US011185645B2

(12) United States Patent
Smutney et al.

(10) Patent No.: US 11,185,645 B2
(45) Date of Patent: Nov. 30, 2021

(54) DRY POWDER INHALER AND SYSTEM FOR DRUG DELIVERY

(71) Applicant: MannKind Corporation, Westlake Village, CA (US)

(72) Inventors: Chad C. Smutney, Watertown, CT (US); P. Spencer Kinsey, Sandy Hook, CT (US); Carl R. Sahi, Coventry, CT (US); Benoit Adamo, North Salem, NY (US); John M. Polidoro, Tolland, CT (US)

(73) Assignee: MannKind Corporation, Westlake Village, CA (US)

( * ) Notice: Subject to any disclaimer, the term of this patent is extended or adjusted under 35 U.S.C. 154(b) by 466 days.

(21) Appl. No.: 15/954,435

(22) Filed: Apr. 16, 2018

(65) Prior Publication Data

US 2018/0228987 A1 Aug. 16, 2018

Related U.S. Application Data

(63) Continuation of application No. 15/098,219, filed on Apr. 13, 2016, which is a continuation of application (Continued)

(51) Int. Cl.

| | |
|---|---|
| ***A61M 15/00*** | (2006.01) |
| ***A61K 47/22*** | (2006.01) |
| ***A61K 9/00*** | (2006.01) |
| ***A61K 38/17*** | (2006.01) |
| ***A61K 38/22*** | (2006.01) |
| ***A61K 38/26*** | (2006.01) |
| *A61K 38/28* | (2006.01) |
| *A61K 38/00* | (2006.01) |

(52) U.S. Cl.

CPC ....... *A61M 15/0045* (2013.01); *A61K 9/0075* (2013.01); *A61K 38/1709* (2013.01); *A61K 38/22* (2013.01); *A61K 38/26* (2013.01); *A61K 38/28* (2013.01); *A61K 47/22* (2013.01); *A61M 15/0021* (2014.02); *A61M 15/0023* (2014.02); *A61M 15/0028* (2013.01); *A61M 15/0043* (2014.02); *A61M 15/0048* (2014.02); *A61M 15/0086* (2013.01); *A61M 15/0091* (2013.01); *A61K 38/00* (2013.01); *A61M 2202/064* (2013.01); *A61M 2205/6081* (2013.01); *A61M 2206/20* (2013.01)

(58) Field of Classification Search

CPC .......... A61M 15/0021; A61M 15/0023; A61M 15/0028; A61M 15/0043; A61M 15/0045; A61M 15/0048; A61M 15/0086; A61M 15/0091; A61M 2202/064; A61M 2205/6081; A61M 2206/20

See application file for complete search history.

(56) References Cited

U.S. PATENT DOCUMENTS 6,748,946 B1 * 6/2004 Rand ................ A61M 15/0065 128/200.23

8,499,757 B2 * 8/2013 Smutney ................ A61K 47/22 128/203.15

(Continued)

*Primary Examiner* — Bradley H Philips

(74) *Attorney, Agent, or Firm* — K&L Gates LLP; Louis C. Cullman; Brian J. Novak

(57) ABSTRACT

A breath-powered, dry powder inhaler, a cartridge, and a pulmonary drug delivery system are provided.

20 Claims, 78 Drawing Sheets

Related U.S. Application Data

No. 13/830,328, filed on Mar. 14, 2013, now Pat. No. 9,339,615, which is a continuation of application No. 12/484,137, filed on Jun. 12, 2009, now Pat. No. 8,424,518.

(60) Provisional application No. 61/157,506, filed on Mar. 4, 2009, provisional application No. 61/061,551, filed on Jun. 13, 2008.

(56) References Cited

U.S. PATENT DOCUMENTS

| | | | | |
|---|---|---|---|---|
| 2006/0239934 | A1* | 10/2006 | Cheatham | A61K 9/0073 424/46 |
| 2007/0181123 | A1* | 8/2007 | Houzego | A61M 15/0068 128/203.15 |
| 2007/0243216 | A1* | 10/2007 | Kepka | A61K 31/557 424/400 |
| 2007/0267010 | A1* | 11/2007 | Fink | A61M 16/08 128/200.23 |

* cited by examiner

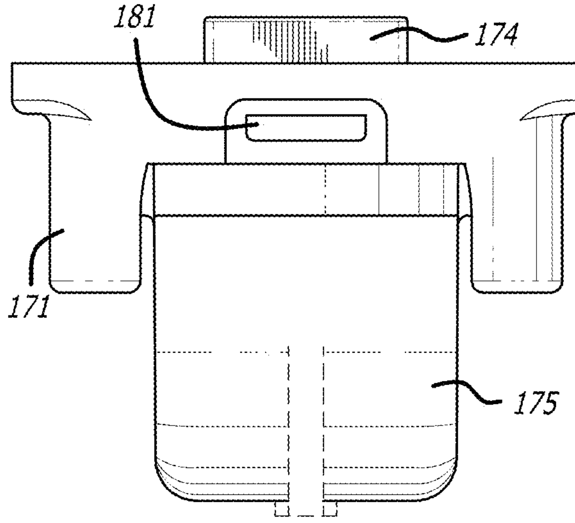
FIG. 39D
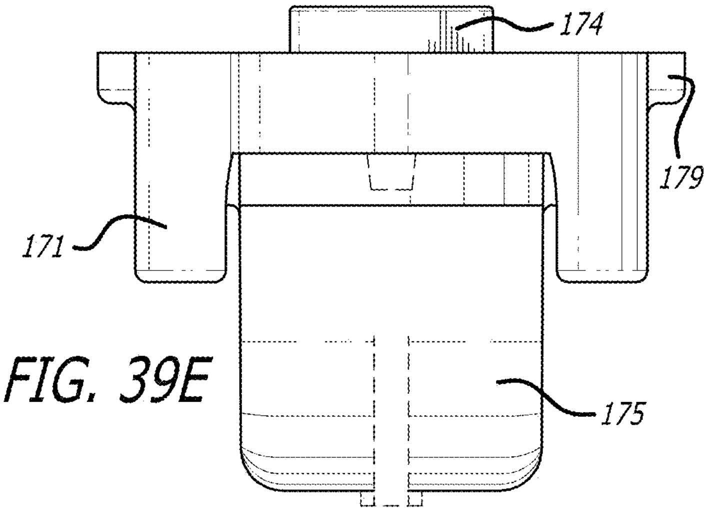
FIG. 39E
FIG. 39F
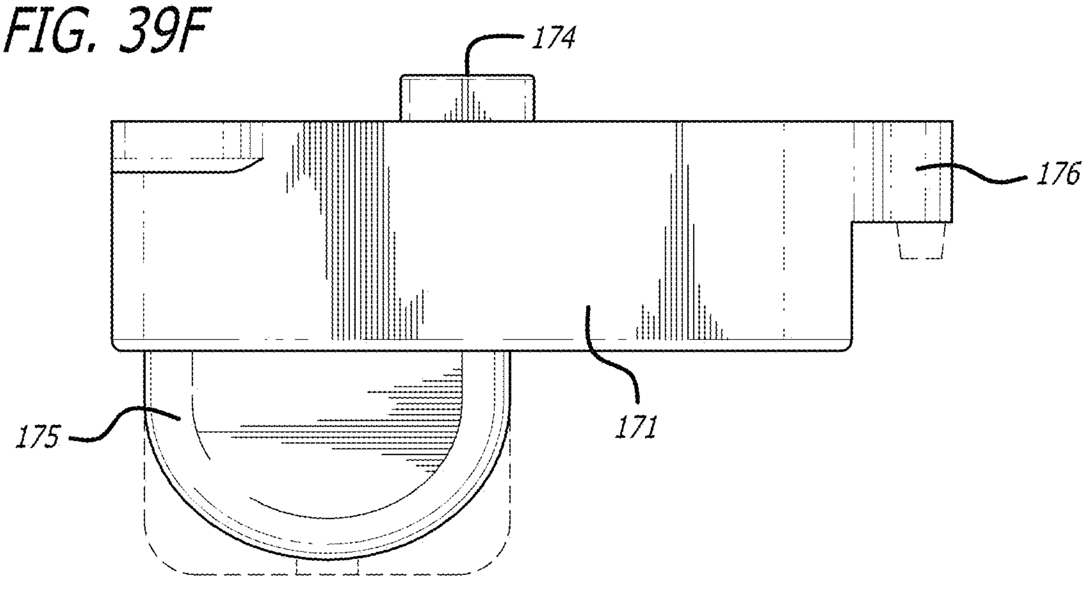

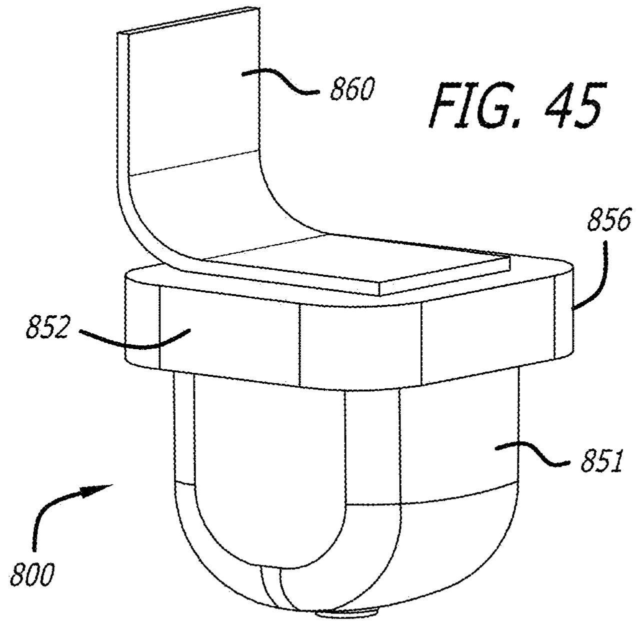
FIG. 45
FIG. 46A
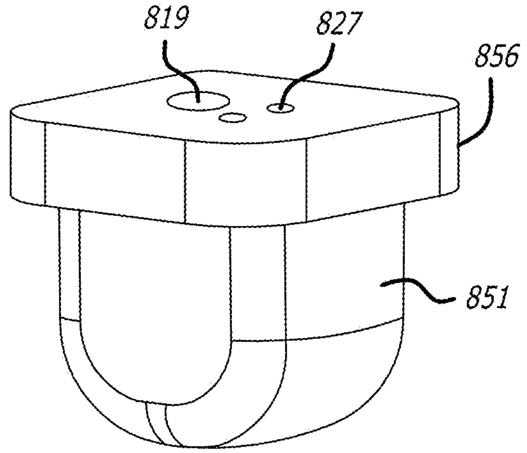
FIG. 46B
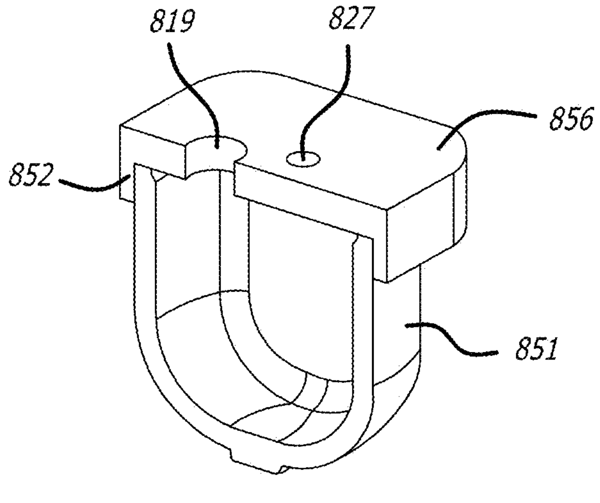

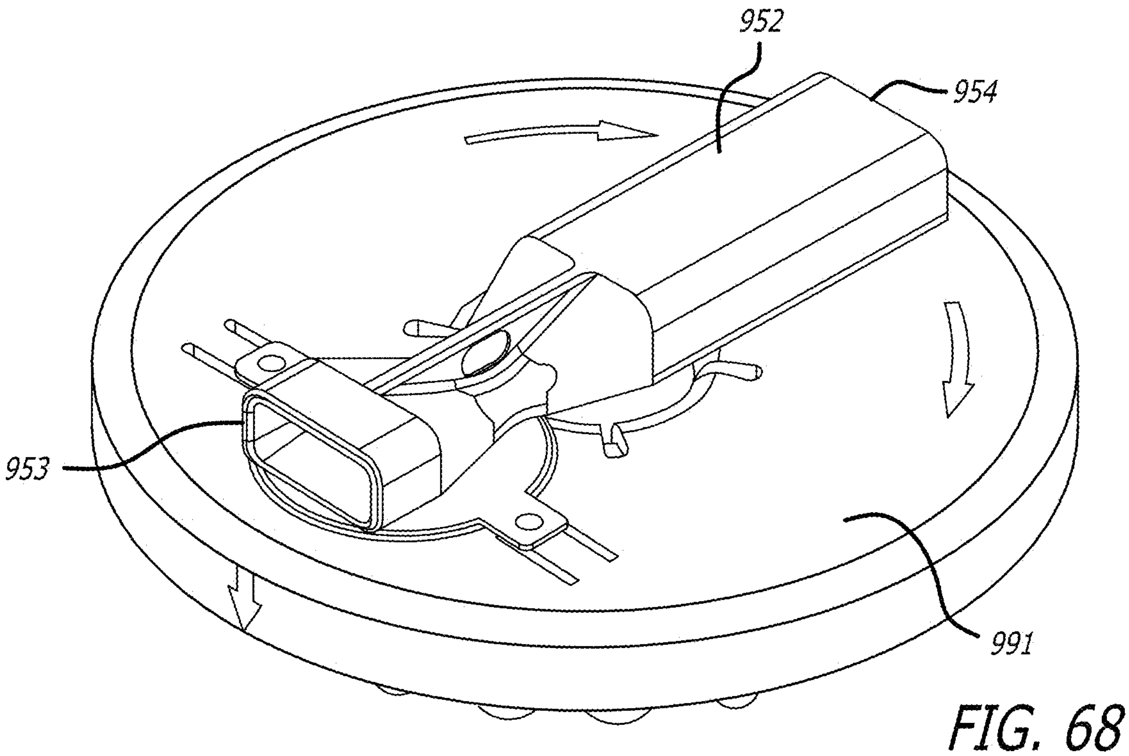
FIG. 68
FIG. 69
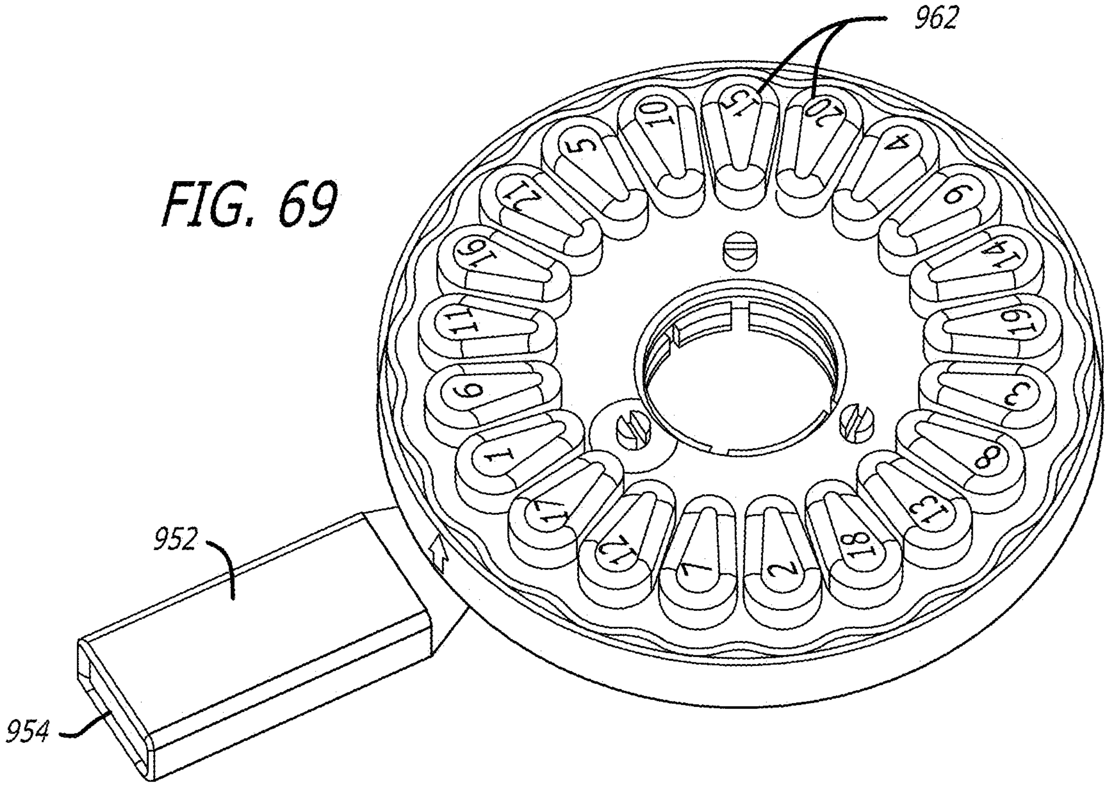

004

131

224

DRY POWDER INHALER AND SYSTEM FOR DRUG DELIVERY

CROSS REFERENCE TO RELATED APPLICATIONS

This Application is a continuation of U.S. patent application Ser. No. 15/098,219, filed Apr. 13, 2016, which is a continuation of U.S. patent application Ser. No. 13/830,328, filed Mar. 14, 2013, now U.S. Pat. No. 9,339,615, which is a continuation of U.S. patent application Ser. No. 12/484,137, filed Jun. 12, 2009, now U.S. Pat. No. 8,424,518, which claims priority from United States Provisional Patent Application Ser. Nos. 61/157,506, filed Mar. 4, 2009, and 61/061,551, filed Jun. 13, 2008, the contents of each of these applications are incorporated herein by reference in their entirety.

TECHNICAL FIELD

The present disclosure relates to dry powder inhalers, cartridges for dry powder inhalers and a system for rapid drug delivery to the pulmonary tract, including dry powder medicament formulations comprising active agents for the treatment of disease such as diabetes and obesity for use with the inhalers. In particular, the system can include a dry powder inhaler with or without a unit dose cartridge, and a drug delivery formulation comprising, for example, a diketopiperazine and an active ingredient such as peptides and proteins, including insulin and glucagon-like peptide 1.

All references cited in this specification, and their references, are incorporated by reference herein in their entirety where appropriate for teachings of additional or alternative details, features, and/or technical background.

BACKGROUND

Drug delivery systems for the treatment of disease which introduce active ingredients into the circulation are numerous and include oral, transdermal, inhalation, subcutaneous and intravenous administration. Drugs delivered by inhalation are typically delivered using positive pressure relative to atmospheric pressure in air with propellants. Such drug delivery systems deliver drugs as aerosols, nebulized or vaporized. More recently, drug delivery to lung tissue has been achieved with dry powder inhalers. Dry powder inhalers can be breath activated or breath-powered and can deliver drugs by converting drug particles in a carrier into a fine dry powder which is entrained into an air flow and inhaled by the patient. Drugs delivered with the use of a dry powder inhaler can no longer be intended to treat pulmonary disease only, but also specific drugs can be used to treat many conditions, including diabetes and obesity.

Dry powder inhalers, used to deliver medicaments to the lungs, contain a dose system of a powder formulation usually either in bulk supply or quantified into individual doses stored in unit dose compartments, like hard gelatin capsules or blister packs. Bulk containers are equipped with a measuring system operated by the patient in order to isolate a single dose from the powder immediately before inhalation. Dosing reproducibility requires that the drug formulation is uniform and that the dose can be delivered to the patient with consistent and reproducible results. Therefore, the dosing system ideally operates to completely discharge all of the formulation effectively during an inspiratory maneuver when the patient is taking his/her dose. However, complete discharge is not required as long as reproducible dosing can be achieved. Flow properties of the powder formulation, and long term physical and mechanical stability in this respect, are more critical for bulk containers than they are for single unit dose compartments. Good moisture protection can be achieved more easily for unit dose compartments such as blisters, however, the materials used to manufacture the blisters allow air into the drug compartment and subsequently the formulation loses viability with long storage. Additionally, dry powder inhalers which use blisters to deliver a medicament by inhalation can suffer with inconsistency of dose delivery to the lungs due to variations in the air conduit architecture resulting from puncturing films or peeling films of the blisters.

Dry powder inhalers such as those described in U.S. Pat. Nos. 7,305,986 and 7,464,706, which disclosure is incorporated herein by reference in their entirety, can generate primary drug particles or suitable inhalation plumes during an inspiratory maneuver by deagglomerating the powder formulation within a capsule. The amount of fine powder discharged from the inhaler's mouthpiece during inhalation is largely dependent on, for example, the interparticulate forces in the powder formulation and the efficiency of the inhaler to separate those particles so that they are suitable for inhalation. The benefits of delivering drugs via the pulmonary circulation are numerous and include rapid entry into the arterial circulation, avoidance of drug degradation by liver metabolism, ease of use, i.e., lack of discomfort of administration by other routes of administration.

Dry powder inhaler products developed for pulmonary delivery have met with limited success to date, due to lack of practicality and/or cost of manufacture. Some of the persistent problems observed with prior art inhalers, include lack of ruggedness of device, propellants use to deliver the powder, consistency in dosing, inconvenience of the equipment, poor deagglomeration, and/or lack of patient compliance. Therefore, the inventors have identified the need to design and manufacture an inhaler with consistent powder delivery properties, easy to use without discomfort, and discrete inhaler configurations which would allow for better patient compliance.

Further, drug delivery to the lungs for agents having systemic effects can also be performed. Advantages of the lungs for delivery of systemic agents include the large surface area and the ease of uptake by the lung's mucosal surface. One problem associated with all of these forms of pulmonary drug delivery is that it is difficult to deliver drugs into the lungs due to problems in getting the drugs past all of the natural barriers, such as the cilia lining the trachea, and in trying to administer a uniform volume and weight of drug.

Accordingly, there is room for improvement in the pulmonary delivery of drugs.

SUMMARY

The present disclosure is directed to dry powder inhalers, cartridges for dry powder inhalers and a system for rapid drug delivery to the pulmonary tract, including dry powders comprising active agents for the treatment of disease, including diabetes and obesity. The dry powder inhaler can be breath-powered, compact, reusable or disposable, has various shapes and sizes, and comprises a system of airflow conduit pathways for the effective and rapid delivery of powder medicament. In one embodiment, the inhaler can be a unit dose, reusable or disposable inhaler that can be used with or without a cartridge. By use without a cartridge we refer to systems in which cartridge-like structures are integral to the inhaler, as opposed systems in which a cartridge is installed for use by, for example, the user. In another embodiment, the inhaler can be a multidose inhaler, disposable or reusable that can be used with single unit dose cartridges installed in the inhaler or cartridge-like structures built-in or structurally configured as part of the inhaler.

The dry powder inhalation system comprises a dry powder inhalation device or inhaler with or without a cartridge, and a pharmaceutical formulation comprising an active ingredient for pulmonary delivery. In some embodiments delivery is to the deep lung (that is, to the alveolar region) and in some of these embodiments the active agents is absorbed into the pulmonary circulation for systemic delivery. The system can also comprise a dry powder inhaler with or without a unit dose cartridge, and a drug delivery formulation comprising, for example, diketopiperazine and an active ingredient such as peptides and proteins, including insulin and glucagon-like peptide 1.

In one embodiment, the dry powder inhaler comprises a housing, a moveable member, and a mouthpiece, wherein the moveable member is operably configured to move a container from a powder containment position to a dosing position. In this and other embodiments, the moveable member can be a sled, a slide tray or a carriage which is moveable by various mechanisms.

In another embodiment, the dry powder inhaler comprises a housing and a mouthpiece, structurally configured to have an open position, a closed position and a mechanism operably configured to receive, hold, and reconfigure a cartridge from a containment position to a dispensing, dosing or dose delivery position upon movement of said inhaler from the open position to the closed position. In versions of this embodiment, the mechanism can also reconfigure a cartridge installed in the inhaler from the dosing position to a containment position after use when the inhaler is opened to unload a used cartridge. In one embodiment, the mechanism can reconfigure a cartridge to a disposable or discarding configuration after use. In such embodiments, the housing is structurally configured to be moveably attached to the mouthpiece by various mechanisms including, a hinge. The mechanism configured to receive and reconfigure a cartridge installed in the inhaler from a containment position to the dosing position can be designed to operate manually or automatically upon movement of the inhaler components, for example, by closing the device from an open configuration. In one embodiment, the mechanism for reconfiguring a cartridge comprises a slide tray or sled attached to the mouthpiece and movably attached to the housing. In another embodiment, the mechanism is mounted or adapted to the inhaler and comprises a geared mechanism integrally mounted within, for example, a hinge of the inhaler device. In yet another embodiment, the mechanism operably configured to receive and reconfigure the cartridge from a containment position to a dosing position comprises a cam that can reconfigure the cartridge upon rotation of, for example, the housing or the mouthpiece.

In an alternate embodiment, the dry powder inhaler can be made as a single use, unit dose disposable inhaler, which can be provided with a powder container configured to hold a powder medicament, wherein the inhaler can have a first and a second configuration in which the first configuration is a containment configuration and the second configuration is a dosing of dispensing configuration. In this embodiment, the inhaler can be provided with or without a mechanism for reconfiguring the powder container. According to aspects of the latter embodiment the container can be reconfigured directly by the user.

In yet another embodiment, an inhaler comprising a container mounting area configured to receive a container, and a mouthpiece having at least two inlet apertures and at least one exit aperture; wherein one inlet aperture of the at least two inlet apertures is in fluid communication with the container area, and one of the at least two inlet apertures is in fluid communication with the at least one exit aperture via a flow path configured to bypass the container area.

In one embodiment, the inhaler has opposing ends such as a proximal end for contacting a users lips or mouth and a distal end, and comprises a mouthpiece and a medicament container; wherein the mouthpiece comprises a top surface and a bottom or undersurface. The mouthpiece undersurface has a first area configured relatively flat to maintain a container in a sealed or containment configuration, and a second area adjacent to the first area which is raised relative to the first area. In this embodiment, the container is movable from the containment configuration to the dosing configuration and vice versa, and in the dosing configuration, the second raised area of the mouthpiece undersurface and the container form or define an air inlet passageway to allow ambient air to enter the internal volume of the container or expose the interior of the container to ambient air. In one embodiment, the mouthpiece can have a plurality of openings, for example, an inlet port, an outlet port and at least one port for communicating with a medicament container in a dispensing or dosing position, and can be configured to have integrally attached panels extending from the bottom surface sides of the inhaler and having flanges protruding towards the center of the inhaler mouthpiece, which serve as tracks and support for the container on the mouthpiece so that the container can move along the tracks from the containment position to a dispensing or dosing position and back to containment if desired. In one embodiment, the medicament container is configured with wing-like projections or winglets extending from its top border to adapt to the flanges on the mouthpiece panels. In one embodiment, the medicament container can be moved manually by a user from containment position to a dosing position and back to the containment position after dosing, or by way of a sled, a slide tray, or a carriage.

In another embodiment, a single use, unit dose, disposable inhaler can be constructed to have a sled incorporated and operably configured to the mouthpiece. In this embodiment, a bridge on the sled can abut or rest on an area of the medicament container to move the container along the mouthpiece panel tracks from the containment position to the dispensing or dosing position. In this embodiment, the sled can be operated manually to move the container on the mouthpiece tracks.

In one embodiment, the dry powder inhaler comprises one or more air inlets and one or more air outlets. When the inhaler is closed, at least one air inlet can permit flow to enter the inhaler and at least one air inlet allows flow to enter a cartridge compartment or the interior of the cartridge or container adapted for inhalation. In one embodiment, the inhaler has an opening structurally configured to communicate with the cartridge placement area and with a cartridge inlet port when the cartridge container is in a dosing position. Flow entering the cartridge interior can exit the cartridge through an exit or dispensing port or ports; or flow entering the container of an inhaler can exit through at least one of the dispensing apertures. In this embodiment, the cartridge inlet port or ports is/are structurally configured so that all, or a portion of the air flow entering the interior of the cartridge is directed at the exit or dispensing port or ports. The medicament container is structurally configured to have two opposing, relatively curvilinear sides which can direct airflow. In this embodiment, flow entering the air inlet during an inhalation can circulate within the interior of the container about an axis relatively perpendicular to the axis of the dispensing ports, and thereby, the flow can lift, tumble and effectively fluidize a powder medicament contained in the cartridge. In this and other embodiments, fluidized powder in the air conduit can be further deagglomerated into finer powder particles by a change in direction or velocity, i.e., acceleration or deceleration of the particles in the flow pathway. In certain embodiments, the change in acceleration or deceleration can be accomplished by changing the angle and geometries of, for example, the dispensing port or ports, the mouthpiece conduit and/or its interfaces. In the inhalers described herewith, the mechanism of fluidization and acceleration of particles as they travel through the inhaler are methods by which deagglomeration and delivery of a dry powder formulation is effectuated.

In particular embodiments, a method for deagglomerating and dispersing a dry powder formulation comprises one or more steps such as tumbling within a primary container region started and enhanced by flow entering the container; a rapid acceleration of powder in the flow through the dispensing ports leaving the container; further accelerating the powder induced by a change in direction or velocity as the powder exits the dispensing port; shearing of powder particles caught within a flow gradient, wherein the flow on the top of the particle is faster than flow on bottom of the particle; deceleration of flow due to expansion of cross-sectional area within the mouthpiece air conduit; expansion of air trapped within a particle due to the particle moving from a higher pressure region to a lower pressure region, or collisions between particles and flow conduit walls at any point in the flow passageways.

In another embodiment, a dry powder inhaler comprises a mouthpiece, a sled, slide tray, or a carriage, a housing, a hinge, and a gear mechanism configured to effectuate movement of the sled or slide tray; wherein the mouthpiece and the housing are moveably attached by the hinge.

Cartridges for use with the dry powder inhaler can be manufactured to contain any dry powder medicament for inhalation. In one embodiment, the cartridge is structurally configured to be adaptable to a particular dry powder inhaler and can be made of any size and shape, depending on the size and shape of the inhaler to be used with, for example, if the inhaler has a mechanism which allows for translational movement or for rotational movement. In one embodiment, the cartridge can be configured with a securing mechanism, for example, having a beveled edge on the cartridge top corresponding to a matching beveled edge in an inhaler so that the cartridge is secured in use. In one embodiment, the cartridge comprises a container and a lid or cover, wherein the container can be adapted to a surface of the lid and can be movable relative to the lid or the lid can be movable on the container and can attain various configurations depending on its position, for example, a containment configuration, a dosing configuration or after use configuration. Alternatively the lid can be removable. An exemplary embodiment can comprise an enclosure to hold medicament configured having at least one inlet aperture to allow flow into the enclosure; at least one dispensing aperture to allow flow out of the enclosure; the inlet aperture configured to direct at least a portion of the flow at the dispensing aperture or at the particles approaching the dispensing aperture within the enclosure in response to a pressure gradient. The dispensing aperture or apertures and the intake gas aperture each independently can have a shape such as oblong, rectangular, circular, triangular, square and oval-shaped and can be in close proximity to one another. During inhalation, a cartridge adapted to the inhaler in a dosing position allows airflow to enter the enclosure and mix with the powder to fluidize the medicament. The fluidized medicament moves within the enclosure such that medicament gradually exits the enclosure through the dispensing aperture, wherein the fluidized medicament exiting the dispensing aperture is sheared and diluted by a secondary flow not originating from within the enclosure. In one embodiment, the flow of air in the internal volume rotates in a circular manner so as to lift a powder medicament in the container or enclosure and recirculate the entrained powder particles or powder mass in the internal volume of the container promoting the flow to tumble prior to the particles exiting dispensing ports of the container or one or more of the inhaler inlet ports or air outlet or dispensing apertures, and wherein the recirculating flow, can cause tumbling, or non-vortical flow of air in the internal volume acts to deagglomerate the medicament. In one embodiment, the axis of rotation is mostly perpendicular to gravity. In another embodiment the axis of rotation is mostly parallel to gravity. The secondary flow not originating from within the enclosure further acts to de-agglomerate the medicament. In this embodiment, the pressure differential is created by the user's inspiration.

A cartridge for a dry powder inhaler, comprising: an enclosure configured to hold a medicament; at least one inlet port to allow flow into the enclosure, and at least one dispensing port to allow flow out of the enclosure; said at least one inlet port is configured to direct at least a portion of the flow entering the at least one inlet port at the at least one dispensing port within the enclosure in response to a pressure differential.

A unit dose cartridge for an inhaler comprising: a substantially flat cartridge top, arrow-like in configuration, having one or more inlet apertures, one or more dispensing apertures, and two side panels extending downwardly and each of the two side panels having a track; and a container moveably engaged to the track of the side panels of the cartridge top, and comprising a chamber configured to have a relatively cup-like shape with two relatively flat and parallel sides and a relatively rounded bottom, and interior surface defining an internal volume; said container configurable to attain a containment position and a dosing position with the cartridge top; wherein in use with a dry powder inhaler during an inhalation a flow entering the internal volume diverges as it enters the internal volume with a portion of the flow exiting through the one or more dispensing apertures and a portion of the flow rotating inside the internal volume and lifting a powder in the internal volume before exiting through the dispensing apertures.

In one embodiment, an inhalation system for pulmonary drug delivery is provided, comprising: a dry powder inhaler comprising a housing and a mouthpiece having an inlet and an outlet port, an air conduit between the inlet and the outlet, and an opening structurally configured to receive a cartridge; a cartridge mounting mechanism such as a sled; a cartridge configured to be adapted to the dry powder inhaler and containing a dry powder medicament for inhalation; wherein the cartridge comprises a container and a lid having one or more inlet ports or one or more dispensing ports; the dry powder inhaler system in use has a predetermined airflow balance distribution through said cartridge relative to total flow delivered to the patient.

In embodiments disclosed herewith, the dry powder inhaler system comprises a predetermined mass flow balance within the inhaler. For example, a flow balance of approximately 10% to 70% of the total flow exiting the inhaler and into the patient is delivered by the dispensing ports or passed through the cartridge, whereas approximately 30% to 90% is generated from other conduits of the inhaler. Moreover, bypass flow or flow not entering and exiting the cartridge can recombine with the flow exiting the dispensing port of the cartridge within the inhaler to dilute, accelerate and ultimately deagglomerate the fluidized powder prior to exiting the mouthpiece.

In the embodiments described herein, the dry powder inhaler is provided with relatively rigid air conduits or plumbing system and high flow resistance levels to maximize deagglomeration of powder medicament and facilitate delivery. Accordingly, effectiveness and consistency of powder medicament discharge is obtained from the inhaler after repeated use since the inhaler are provided with air conduit geometries which remain the same and cannot be altered. In some embodiments, the dry powder medicament is dispensed with consistency from the inhaler in less than about 3 seconds, or generally less than one second. In some embodiments, the inhaler system can have a high resistance value of, for example, approximately 0.065 to about 0.200 (√kPa)/liter per minute. Therefore, in the system, peak inhalation pressure drops of between 2 and 20 kPa produce resultant peak flow rates of about between 7 and 70 liters per minute. These flow rates result in greater than 75% of the cartridge contents dispensed in fill masses between 1 and 30 mg. In some embodiments, these performance characteristics are achieved by end users within a single inhalation maneuver to produce cartridge dispense percentage of greater than 90%. In certain embodiments, the inhaler and cartridge system are configured to provide a single dose by discharging powder from the inhaler as a continuous flow, or as one or more pulses of powder delivered to a patient.

In one embodiment, a method for effectively deagglomerating a dry powder formulation during an inhalation in a dry powder inhaler is provided. The method can comprise the steps of providing a dry powder inhaler comprising a container having an air inlet, dispensing ports communicating with a mouthpiece air conduit and containing and delivering a formulation to a subject in need of the formulation; generating an airflow in the inhaler by the subject's inspiration so that about 10 to about 70% of the airflow entering the inhaler enters and exits the container; allowing the airflow to enter the container inlet, circulate and tumble the formulation in an axis perpendicular to the dispensing ports to fluidize the formulation so as to yield a fluidized formulation; accelerating metered amounts of fluidized formulation through the dispensing ports and in the air conduit, and decelerating the airflow containing fluidized formulation in the mouthpiece air conduit of the inhaler prior to reaching the subject.

In another embodiment, a method for deagglomerating and dispersing a dry powder formulation for inhalation is provided, comprising the steps of: generating an airflow in a dry powder inhaler comprising a mouthpiece and a container having at least one inlet port and at least one dispensing port and containing a dry powder formulation; said container forming an air passage between at least one inlet port and at least one dispensing port and the inlet port directs a portion of the airflow entering the container to at least one dispensing port; allowing airflow to tumble powder within the container in a substantially perpendicular axis to the at least one dispensing port so as to lift and mix the dry powder medicament in the container to form an airflow medicament mixture; and accelerating the airflow exiting the container through at least one dispensing port. In one embodiment, the inhaler mouthpiece is configured to have a gradual expanding cross-section to decelerate flow and minimize powder deposition inside the inhaler and promote maximal delivery of powder to the patient. In one embodiment, for example, the cross-sectional area of the oral placement region of an inhaler can be from about 0.05 $cm^2$ to about 0.25 $cm^2$ over an approximate length of about 3 cm. These dimensions depend on the type of powder used with the inhaler and the dimensions of the inhaler itself.

A cartridge for a dry powder inhaler, comprising: a cartridge top and a container defining an internal volume; wherein the cartridge top has an undersurface that extends over the container; said undersurface configured to engage said container, and comprising an area to contain the internal volume and an area to expose the internal volume to ambient air.

In an alternate embodiment, a method for the delivery of particles through a dry powder delivery device is provided, comprising: inserting into the delivery device a cartridge for the containment and dispensing of particles comprising an enclosure enclosing the particles, a dispensing aperture and an intake gas aperture; wherein the enclosure, the dispensing aperture, and the intake gas aperture are oriented such that when an intake gas enters the intake gas aperture, the particles are deagglomerated, by at least one mode of deagglomeration as described above to separate the particles, and the particles along with a portion of intake gas are dispensed through the dispensing aperture; concurrently forcing a gas through a delivery conduit in communication with the dispensing aperture thereby causing the intake gas to enter the intake gas aperture, de-agglomerate the particles, and dispense the particles along with a portion of intake gas through the dispensing aperture; and, delivering the particles through a delivery conduit of the device, for example, in an inhaler mouthpiece. In embodiment described herein, to effectuate powder deagglomeration, the dry powder inhaler can be structurally configured and provided with one or more zones of powder deagglomeration, wherein the zones of deagglomeration during an inhalation maneuver can facilitate tumbling of a powder by air flow entering the inhaler, acceleration of the air flow containing a powder, deceleration of the flow containing a powder, shearing of a powder particles, expansion of air trapped in the powder particles, and/or combinations thereof.

In another embodiment, the inhalation system comprises a breath-powered dry powder inhaler, a cartridge containing a medicament, wherein the medicament can comprise, for example, a drug formulation for pulmonary delivery such as a composition comprising a diketopiperazine and an active agent. In some embodiments, the active agent comprises peptides and proteins, such as insulin, glucagon-like peptide 1, oxyntomodulin, peptide YY, exendin, analogs thereof, and the like. The inhalation system of the invention can be used, for example, in methods for treating conditions requiring localized or systemic delivery of a medicament, for example, in methods for treating diabetes, pre-diabetes conditions, respiratory track infection, pulmonary disease and obesity. In one embodiment, the inhalation system comprises a kit comprising at least one of each of the components of the inhalation system for treating the disease or disorder.

The present disclosure also provides systems, microparticles and methods that allow for improved delivery of drugs to the lungs. Embodiments disclosed herein achieve improved delivery by providing fumaryl diketopiperazine (FDKP) microparticles with a trans isomer content of about 45 to about 65%. Microparticles with a trans isomer content in this range exhibit characteristics beneficial to drug delivery to the lungs such as improved aerodynamic performance.

One embodiment disclosed herein comprises FDKP microparticles comprising a trans isomer content of about 45 to about 65%. In another embodiment of the FDKP microparticles, the trans isomer content is from about 45 to about 63%. In another embodiment of the FDKP microparticles, the trans isomer content is from about 53 to about 65%. In another embodiment of the FDKP microparticles, the trans isomer content is from about 53 to about 63%. In another embodiment of the FDKP microparticles, the trans isomer content is from about 50 to about 56%. In another embodiment of the FDKP microparticles, the trans isomer content is from about 54 to about 56%.

In another embodiment, the FDKP microparticles comprise a drug. In another embodiment of the FDKP microparticles, the drug is insulin. In another embodiment of the FDKP microparticles, the insulin content is from about 3 to about 4 U/mg.

Embodiments disclosed herein also include dry powders. In one embodiment, the dry powders comprise FDKP microparticles comprising a trans isomer content of about 45 to about 65%. In another embodiment of the dry powders, the trans isomer content is from about 45 to about 63%. In another embodiment of the dry powders, the trans isomer content is from about 50 to about 63%. In another embodiment of the dry powders, the trans isomer content is from about 53 to about 65%. In another embodiment of the dry powders, the trans isomer content is from about 53 to about 63%. In another embodiment of the dry powders, the trans isomer content is from about 50 to about 56%. In another embodiment of the dry powders, the trans isomer content is from about 54 to about 56%.

In another embodiment of the dry powders, the FDKP microparticles comprise a drug. In another embodiment of the dry powders, the drug is insulin. In another embodiment of the dry powders, the insulin content of the FDKP microparticles is from about 3 to about 4 U/mg.

Further embodiments concern drug delivery systems comprising an inhaler, a unit dose dry powder medicament container, and a powder comprising the microparticles disclosed herein and an active agent.

Embodiments disclosed herein also include methods. One embodiment includes a method of treating an insulin-related disorder comprising administering a dry powder described above to a person in need thereof.

Another embodiment disclosed herein includes a method of making microparticles suitable for pulmonary administration as a dry powder comprising: a) providing a solution of FDKP wherein the trans isomer content is from about 45 to about 65%, b) providing a solution of a volatile acid, and c) mixing the solutions together in a high-shear mixer to produce the microparticles.

Also disclosed herein is a method for preparing FDKP microparticles comprising recrystallizing FDKP from a solvent to obtain FDKP microparticles, wherein the trans-FDKP isomer content of the microparticles is about 45% to about 65%, or about 53% to about 63%, or about 54% to about 56%. Further embodiments include FDKP microparticles comprising a drug, and having a manufacturing specification of about 53% to about 63% trans-FDKP isomer content, based on the total content of FDKP.

Another embodiment disclosed herein includes a method of delivering insulin to a patient in need thereof comprising administering a dry powder comprising diketopiperazine microparticles disclosed herein to the deep lung by inhalation of the dry powder by the patient. In aspects of this embodiment particular features of an inhaler system are specified.

BRIEF DESCRIPTION OF THE DRAWINGS

FIG. 39B through 39F depict the cartridge embodiment shown in FIG. 39A in a top, bottom, proximal, distal and side views, respectively.

FIG. 45 illustrates a perspective view of an alternate cartridge embodiment for use with a dry powder inhaler showing the cartridge in a containment configuration.

FIG. 46A illustrates a perspective view of the cartridge embodiment of FIG. 45 for use with a dry powder inhaler showing the cartridge in a dosing configuration.

FIG. 46B illustrates a perspective view of a cartridge embodiment of FIG. 45 in a mid-longitudinal cross-section and in a dosing configuration.

FIG. 68 illustrates a perspective view of an alternate embodiment of a multidose dry powder inhaler.

FIG. 69 illustrates a perspective bottom view of the inhaler depicted in FIG. 68.

DETAILED DESCRIPTION

Figure 1:
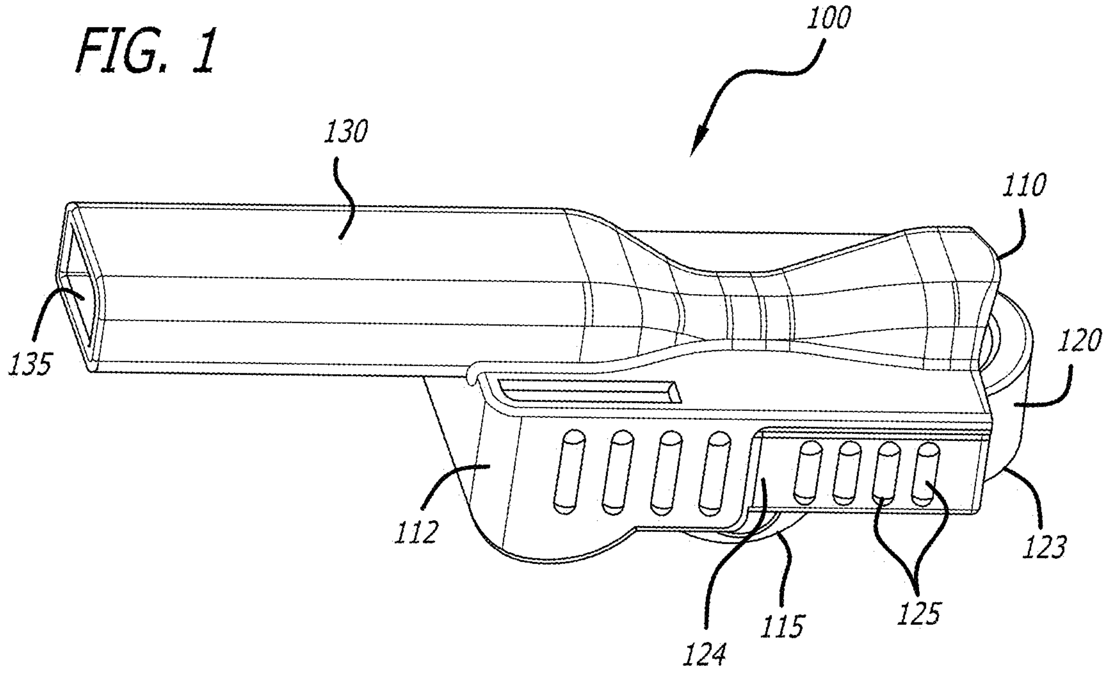
FIG. 1 depicts a perspective view of an embodiment of a dry powder inhaler in a closed position.

In embodiments disclosed herein, there is disclosed a dry powder inhaler, a cartridge for a dry powder inhaler and an inhalation system for delivering pharmaceutical medicaments to a patient via inhalation. In one embodiment, the inhalation system comprises a breath-powered dry powder inhaler, and a cartridge containing a pharmaceutical formulation comprising a pharmaceutically active substance or active ingredient and a pharmaceutically acceptable carrier. The dry powder inhaler is provided in various shapes and sizes, and can be reusable or for single use, easy to use, is inexpensive to manufacture and can be produced in high volumes in simple steps using plastics or other acceptable materials. In addition to complete systems, inhalers, filled cartridges and empty cartridges constitute further embodiments disclosed herein. The present inhalation system can be designed to be used with any type of dry powder. In one embodiment, the dry powder is a relatively cohesive powder which requires optimal deagglomeration condition. In one embodiment, the inhalation system provides a re-useable, miniature breath-powered inhaler in combination with single-use cartridges containing pre-metered doses of a dry powder formulation.

As used herein the term “a unit dose inhaler” refers to an inhaler that is adapted to receive a single container a dry powder formulation and delivers a single dose of a dry powder formulation by inhalation from container to a user. It should be understood that in some instance multiple unit doses will be required to provide a user with a specified dosage.

As used herein the term “a multiple dose inhaler” refers to an inhaler having a plurality of containers, each container comprising a pre-metered dose of a dry powder medicament and the inhaler delivers a single dose of a medicament powder by inhalation at any one time.

As used herein a "container" is an enclosure configured to hold or contain a dry powder formulation, a powder containing enclosure, and can be a structure with or without a lid.

As used herein a "powder mass" is referred to an agglomeration of powder particles or agglomerate having irregular geometries such as width, diameter, and length.

As used herein, the term "microparticle" refers to a particle with a diameter of about 0.5 to about 1000 μm, irrespective of the precise exterior or interior structure. However four pulmonary delivery microparticles that are less than 10 μm are generally desired, especially those with mean particles sizes of less than about 5.8 μm in diameter. Microparticles having a diameter of between about 0.5 and about 10 microns can reach the lungs, successfully passing most of the natural barriers. A diameter of less than about 10 microns is required to navigate the turn of the throat and a diameter of about 0.5 microns or greater is required to avoid being exhaled. To reach the deep lung (or alveolar region) where most efficient absorption is believed to occur, it is preferred to maximize the proportion of particles contained in the "respirable fraction" (RF), generally accepted to be about 0.5 to about 5.7 microns, though some references use somewhat different ranges. Embodiments disclosed herein show that FDKP microparticles with a trans isomer content of between about 45 to about 65% exhibit characteristics beneficial to delivery of drugs to the lungs such as improved aerodynamic performance.

Respirable fraction on fill (RF/fill), representing the % of powder in a dose that emitted from an inhaler upon discharge, is a measure of microparticle aerodynamic performance. As described herein, a RF/fill score of 40% or greater reflects acceptable aerodynamic performance characteristics.

It should be understood that specific RF/fill values can depend on the inhaler used to deliver the powder. Powders generally tend to agglomerate and crystalline DKP microparticles form particularly cohesive powders. One of the functions of a dry powder inhaler is to deagglomerate the powder. However deagglomeration is not typically complete so that the particle size distribution seen when measuring the respirable fraction as delivered by an inhaler will not match the size distribution of the primary particles, that is the profile will be shifted toward larger particles. Although inhaler designs vary in their efficiency of deagglomeration and thus the absolute value of RF/fill observed using such different designs will also vary, it is expected that optimal RF/fill as a function of surface area (or other variables impacting aerodynamic performance) will be similar from inhaler to inhaler.

As used herein a "unit dose" refers to a pre-metered dry powder formulation for inhalation. Alternatively, a unit dose can be a single container having multiple doses of formulation that can be delivered by inhalation as metered single amounts. A unit dose cartridge/container contains a single dose. Alternatively it can comprise multiple individually accessible compartments, each containing a unit dose.

As used herein, the term "about" is used to indicate that a value includes the standard deviation of error for the device or method being employed to determine the value.

The present devices can be manufactured by several methods, however, in one embodiment, the inhalers and cartridges are made, for example, by injection molding techniques, thermoforming, using various types of plastic materials, including, polypropylene, cyclicolephin co-polymer, nylon, and other compatible polymers and the like. In certain embodiments, the dry powder inhaler can be assembled using top-down assembly of individual component parts. In some embodiments, the inhalers are provided in compact sizes, such as from about 1 inch to about 5 inches in dimension, and generally, the width and height are less than the length of the device. In certain embodiments the inhaler is provided in various shapes including, relatively rectangular bodies, cylindrical, oval, tubular, squares, oblongs, and circular forms.

In embodiments described and exemplified herewith, the inhalers effectively fluidize, deagglomerate or aerosolize a dry powder formulation by using at least one relatively rigid flow conduit pathway for allowing a gas such as air to enter the inhaler. For example, the inhaler is provided with a first air/gas pathway for entering and exiting a cartridge containing the dry powder, and a second air pathway which can merge with the first air flow pathway exiting the cartridge. The flow conduits, for example, can have various shapes and sizes depending on the inhaler configuration.

Figure 2:
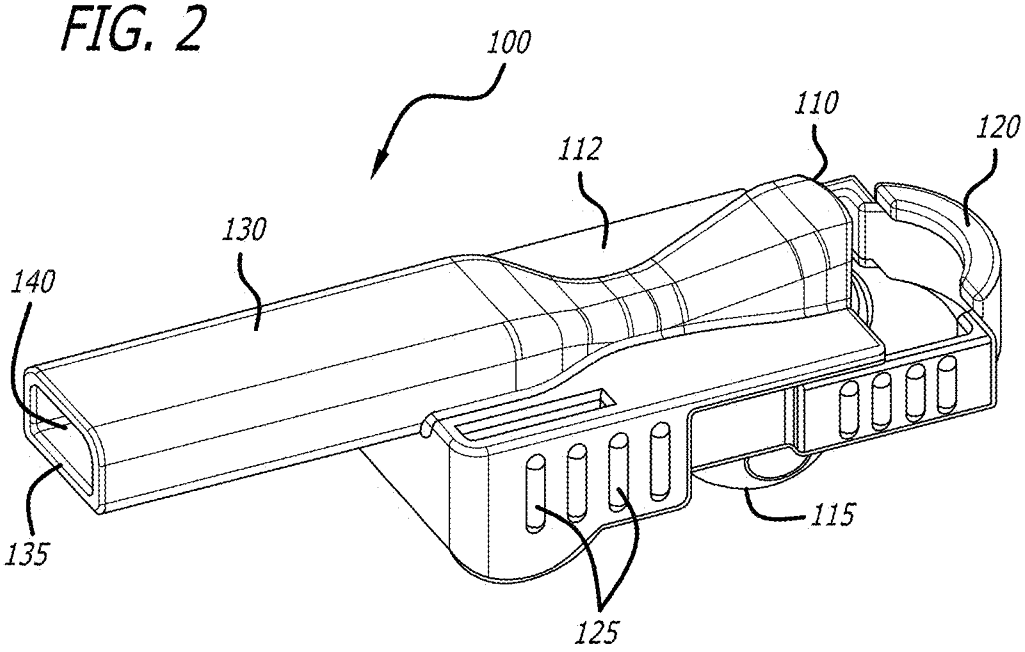
FIG. 2 depicts a perspective view of the dry powder inhaler of FIG. 1 showing the dry powder inhaler in a partially opened position.
Figure 4A:
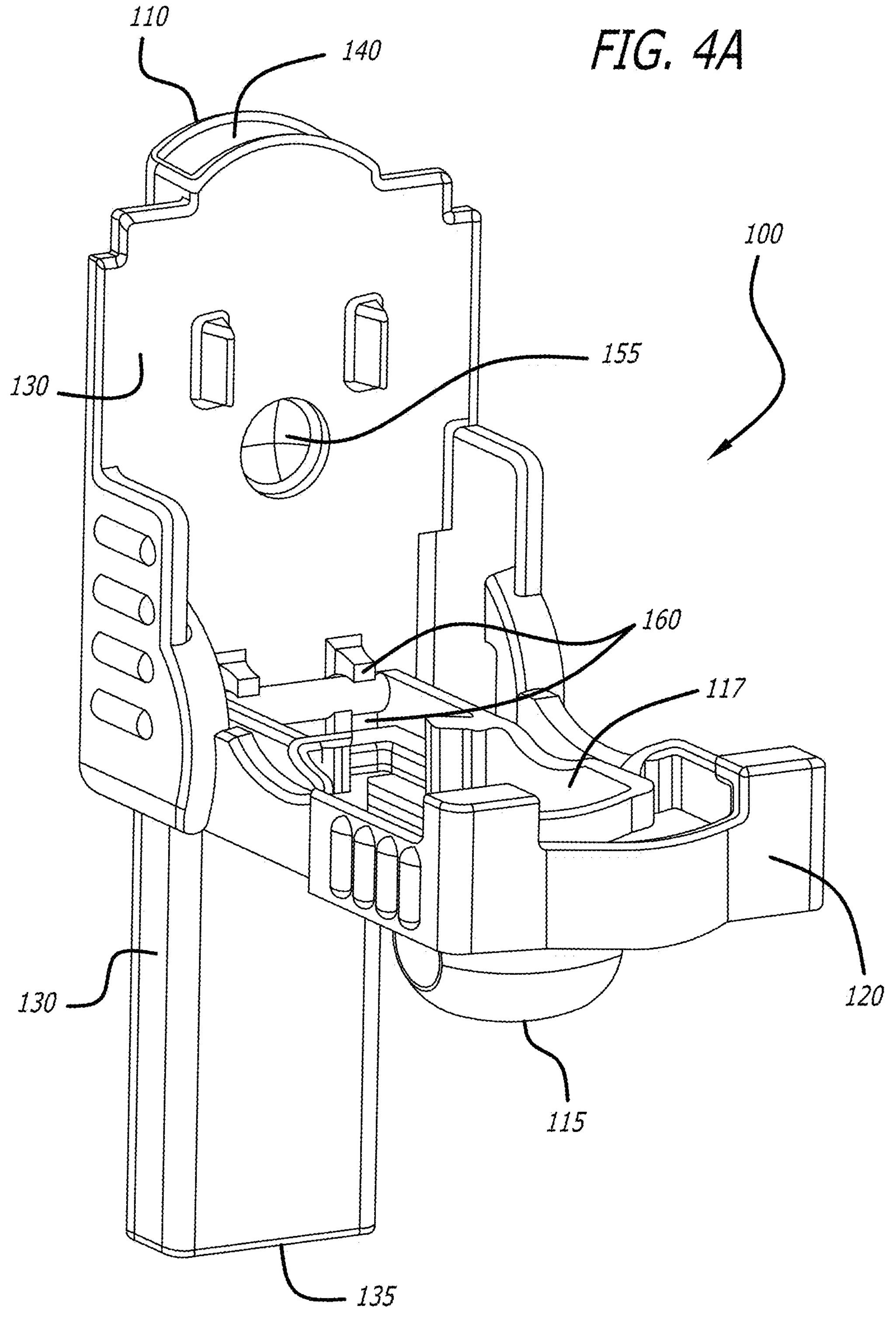
FIG. 4A depicts a perspective view of the inhaler in FIG. 1 showing the inhaler in a fully opened, cartridge loading/unloading position, depicting its internal surface including the interior surface of the inhaler mouthpiece.
Figure 4B:
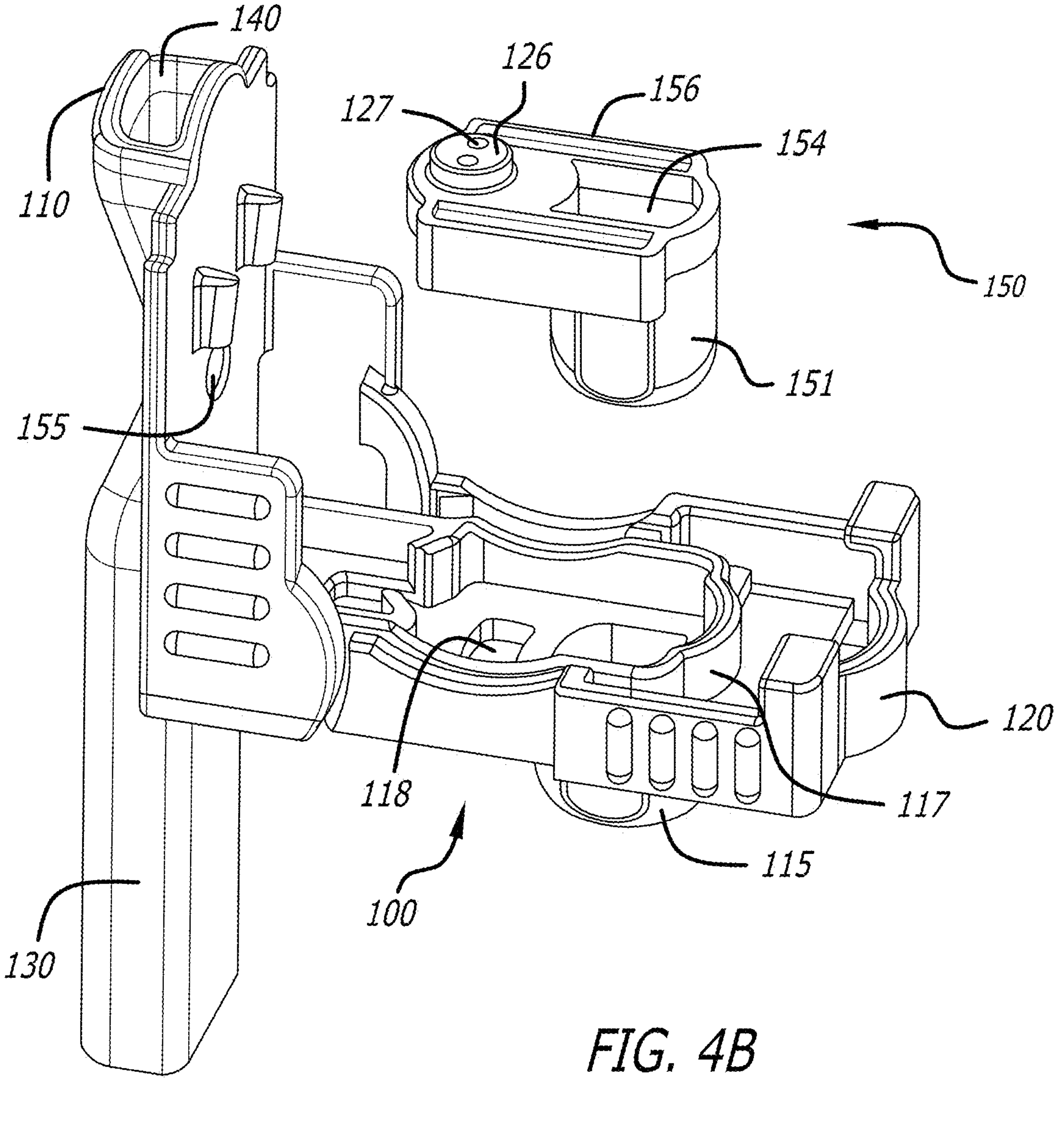
FIG. 4B depicts a perspective view of the dry powder inhaler of FIG. 4A showing the inhaler in the fully opened, cartridge loading/unloading position and the cartridge configured for placement into the inhaler.
Figure 4C:
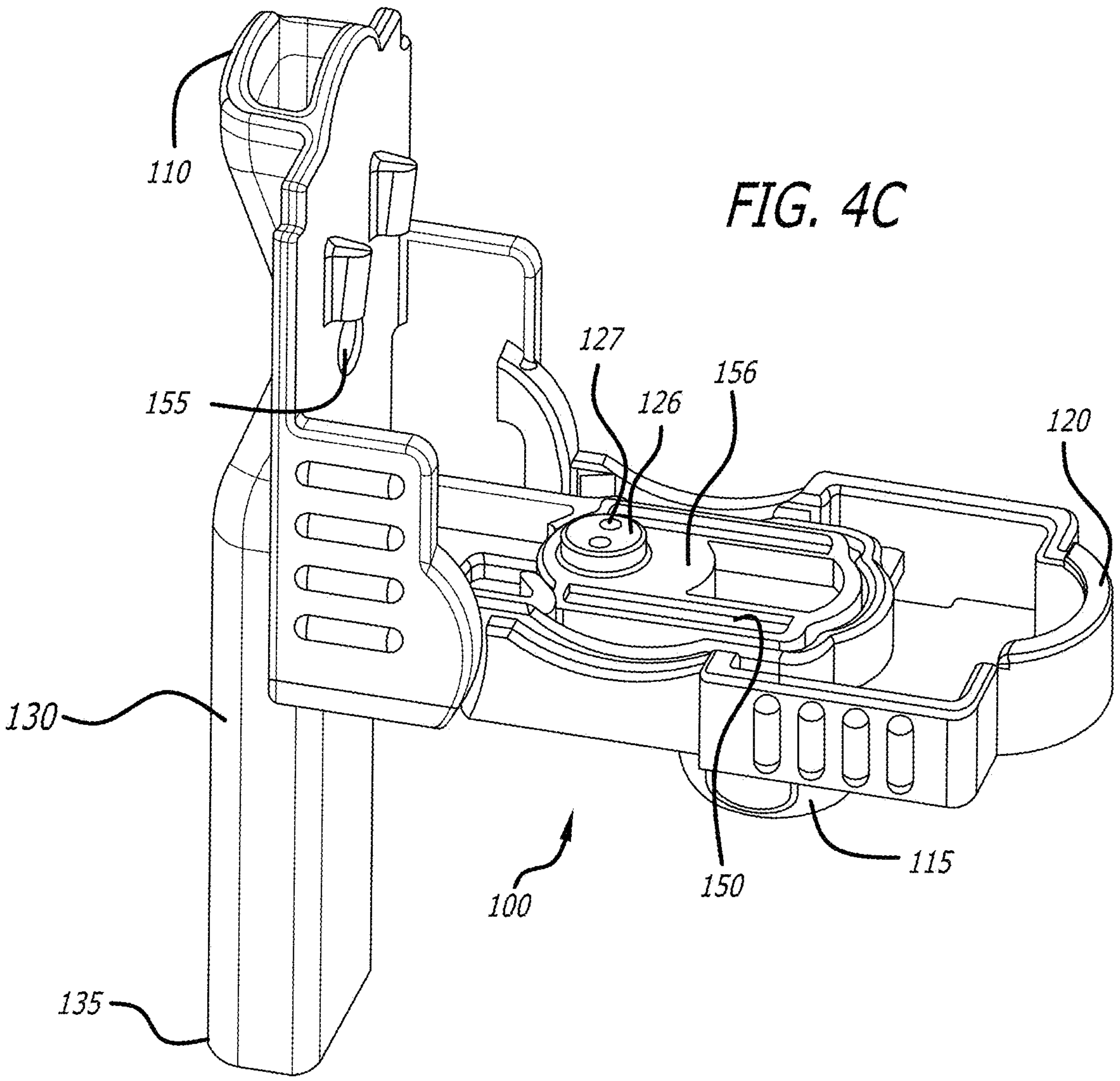
FIG. 4C is the inhaler shown in FIGS. 4A and 4B showing a cartridge loaded into the cartridge holder.
Figure 5:
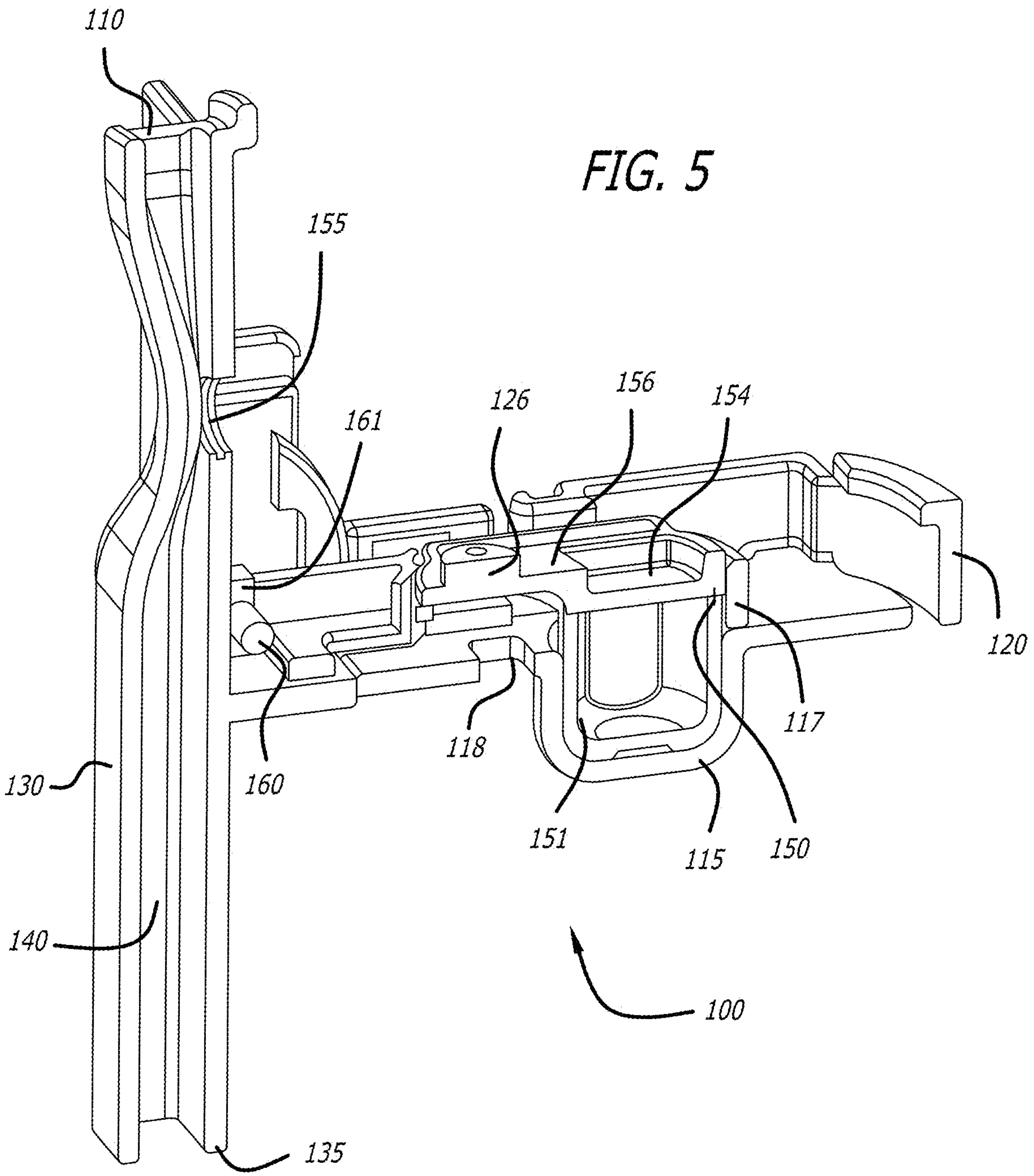
FIG. 5 depicts the dry powder inhaler of FIG. 1 with a cartridge and in a fully opened position, shown in mid-longitudinal section and containing a cartridge in the holder, wherein the cartridge container is in the containment position.
Figure 6:
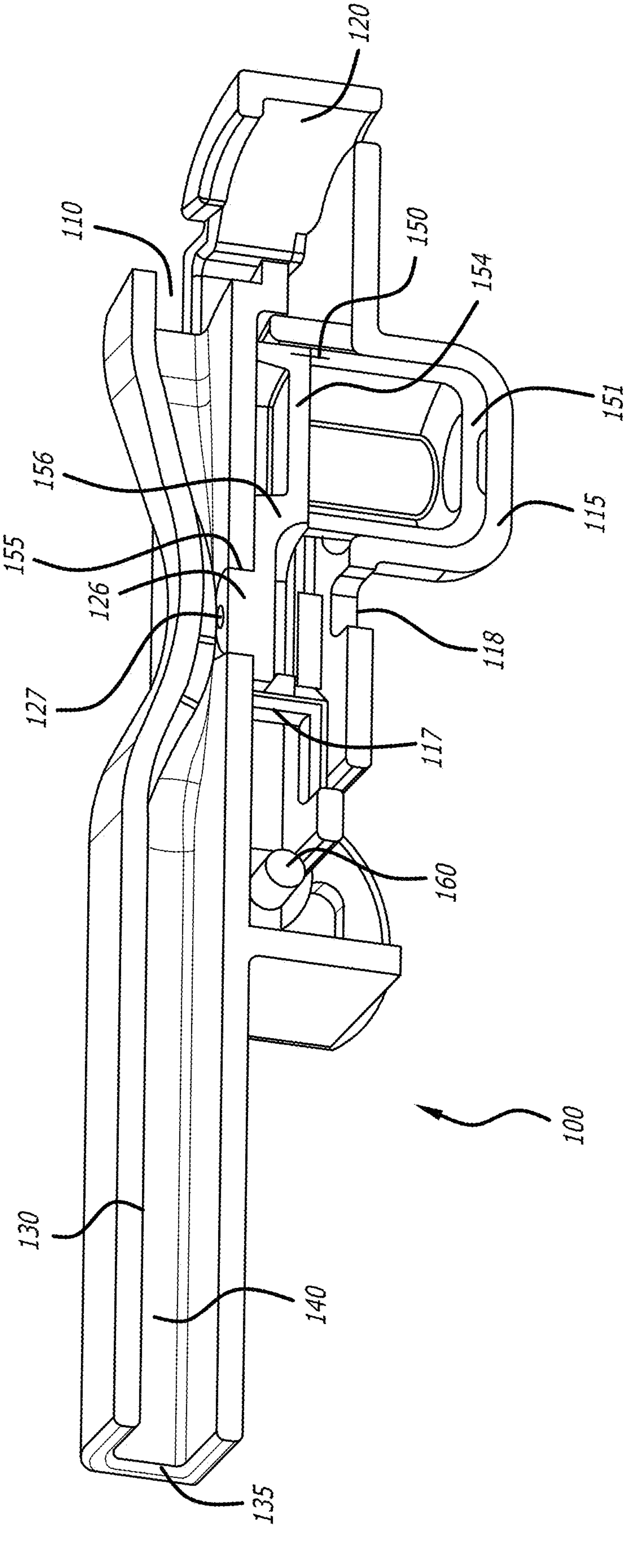
FIG. 6 depicts the dry powder inhaler of FIG. 1 with a cartridge and in a partially opened position shown in mid-longitudinal section and containing a cartridge in the holder, wherein the cartridge is in a containment position.
Figure 7:
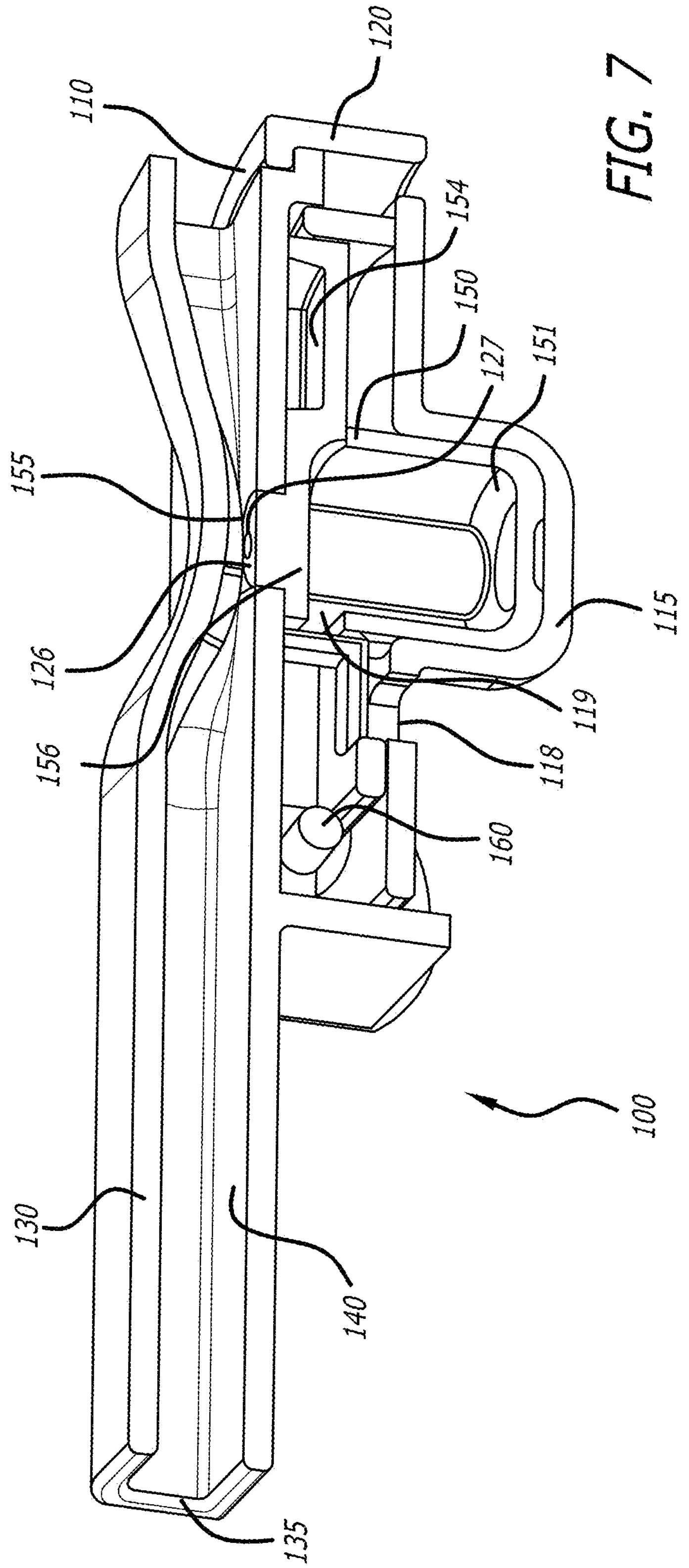
FIG. 7 depicts the dry powder inhaler of FIG. 1 with a cartridge and in a closed position, shown in mid-longitudinal section and containing a cartridge in the holder, wherein the cartridge is in a dosing position.

An embodiment of the dry powder inhaler is exemplified in FIGS. 1-8. In this embodiment, the dry powder inhaler has three configurations, i.e., a closed configuration is illustrated in FIGS. 1 and 7, a partially opened configuration is illustrated in FIGS. 2 and 6 and an open configuration is illustrated in FIGS. 3-5 and 8. The dry powder inhaler 100 as depicted in FIGS. 1-8 has a relatively rectangular body having a proximal end for contacting the user's lips or oral cavity and a distal end, with top and bottom sides, a housing 120, mouthpiece 130 and carriage, slide tray or sled 117. FIG. 1 illustrates the dry powder inhaler in a closed position, wherein the mouthpiece 130 comprises a body 112 and has one or more air inlets 110 (see also FIGS. 5 and 7) and an oral placement section having an outlet 135. An air conduit runs the length of the inhaler mouthpiece 130 from air inlet 110 to outlet 135. Mouthpiece 130 can be configured having a narrowing in the shape of an hourglass at approximately its mid to distal section to accelerate airflow, and then it is configured of a wider diameter at its proximal end, or oral placement section to decelerate airflow towards outlet or opening 135 (see FIG. 7). Air conduit 140 (FIG. 4A) has an opening 155 for adapting an area or boss 126 of cartridge top 156 (FIG. 4B) and is in communication with a mounted cartridge 150 in the inhaler in the closed position (FIGS. 6 and 7). When the inhaler is in a closed or inhalation position as shown in FIG. 1, body 112 encloses a portion of the housing 120 of the inhaler 100. FIG. 1 also depicts a cartridge holder 115 extending downwardly from the inhaler body. In the embodiment of FIG. 1, the housing 120 is structurally configured to be relatively rectangular in shape and has a bottom wall 123, side walls 124 with riblet projections 125 which facilitate a stable grip for opening and closing the inhaler 100.

Figure 3:
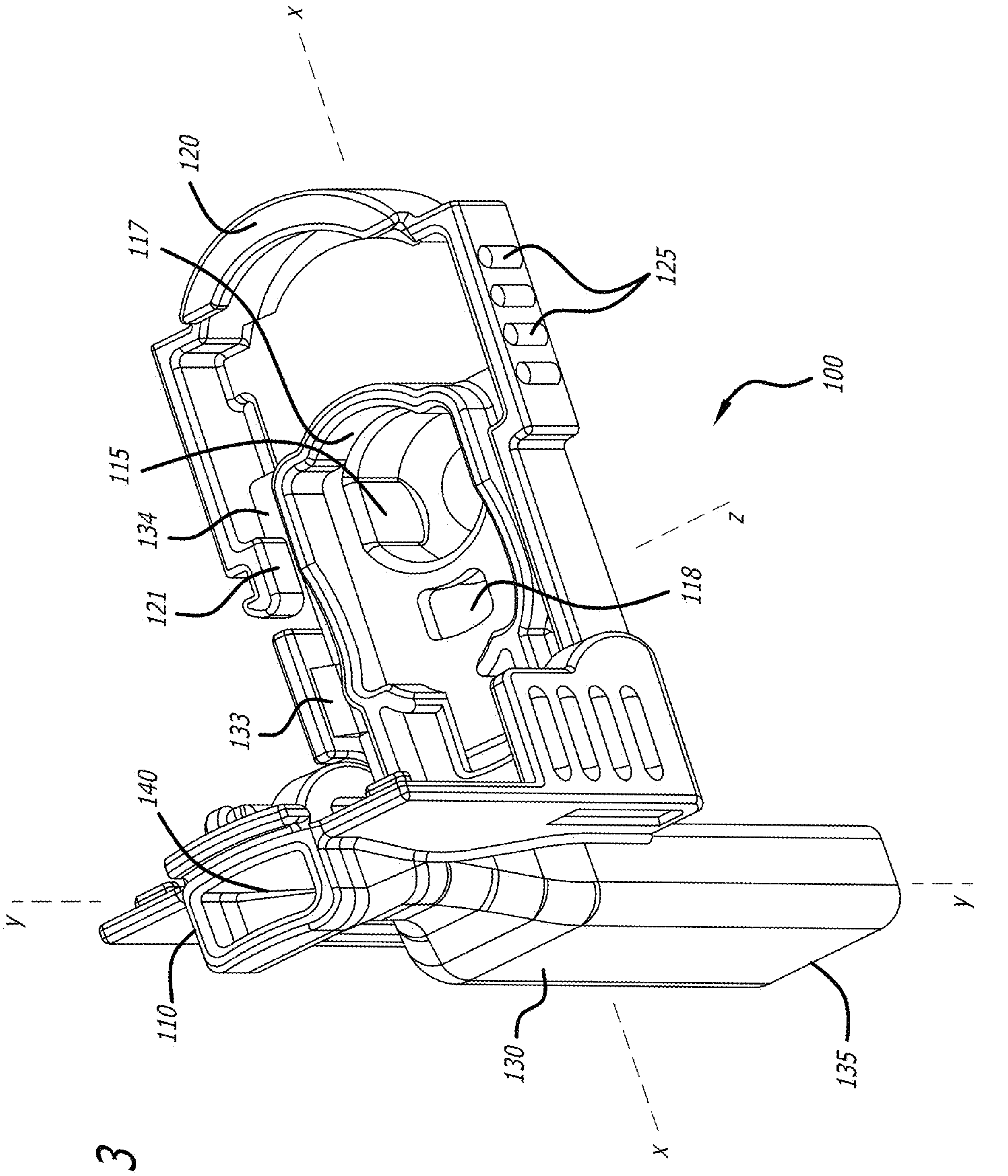
FIG. 3 depicts a perspective view of the dry powder inhaler of FIG. 1 showing the inhaler in a fully opened, cartridge loading/unloading position and depicting the interior compartment of the inhaler.

FIG. 2 is the dry powder inhaler embodiment depicted in FIG. 1, showing the inhaler in a partially opened containment position, wherein mouthpiece 130 shows a portion of the housing 120 protruding slightly outwardly. In this position, mouthpiece 130 can pivot by angular rotation to an opened configuration for loading a cartridge, or can be closed to a dosing configuration if a cartridge is contained in the holder, or for storage. In FIG. 2, a cartridge mounted in the cartridge holder 115 is in a closed, powder containment configuration. FIG. 3 illustrates a perspective view of the dry powder inhaler of FIG. 1, showing the inhaler in a fully opened, cartridge loading/unloading position and depicting the interior compartment areas of the inhaler. As seen in FIG.

3, mouthpiece 130, in the fully opened position of the inhaler, can be relatively moved about 90° from vertical plane Y-Z to a horizontal plane X-Z. As mouthpiece 130 rotates from the opened to the closed position, aperture 155 (FIG. 4A) can engage cartridge boss 126 (FIG. 4B) allowing exit or dispensing ports 127 to be in communication and within the floor of the flow conduit 140 with a cartridge adapted in the inhaler.

As illustrated in FIG. 3, housing 120 comprises the bottom portion of the inhaler body, which comprises a cartridge holder 115 in the shape of a cup, a securing mechanism to secure the inhaler in the closed position, such as snap 121, and an air inlet aperture 118 which communicates with the mouthpiece air conduit 140 at opening 155 in the mouthpiece floor without a cartridge in the holder 115 in the closed position of the inhaler. With a cartridge installed in the inhaler and in the closed position, inlet aperture 118 communicates with the cartridge inlet port 119 when the cartridge 150 is in the dosing configuration (see FIG. 7). In the closed position of the inhaler, the sled 117 is configured at its proximal end to correspond in shape to air inlet aperture 118 of housing 120 so that the air inlet is not obstructed in the closed position of the inhaler. In this embodiment, movement of mouthpiece 130 from a partially opened to a closed position is accomplished through a sliding motion in the X-Z plane, and movement of mouthpiece 130 from a partially open to a fully open configuration is angular rotating about the Z axis. To achieve full closure of the inhaler, mouthpiece 130 is moveable in the horizontal axis X and moves or slides distally relative to housing 120. In this manner, the translational movement of slide tray or sled 117 against the cartridge top 156 of cartridge 150 being held in the cartridge container 115 (see FIG. 4) moves and places the boss 126 over the cartridge container, so that cartridge container 151 is under dispensing ports 127 and in alignment over mouthpiece opening 155. This translational movement also configures the cartridge 150 to form an opening or an air inlet 119 into the container 151. A flow pathway is then established with air conduit 140 and inlet 118 through dispensing ports 127. Cartridge boss 126 is structurally configured to correspond and fit the opening 155 (FIG. 4A) in the waist section of the air conduit 140 of mouthpiece 130 so that it is within the internal wall of the air conduit 140.

FIGS. 4A-4C depict the perspective views of the dry powder inhaler of FIG. 1 showing the inhaler in the fully opened, cartridge loading/unloading position. FIG. 4A is a front view of the inhaler showing mouthpiece 130 comprising the top portion of the body of the inhaler; an aperture 155 relatively centrally located in the mouthpiece inner surface communicates with air conduit 140; an air inlet 110 and an air outlet 135 are in communication with the air conduit 140 of the inhaler 100. Housing 120 forms the bottom portion of the inhaler body and comprises a cartridge holder 115 and holds a slide tray or sled 117 which moves relative to the housing 120. A hinge 160 (FIG. 4A) formed by a snap and a rod engages the slide tray or sled 117 onto mouthpiece 130. FIG. 4B illustrates the inhaler of FIG. 4A and a cartridge 150 configured to be adaptable into inhaler 100. The inhaler is shown in the fully open position with a cartridge above the cartridge holder container 115 yet to be installed in the inhaler; housing 120 comprising an air aperture or inlet 118, slide tray or sled 117, which is engaged to mouthpiece 130 having aperture 155 and air inlet 110. Cartridge 150 comprises a medicament container 151 and a top 156 comprising a boss 126 with dispensing ports 127. The cartridge top 156 comprises a first area 154 which is recessed such that its bottom wall is in contact with container 151 top border and seals the container 151 in a containment position. While in this embodiment, first area 154 is recessed for ease of manufacturing, the first area 154 can have alternate designs as long as it forms an acceptable seal for containing a dry powder. A second area of cartridge top 156 contains boss 126 and this portion of the cartridge top is slightly raised and hollow in its undersurface so that when the cartridge container 151 is moved to a dispensing position, the top border of container 151 forms an opening or air inlet with cartridge top 156 to create a passageway through the cartridge inlet and the dispensing ports. FIG. 4B shows cartridge 150 in a containment position, which is the position in which the cartridge is closed and does not allow a flow path to be established through its interior compartment. As seen in the FIG. 4C, cartridge 150 is installed in inhaler 100 and the inhaler is in the opened configuration.

FIG. 5 also depicts the dry powder inhaler of FIG. 4C in a fully opened position, shown in mid-longitudinal section and containing cartridge 150 in the holder, wherein cartridge container 151 is in the containment position and fits into container holder 115. Cartridge top 156 and recessed area 154 are clearly depicted as forming a tight seal with the container 151. The area of the cartridge top 156 under the boss can be seen as concave-like in shape and raised when compared to the area 154.

FIG. 6 depicts the dry powder inhaler of FIG. 4A in a partially opened position in mid-longitudinal section and containing cartridge 150 with cartridge container 151 installed in cartridge holder 115. In this embodiment, cartridge container 151 is in a containment position; boss 126 snuggly fitting in aperture 155 of airflow conduit 140, which allows dispensing port 127 to be in fluid communication with air conduit 140. As seen in FIG. 6, sled or slide tray 117 abuts cartridge top 156, and the mouthpiece and slide tray 117 can move as a unit so that the cartridge top can move over container 151 upon closure of the device to attain the dispensing position. In the closed or dispensing position, the securing mechanism illustrated by snaps 121 (FIG. 3) maintain housing 120 and mouthpiece 130 securely engaged. In this embodiment, housing 120 can be disengaged from mouthpiece 130 by releasing the snaps and moving mouthpiece 130 over housing 120 in the opposite direction to attain a partially opened configuration which causes cartridge 150 to be reconfigured from the dosing position to the containment configuration.

Cartridge 150 can be movably configured from a containment position to a dosing position within the inhaler upon reconfiguration of the inhaler unit to a closed position as shown in FIG. 7. In the dosing position, cartridge container 151 is in alignment with boss 126, and air inlet port 119 is formed by cartridge container 151 and cartridge top 156, which is in communication with dispensing ports 127 establishing an air conduit through cartridge 150.

FIG. 7 further depicts a mid-longitudinal section of the dry powder inhaler of FIG. 1 in a closed position and ready for inhalation and containing cartridge 150 in holder 115, wherein the cartridge container 151 is in a dosing position. As seen in FIG. 7, cartridge boss 126 is structurally configured to fit in inhaler aperture 155 so that air flow exiting the cartridge through dispensing or exit ports 127 enters the flow path of air entering air conduit at 110. FIG. 7 also illustrates cartridge air inlet 119 formed by cartridge top 156 and cartridge container 151 in the dosing configuration and proximity of air inlet 119 to dispensing ports 127. In one embodiment, boss 126 with dispensing ports 127 are positioned at the narrowest section of air conduit 140 of mouthpiece 130.

Figure 8:
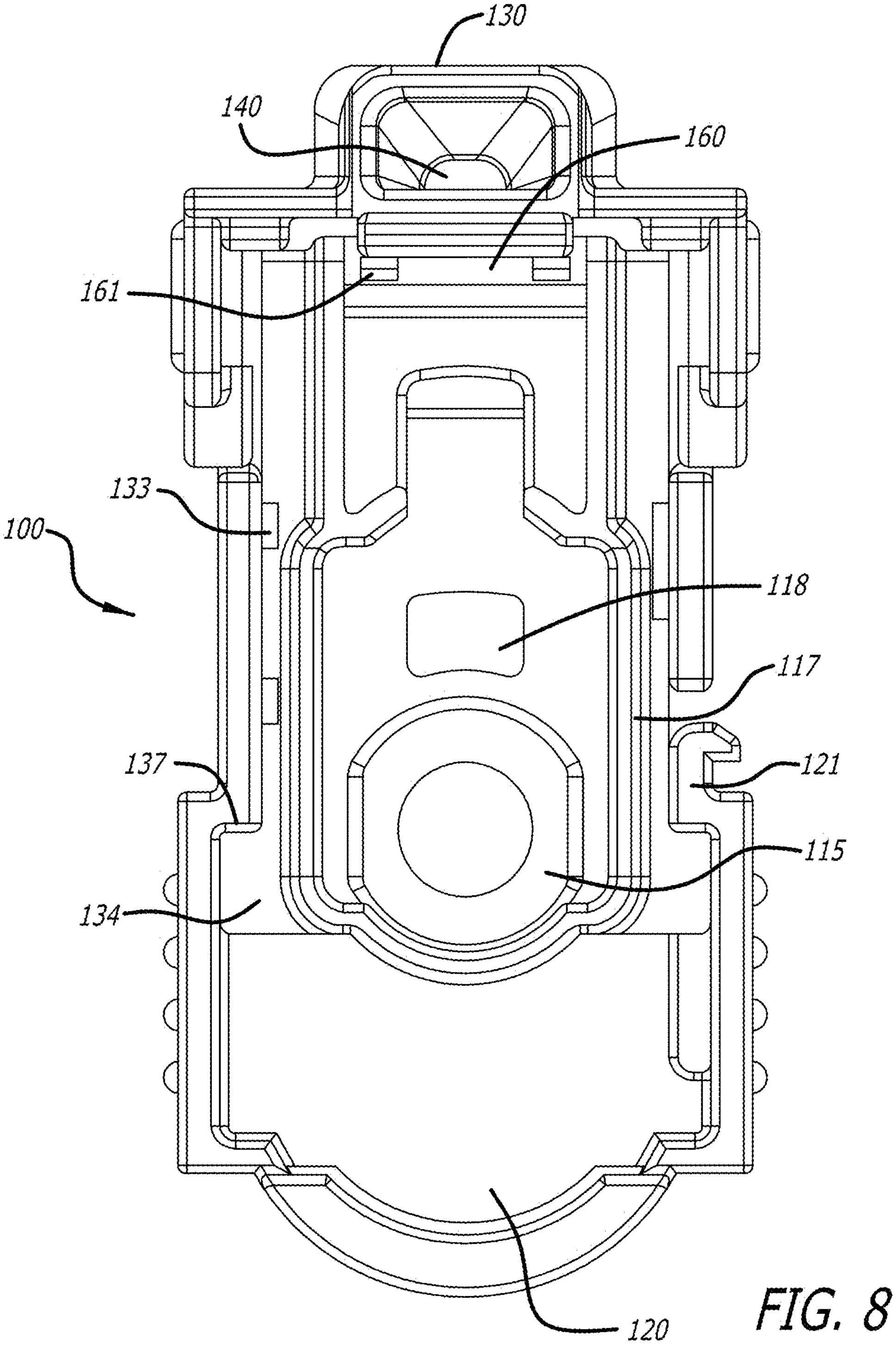
FIG. 8 depicts a top view of the dry powder inhaler of FIG. 1 in a fully opened configuration and showing the inner compartment components of the inhaler.

FIG. 8 depicts a top view of the dry powder inhaler of FIG. 1 in a fully opened configuration and showing the inner compartment components of the inhaler. As seen in FIG. 8, mouthpiece 130 is moveably attached or articulated to housing 120 by hinge assembly 160, via slide tray or sled 117 which is engageably connected to mouthpiece 130 by hinge 160, 161 and to housing 120 interior. Sled 117 is movable in the horizontal plane of housing 120 and can be prevented from moving further in the direction of the mouthpiece by flanges 134, which protrude outwardly and can be stopped by recess 137 of the housing. Cartridge container holder 115 is integrally formed within the bottom wall of housing 120 which has aperture 118 which allows ambient air into the inhaler to supply airflow into the cartridge in a dosing position. Sled 117 is held within the housing by, for example, protrusions or flanges 133 extending from the side walls of the housing into its interior space.

Figure 9:
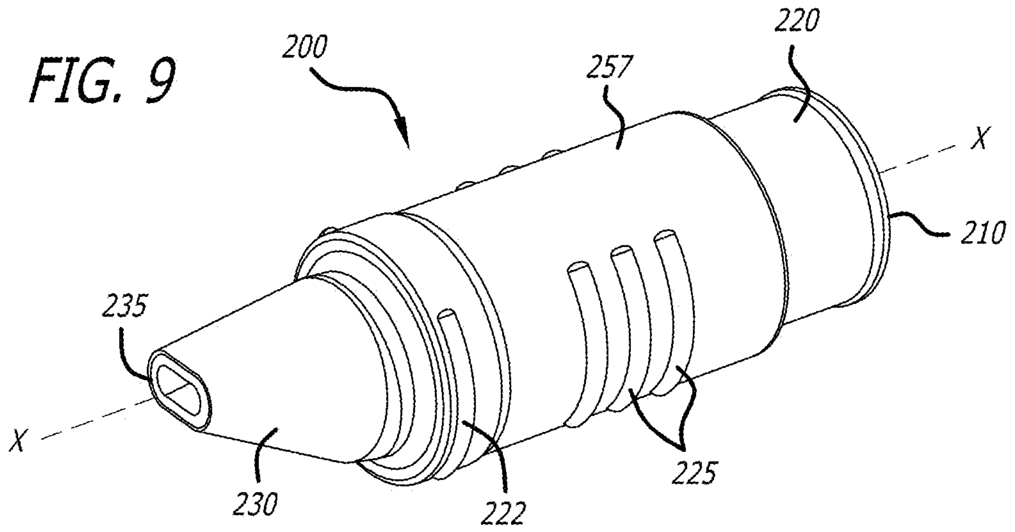
FIG. 9 depicts a perspective view of an alternate embodiment of the dry powder inhaler in the closed or inhalation position.
Figure 10:
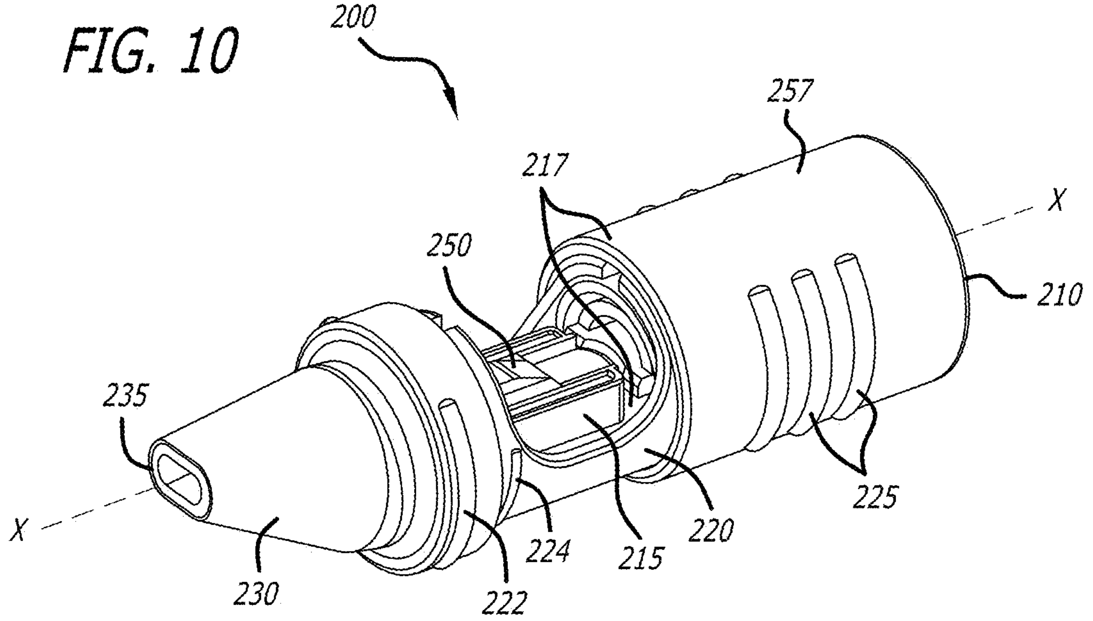
FIG. 10 depicts the dry powder inhaler of FIG. 9 in an opened position, showing a cartridge installed in the cartridge holder, wherein the cartridge is in a containment position.

In another embodiment, a dry powder inhaler is provided with a relatively cylindrical shape. FIG. 9 through FIG. 11B illustrate this embodiment, wherein the inhaler comprises a housing 220 integrally attached to mouthpiece 230, and a sled or slide tray 217. In FIGS. 9 and 10, sled 217 is depicted comprising outer shell 257 which is in telescopic arrangement and concentrically positioned and partially covering housing 220. Sled 217 further comprises a gripping mechanism such as ribs 225 on the outer surface of shell 257 for securely gripping inhaler sled 217 while sliding over housing 220 to open and close the device. Sled 217 further comprises groove 221 in its inner surface at its end facing the mouthpiece for engageably attaching with snap ring 224 segments of mouthpiece 230 for securing the inhaler in a closed configuration.

Figure 11A:
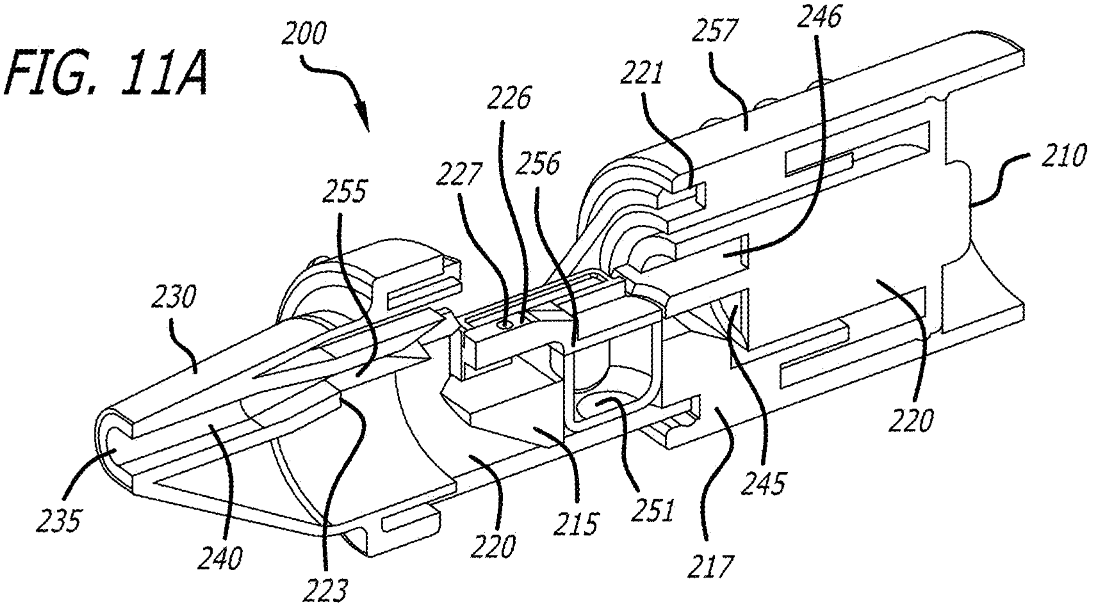
FIG. 11A and FIG. 11B depict the dry powder inhaler embodiment of FIG. 9 in an opened (FIG. 11A) and closed (FIG. 11B) position, shown in a mid-longitudinal section with the cartridge in the cartridge holder in the containment position and dosing position, respectively.
Figure 11B:
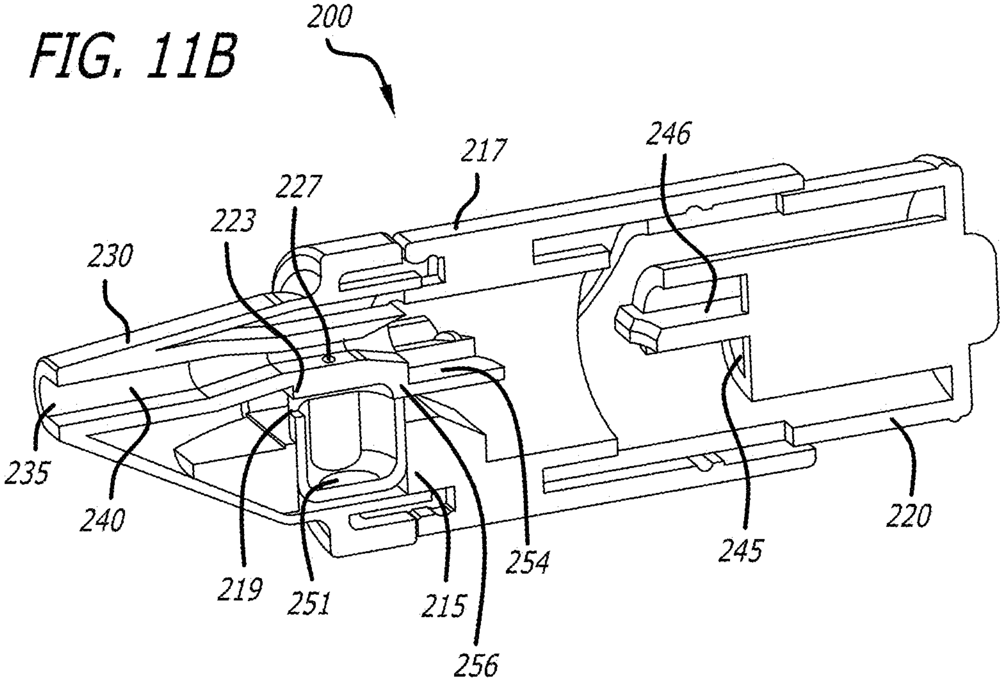

As seen in FIG. 11A, sled 217 also comprises cartridge holder 215 configured to receive cartridge 250. Cartridge holder 215 is integrally structured with outer shell 257 so that movement of outer shell 257 moves the cartridge holder while closing the inhaler. FIG. 11A also illustrates the positioning of cartridge 250 within the inhaler and wherein the cartridge can be seen as having top 256, boss 226, dispensing ports 227 and a container 251 in a containment position. In this embodiment, movement of sled 217 effectuates translation of cartridge container 251 to the dosing position in alignment with dispensing ports 227 and configuration of inlet port 219 as seen in FIG. 11B.

In this embodiment, housing 220 is tubular in shape and it is structurally configured to have air inlet 210 with one or more air conduits, for example, air conduits such as, air conduits 245, 246. Surface projections or ribs 225 from the outer surface of sled shell 257 allow for ease of gripping the inhaler device 200 in use. As seen in FIG. 9, the inhaler comprises mouthpiece portion 230 and housing 220, air inlet 210 and air outlet 235. As shown in FIG. 10, inhaler 200 can be configured to an open configuration wherein a user can load and/or unload a cartridge. By gripping ribs 222 and 225, sled outer shell 257 can be moved away from mouthpiece 230, and the cartridge holder can then be accessed. FIG. 10 shows inhaler 200 in an opened, cartridge loading/unloading position and depicting sled 217 fully retracted from mouthpiece 230 to allow access to the internal compartment to load or unload a cartridge. FIG. 10 also illustrates cartridge 250 installed in cartridge holder 215 of sled 217 and the mechanism such as outer shell 257 for actuating and opening the cartridge to the airflow path upon engagement of the sled outer shell 257 in snap ring 224 of the mouthpiece so that the device is in the closed, or inhalation position. Closing of the device is effectuated by translational movement of sled 217 over the housing 220 and engagement of sled 217 with mouthpiece 230 along horizontal axis X. As can be seen in FIG. 11B, the closing action of the sled 217 moves the cartridge 250 until the cartridge top 256 abuts mouthpiece recess surface 223, after which time continuous movement of sled 217 to a closed position causes the container 251 portion of cartridge 250 to be moved from a containment position to the opposite side of cartridge cover 256 so that dispensing ports 227 are aligned relatively over container or cup 251. An air inlet passage is then created between container 251 and the cartridge top 256 which air inlet is in communication with the interior of container 251 and exit or dispensing ports 227 of boss 226.

FIG. 11A is a perspective view of a mid-longitudinal section of the embodiment of FIG. 10 in an open configuration. FIG. 11B is a perspective view of a mid-longitudinal section of the embodiment of FIG. 10 in a closed, dosing configuration. As seen in FIGS. 11A and 11B, the inhaler comprises mouthpiece 230 having a frustoconical shape, air conduit 240 which is tapered to aperture 255 for engaging with cartridge boss 226 on cartridge top 256 of cartridge 250 in a closed position. Mouthpiece 230 also comprises air outlet 235. FIGS. 10 and 11 also show that housing 220 can be integrally attached to mouthpiece 230 and comprises a snap ring segments 224 for engaging sled 217 in the closed position. FIG. 11B shows inhaler 200 in the dosing configuration having airway conduit 240 in communication with cartridge 250 through dispensing port 227 and cartridge inlet 219. In the closed configuration, inhaler housing 220 protrudes beyond sled 217 and the cartridge container is translocated to a dosing position under boss 226.

Figure 12:
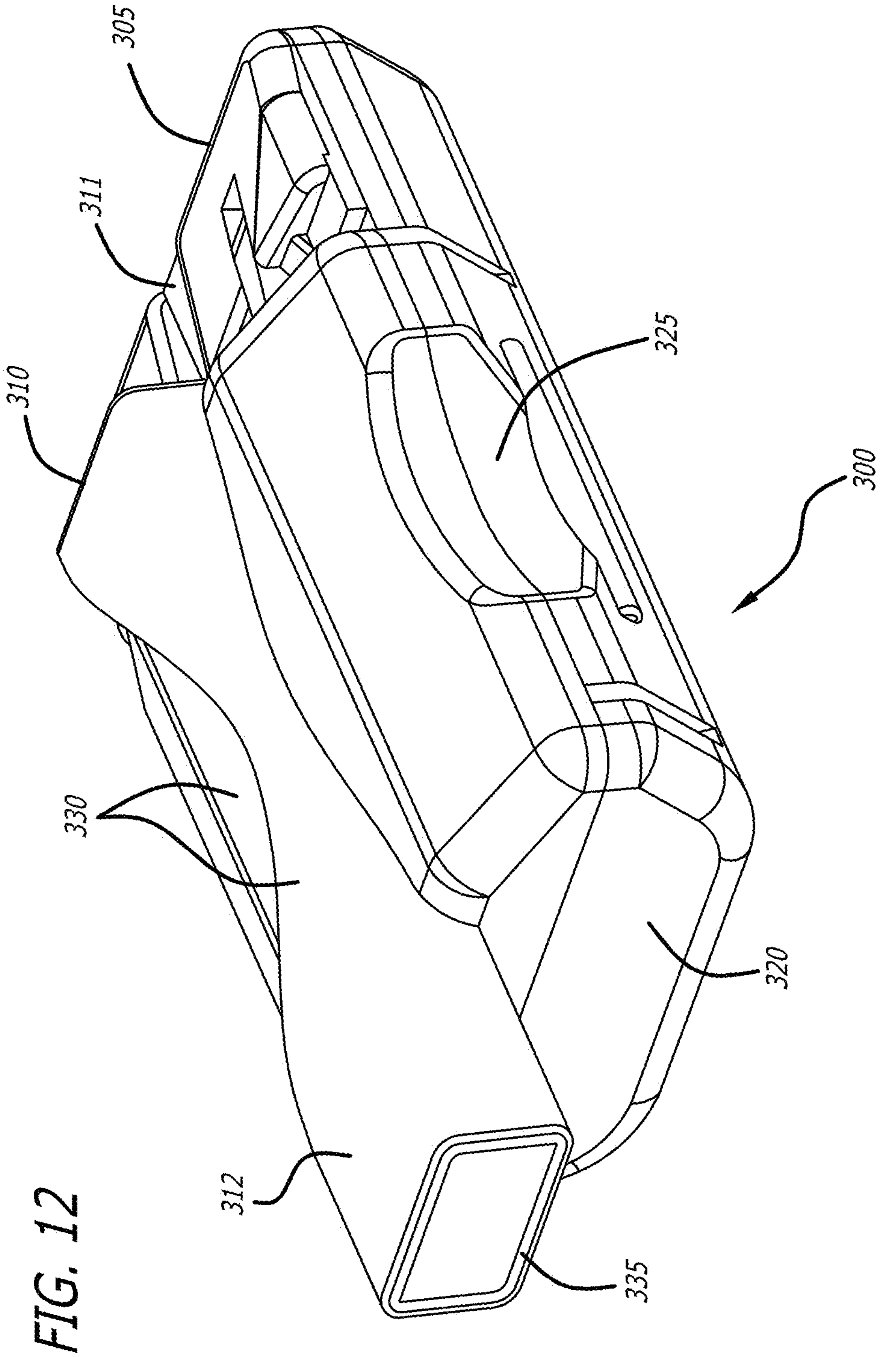
FIG. 12 depicts a perspective view of an alternate embodiment of the dry powder inhaler in the closed position.

In an alternate embodiment, there is provided a dry powder inhaler 300, comprising a mouthpiece, a sled or slide tray mechanism and a housing. In this embodiment illustrated in FIGS. 12 through 15, the inhaler is relatively rectangular in shape with the mouthpiece 330 comprising the top portion of inhaler body 305; an oral placement section 312; air inlet 310; air conduit 340 which extends from air inlet 310 to air outlet 335. FIG. 12 illustrates the inhaler in the closed position showing the various features of the outside of inhaler 300 including, air channel 311 which can direct air into inlet port 375. An area 325 for holding the inhaler is configured into inhaler body 305 for ease of use, and also serves as a surface to push or squeeze to release latches 380.

Figure 13:
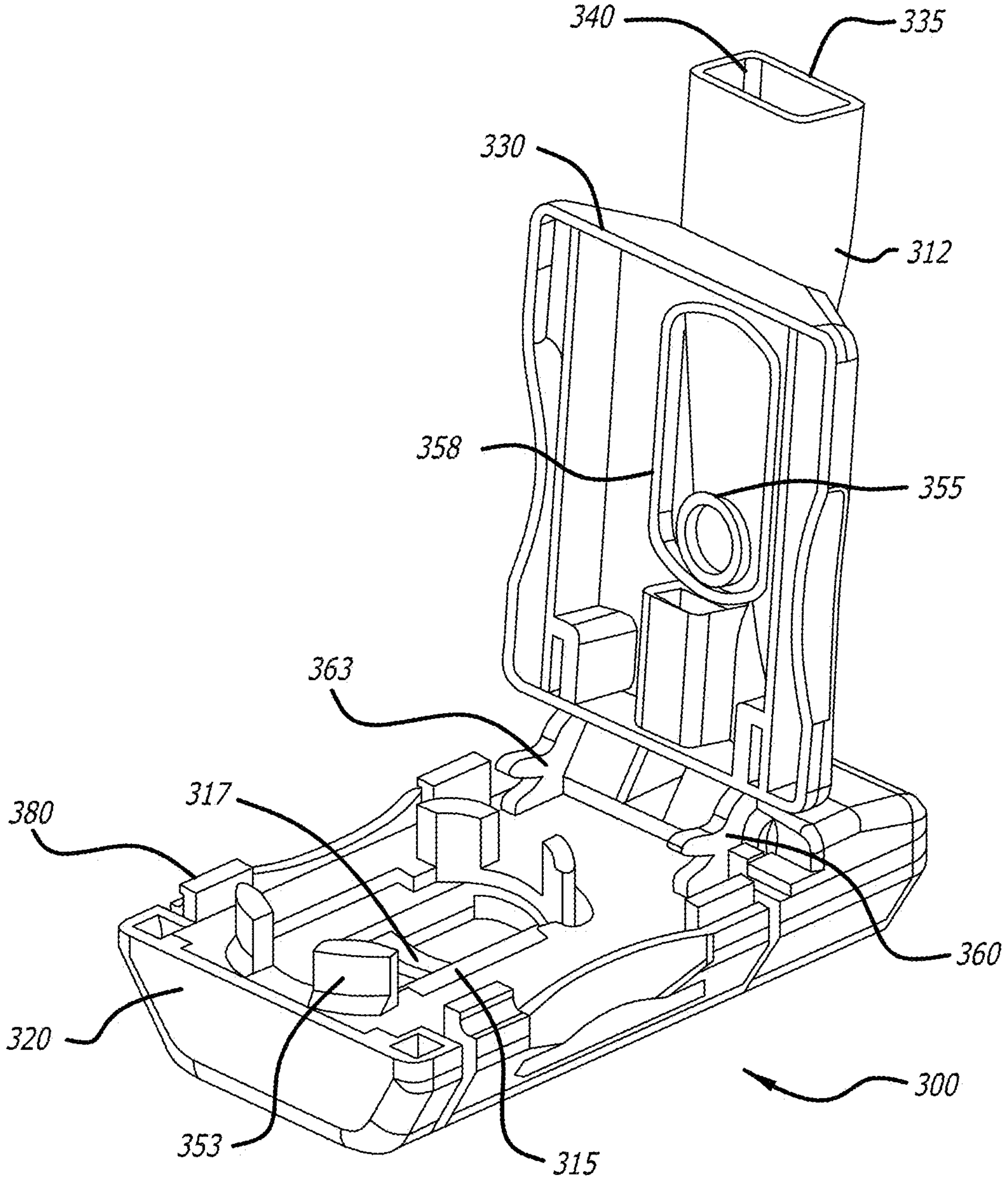
FIG. 13 depicts a perspective view of the dry powder inhaler embodiment of FIG. 12 in an open position showing the interior compartment of the inhaler.

FIG. 13 illustrates a perspective view of the embodiment of FIG. 12 in an open configuration, or cartridge loading and unloading position. As illustrated in FIG. 13, mouthpiece 330 is engageably attached to housing 320 by a hinge attached to gear mechanism 360, 363. Mouthpiece 330 has an aperture 355 which is in fluid communication with air conduit 340; an air outlet 335 and flange 358 define a rectangular structure surrounding aperture 355. FIG. 13 also depicts housing 320 as comprising a cartridge holder 315; with a section of sled 317 showing through the cartridge container placement area, projections 353 for holding cartridge top 356 in place and snaps 380 for closing the body portion of the inhaler mouthpiece.

Figure 14:
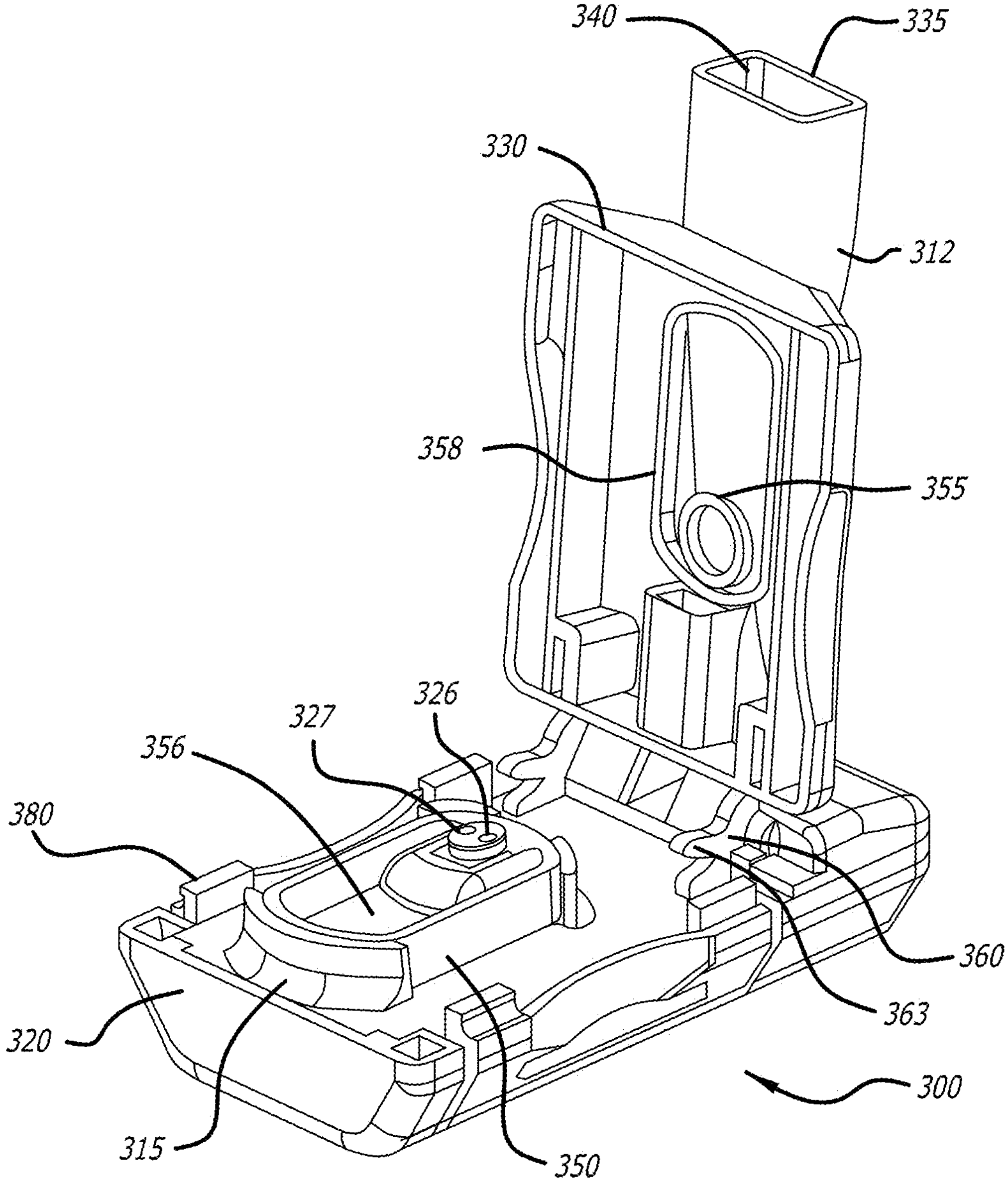
FIG. 14 depicts the embodiment of FIG. 12 in an opened, loading/unloading position having a cartridge installed in the holder in the containment position.

FIG. 14 illustrates a perspective view of the embodiment of FIG. 13 in an open configuration wherein a cartridge can be loaded or unloaded into the cartridge holder. FIG. 14 illustrates an inhaler comprising a mouthpiece 330 comprising the top portion of body 305 of the inhaler and having an aperture 355 relatively centrally located in the body and surrounded by flange 358; mouthpiece oral placement section 312 is configured to extend from the inhaler body and has an air outlet for placing in the oral cavity of a patient at dosing. The inhaler further comprises housing 320 which is engageably attached to mouthpiece 330 by a geared mechanism. In this embodiment, the geared mechanism is, for example, a rack and pinion 363 (see also FIG. 15A) which allows for an angular movement of the mouthpiece relative to the housing. Rack mechanism 363 is engaged to sled 317 to effectuate movement of container 351 of cartridge 350 to move slideably under the cartridge top and under the cartridge boss 326 when the inhaler is in the closed position. FIG. 14 also illustrates the position of cartridge 350 installed in holder 315 and showing the internal compartment parts, including boss 326 with dispensing ports 327; gear mechanism 360, 363 and snaps 380 which assist in maintaining the device in a closed configuration. As seen in FIG. 13, mouthpiece 330 forms the inhaler body top portion, and comprises an oral placement section 312 with air conduit 340 and air inlet 310 and air outlet 335.

Figure 15A:
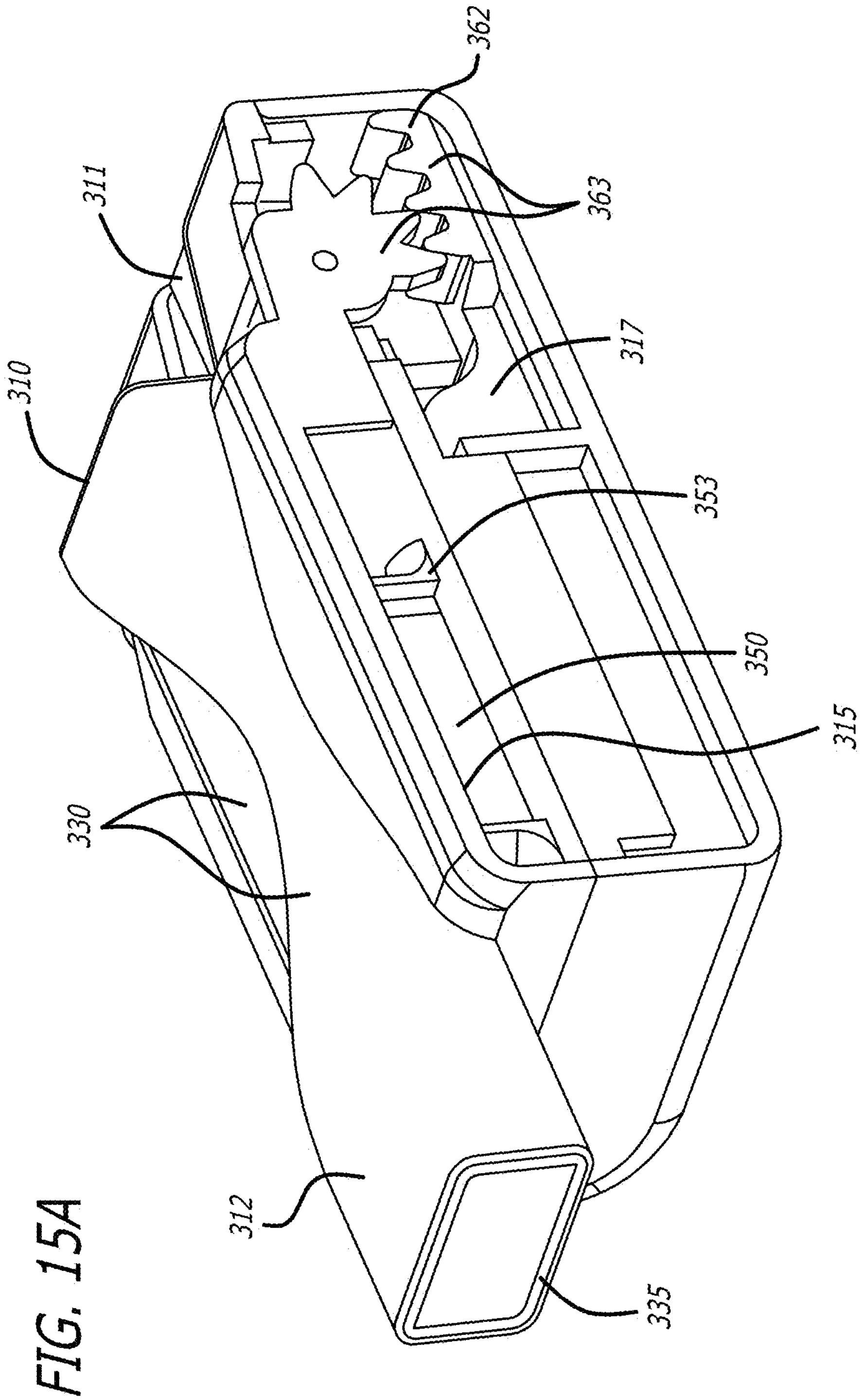
FIG. 15A depicts the embodiment of FIG. 12 showing the dry powder inhaler in the closed position as a cross-section through the longitudinal axis. The geared mechanism for opening and closing a cartridge and opening and closing the inhaler can be seen.
Figure 15B:
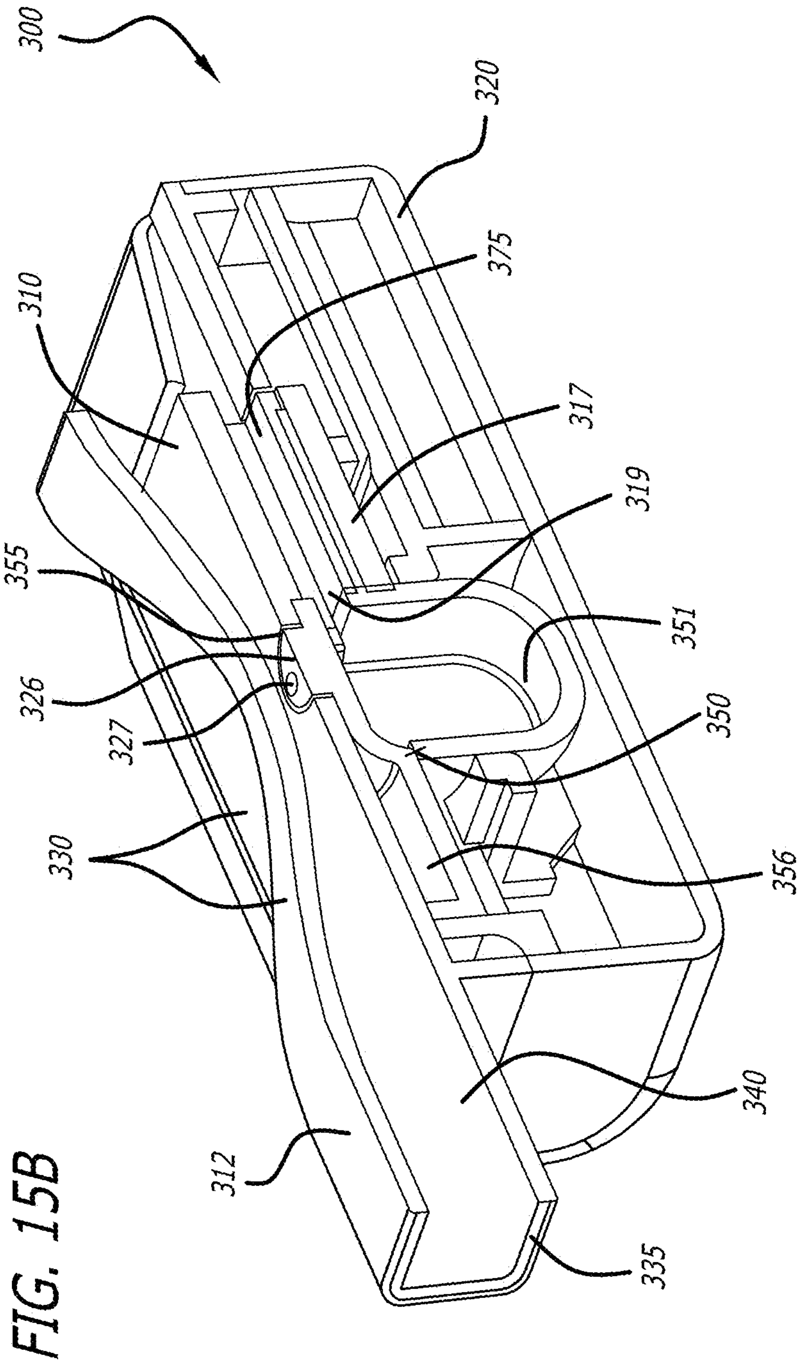
FIG. 15B depicts the embodiment of FIG. 12 showing the dry powder inhaler in the closed position as a cross-section through the mid-longitudinal axis.

FIG. 15A and FIG. 15B depicts the embodiment of FIG. 12 showing the dry powder inhaler in the dosed/inhalation position as cross-sections through the longitudinal axis with a cartridge 350 in the dosing position inside the cartridge holder 315 of housing 320. FIG. 15A illustrates gear mechanism 362, 363 engageably connected to sled 317 for opening and closing the inhaler and which simultaneously will move a cartridge container to the dosing or dispensing position upon closing the device.

FIG. 15B depicts the embodiment of FIG. 12 and FIG. 14 showing the dry powder inhaler in the closed/inhalation position as a cross-section through the mid-longitudinal axis. As can be seen, cartridge 350 is in the dosing position, wherein boss 326 fits or engages with aperture 355 of air conduit 340 to allow flow from dispensing ports 327 to exit cartridge 350 and merge into the flow path in conduit 340. FIG. 14 also shows cartridge top 359 securely held in position by projections 353 in the cartridge placement area. FIGS. 15A and 15B show cartridge container 351 configured in the dosing position and having air inlet port 356 in close proximity to and in communication with dispensing ports 327. Sled 317 abuts the cartridge container to maintain it in place for inhalation. In this embodiment, air inlet port 375 leading to cartridge inlet 319 is configured to run beneath and parallel to air conduit 340. Movement of the cartridge in this embodiment is effectuated by the opening and closing of the mouthpiece 330 relative to the housing wherein the gear mechanism opens and closes the cartridge by translational movement of sled 317. As shown in FIG. 15B and in use, airflow enters the inhaler through air inlet 310 and simultaneously into air inlet 375 which enters cartridge 350 through air inlet 319. In one example embodiment, the internal volume extending from inlet port 310 to outlet port 335 is greater than about 0.2 $cm^3$. In other example embodiments, the internal volume is about 0.3 $cm^3$, or about 0.3 $cm^3$, or about 0.4 $cm^3$ or about 0.5 $cm^3$. In another example embodiment, this internal volume of greater than 0.2 $cm^3$ is the internal volume of the mouthpiece. A powder contained within cartridge container 351 is fluidized or entrained into the airflow entering the cartridge through tumbling of the powder content. The fluidized powder then gradually exits through dispensing port 327 and into the mouthpiece air conduit 340 and further deagglomerated and diluted with the airflow entering at air inlet 310, prior to exiting outlet port 335.

Figure 15C:
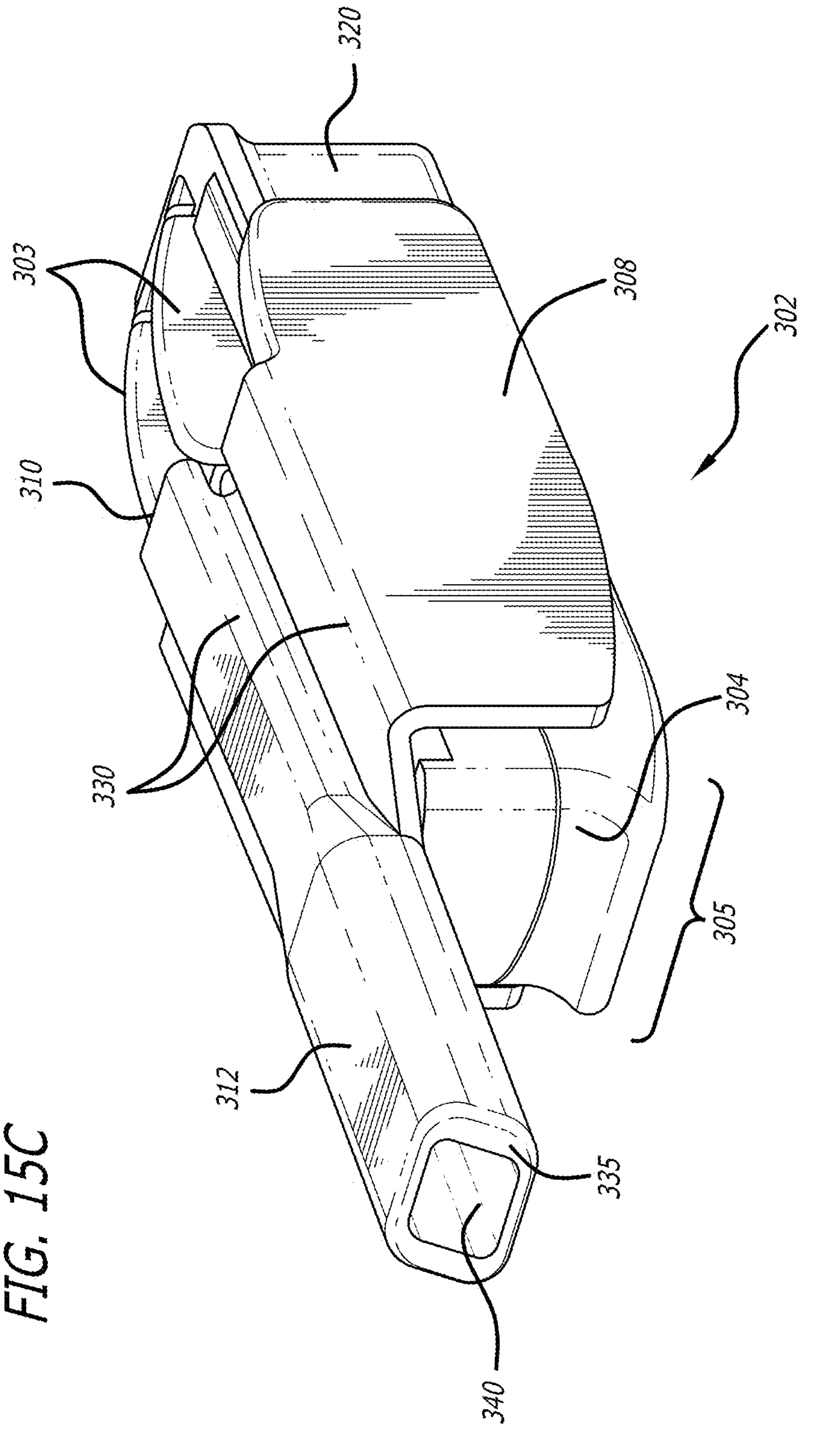
FIG. 15C depicts an alternate embodiment of the inhaler of FIG. 12 showing an isometric view of the inhaler in a closed position.
Figure 15D:
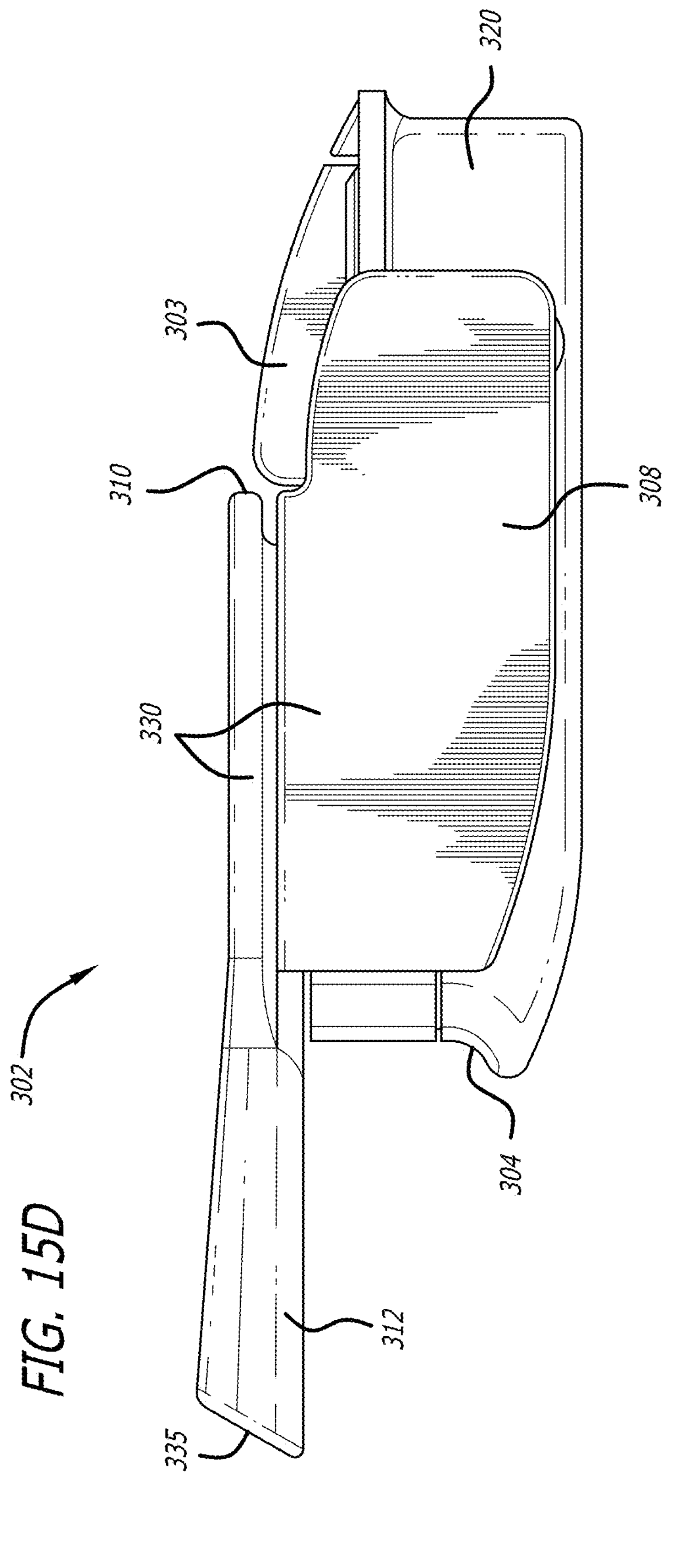
FIGS. 15D, 15E, 15F, 15G, and 15H depict side, top, bottom, proximal and distal views, respectively, of the inhaler of FIG. 15C.
Figure 15E:
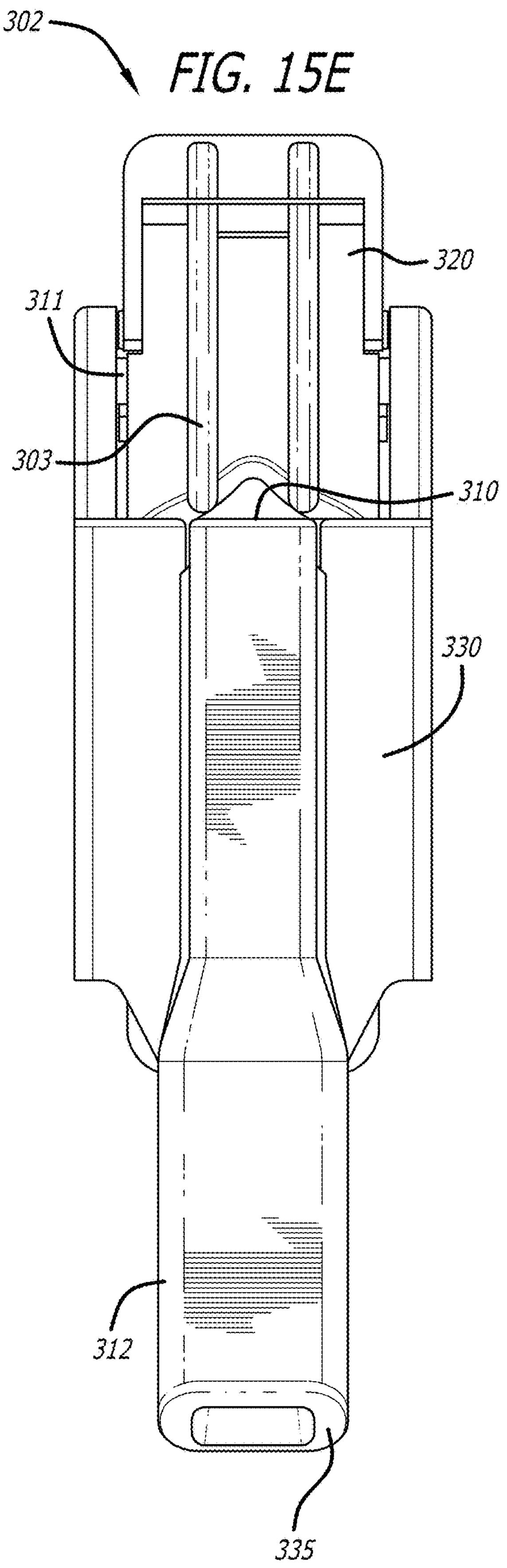
Figure 15F:
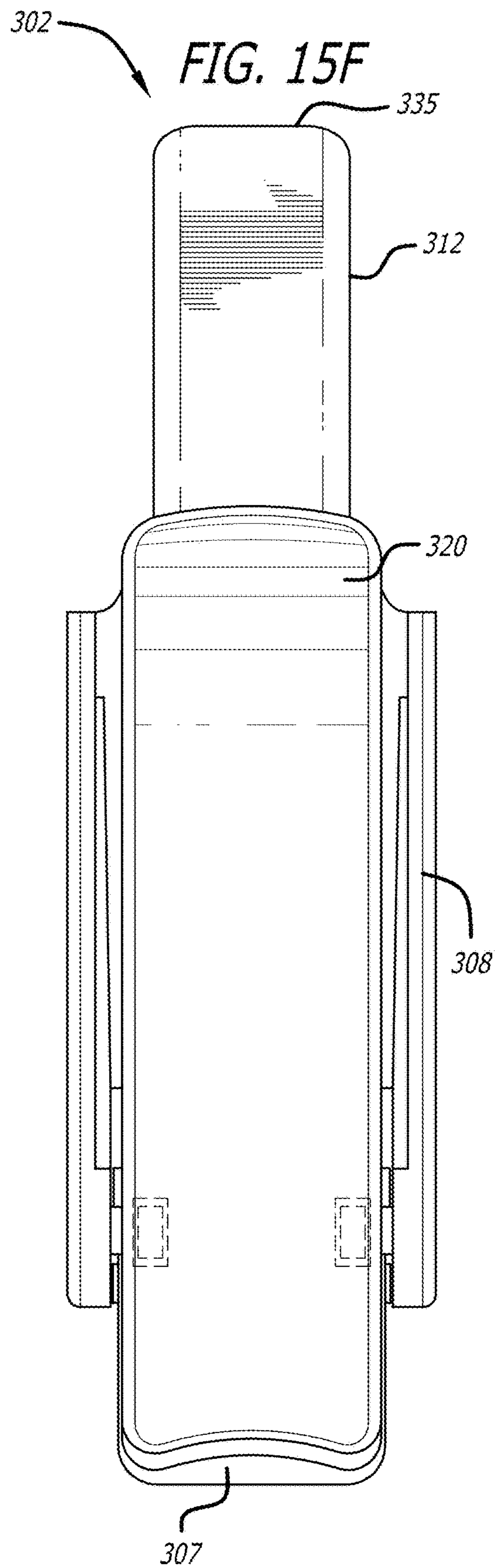
Figure 15G:
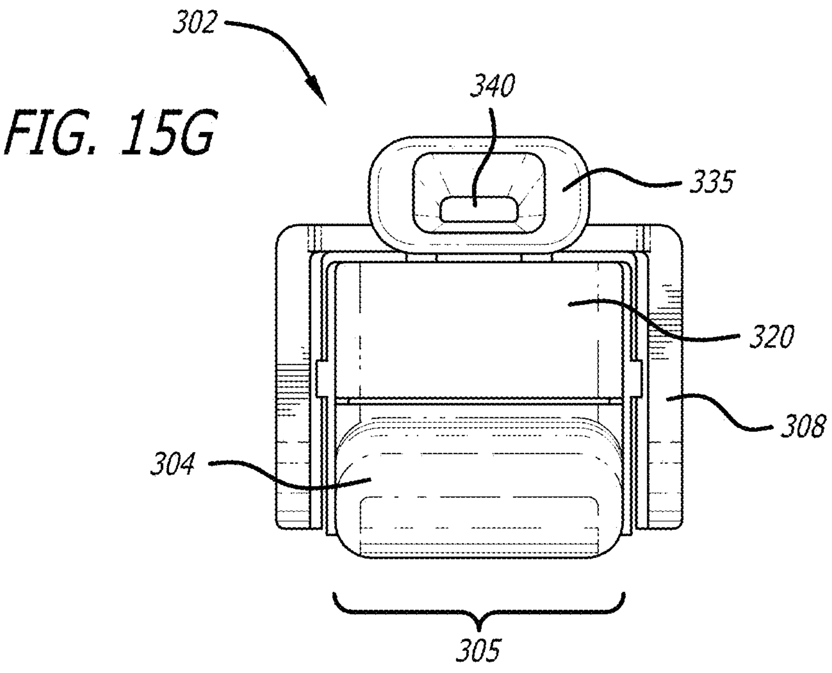
Figure 15H:
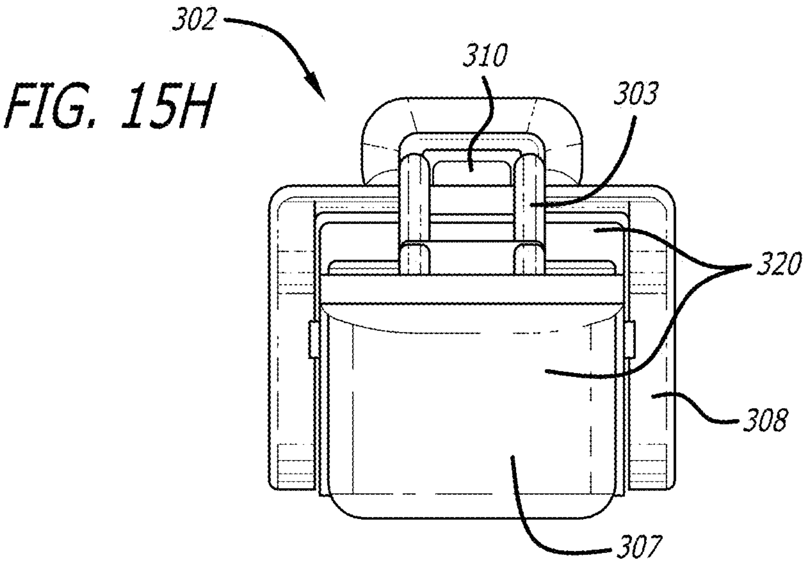
Figure 15I:
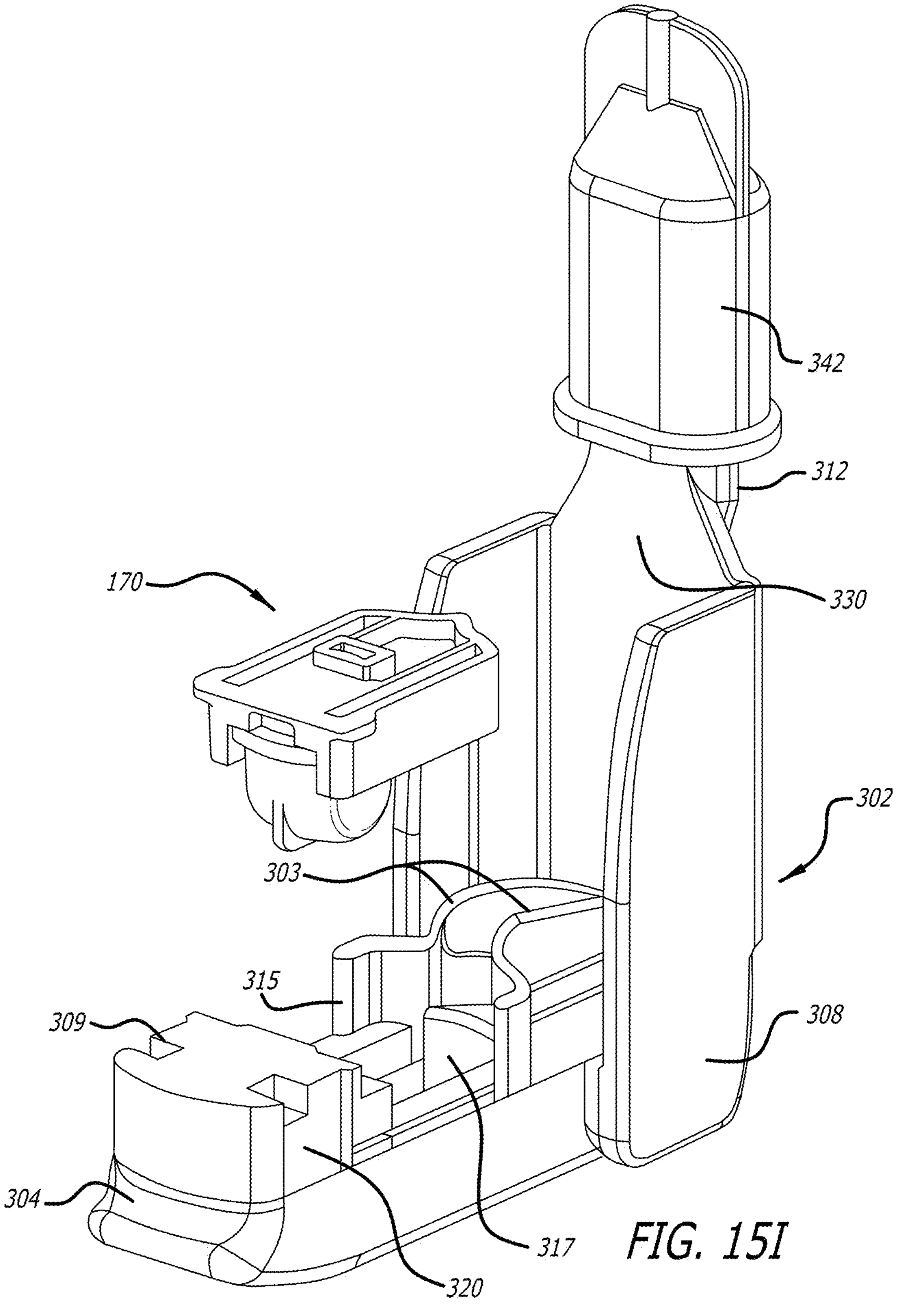
FIG. 15I depicts a perspective view of the inhaler in FIG. 15C in an open configuration showing a corresponding cartridge and a mouthpiece covering.
Figure 15J:
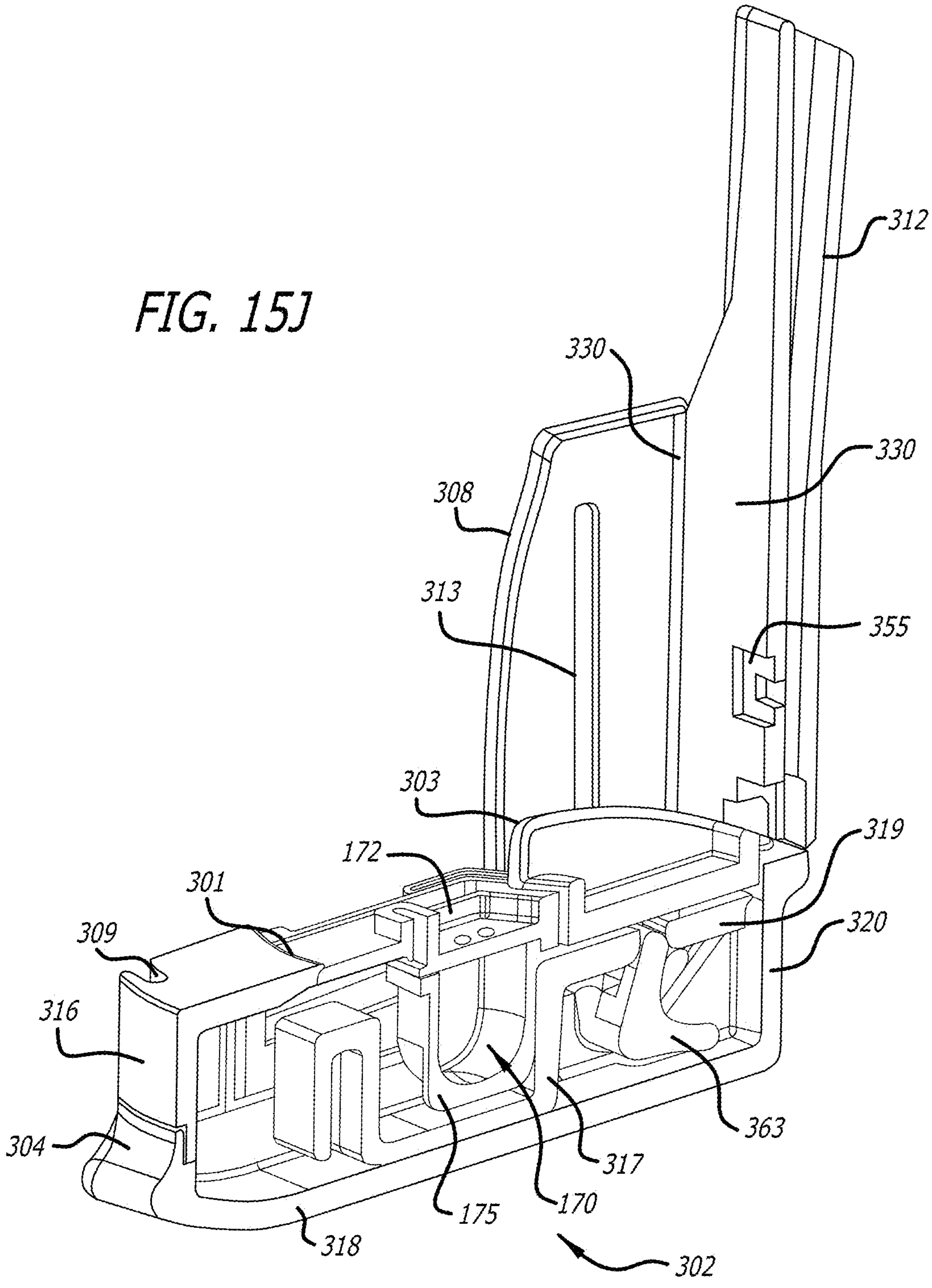
FIG. 15J depicts an isometric view of the inhaler of FIG. 15I in an open configuration with a cartridge installed in the holder.

FIGS. 15C-15K depict an alternate embodiment 302 of inhaler 300 depicted in FIGS. 12-15B. The inhaler comprises housing 320, mouthpiece 330, a gear mechanism, and a sled and can be manufactured using, for example, four parts in a top down assembly manner. Mouthpiece 330 further comprises air conduit 340 configured to run along the longitudinal axis of the inhaler and having an oral placement portion 312, air inlet 310 and air outlet 335 configured to have its surface angular or beveled relative to the longitudinal axis of the air conduit, and cartridge port opening 355 which is in fluid communication with housing 320 and/or a cartridge installed in housing 320 for allowing airflow to enter air conduit 340 from the housing or from a cartridge installed in the inhaler in use. FIG. 15C illustrates inhaler 302 in isometric view in a closed position having a more slender body 305 than inhaler 300 formed by housing 320 and cover portion 308 of mouthpiece 330, which extends over and engages housing 320 by a locking mechanism 312, for example, a protrusion. FIGS. 15D, 15E, 15F, 15G, and 15H depict side, top, bottom, proximal and distal views, respectively, of the inhaler of FIG. 15C. As shown in the figures, inhaler 302 comprises mouthpiece 330 having an oral placement section 312, an extended portion configured as a cover 308 that can attach to housing 320 at at least one location as shown in FIG. 15J. Mouthpiece 330 can pivot to open from a proximal position from a users hands in an angular direction by hinge mechanism 313. In this embodiment, inhaler 302 is configured also to have a gear mechanism 363 as illustrated in FIG. 15J. Gear mechanism 317 can be configured with the mouthpiece as part of the hinge mechanism to engage housing 320, which housing can also be configured to engage with sled 317. In this embodiment, sled 317 is configured with a rack which engages the gearwheel configured on the hinge mechanism. Hinge mechanism 363 allows movement of mouthpiece 330 to an open or cartridge loading configuration, and close configuration or position of inhaler 302 in an angular direction. Gear mechanism 363 in inhalers 300, 302 can actuate the sled to allow concurrent movement of sled 317 within housing 320 when the inhaler is effectuated to open and close by being integrally configured as part of gear mechanism 363. In use with a cartridge, the inhalers gear mechanism 363 can reconfigure a cartridge by movement of sled 317 during closing of the inhaler, from a cartridge containment configuration after a cartridge is installed on the inhaler housing, to a dosing configuration when the inhaler is closed, or to a disposable configuration after a subject has effectuated dosing of a dry powder formulation. In the embodiment illustrated herein, the hinge and gear mechanism are provided at the distal end of the inhaler, however, other configurations can be provided so that the inhaler opens and closes to load or unload a cartridge as a clam.

In one embodiment, housing 320 comprises one or more component parts, for example, a top portion 316 and a bottom portion 318. The top and bottom portions are configured to adapt to one another in a tight seal, forming an enclosure which houses sled 317 and the hinge and/or gear mechanisms 363. Housing 320 is also configured to have one or more openings 309 to allow air flow into the interior of the housing, a locking mechanism 313, such as protrusions or snap rings to engage and secure mouthpiece cover portion 308 in the closed position of inhaler 302. Housing 320 is also configured to have a cartridge holder or cartridge mounting area 315 which is configured to correspond to the type of cartridge to be used with the inhaler. In this embodiment, the cartridge placement area or holder is an opening in the top portion of housing 320 which opening also allows the cartridge bottom portion or container to lie on sled 317 once a cartridge is installed in inhaler 302. The housing can further comprise grasping areas 304, 307 configured to aid a user of the inhaler to firmly or securely grip the inhaler to open it to load or unload a cartridge. Housing 320 can further comprise flanges configured to define an air channel or conduit, for example, two parallel flanges 303 which are also configured to direct air flow into the inhaler air inlet 310 and into a cartridge air inlet of the cartridge air conduit positioned in the inhaler. Flanges 310 are also configured to prevent a user from obstructing inlet port 310 of inhaler 302.

Figure 15K:
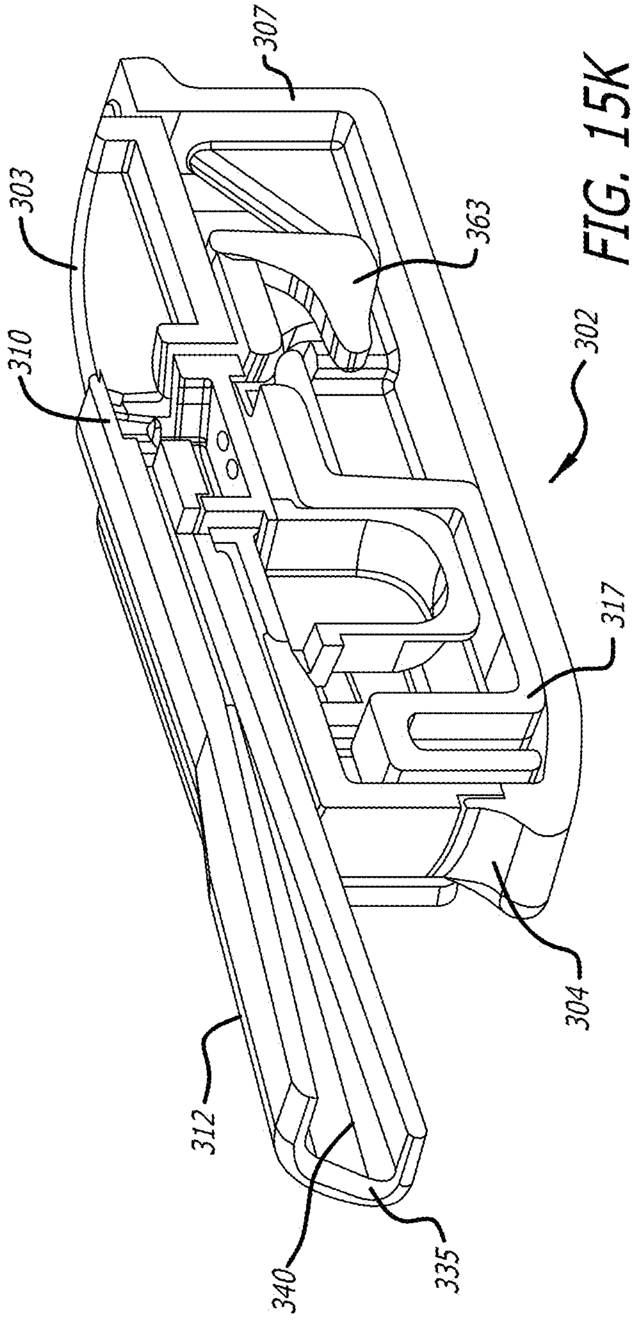
FIG. 15K depict the inhaler of FIG. 15C in cross-section through the mid-longitudinal axis with a cartridge installed in the cartridge holder and in a dosing configuration, and the closed configuration FIG. 15J.

FIG. 15I depicts an isometric view of the inhaler of FIG. 15C in an open configuration with mouthpiece covering, for example, cap 342 and cartridge 170 which are configured to correspond to the cartridge mounting area and allow a cartridge to be installed in cartridge holder 315 for use. In one embodiment, reconfiguration of a cartridge from a containment position, as provided after manufacturing, can be effectuated once the cartridge is installed in cartridge holder 315, which is configured within housing 320 and to adapt to the inhaler so that the cartridge has the proper orientation in the inhaler and can only be inserted or installed in only one manner or orientation. For example, cartridge 170 can be configured with locking mechanism 301 that matches a locking mechanism configured in the inhaler housing, for example, the inhaler mounting area, or holder can comprise a beveled edge 301 which would correspond to a beveled edge 180 on the cartridge of, for example, cartridge 170 to be installed in the inhaler. In this embodiment, the beveled edges form the locking mechanism which prevents the cartridge from popping out of holder 315 during movement of sled 317. In one particular embodiment illustrated in FIGS. 15J and 15K, the cartridge lid is configured with the beveled edge so that it remains secure in the housing in use. FIGS. 15J and 15K also show rack mechanism 319 configured with sled 317 to effectuate movement of a cartridge container 175 of cartridge 170 slideably under the cartridge top to align the container under the cartridge top undersurface configured to have dispensing port in a closed dosing position or configuration of the inhaler when inhaler 302 is ready for dosing a user. In the dosing configuration, an air inlet port forms by the border of the cartridge top and the rim of the container, since the undersurface of the cartridge top is raised relative to the containment undersurface. In this configuration, an air conduit is defined through the cartridge by the air inlet, the internal volume of the cartridge which is exposed to ambient air and the openings in the cartridge top or dispensing port in the cartridge top, which air conduit is in fluid communication with air conduit 340 of the mouthpiece.

Inhaler 302 can further include a mouthpiece cap 342 to protect the oral placement portion of the mouthpiece. FIG. 15K depict the inhaler of FIG. 15C in cross-section through the mid-longitudinal axis with a cartridge installed in the cartridge holder and in an open configuration, and in the closed configuration FIG. 15K.

FIG. 15J illustrates the position of cartridge 350 installed in holder or mounting area 315 and showing the internal compartment parts, including boss 326 with dispensing ports 327; gear mechanism 360, 363 and snaps 380 which assist in maintaining the device in a closed configuration.

Figure 16:
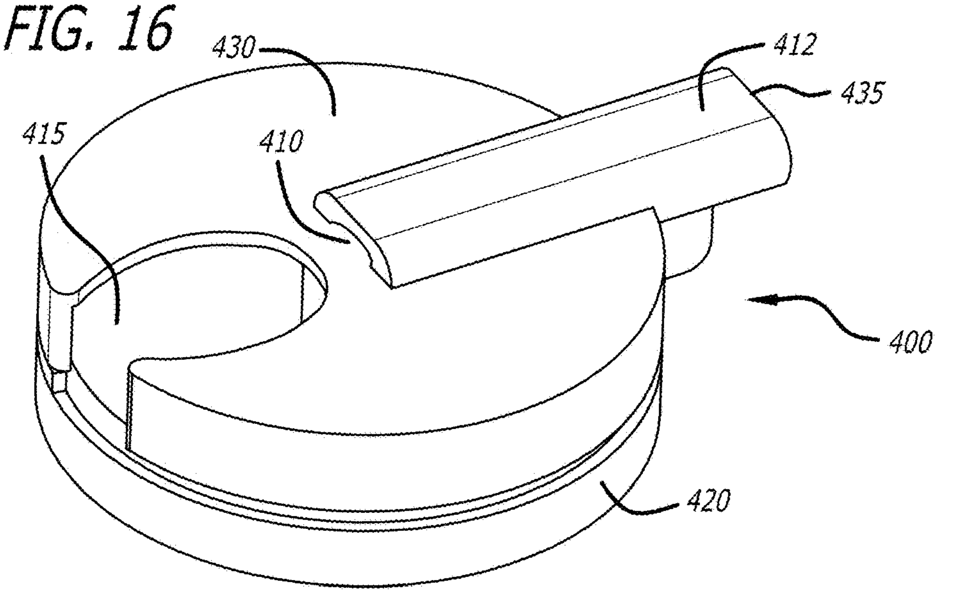
FIG. 16 illustrates a perspective view of an alternate embodiment of the dry powder inhaler in the closed position.
Figure 17:
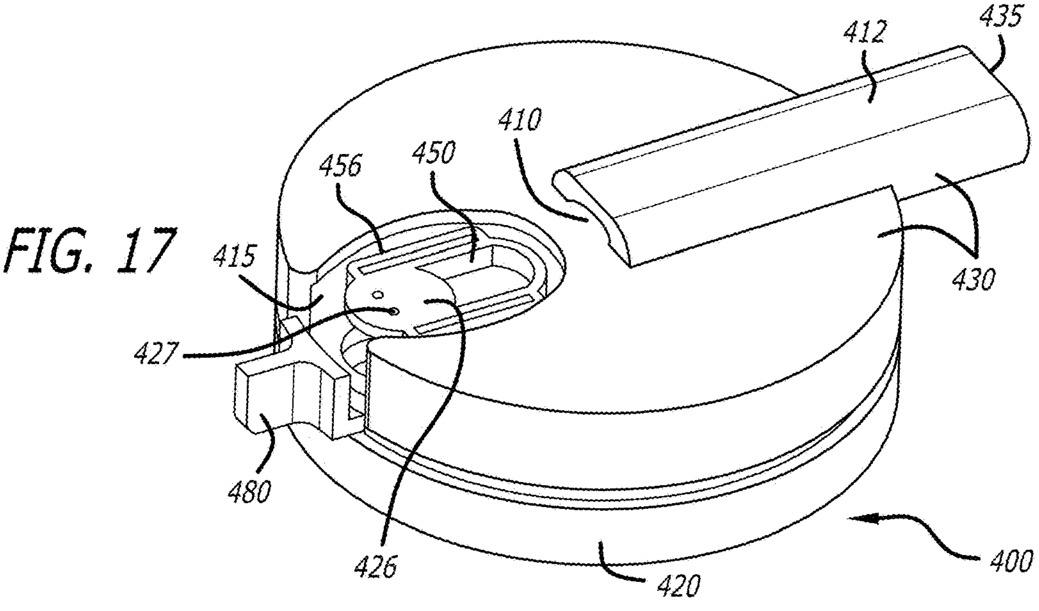
FIG. 17 illustrates the embodiment FIG. 16 in an opened, loading/unloading position having a cartridge installed in the cartridge holder.
Figure 18:
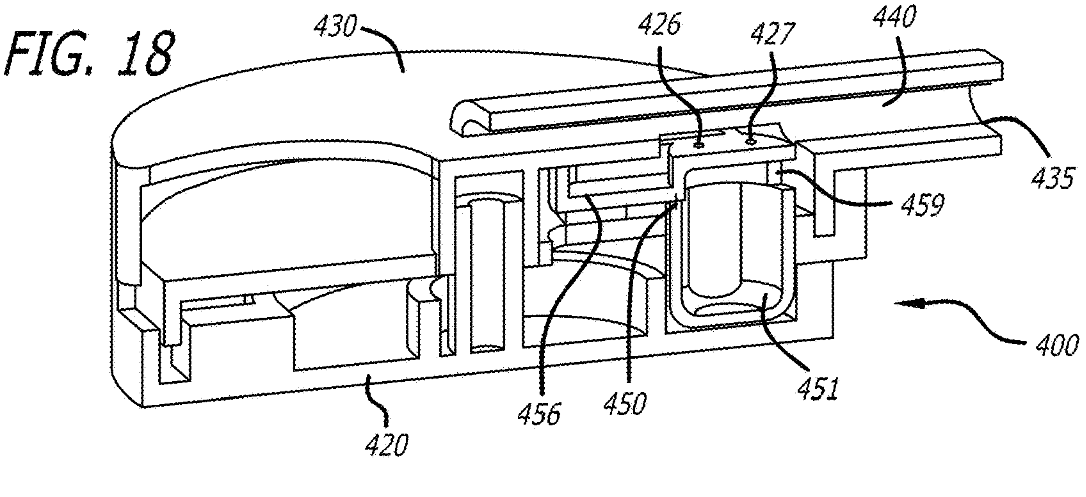
FIG. 18 illustrates the embodiment FIG. 16 in a closed, inhalation position having a cartridge installed in the cartridge holder in a dosing configuration.

In yet another embodiment, dry powder inhaler 400 is disclosed having a relatively round body and comprising mouthpiece 430; cartridge holder section 415 and housing 420 as illustrated in FIGS. 16-18. FIG. 16 illustrates a perspective view of an alternate embodiment of the dry powder inhaler in the closed position, wherein mouthpiece 430 comprises the top portion of the body of the inhaler and housing 420 comprises the bottom portion of the inhaler in the dosing position. Mouthpiece 430 also comprises oral placement section 412 having air outlet port 435.

FIG. 17 illustrates the embodiment of FIG. 16 in an opened, loading/unloading configuration showing cartridge 450 seated in cartridge holder 415, showing top 456 of cartridge 450. In this embodiment, the mechanism for actuating movement of cartridge 450 from a containment position to an open configuration is, for example, a cam. Handle or lever 480 containing cartridge 450 can be moved by rotation of lever 480 to the closed position. In the closed position, cartridge 450 within the lever 480 is moved under oral placement portion 412 of mouthpiece 430.

FIG. 18 illustrates a mid-longitudinal section of the embodiment depicted in FIG. 16 in a closed, inhalation position having cartridge 450 installed in cartridge holder 415 in an open configuration. As seen in FIG. 18, in the cartridge dosing configuration, air inlet 459 is formed or defined by a gap between cartridge top 456 and container 451, which is in communication with dispensing ports 427 on boss 426. Dispensing ports 427 are in fluid communication with air conduit 440, thereby during an inhalation maneuver, airflow entering air conduit 440 from cartridge 450 exits the cartridge and combines with airflow in the air conduit entering air inlet 410 and a flow is swept in the direction of air outlet 435.

FIG. 19 through FIG. 28 illustrate two alternative embodiments of the dry powder inhaler. In these embodiments, the dry powder inhaler is structurally configured for single use as a unit dose inhaler and cartridge assembled together into a disposable, non-reusable unit. The inhalers in this embodiment are manufactured to contain the desired pre-metered, unit dose, drug formulation within the formed cartridge container. In this embodiments, the container is also capable of movement from a containment position to a dosing or dispensing configuration.

Figure 19:
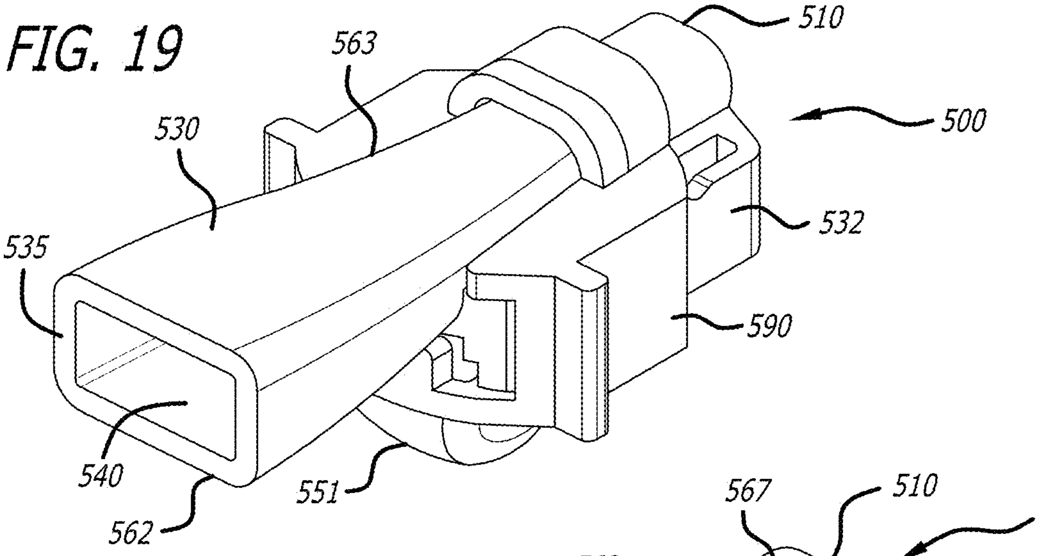
FIG. 19 illustrates a perspective view of an alternate embodiment of a dry powder inhaler for single use, showing the container in a containment configuration.

FIGS. 19-23 illustrate perspective views of an embodiment of a dry powder inhaler for single use. FIG. 19 shows the inhaler in a containment configuration. In this embodiment, inhaler 500 comprises a top surface 563 and a bottom or undersurface 562; a mouthpiece 530 and a mounted cartridge assembly or sled 590. Mouthpiece 530 has an elongated shape and it is structurally configured with an air inlet 510 and an air outlet port 535. An air conduit extends from air inlet 510 to air outlet 535 which creates a secondary pathway for airflow entering inhaler 500 during inhalation.

Figure 20:
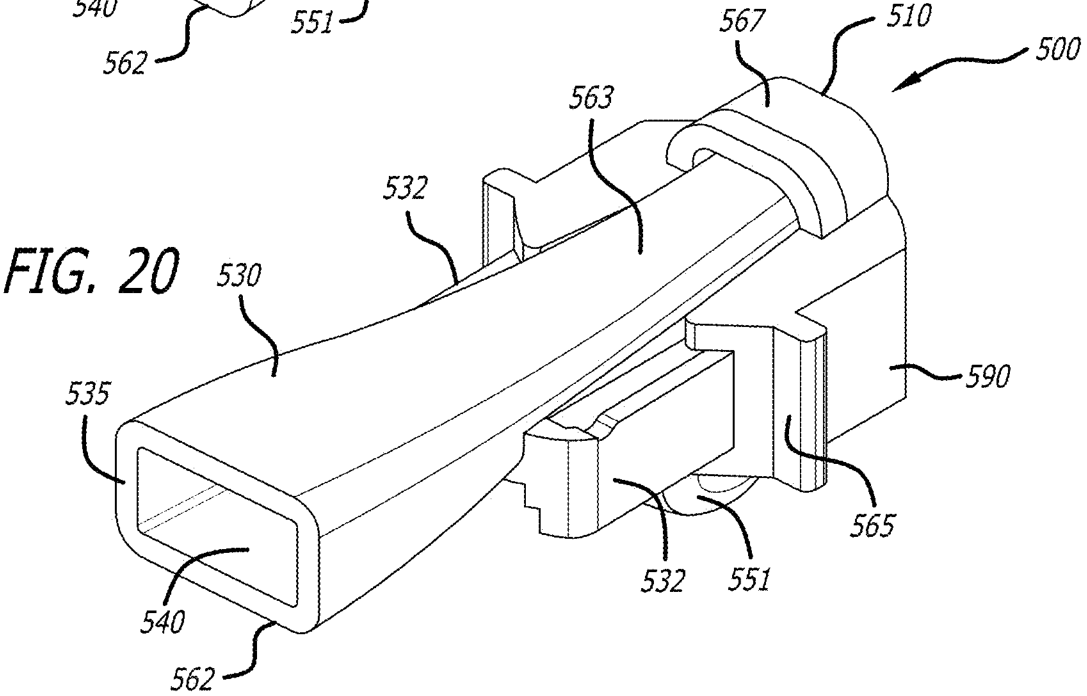
FIG. 20 illustrates a perspective view of the inhaler shown in FIG. 19 wherein the inhaler is in the dosing configuration, which allows air to flow through the interior of the powder containment cup.

FIG. 20 illustrates a perspective view of the inhaler embodiment shown in FIG. 19, wherein the inhaler is in the dose configuration establishing a flow pathway through the interior of the cartridge and the dispensing ports wherein the inhaler is ready for use. FIG. 20 depicts mouthpiece 530 having an increasingly wider cross-sectional area of air conduit 540 from air inlet port 510 to air outlet port 535, being narrower at the inlet port end 510. Mouthpiece 530 also is structurally configured to have side extension or panels 532 integrally extending from the walls of mouthpiece conduit 540 which support sled 590. A space between the mouthpiece air conduit wall 540 and the panel is provided which allows the sled 590 to slide over mouthpiece 530. Sled 590 has a first bridge 567 spanning mouthpiece 530 on the top side, and has wings or flanges 565 which allow manual gripping or grasping of the sled 590 to configure the device from the containment to the dose position, and vice versa.

Figure 21:
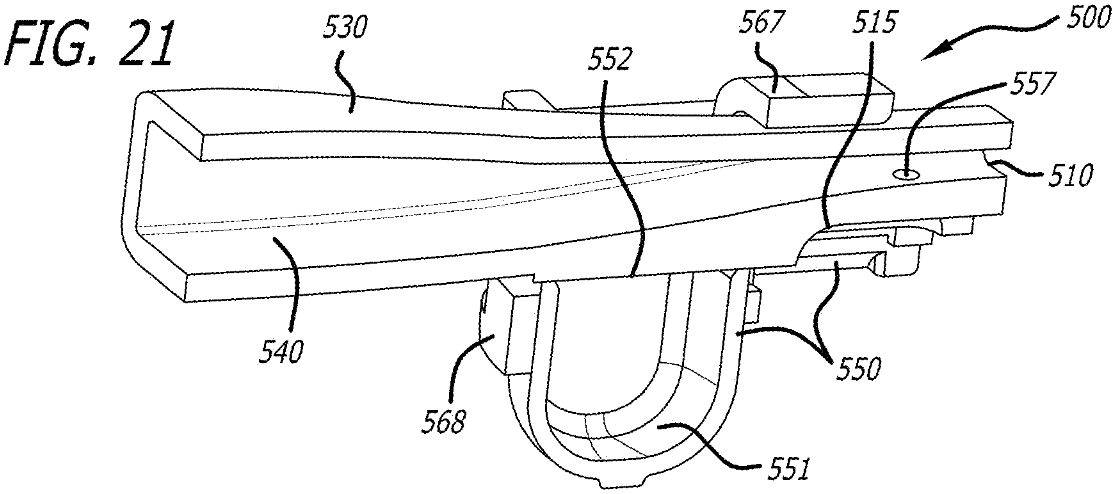
FIG. 21 illustrates a perspective view of the inhaler shown in FIG. 19 in mid-longitudinal section wherein the inhaler is in a containment configuration.
Figure 22:
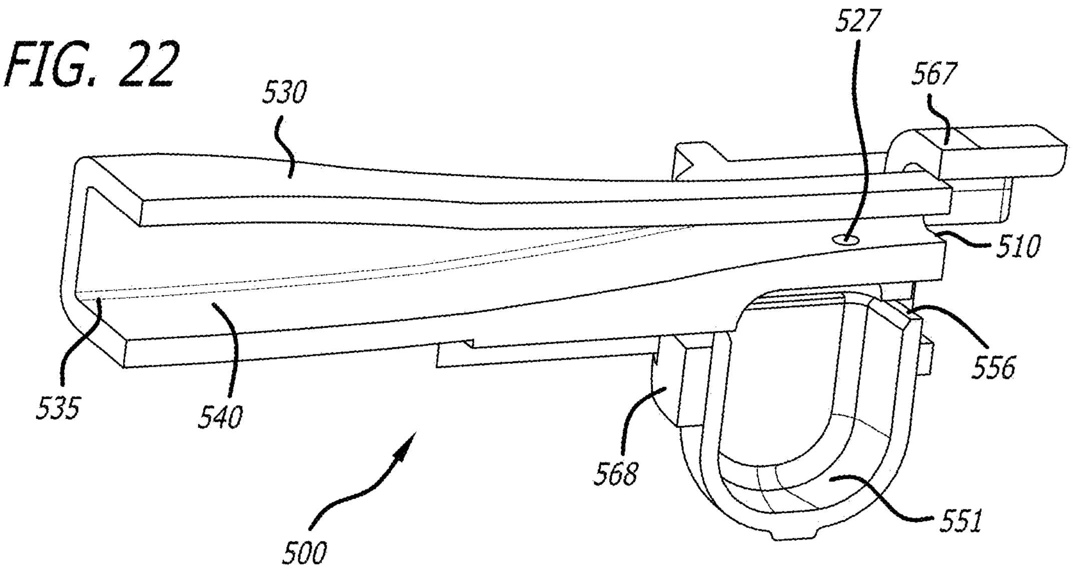
FIG. 22 illustrates a perspective view of the inhaler shown in FIG. 20 in longitudinal section wherein the inhaler is the dosing configuration.
Figure 23:
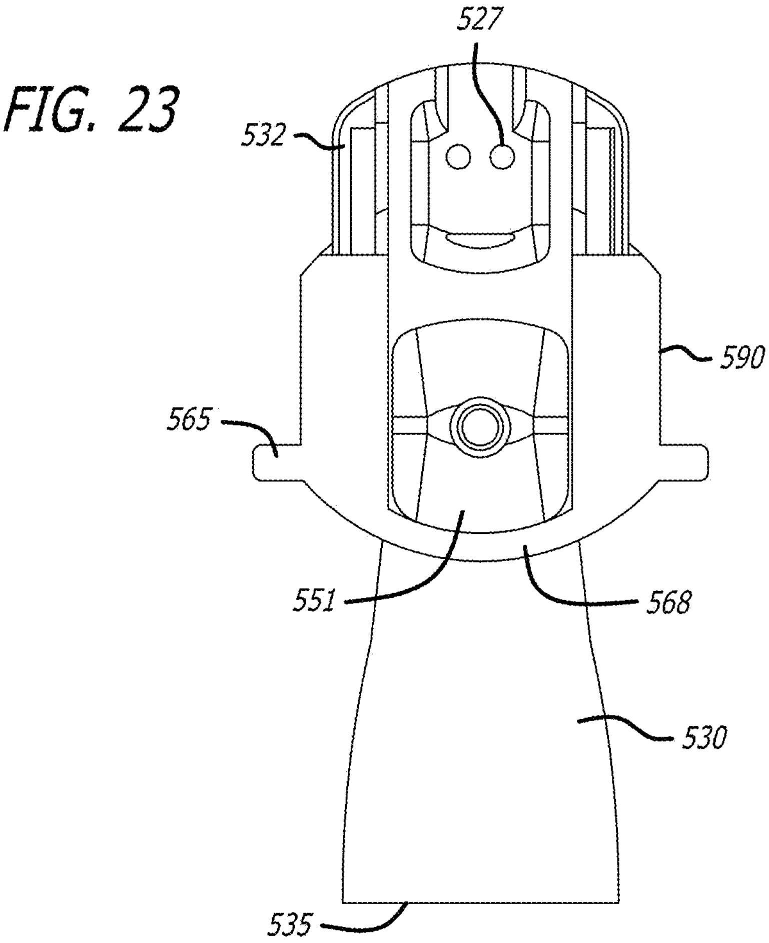
FIG. 23 depicts a bottom view of the embodiment of FIG. 19, showing the undersurface of the dry powder inhaler components.

FIG. 21 illustrates a perspective view of the inhaler shown in FIG. 19 in mid-longitudinal section in a containment position. In FIG. 21, cartridge container 551 is integrally adapted to the mouthpiece 530 so that it is flushed and sealed against the surface of mouthpiece 530. Container 551 has wing-like structures that can be suspended and moveable on tracts configured on the bottom surface of the mouthpiece panels or extensions 532. The mouthpiece panels 532 are structurally configured so that movement of container 551 is contained within panels 532. FIG. 23 depicts undersurface 562 showing sled 590 configured to have a second bridge 568 on the bottom side of inhaler 500 which can be configured to be in contact with container 551 for translational movement from the containment position to the dispensing or dosing position. When sled 590 is moved towards inlet port 510, it carries container 551 translationally to an open position and for alignment with dispensing ports 527 located in the floor of mouthpiece conduit 540. In the dosing configuration an inlet port is defined by the container rim and the mouthpiece undersurface to allow the internal volume to be exposed to ambient air. The dosing configuration also defines an air conduit between the inlet port, the internal volume of the container and the dispensing ports to allow a flow to transit the container and deliver a powder dose contained therein. Full alignment of container 551 and dispensing ports 527 is achieved by moving the sled from the containment position to the dose position until the sled cannot move further in panel 532. FIG. 22 illustrates a perspective view of the inhaler shown in FIG. 20 in longitudinal section wherein the cartridge is in the open or dosing position. In this configuration, a primary air passage is established through the container as represented by inlet 556 and dispensing port 527 with the container's internal volume. A secondary flow passage is provided by mouthpiece conduit 540 from air inlet 510 to outlet 535 which is configured to provide a flow that impinges a flow exiting the dispensing ports to prove shear force and promote deagglomeration of powder particles as they exit the dispensing ports in use.

Figure 24:
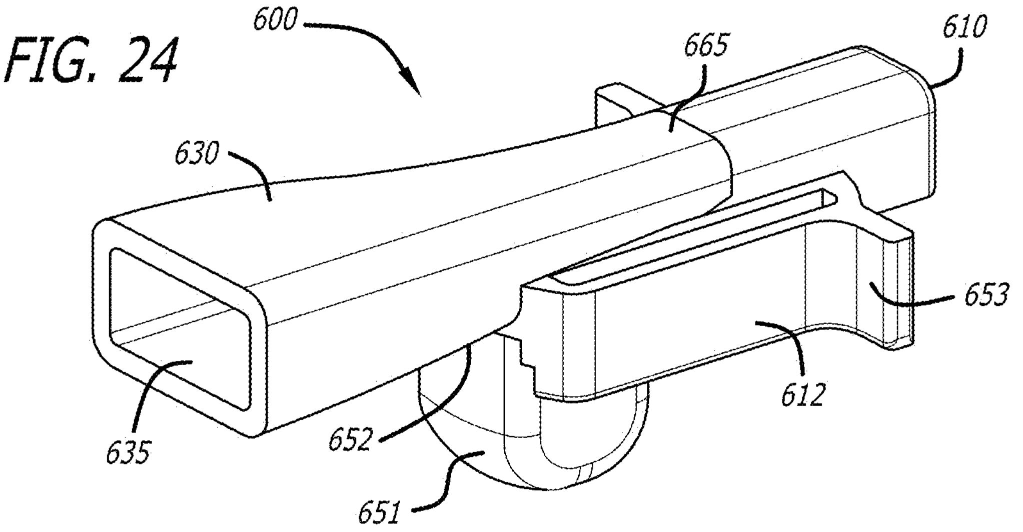
FIG. 24 illustrates a perspective view of yet another embodiment of a dry powder inhaler for single use, showing the containment configuration.
Figure 25:
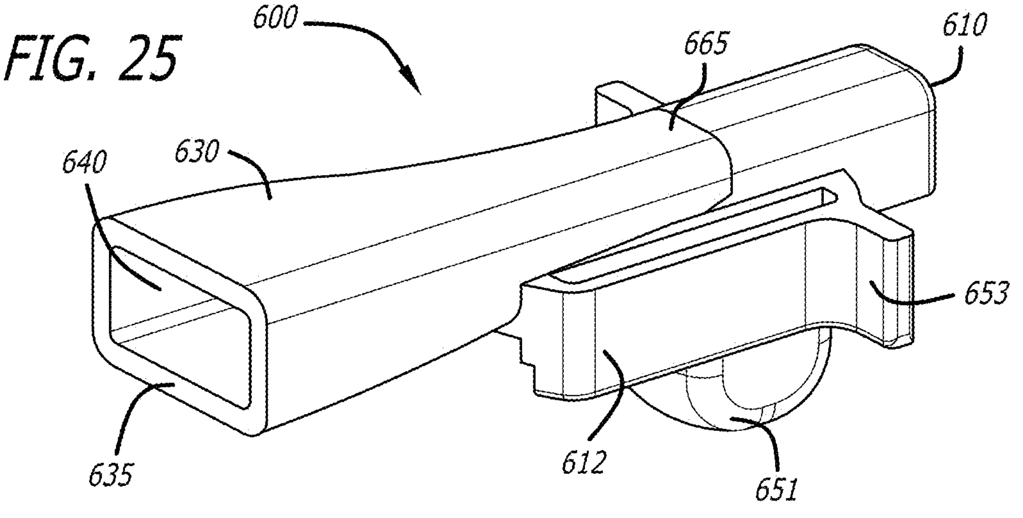
FIG. 25 illustrates a perspective view of the inhaler of FIG. 23 wherein the dosing configuration, which allows air to flow through the interior of the medicament container is shown.
Figure 26:
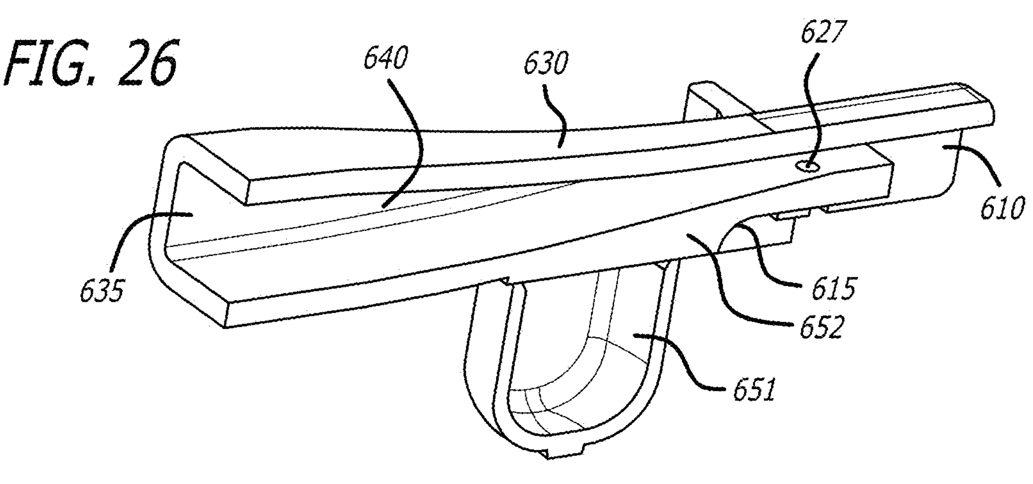
FIG. 26 illustrates a perspective view of the inhaler shown in FIG. 24 in mid-longitudinal section wherein the medicament container in a containment or closed position is displayed.
Figure 27:
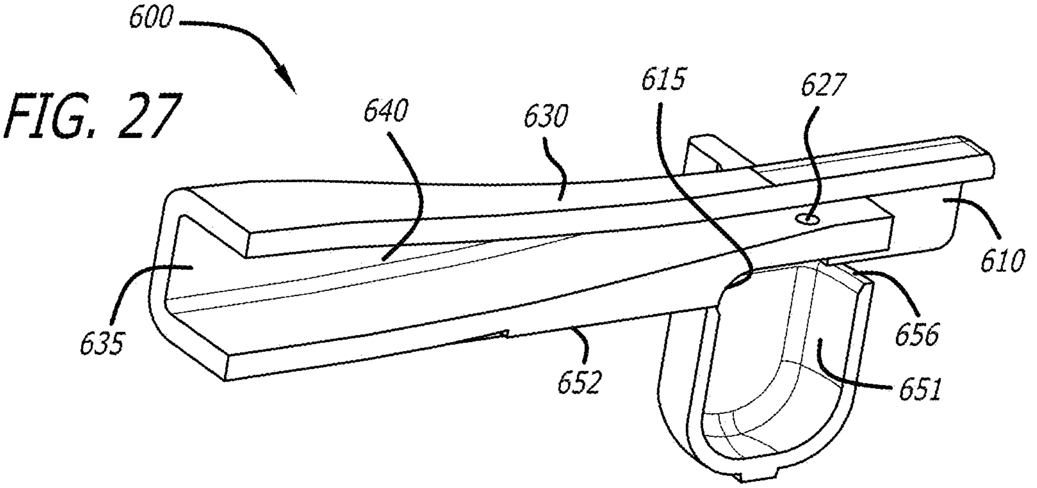
FIG. 27 illustrates a perspective view of the inhaler shown in FIG. 24 in mid-longitudinal section wherein the medicament container in a dosing position is displayed.
Figure 28:
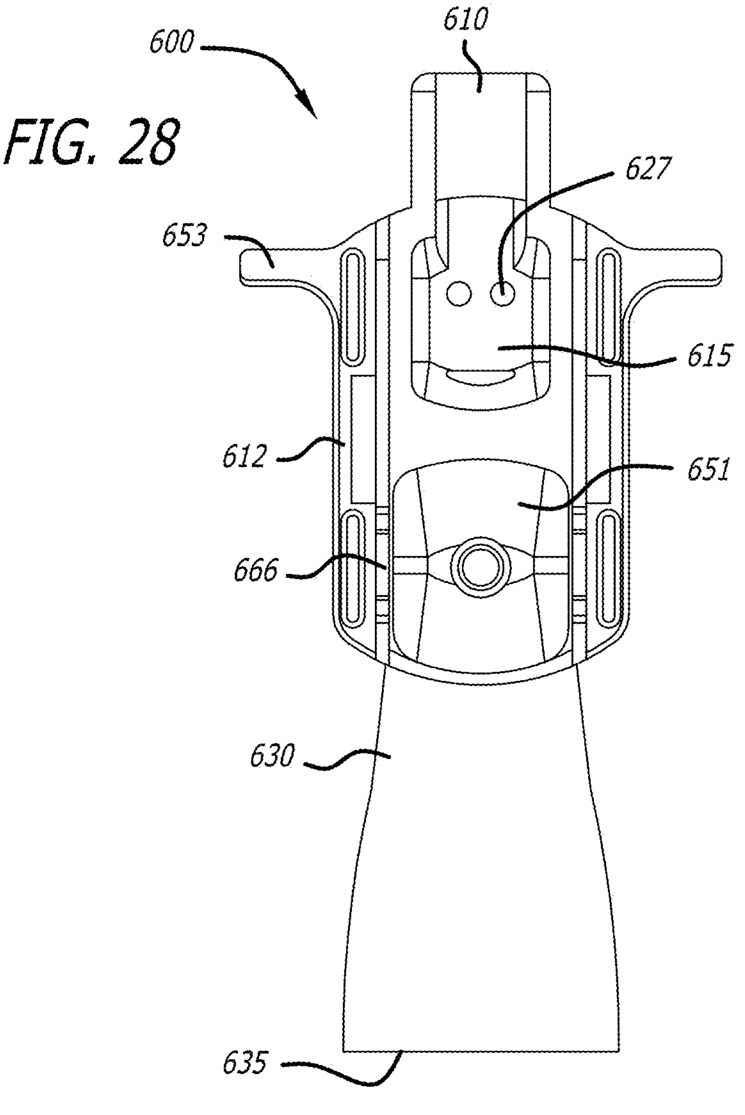
FIG. 28 is a perspective and bottom view of the inhaler of FIG. 24, showing the undersurface components of the inhaler.

FIGS. 24-28 illustrate perspective views of yet another embodiment of a dry powder inhaler for single use. In this embodiment, the inhaler 600 has top surface 665 and bottom or undersurface 652 and comprises mouthpiece 630 and container 651. FIG. 24 shows the container 651 component in a containment configuration. In this embodiment, inhaler 600 comprises mouthpiece 630 and mounted container 651 attached and moveable relative to mouthpiece 630. Mouthpiece 630 has an elongated shape and it is structurally configured with air inlet 610 and air outlet port 635. An air conduit 640 extends from air inlet 610 to air outlet 635 which is configured to create an additional or secondary pathway for airflow entering inhaler 600 during inhalation. FIG. 28 shows mouthpiece 630 undersurface 652 which is configured with parallel side panels 612 at each side of the inhaler, configured to have projections or wings 653 for holding or securely gripping inhaler 600. Panels 612 are configured on their bottom ends with, for example, a flange to form a track for adapting and supporting side wings 666 on the cartridge container. FIG. 26 shows undersurface 652 of mouthpiece 630 configured to hold the cartridge container in a sealed or containment position, and in this area, undersurface 652 is flushed against the top of cartridge container 651. Mouthpiece undersurface 615 is configured to have a concave-like or hollow form so that when the container 651 is moved to the inhalation or dosing position, air inlet 656 is created by the container wall and the mouthpiece undersurface. An air flow pathway is then established between inlet 656 and dispensing port 627.

FIG. 25 illustrates a perspective view of the inhaler shown in FIG. 24 wherein the cartridge component is in the open configuration which allows air to flow through the interior of the cartridge. FIG. 26 illustrates a perspective view of the inhaler shown in FIG. 24 in mid-longitudinal section wherein container 651 is in the containment position. FIG. 27 illustrates a perspective view of the inhaler shown in FIG. 25 in mid-longitudinal section wherein the cartridge is in the open or dosing position. In a dosing configuration, container inlet port 656 forms an air conduit with dispensing port 627 which is in communication with mouthpiece air conduit 640. Container 651 is supported by container wings 666 through parallel tracks and the undersurface of the device.

Figure 31:
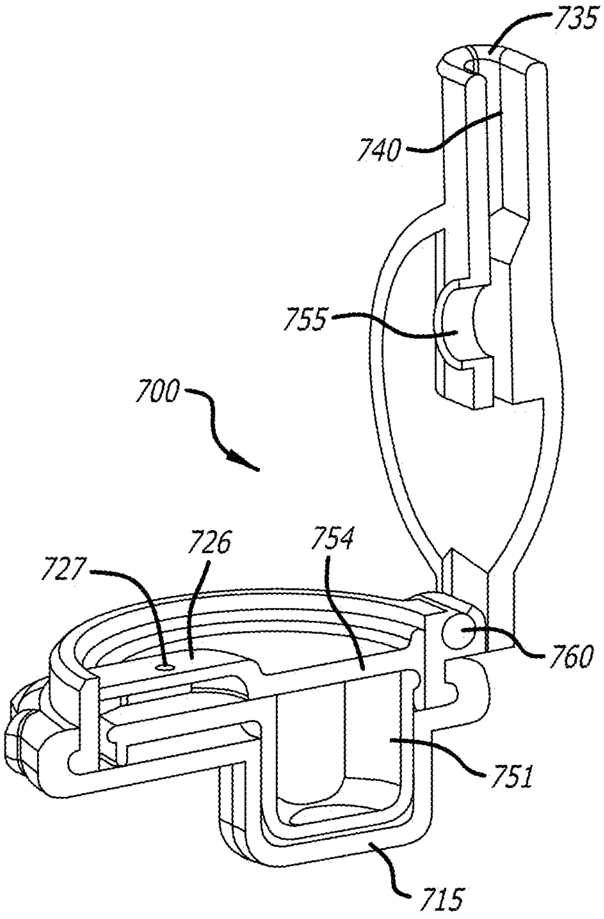
FIG. 31 illustrates a perspective view of the inhaler shown in FIG. 30 in mid-longitudinal section in the open configuration wherein the medicament container in a containment position is displayed.
Figure 32:
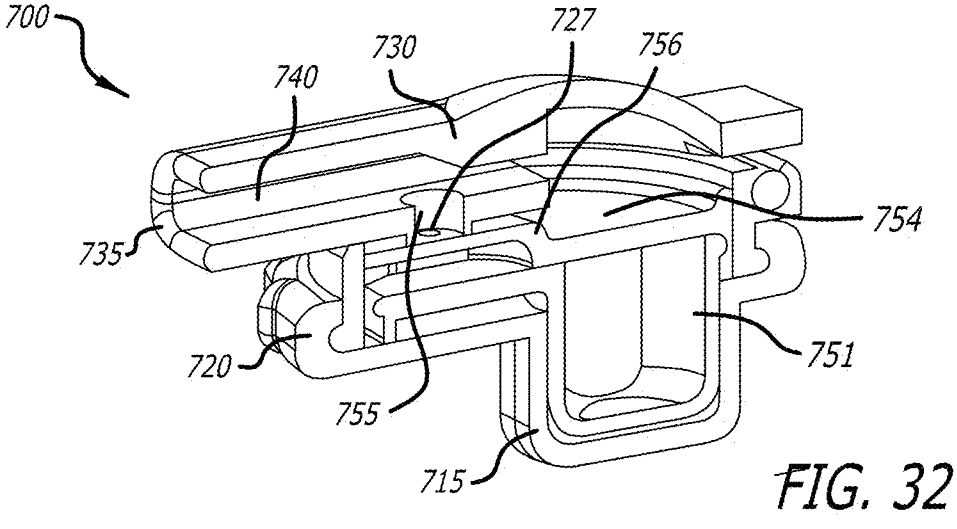
FIG. 32 illustrates a perspective view of the inhaler shown in FIG. 31 in mid-longitudinal section wherein the medicament container in a containment position is displayed and the mouthpiece section has been secured with the housing.
Figure 33:
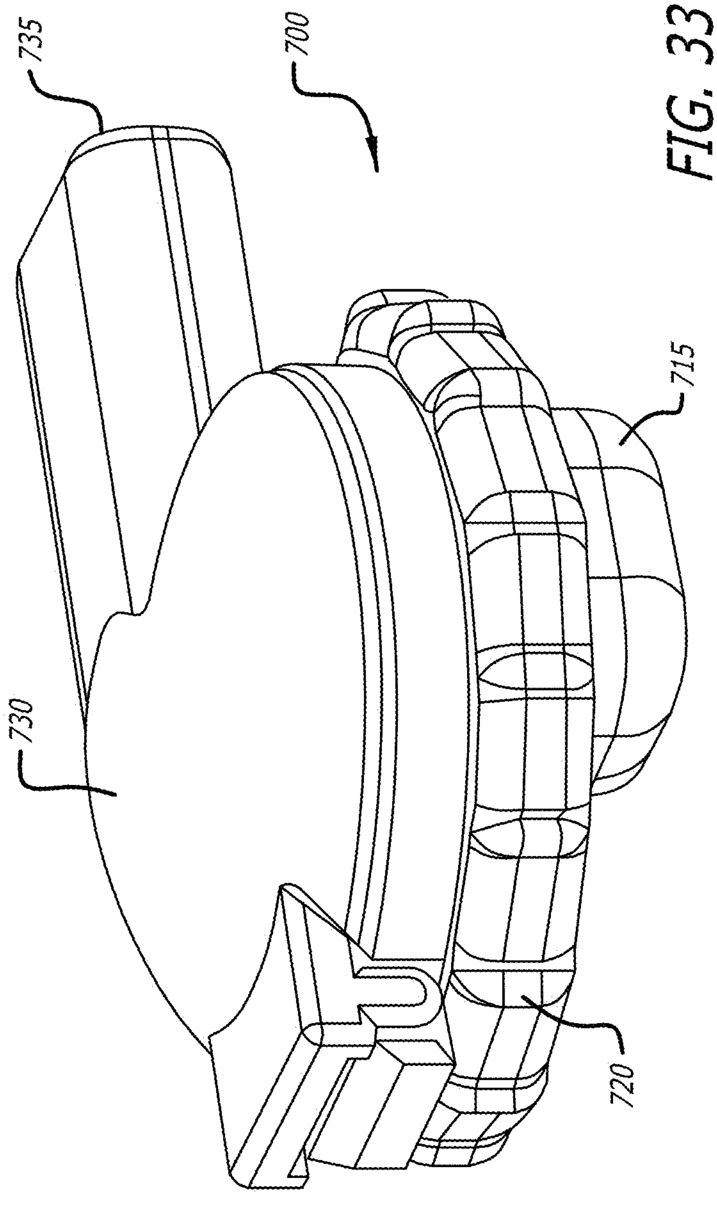
FIG. 33 illustrates a perspective view of the inhaler shown in FIG. 29 showing the inhaler in a dosing position.
Figure 34:
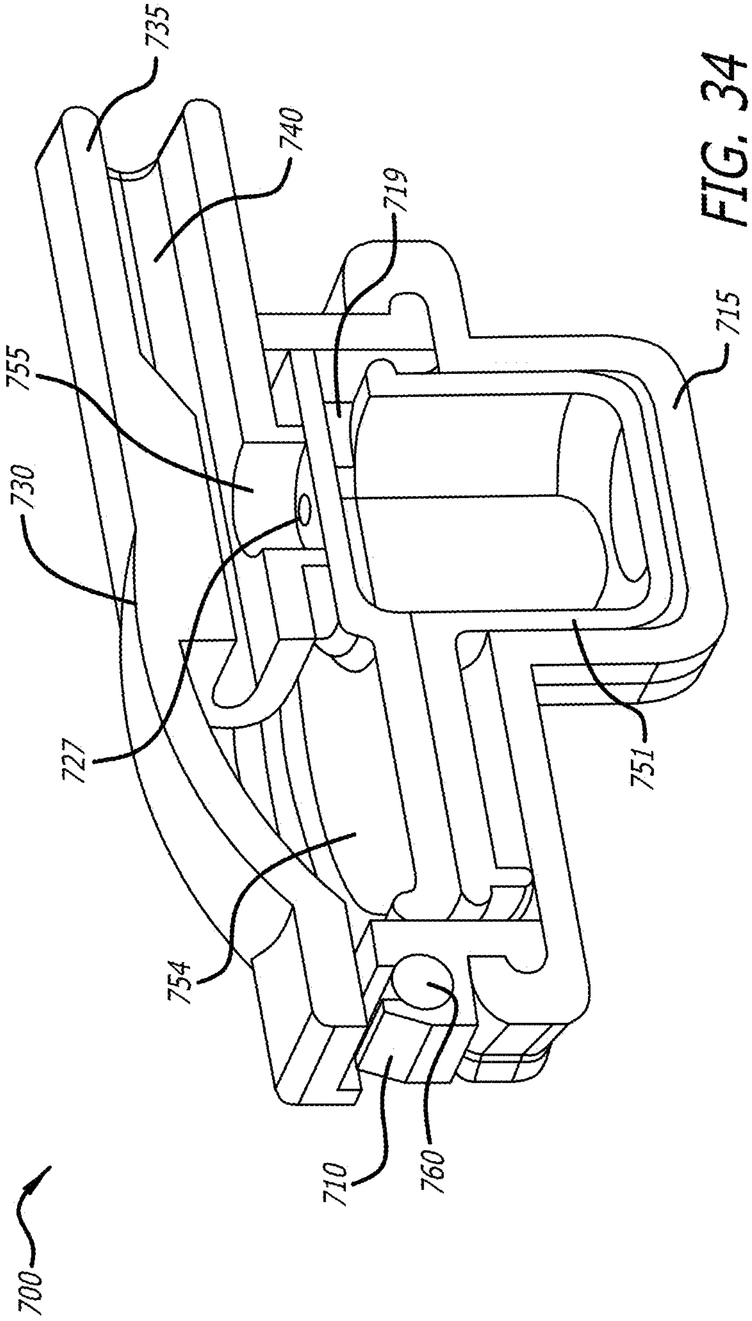
FIG. 34 illustrates a perspective view of the inhaler shown in FIG. 33 in mid-longitudinal section wherein the medicament container in a dosing position is displayed.

Perspective views of an alternate embodiment of the dry powder inhaler are illustrated in FIGS. 29-34. In this embodiment, the inhaler can be in a closed-containment configuration and in a closed-dosing configuration. The figures depict the inhaler with or without a cartridge, and depicting its relatively circular, disk-like body formed by a portion of mouthpiece 730 and housing 720, and having top and bottom surfaces. Mouthpiece 730 has an inlet port 710 and outlet port 735, and opening 755 in its undersurface. Mouthpiece 730 is configured to define the top portion 731 of the inhaler body and is movably attached by a hinge 760, which allows the inhaler to be opened from a containment position in an angular motion to load and unload a cartridge. Mouthpiece 730 can also be rotatably movable relative to housing 720 from a containment position to a closed, dosing positing of the inhaler through and angle of about 180°. FIG. 30A also illustrates a medicament cartridge 780 for use with this inhaler which is also depicted in FIGS. 40 through 44 and comprises a top or lid 756 and container 751 configured to fit in holder 715 within housing 720. Housing 720 comprises cartridge holder 715 and and is configured to define the bottom portion of the inhaler body. FIGS. 30A, 30B and 31 show the inhaler in a containment configuration wherein mouthpiece 730 and the housing 720 are can allow a cartridge to be loaded. When a medicament cartridge is installed in holder 715 as illustrated in FIGS. 30B, 31, 32 and 34 mouthpiece 730 has an engagement mechanism with the housing such as a snap ring and can rotate relative to housing 720. FIG. 30A additionally shows that mouthpiece 730 can engage with an intermediate structure or rotator 717 which is configured to adapt to the housing 720 by a ring and groove mechanism and is configured to hold a cartridge. As shown in FIG. 32, mouthpiece 730 also engages cartridge top 756 defining an air conduit between the cartridge top and mouthpiece air conduit 740, wherein movement of mouthpiece 730 and cartridge top 756 move together relative to housing 720 to position cartridge boss 726 over container 751, aligning dispensing ports 727 over container 751 and holder 715. An inlet port 719 is defined by the cartridge top 756 over container 751 to allow air entry into the cartridge 780 and through the dispensing ports 727 in a dosing configuration. FIGS. 33 and 34 illustrate the inhaler in a closed-dosing configuration wherein rotation of the inhaler over cartridge container 751 also defines an air flow communication between an inhaler inlet port 710 of the inhaler body located over hinge 760 and the interior of the inhaler body with the cartridge inlet 719 which places the inhaler in a closed-dosing configuration. A portion of air flow entering the inhaler body through inlet port 710 enters the cartridge inlet 719 and exits through dispensing ports 727 into mouthpiece aperture 755 which then meets bypass air that enters the mouthpiece conduit 740 before reaching outlet port 735 and into a user. In this embodiment, the inhaler is configured to have a registration structure at predetermined sites to indicate the dosing position and the containment position once they are reached during rotational movement of the mouthpiece. As with other embodiments herein, a portion of the flow in use diverges and remains circulating in the internal volume of the container to promote entrainment and lifting of a powder medicament in the container and promote deagglomeration of the powder to form small masses of the powder that can exit through the dispensing ports.

Figure 35:
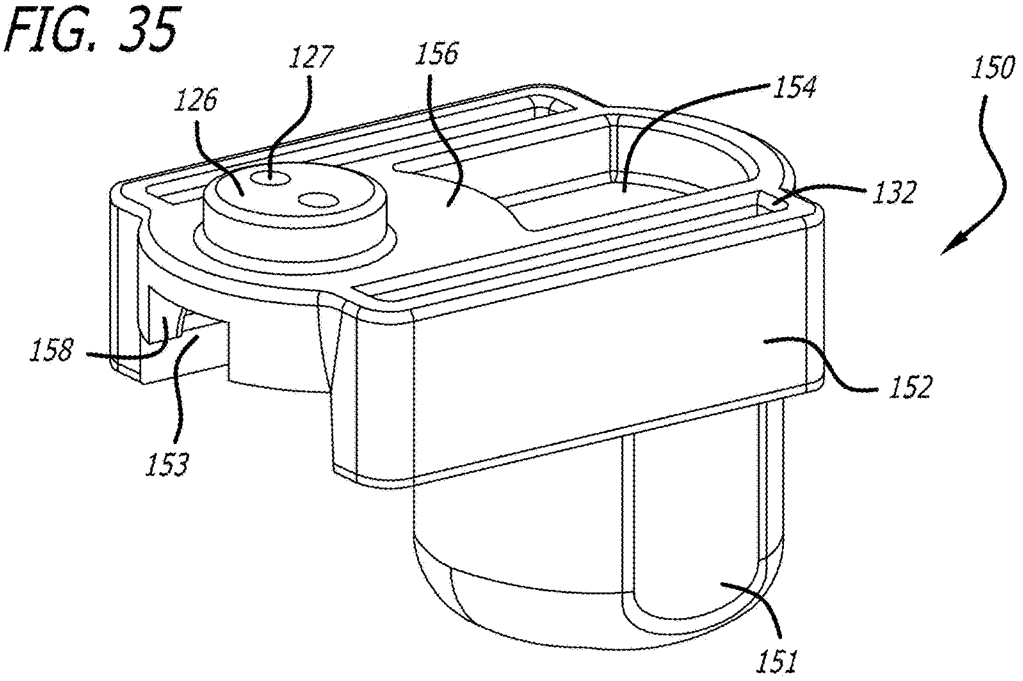
FIG. 35 illustrates a perspective view of a cartridge embodiment for use with the inhaler of FIG. 1 as also shown in FIG. 4B depicting the cartridge in a containment configuration.
Figure 39A:
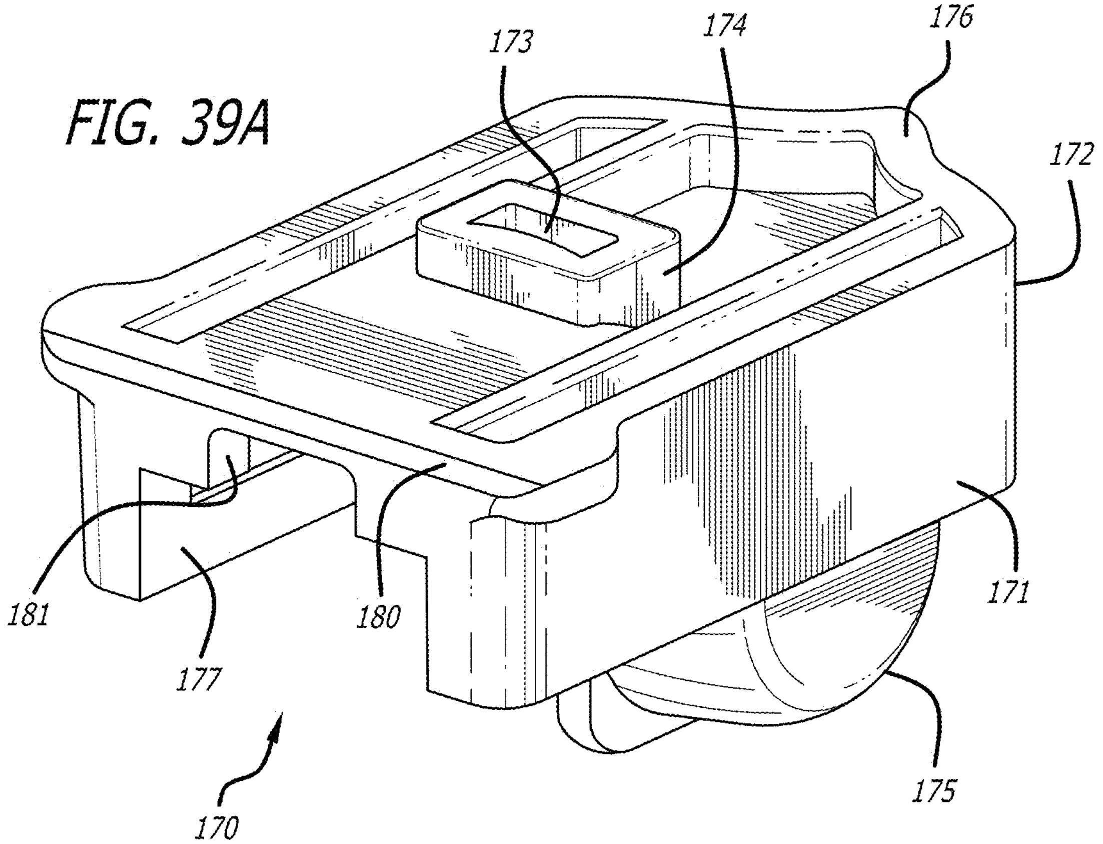
FIG. 39A depicts a perspective view of an alternate embodiment of a cartridge in a containment configuration.
Figure 40:
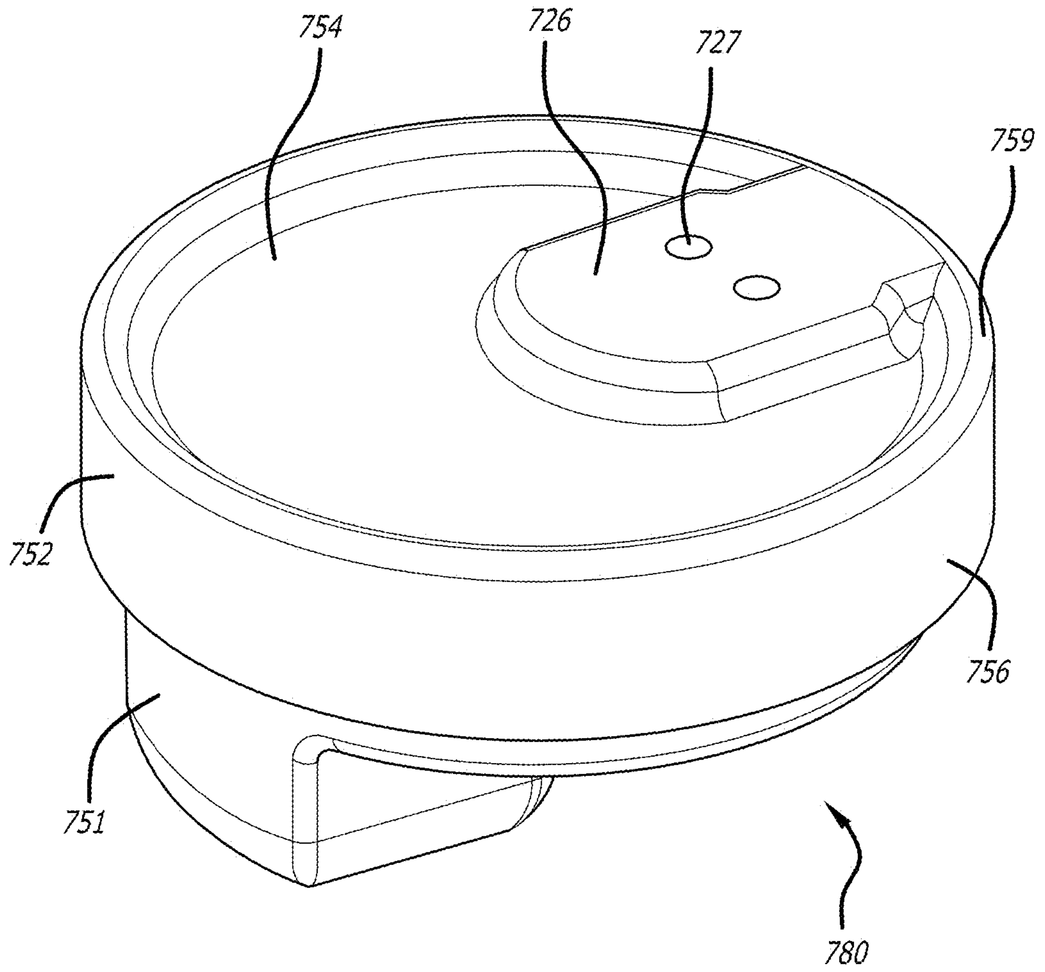
FIG. 40 illustrates a perspective view of a cartridge embodiment for use with the inhaler of FIG. 29 showing the cartridge in a containment configuration.

Cartridge embodiments for use with the inhalers are describe above, such as cartridges 150, 170, 780, and 800 illustrated, respectively, in FIGS. 4B and 35; FIGS. 15I and 39A; FIG. 40 and FIG. 45. The present cartridges are configured to contain a dry powder medicament in a storage, tightly sealed or contained position and can be reconfigured within an inhaler from a powder containment position to an inhalation or dosing configuration. In certain embodiments, the cartridge comprises a lid or top and a container having one or more apertures, a containment configuration and dosing configuration, an outer surface, an inner surface defining an internal volume; and the containment configuration restricts communication to the internal volume and the dispensing configuration forms an air passage through said internal volume to allow an air flow to enter and exit the internal volume in a predetermined manner. For example, the cartridge container can be configured so that an airflow entering the cartridge air inlet is directed across the air outlets within the internal volume to meter the medicament leaving the cartridge so that rate of discharge of a powder is controlled; and wherein airflow in the cartridge can tumble substantially perpendicular to the air outlet flow direction, mix and fluidize a powder in the internal volume prior to exiting through dispensing apertures.

Figure 36:
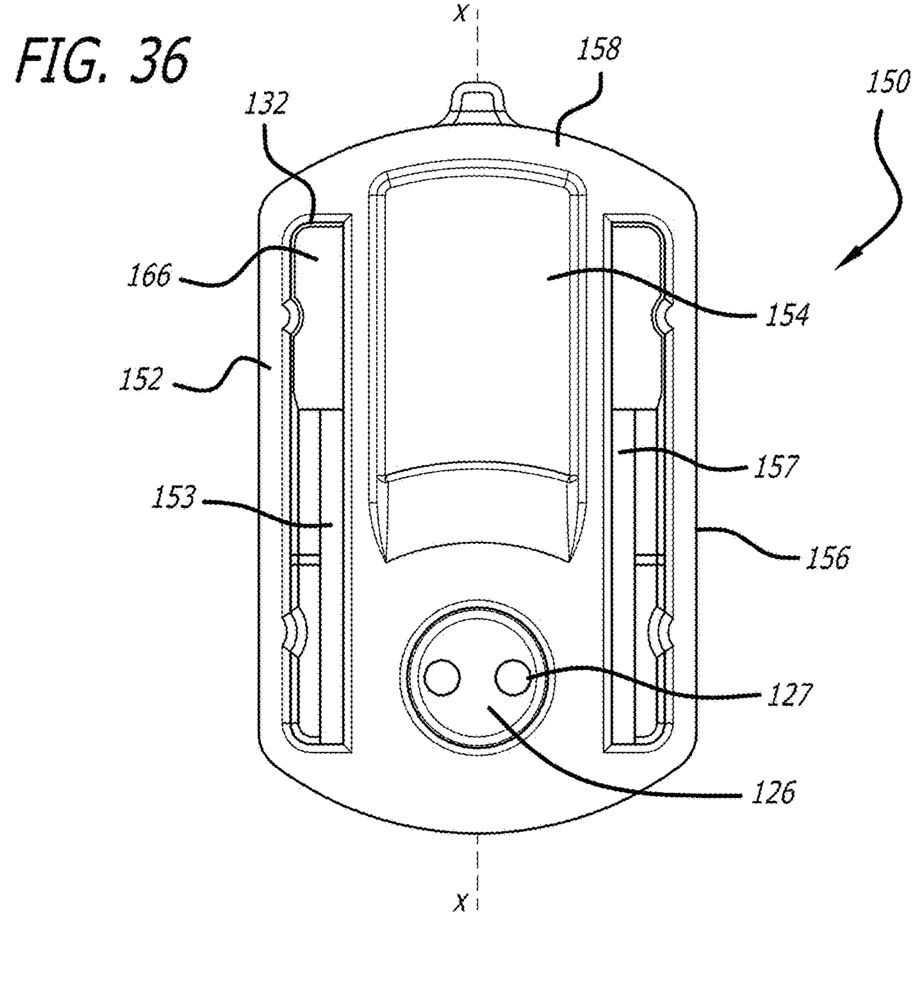
FIG. 36 illustrates a top view of the cartridge embodiment of FIG. 35, showing the component structures of the cartridge top surface.
Figure 37:
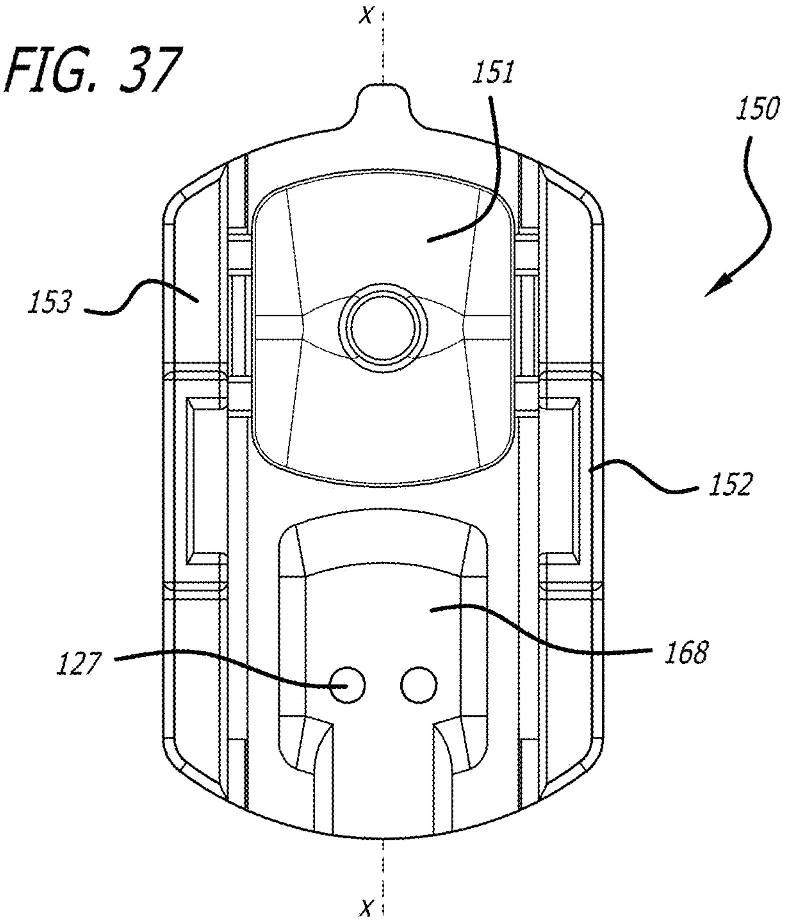
FIG. 37 illustrates a bottom view of the cartridge embodiment of FIG. 35, showing the component structures of the cartridge undersurface.

FIG. 35-38B further illustrate cartridge 150 comprising top or lid 156 and container 151 defining an interior space or volume. FIG. 36 exemplifies the cartridge top 156 having opposing ends and comprising recess area 154 and boss 126 at opposing ends of a longitudinal axis X, and relatively rectangular set of panels 152 along the sides and in the longitudinal axis X, which are integrally configured and attached to top 156 at their ends. The border 158 of cartridge top 156 extends downwardly and is continuous with panels 152. Panels 152 extend downwardly from either side of top 156 in the longitudinal axis X and are separated from the area of boss 126 and recess area 154 by a longitudinal space or slit 157. FIGS. 35-37 also show each panel 152 further comprising a flange 153 structurally configured to engage with projections or wings 166 of container 151, support container 151 and allow container 151 to be movable from a containment position under recess area 154 to a dosing position under area of boss 126. Panels 152 are structurally configured with a stop 132 at each end to prevent container 151 from moving beyond their end where they are attached to border 158. In this embodiment, container 151 or lid 156 can be movable, for example, by translational movement upon top 156, or top 156 can be movable relative to the container 151. In one embodiment, container 151 can be movable by sliding on flanges 153 on lid 156 when lid or top 156 is stationary, or lid 156 can be movable by sliding on a stationary container 151 depending on the inhaler configuration. Border 158 near the boss 126 has a recess area which forms part of the perimeter of inlet port 119 in the dosing configuration of the cartridge.

Figure 38A:
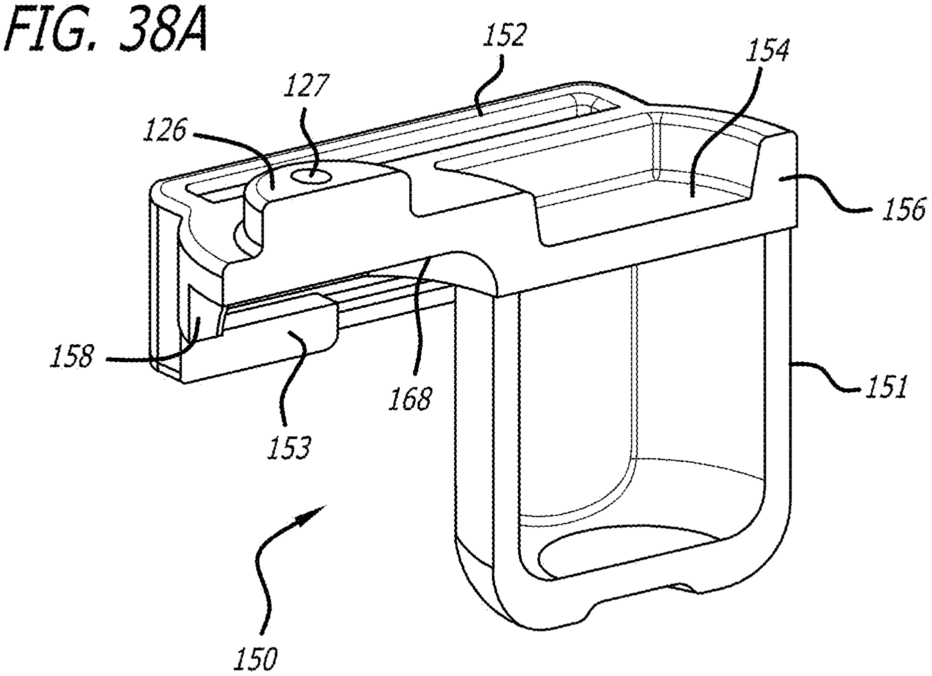
FIG. 38A illustrates a perspective view of a cartridge embodiment of FIG. 35 in mid-longitudinal cross-section and in a containment configuration.
Figure 38B:
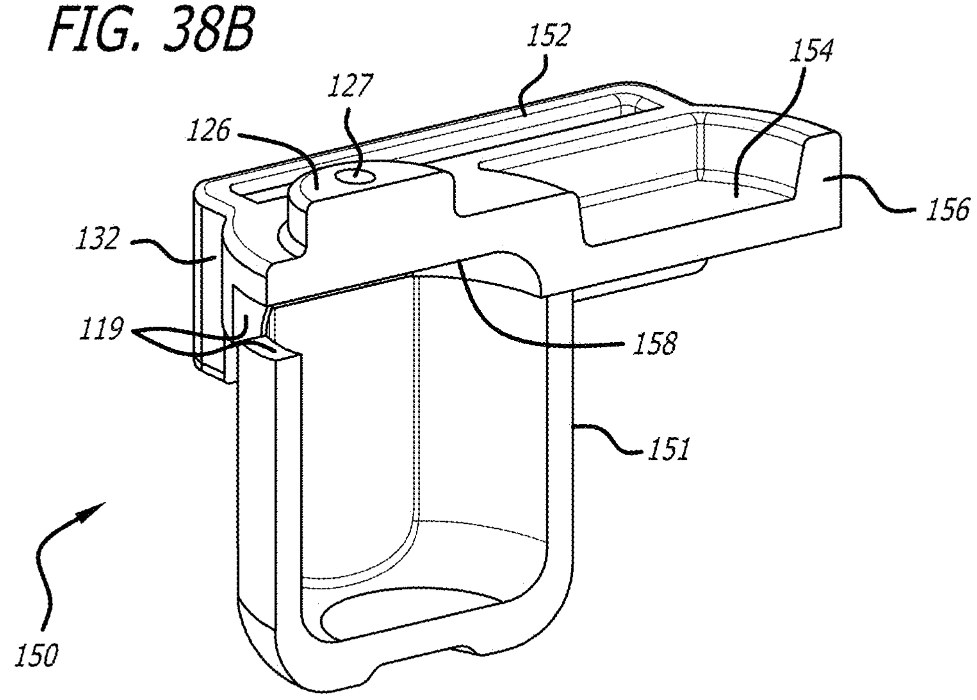
FIG. 38B illustrates a perspective view of a cartridge embodiment of FIG. 35 in a mid-longitudinal cross-section and in a dosing configuration.

FIG. 37 illustrates a bottom view of cartridge 150 showing the relationship of the structures in a containment configuration, such as container 151, dispensing ports 127, panels 152, flanges 153 and area under the boss 126 or undersurface 168 which is relatively hollow or recessed. FIG. 38A illustrates a cross-section through the mid-longitudinal axis X of cartridge 150 in a containment configuration and showing container 151 in tight contact with lid 156 at recess area 154 and supported by flanges 153. The undersurface of the boss 126 is hollow and can be seen relatively at a higher position than the top border of container 151. FIG. 38B illustrates cartridge 150 in a dosing configuration wherein the upper border of container 151 and panel 158 under the area of boss 126 form an inlet port 119 which allows flow entry into the interior of cartridge 151.

In another embodiment, a translational cartridge 170 is illustrated in FIGS. 39A-39I, which is an alternate embodiment of cartridge 150 and can be used with, for example, inhaler 302 depicted in FIGS. 15C-15L. FIG. 39A depicts cartridge 170 comprising an enclosure comprising a top or lid 172 and a container 175 defining an interior space, wherein the cartridge is shown in a containment configuration. In this cartridge configuration, the cartridge top 172 is configured to form a seal with container 175 and container or lid is movable relative to one another. Cartridge 170 can be configured from a containment position (FIGS. 39A and 39H) to a dosing position (FIGS. 39C-39G and 39I) and to a disposable position (not shown), for example, in the middle of the cartridge, to indicate that the cartridge has been used. FIG. 39A also illustrates the various features of cartridge 170, wherein top 172 comprises side panels 171 configured to partially cover the exterior of the container. Each side panel 172 comprises a flange 177 at its lower edge which forms a track to support wing-like structures of container 175, which allows movement of container 175 along the lower border of top 172. The cartridge top 172 further comprises an exterior relatively flat surface at one end, a relatively rectangular boss 174 having an opening or dispensing port 173, and a concave or recess area configured internally to maintain the contents of container 175 in a tight seal. In one embodiment, the dispensing port can be configured to have various sizes, for example, the width and length of the opening can be from about 0.025 cm to about 0.25 cm in width and from about 0.125 cm to about 0.65 cm in length at its entry within the interior of the cartridge. In one embodiment, the dispensing port entry measures approximately 0.06 cm in width to 0.3 cm in length. In certain embodiments, cartridge top 172 can comprise various shapes which can include grasping surfaces, for example, tabs 176, 179 and other configurations to orient the cartridge in the right orientation for proper placement in the holder, and a securing mechanism, for example, a chamfered or beveled edge 180 to adapt securely to a corresponding inhaler. The flanges, external geometry of the boss, tabs, and various other shapes can constitute keying surfaces that can indicate, facilitate, and/or necessitate proper placement of the cartridge in the inhaler. Additionally, these structures can be varied from one inhaler-cartridge pairing system to another in order to correlate a particular medicament or dosage provided by the cartridge with a particular inhaler. In such manner, a cartridge intended for an inhaler associated with a first medicament or dosage can be prevented from being placed into or operated with a similar inhaler associated with a second medicament or dosage.

Figure 39B:
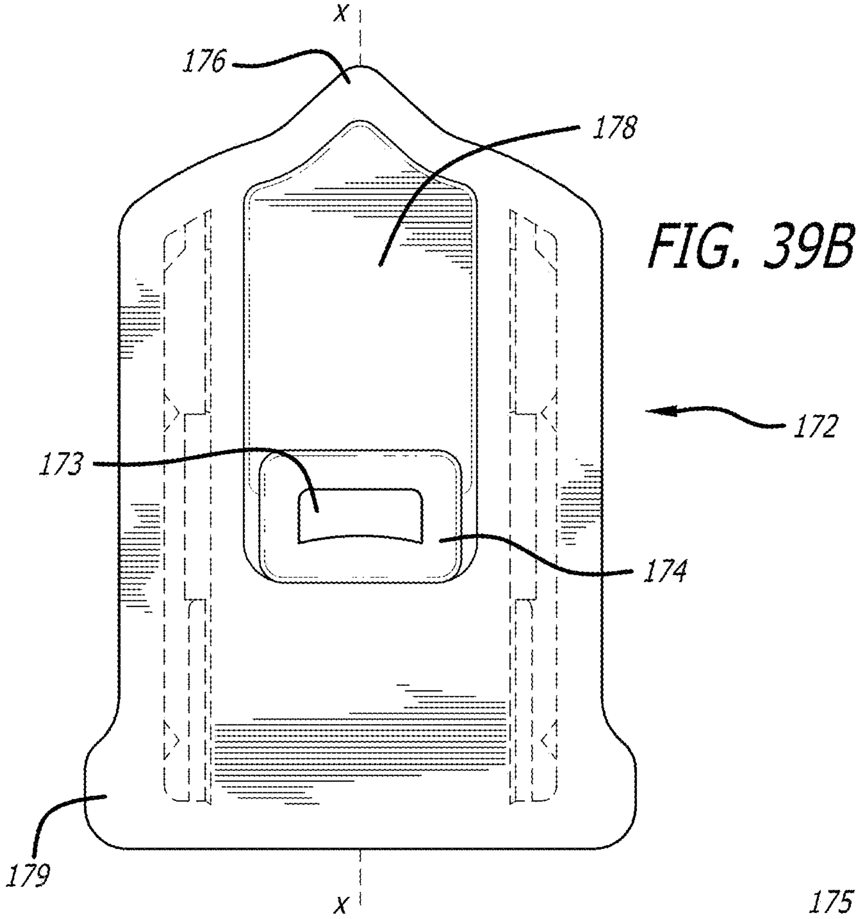
Figure 39C:
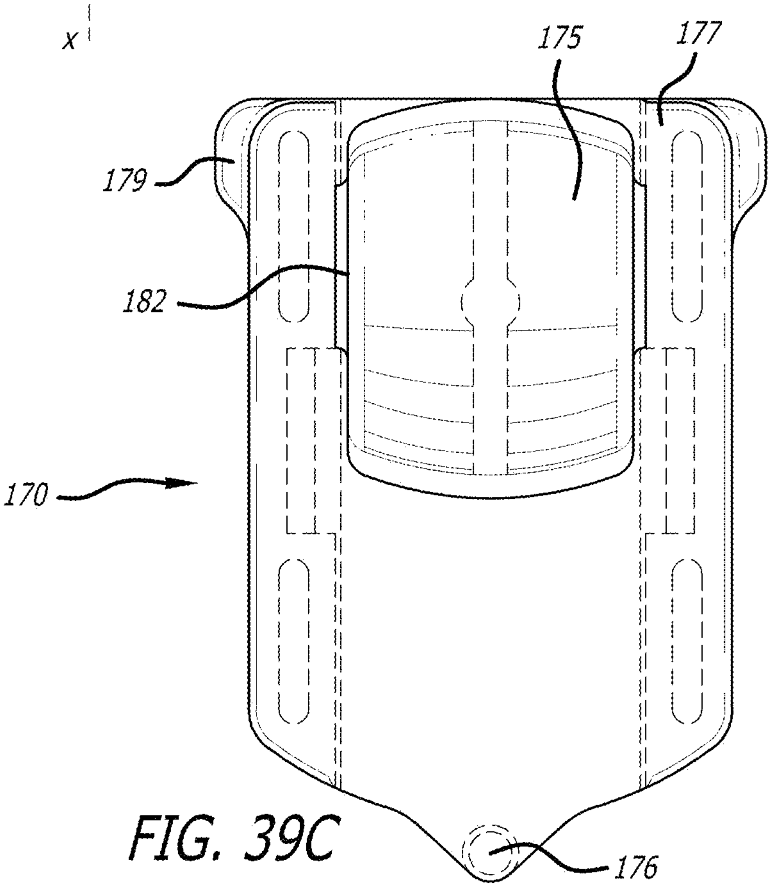

FIG. 39B is a top view of exemplifying the general shape of a cartridge top 172 with boss 174, dispensing port 173, recess area 178 and tabs 176 and 179. FIG. 39C is a bottom view of cartridge 170 showing container 175 in a containment position being supported by its wing-like projections 182 by each flange 177 from top 172. FIG. 39D depicts cartridge 170 in a dosing configuration further comprising an air inlet 181 formed by a notch on the cartridge top 172 and the container 175 upper border. In this configuration, air inlet 181 is in communication with the interior of the cartridge and forms and air conduit with dispensing port

173. In use, the cartridge air inlet 181 is configured to direct airflow entering the cartridge interior at the dispensing port 173.

Figure 39G:
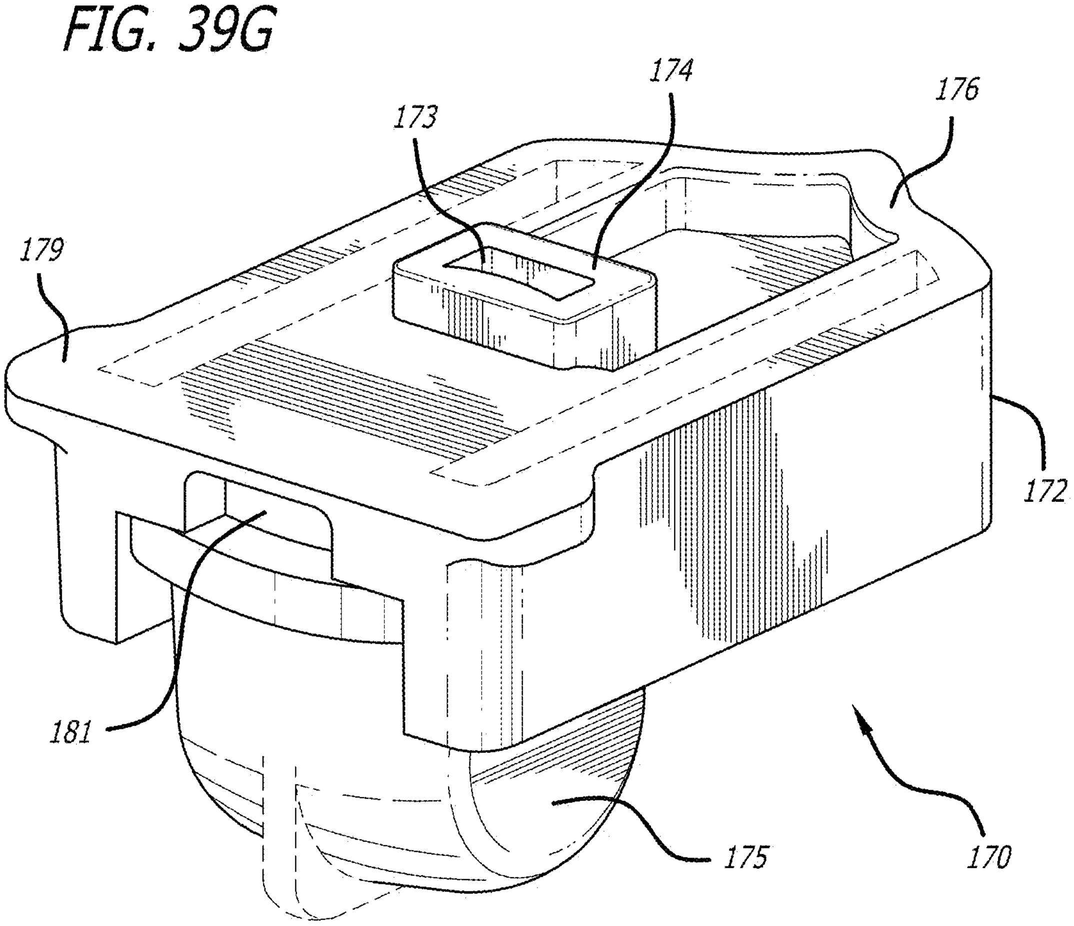
FIG. 39G depicts a perspective view of the cartridge embodiment shown in FIG. 39A in a dosing configuration.
Figure 39H:
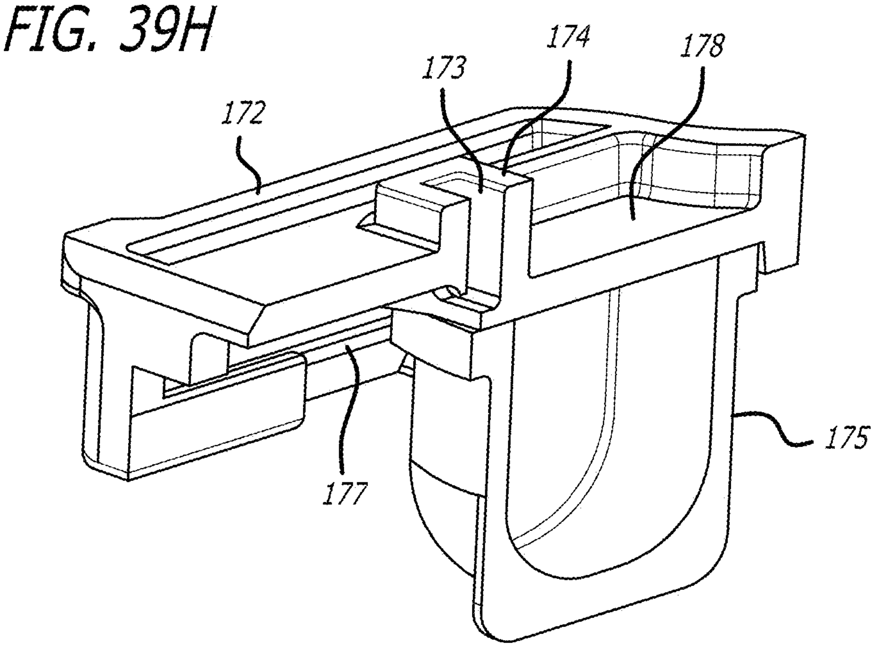
FIGS. 39H and 39I are cross-sections through the longitudinal axis of the cartridge embodiment of FIGS. 39A and 39G, respectively.
Figure 39I:
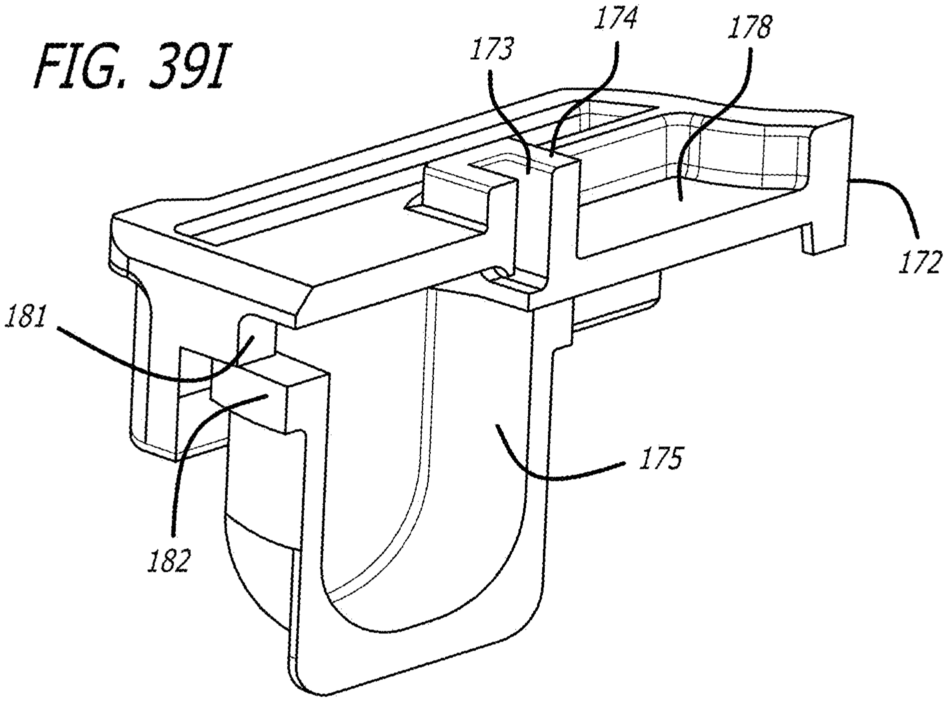

FIG. 39F illustrates a side view of cartridge 150, showing the relationship of the structures in a dosing configuration, such as container 175, boss 174, side panels 172, and tab 176. FIG. 39G illustrates a cartridge 170 in a dosing configuration for use and comprising a container 175 and a top 172 having a relatively rectangular air inlet 181 and a relatively rectangular dispensing port 173 piercing through a boss 174 which is relatively centrally located on the cartridge top 172 upper surface. Boss 174 is configured to fit into an aperture within a wall of a mouthpiece of an inhaler. FIGS. 39H and 39I illustrate cross-sections through the mid-longitudinal axis X of cartridge 170 in a containment configuration and dosing configuration, respectively, showing container 175 in contact with the lid 172 undersurface of the recess area 178 and supported by flanges 177 which form tracks for the container to slide from one position to another. As shown in FIG. 39H, in the containment configuration, container 175 forms a seal with the undersurface of the cartridge top 172 at recess area 178. FIG. 39I depicts the cartridge 170 in the dosing configuration wherein the container is at opposing end of the recess area 181 and the container 175 and cartridge top form an air inlet 181 which allows ambient air to enter cartridge 170 as well as to form an air conduit with dispensing port 173 and the interior of tcontainer 175. In this embodiment, the cartridge top undersurface wherein the dosing position is attained is relatively flat and container 175 interior surface is configured to have somewhat of a U-shape. The boss 174 is configured to slightly protrude above the top surface of cartridge top 172.

In another embodiment of the cartridge, cartridge 780 is described above with reference to FIG. 30A and herewith illustrated in FIGS. 40-44. Cartridge 780 can be adapted to the dry powder inhalers disclosed herewith and is particularly suitable for use with an inhaler with a rotatable mechanism for moving the inhaler from a containment configuration to a dosing position, wherein the cartridge top is movable relative to the container, or for moving the container relative to the top in achieving alignment of the dispensing ports with the container to a dosing position, or moving either the container or the top to the containment configuration.

Figure 29:
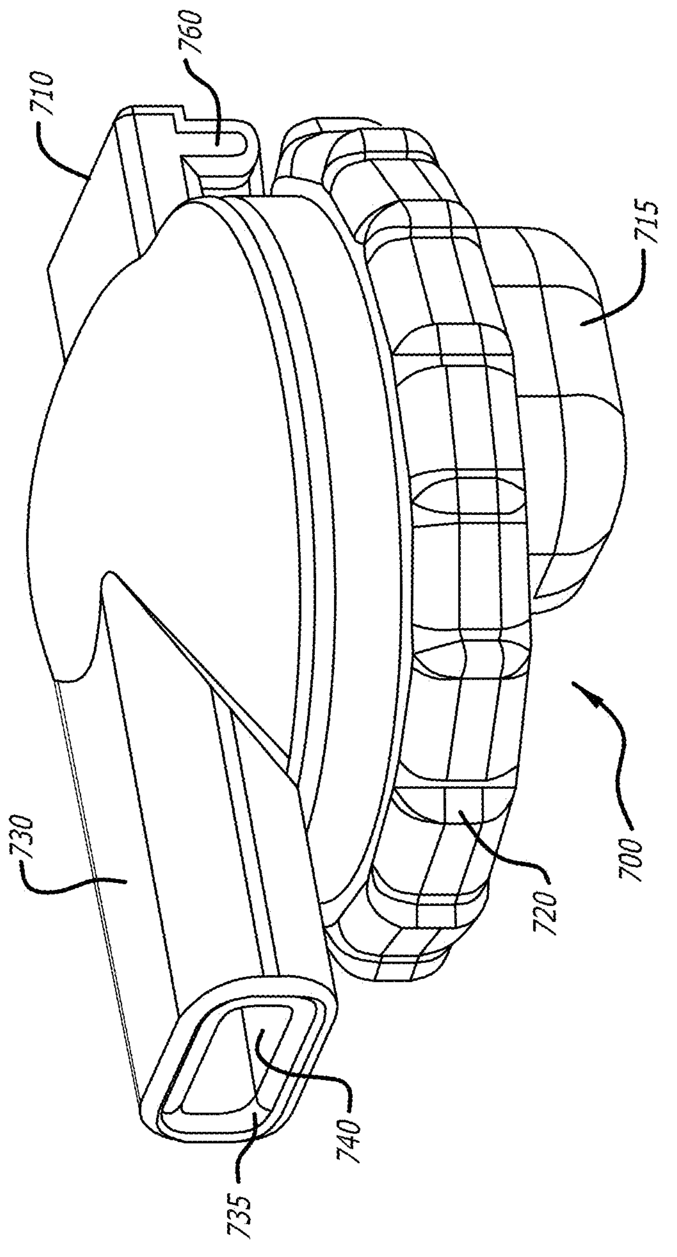
FIG. 29 illustrates a perspective view of yet an alternate embodiment of a dry powder inhaler showing the containment configuration.
Figure 30A:
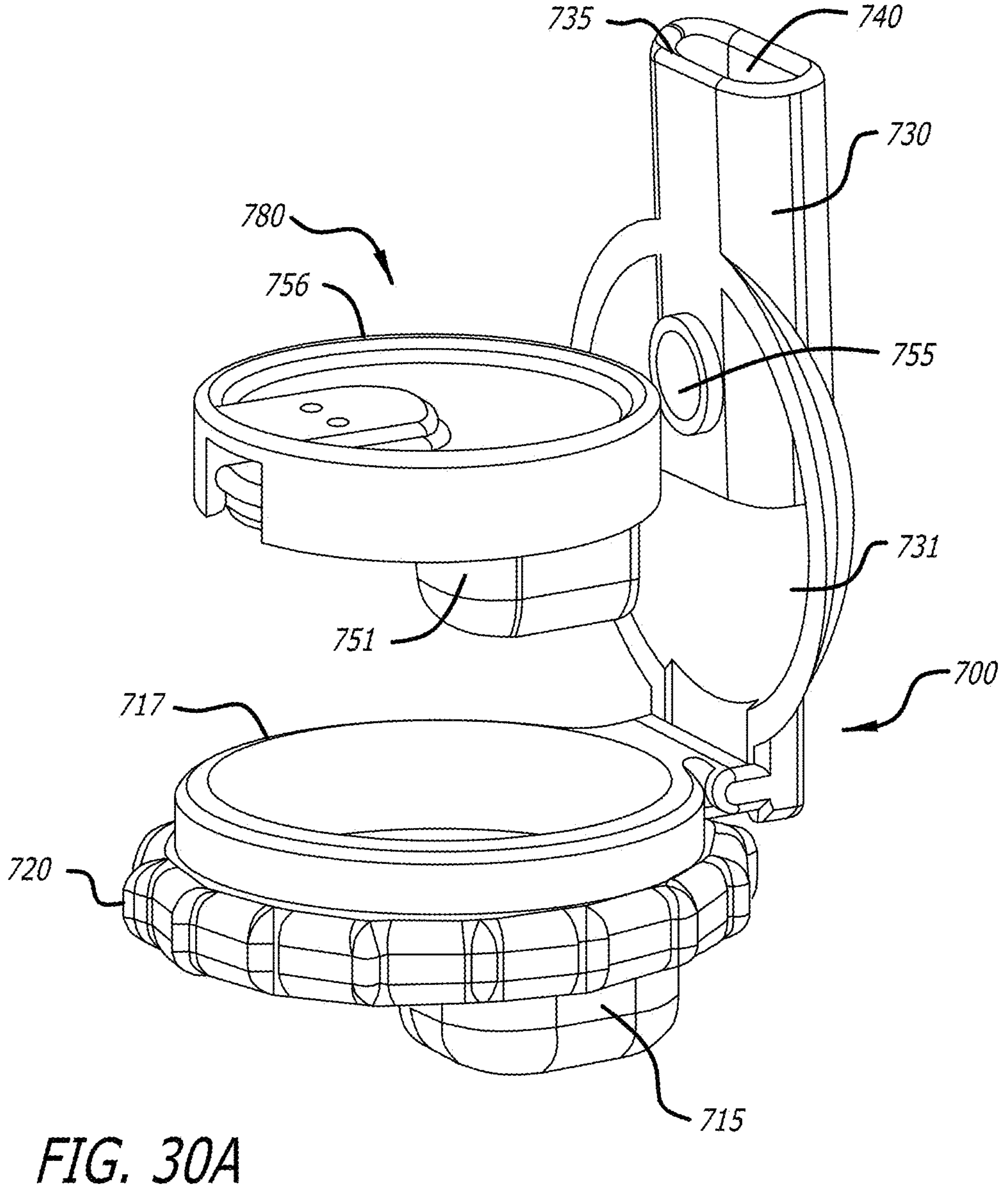
FIG. 30A and FIG. 30B illustrate perspective views of the inhaler of FIG. 29 in an opened position and showing a cartridge installed in a containment or closed position.
Figure 30B:
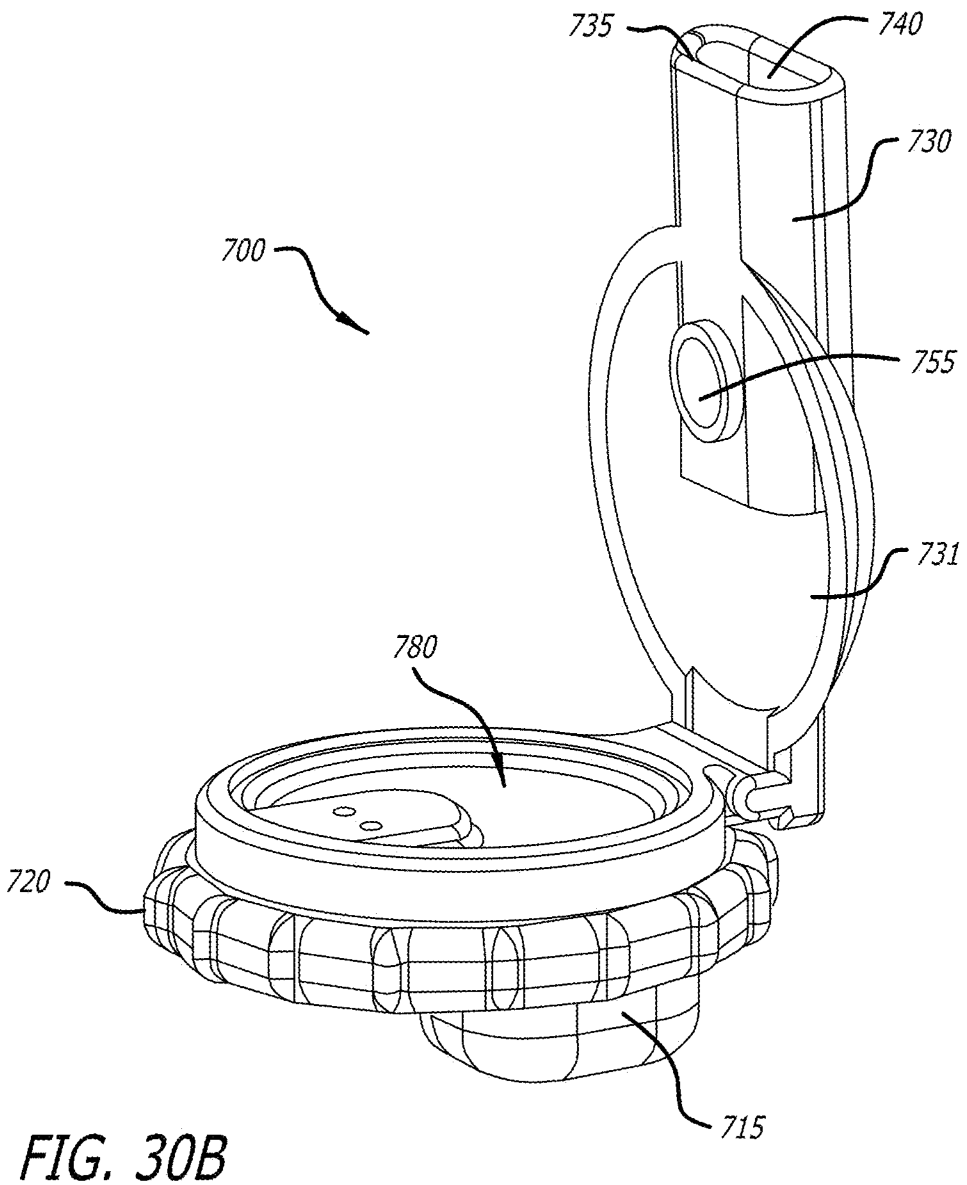

As described above, FIG. 40-44 further illustrate perspective views of cartridge 780 embodiment for use with, for example, the inhaler of FIG. 29, and show a cartridge in a containment configuration comprising a cartridge top or lid 756 and container 751 integrally attached to one another. Container 751 and top 756 are movable relative to one another in a rotating motion from a containment position to a dosing or inhalation position and back. Cartridge top 756 is relatively circular in form and also comprises a recessed area 754 and a raised area or boss 726 having dispensing ports 727 and a circular panel 752 extending downwardly to enclose and attach to container 751 and defining an interior space. Top 756 also has a raised top border or top edge 759 configured to adapt with an inhaler and a groove in the inside surface of panel 752 for engaging with container 751.

Figure 41:
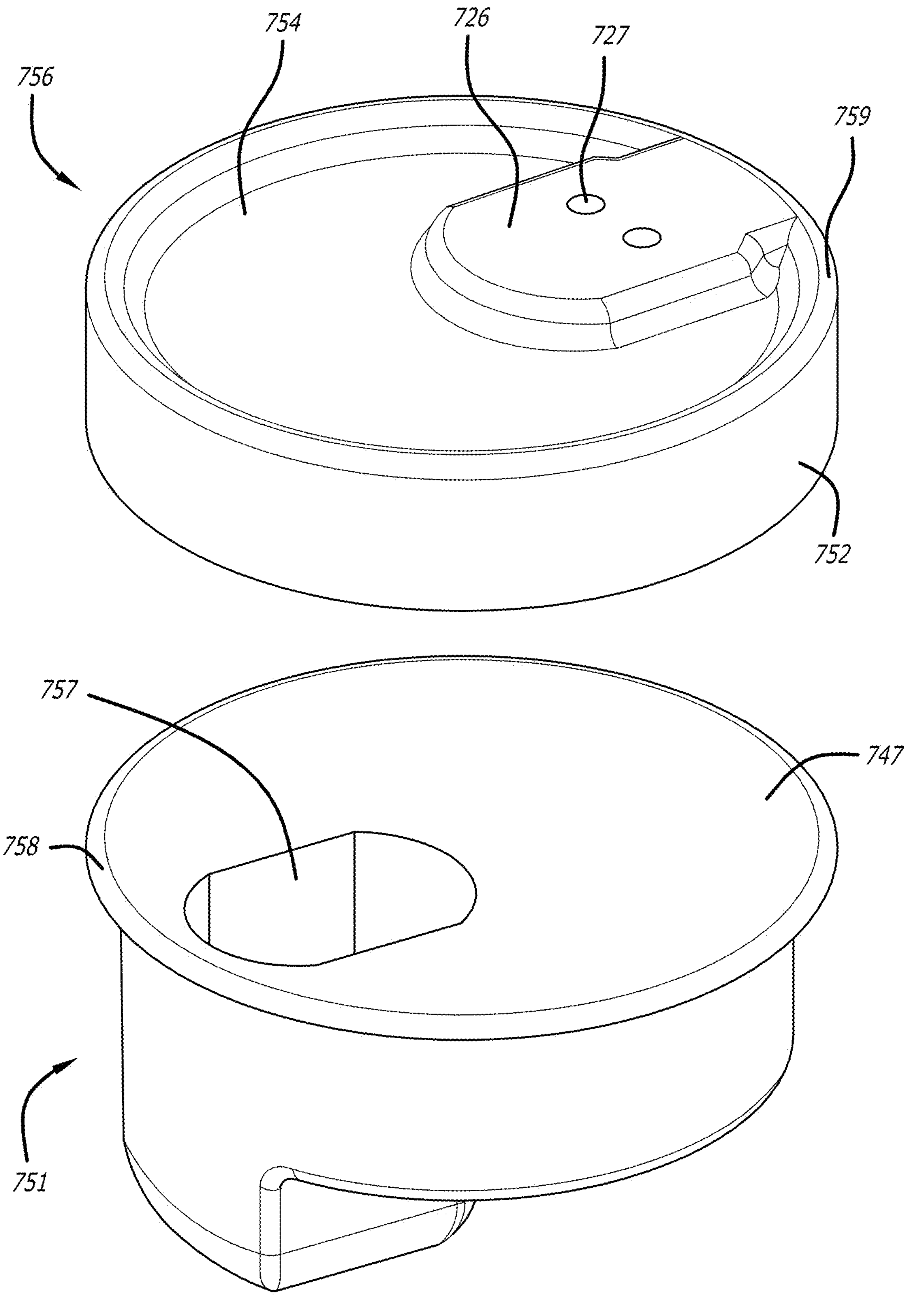
FIG. 41 illustrates an exploded view of the cartridge embodiment of FIG. 40, showing the component parts of the cartridge.
Figure 42:
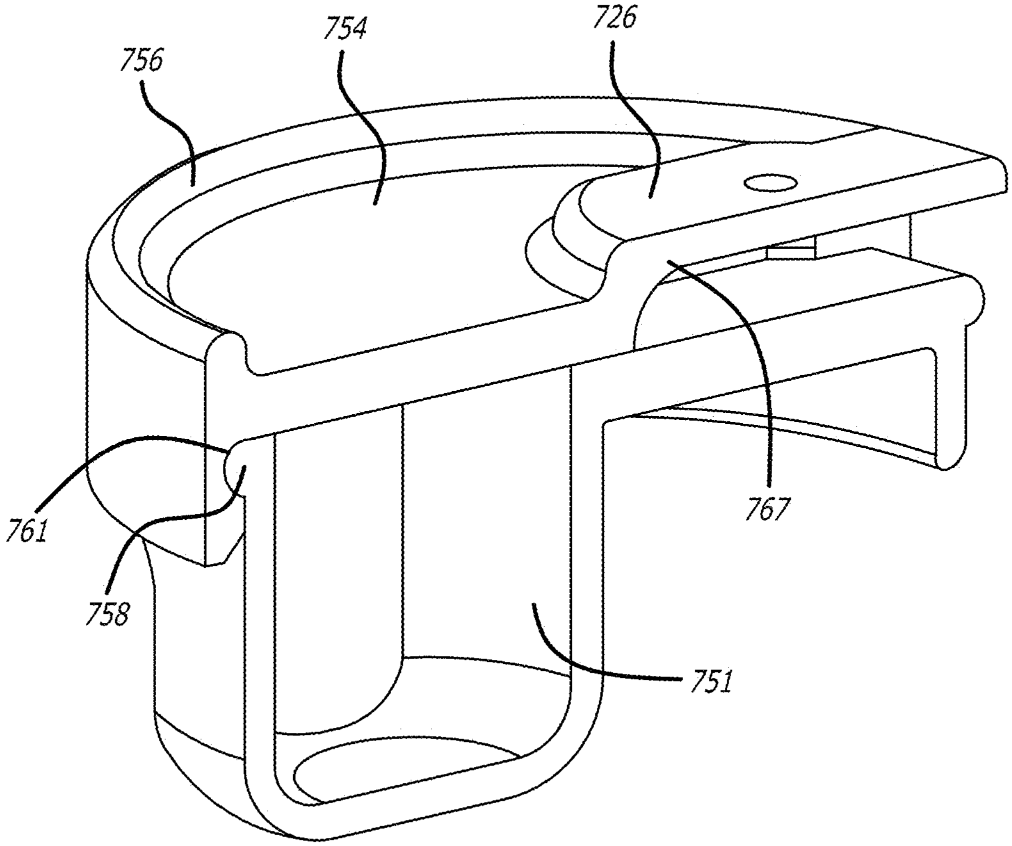
FIG. 42 illustrates a perspective view of a cartridge embodiment of FIG. 40 in mid-longitudinal cross-section in a containment configuration.

FIG. 41 illustrates an exploded view of the cartridge embodiment of FIG. 40, showing container 751 defining a chamber 757 for containing a medicament which is continuous with a relatively circular, top portion 747 of wider diameter to said chamber and configured to have an engaging mechanism to engage and move relative to cartridge top 756. FIG. 42 shows, for example, that upper border 758 of the container can have a circular configuration, for example, a snap ring for engaging with groove 761 of panel 752 to form cartridge 780. FIG. 42 also illustrates a perspective view of the cartridge embodiment of FIG. 40 in cross-section through the perpendicular axis and in the containment configuration, showing recess area 754 sealing container 751 and undersurface 767 of boss 726 being hollow. When recessed area 754 is over container chamber or internal volume 757, the cartridge is in a containment configuration as illustrated in FIG. 42.

Figure 43:
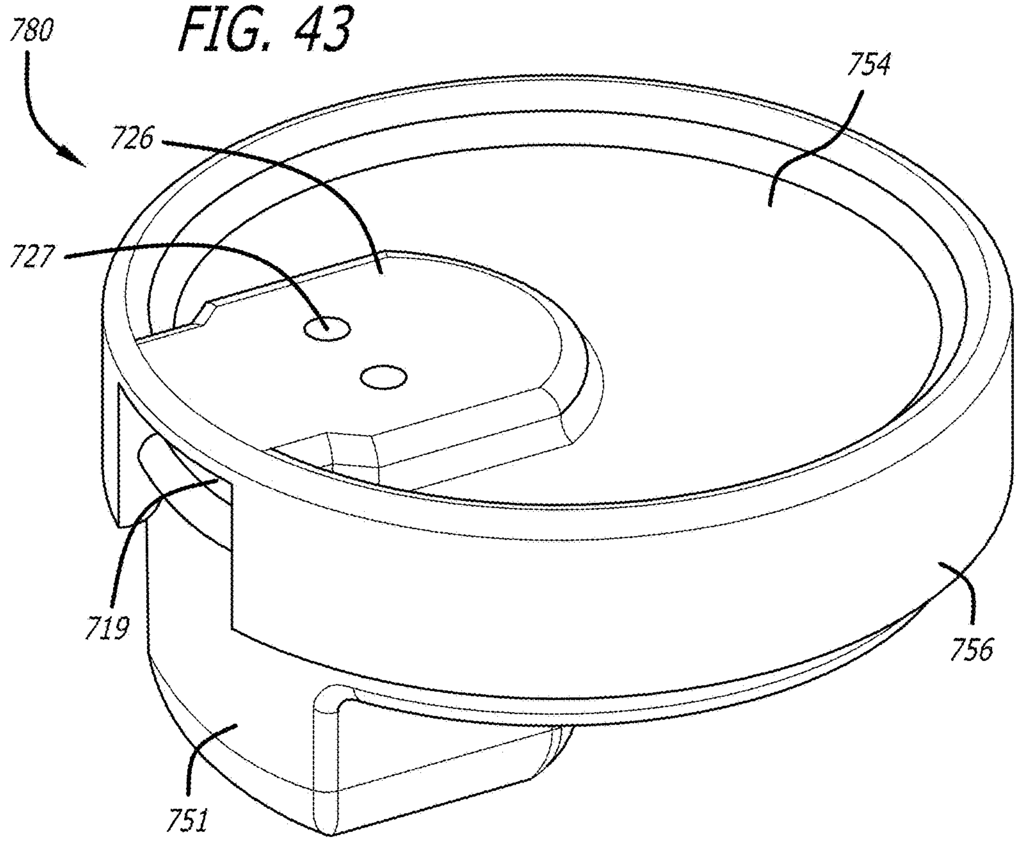
FIG. 43 illustrates a perspective view of a cartridge embodiment of FIG. 40 in a dosing configuration.
Figure 44:
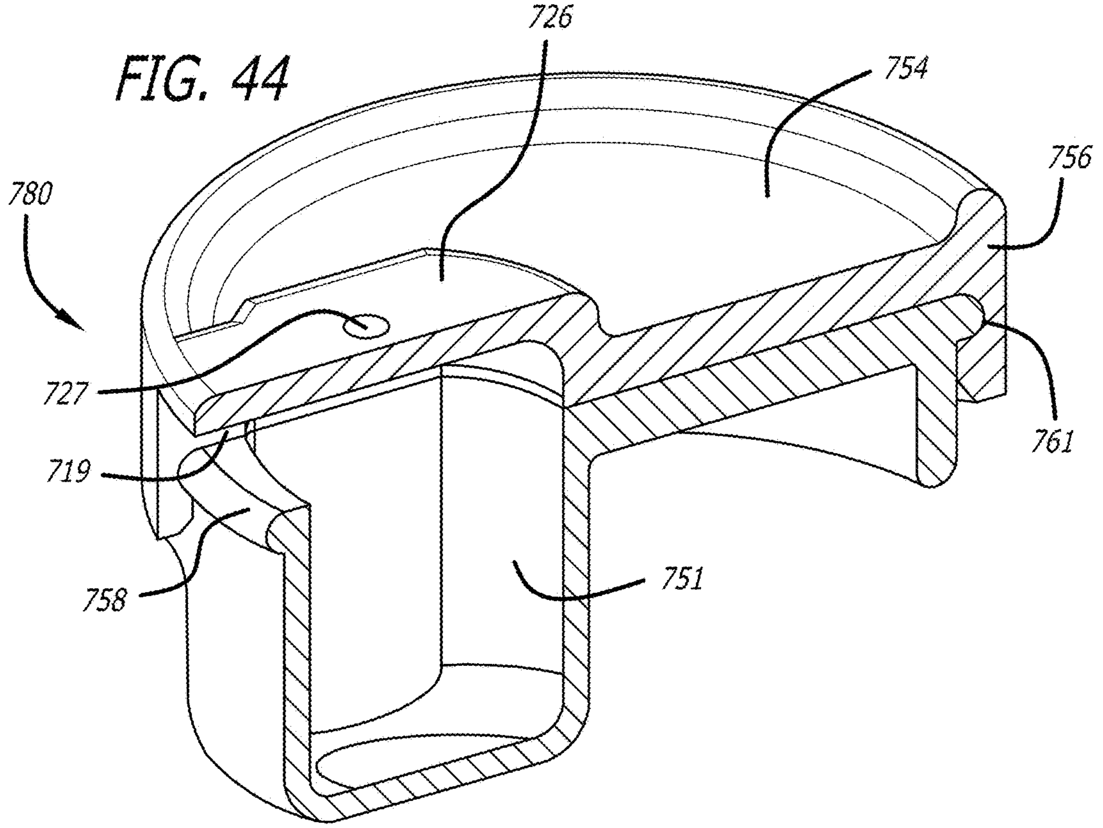
FIG. 44 illustrates a perspective view of a cartridge embodiment of FIG. 38 in a mid-longitudinal cross-section and in a dosing configuration.

FIG. 43 illustrates a perspective view of a cartridge embodiment of FIG. 40 in a dosing configuration, wherein the chamber 757 of container 751 is directly under the boss 726 and the cartridge is configured to have an inlet port 719 in communication with dispensing ports 727. FIG. 44 illustrates a perspective view of this embodiment in cross-section and in a dosing configuration to show the air inlet 719 and the position of the container and boss 726 with dispensing ports 727. In this embodiment, recess area 754 of lid 756 and area 747 of container form a tight abutment or seal on each other.

Figure 47A:
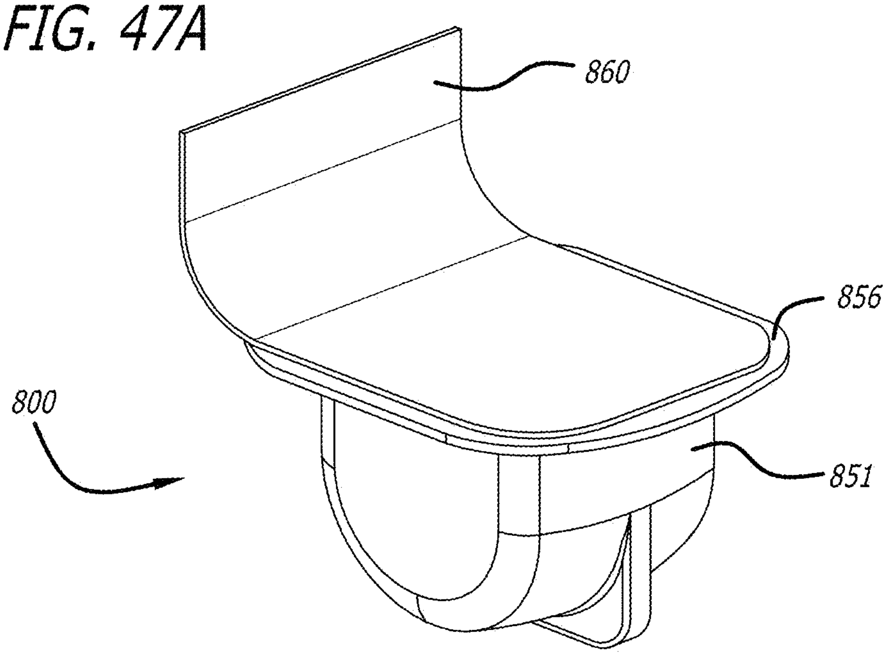
FIG. 47A illustrates a perspective view of an alternate cartridge embodiment for use with a dry powder inhaler showing the cartridge in a containment configuration.
Figure 47B:
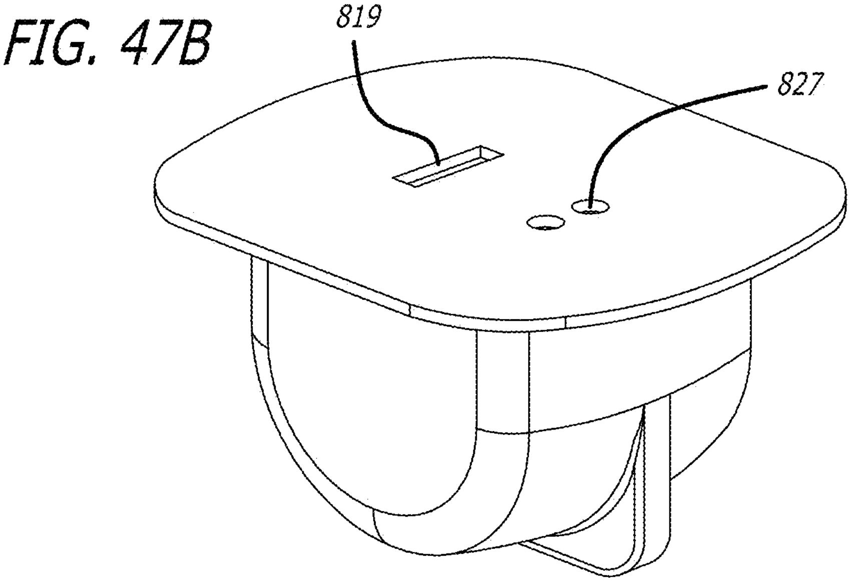
FIG. 47B illustrates a perspective view of the cartridge embodiment of FIG. 47A for use with a dry powder inhaler showing the cartridge in a dosing configuration.

The air inlet port of a cartridge for use with the present inhalers can be configured at any point on the cartridge so that a powder medicament within the container can remain in a containment position prior to inhalation. For example, FIGS. 45, 46A, 46B, 47A and 47B illustrate two alternate embodiments of a cartridge for use with the dry powders inhaler, comprising a lid or top 856, a container 851 structurally configured as in FIG. 35-39 above. In this embodiment, however, air inlet 819 into the cartridge interior can be incorporated within the cartridge top or lid 851 along with one or more dispensing ports 827. In this embodiment, the cartridge comprises a container 851 and a lid or top 856. Lid or top 856 can be provided with a groove in its interior surface to engage with the upper border of the container 851 as locking mechanism. The cartridge can also be provided with a seal 860 to contain a powder medicament within the cartridge and can be made from, for example, plastic film or laminated foil. Seal 860 can be made to contain a single cartridge for single dose use or multiple, single dose cartridges on a strip. Lid 856 contains at least two ports which at least one works as an air inlet and another as a dispensing port. FIGS. 46A and 46B illustrate the embodiment of the cartridge in FIG. 45 comprising a container 851 which can be adapted to a lid 856 wherein the relatively square lid has an inlet port 819 relative round and two outlet ports 827 and a side panel 852 configured to have a groove to adapt to container 851, wherein container 851 is relatively shaped as a cup and has a protrusion on his upper border for engaging lid 856. FIG. 46B illustrates a perspective view of a cartridge embodiment of FIG. 45 in a cross-section and dosing configuration. In this embodiment, the cartridge top air inlet can have various configurations. For example, FIGS. 47A and 47B illustrate and alternate embodiment of cartridge 800, in which the cartridge top 856 is relatively semicircular and flat in shape having an air inlet port rectangular in shape. In this embodiment, the container and cartridge top can be manufactured from a thermoform material, for example, polyethylene pterephthalate, stock to facilitate production.

In embodiments described herein, cartridges can be configured to deliver a single unit, pre-metered dose of a dry powder medicament. Cartridges such as cartridge 150, 170, 780 and 800 can be structurally configured to contain a dose of, for example, from 0.1 mg to about 50 mg of a dry powder formulation. Thus the size and shape of the container can vary depending on the size of the inhaler and the amount or mass of powder medicament to be delivered. For example, the container can have a relatively cylindrical shape with two opposing sides relatively flat and having an approximate distance between of from about 0.4 cm to about 2.0 cm. To optimize the inhaler performance, the height of the inside of the cartridge along the Y axis may vary depending on the amount of powder that is intended to be contained within the chamber. For example, a fill of 5 mg to 15 mg of powder may optimally require a height of from about 0.6 cm to about 1.2 cm.

In an embodiment, a medicament cartridge for a dry powder inhaler is inhaler is provided, comprising: an enclosure configured to hold a medicament; at least one inlet port to allow flow into the enclosure, and at least one dispensing port to allow flow out of the enclosure; the at least one inlet port is configured to direct at least a portion of the flow entering the at least one inlet port at the at least one dispensing port within the enclosure in response to a pressure differential. In one embodiment, the inhaler cartridge is formed from a high density polyethylene plastic. The cartridge has a container which has an internal surface defining an internal volume and comprising a bottom and side walls contiguous with one another, and having one or more openings. The can have a cup-like structure and has one opening with a rim and it is formed by a cartridge top and a container bottom which are configurable to define one or more inlet ports and one or more dispensing ports. The cartridge top and container bottom are configurable to a containment position, and a dispensing or dosing position.

In embodiments described herein, the dry powder inhaler and cartridge form an inhalation system which can be structurally configured to effectuate a tunable or modular airflow resistance, as it can be effectuated by varying the cross-sectional area at any section of the airflow conduits of the system. In one embodiment, the dry powder inhaler system can have an airflow resistance value of from about 0.065 to about 0.200 (√kPa)/liter per minute. In other embodiments, a check valve may be employed to prevent air flow through the inhaler until a desired pressure drop, such as 4 kPa has been achieved, at which point the desired resistance reaches a value within the range given herewith.

Figure 48:
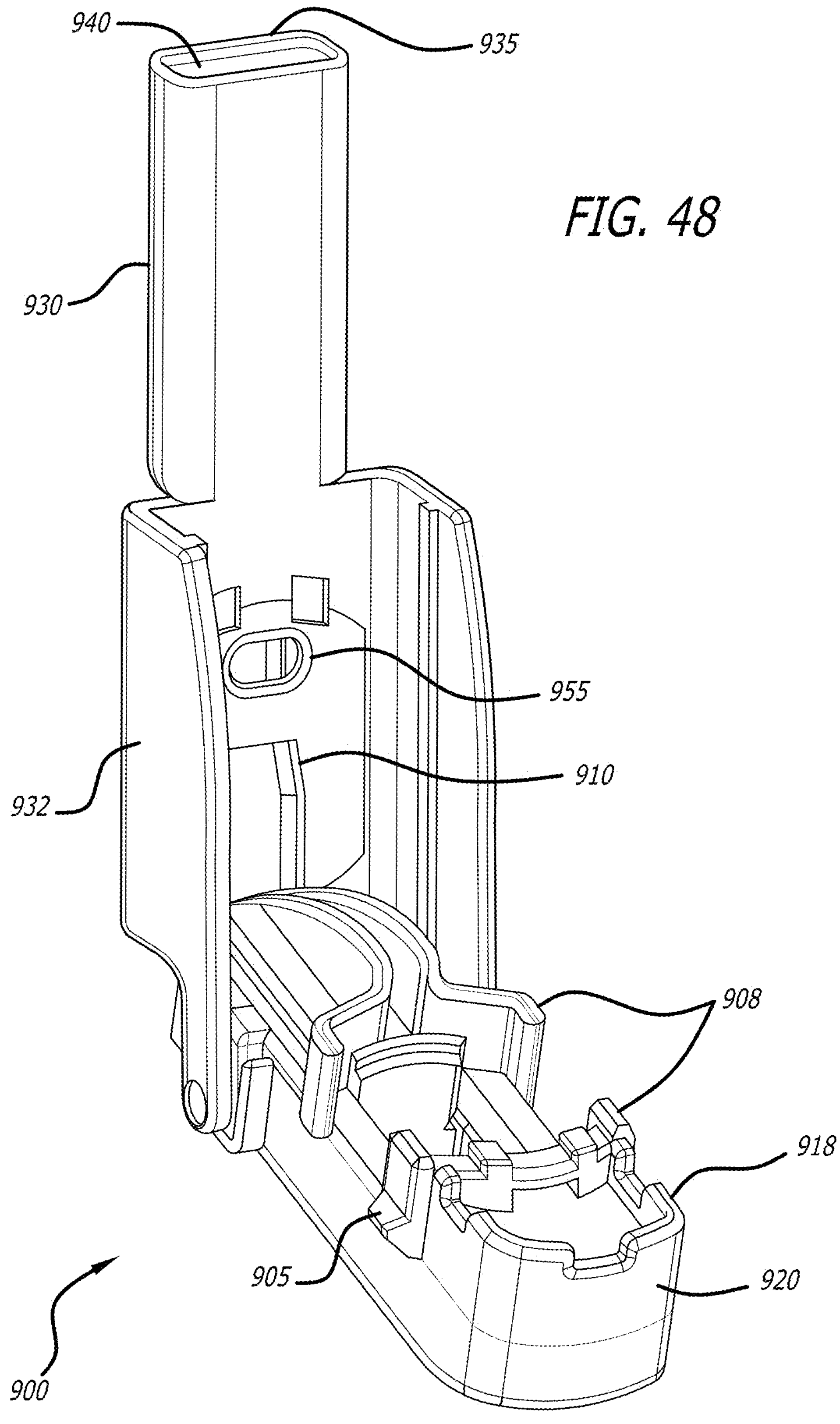
FIG. 48 illustrates a perspective view of an alternate embodiment of a dry powder inhaler shown in an opened configuration.
Figure 49:
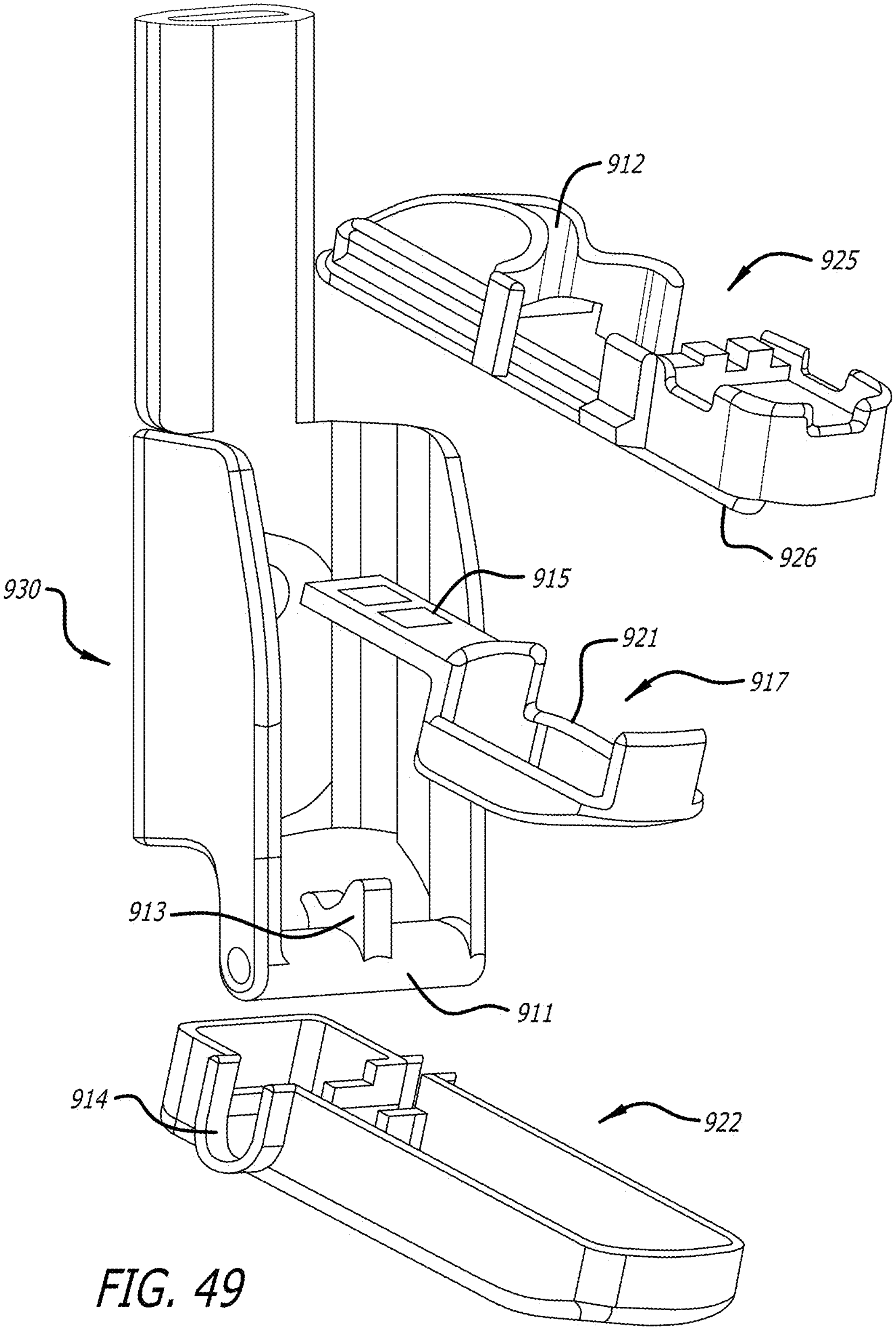
FIG. 49 illustrates an exploded view of the inhaler embodiment of FIG. 48 showing the inhaler component parts.

FIGS. 48-54 illustrate yet another embodiment of the dry powder inhaler. FIG. 48 depicts an inhaler 900 in an open configuration which is structurally configured similarly as inhaler 300 shown in FIGS. 12-15B. Inhaler 900 comprises mouthpiece 930 and housing subassembly 920 which are attached to one another by a hinge so that mouthpiece 930 pivots relative to the housing subassembly 920. Mouthpiece 930 further comprises integrally formed side panels 932 wider than housing 920, which engage with housing protrusions 905 to attain the closed configuration of inhaler 900. Mouthpiece 930 further comprises air inlet 910, air outlet 935; air flow conduit 940 extending from air inlet 910 to air outlet 935 for contacting a users lips or mouth, and aperture 955 on the floor or bottom surface which communicates with airflow conduit 940 of the inhaler. FIG. 49 illustrates inhaler 900 in an exploded view, showing the component parts of the inhaler, including the mouthpiece 930 and housing subassembly 920. As depicted in FIG. 49, the mouthpiece is configured as a single component and further comprises a bar, cylinder or tube 911 configured with teeth or gear 913 for articulating with housing 920 so that movement of mouthpiece 930 relative to housing 920 in an angular direction attains closure of the device. An air channel 912 can be provided to the housing which can direct an air flow towards mouthpiece air inlet 910. Air channel 912 is configured so that in use, a users finger placed over the channel cannot limit or obstruct airflow into air conduit 940.

Figure 50:
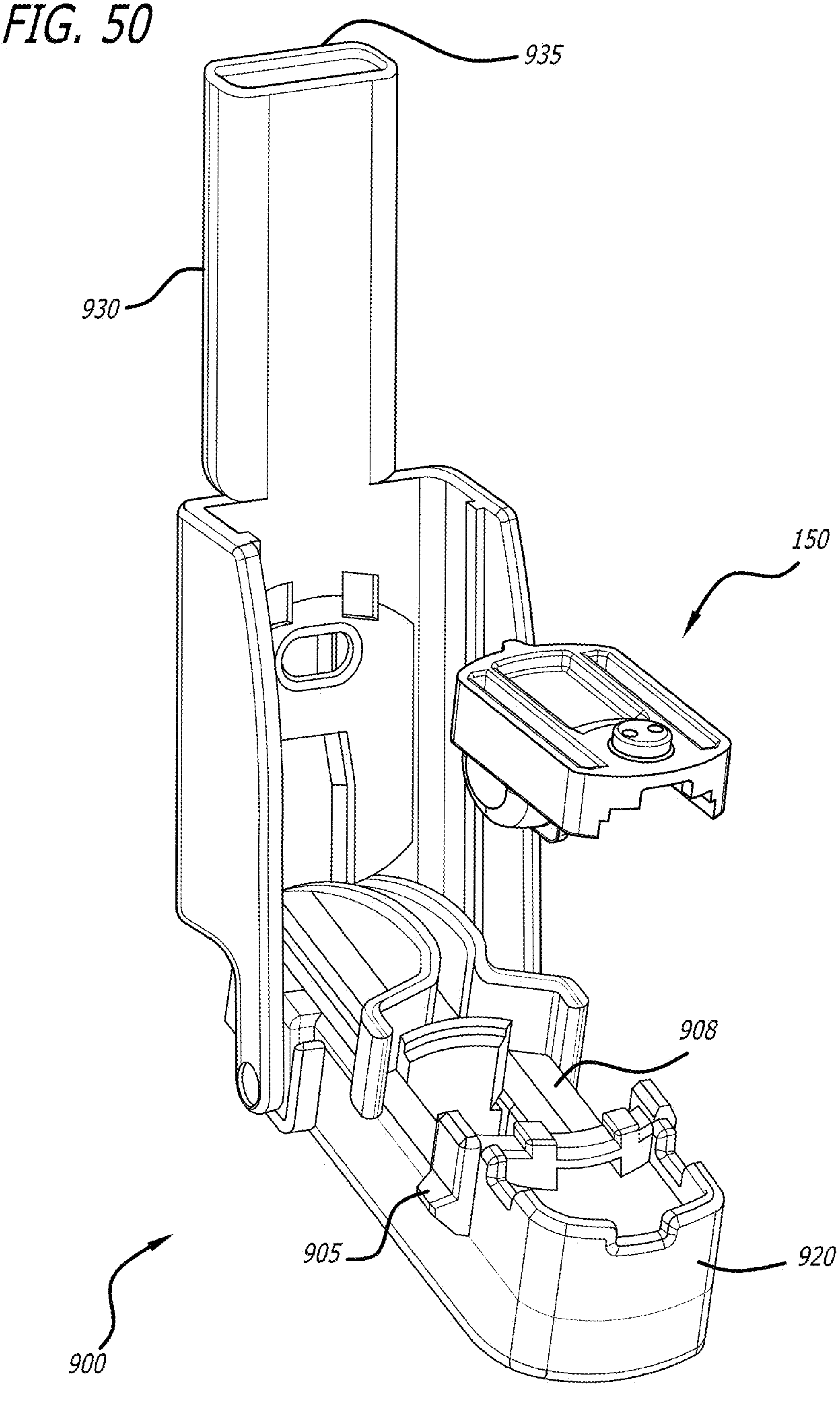
FIG. 50 illustrates a perspective view of the inhaler in FIG. 48 in the open configuration and showing the type and orientation of a cartridge to be installed in the inhaler holder.
Figure 51:
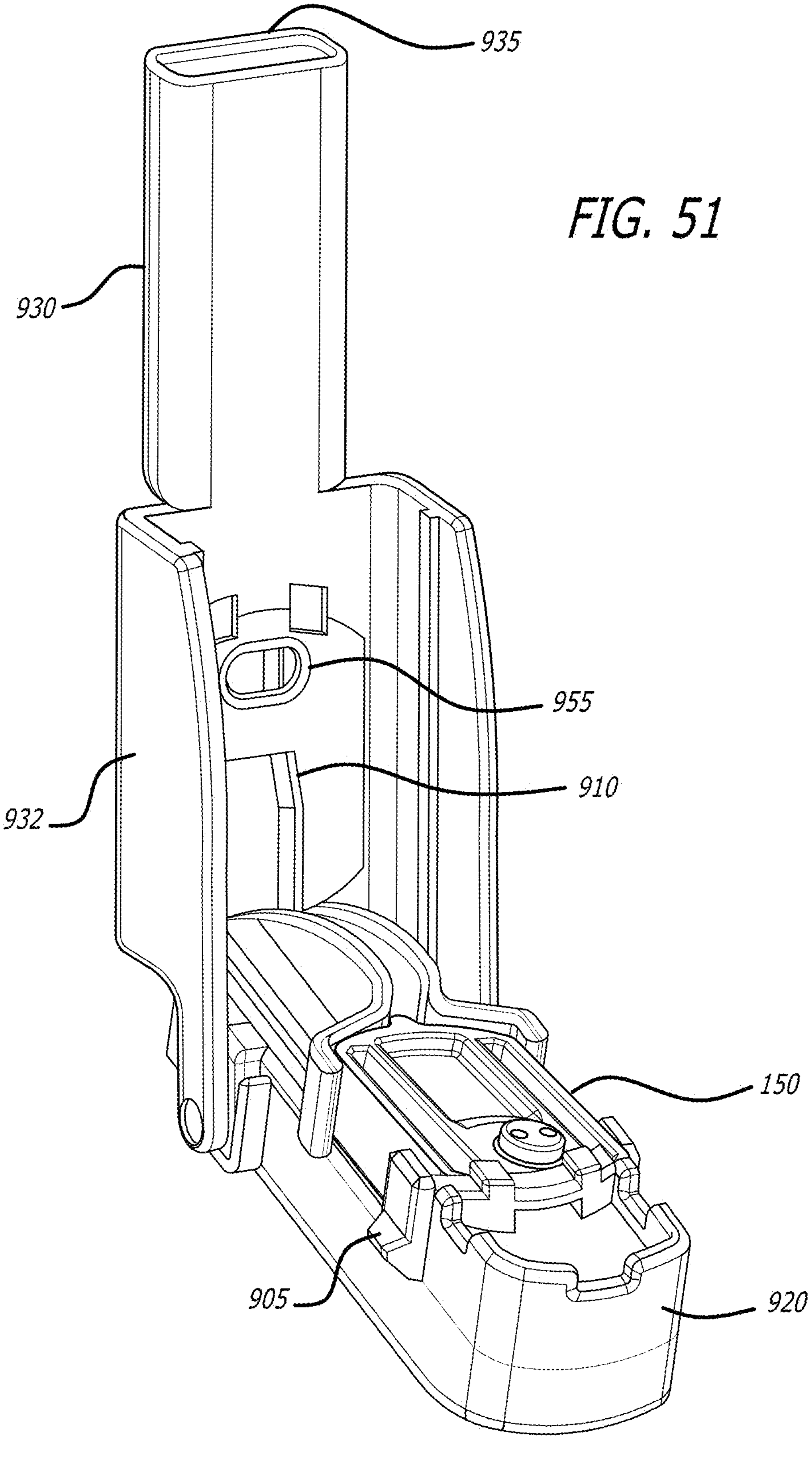
FIG. 51 illustrates a perspective view of the inhaler in FIG. 50 in the open configuration and showing a cartridge installed in the inhaler.
Figure 52:
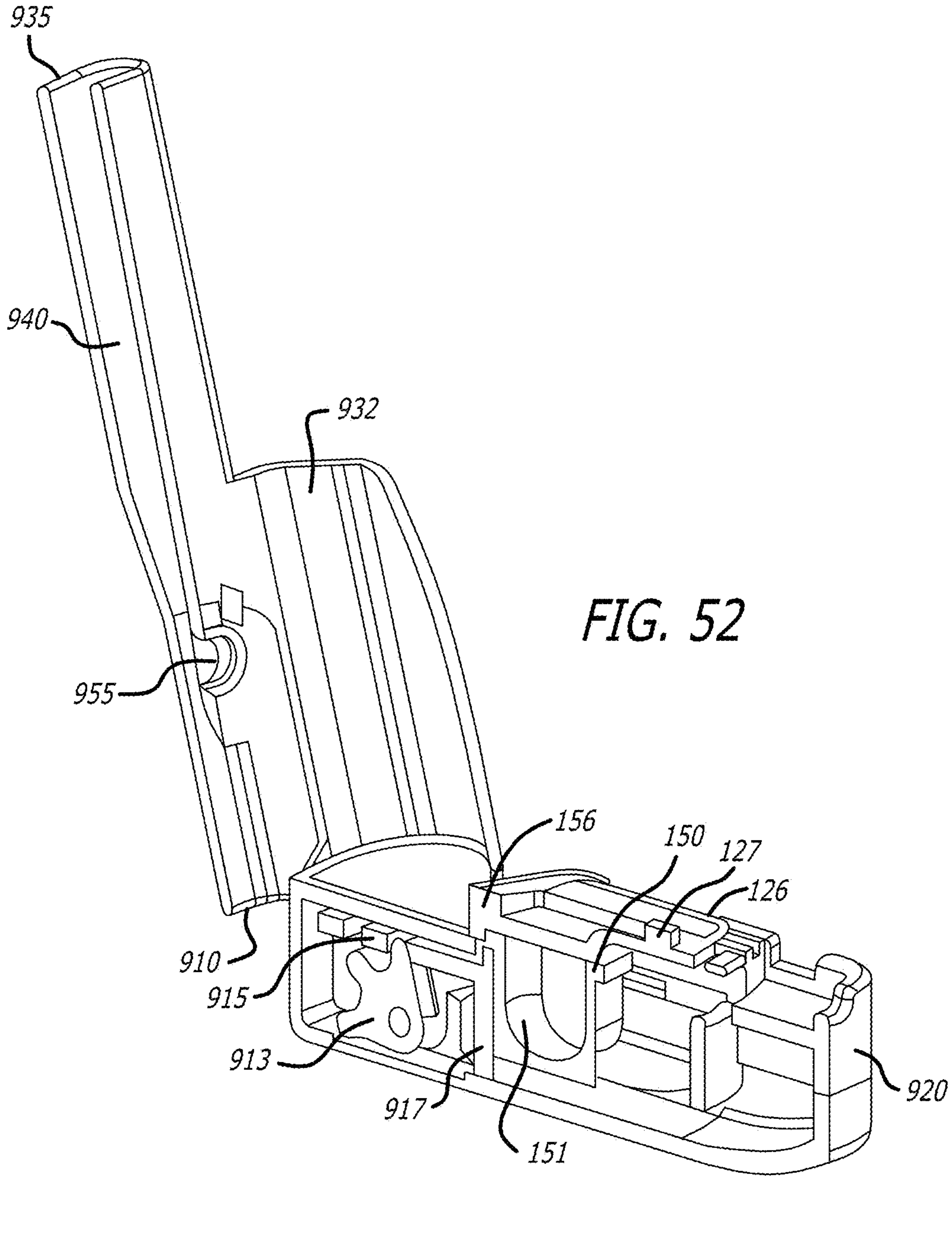
FIG. 52 illustrates a mid-longitudinal section of the inhaler depicted in FIG. 51 showing the cartridge container in the containment configuration and in contact with the sled and the gear mechanism in contact with the sled.
Figure 53:
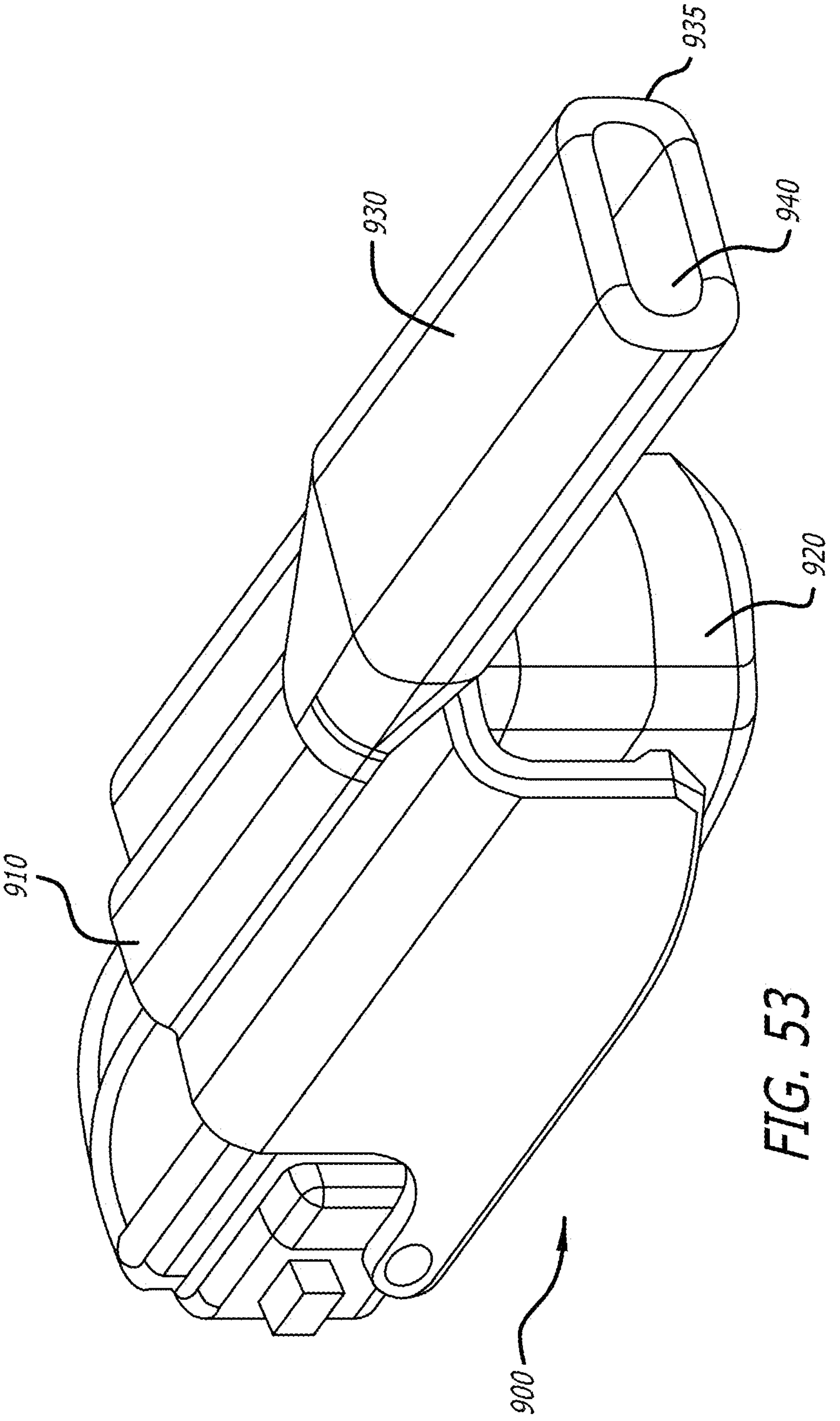
FIG. 53 illustrates a perspective view of the inhaler in FIG. 50 in the closed configuration and with a cartridge in the holder.
Figure 54:
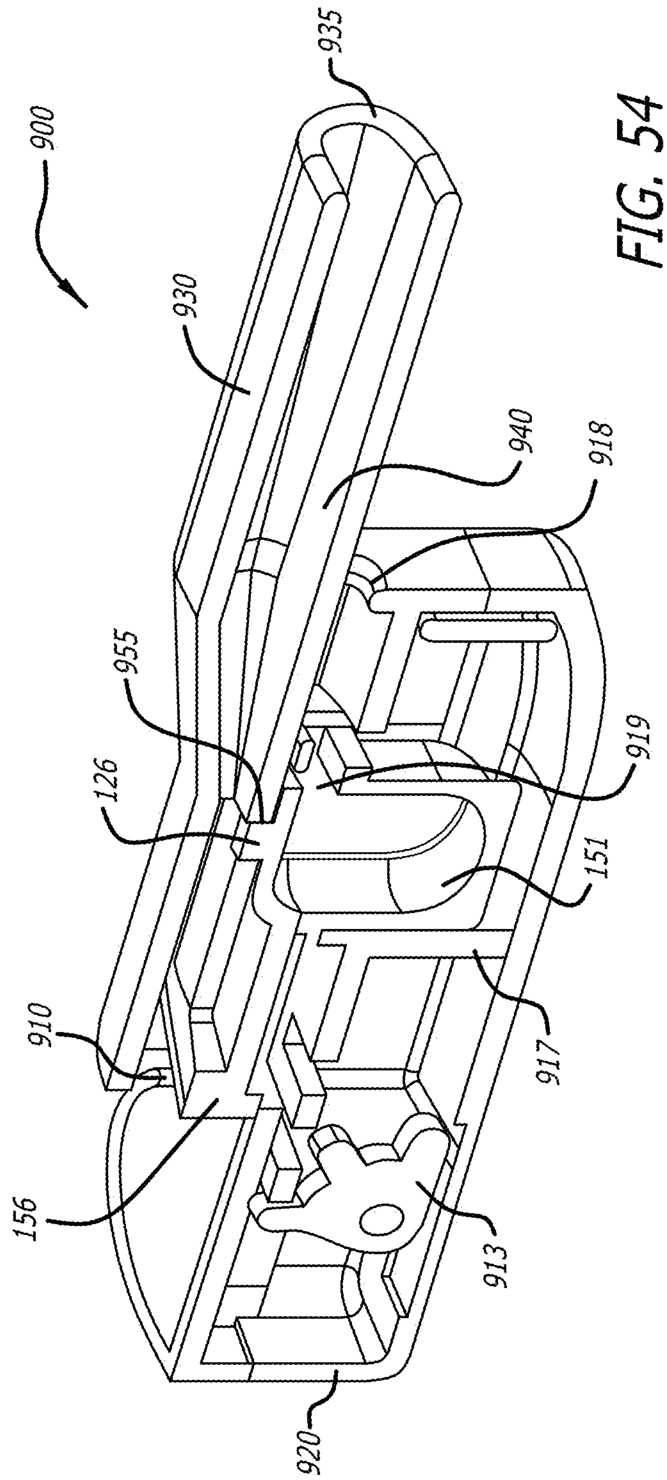
FIG. 54 illustrates a mid-longitudinal section of the inhaler depicted in FIG. 53 showing the cartridge container in the dosing configuration and the air flow pathway established through the container.

FIG. 48 illustrates the housing subassembly 920 comprising a cartridge placement or mounting area 908 and a notch 918 which is configured to define an air inlet when the inhaler is in a closed configuration. FIG. 49 illustrates housing 920 as an enclosure, further comprising two component parts for ease of manufacturing, although less or more parts can be used, including a tray 922, and a cover 925. Tray 922 is configured with notches 914 configured near its distal end which houses bar, cylinder or tube 911 in forming a hinge with mouthpiece 930. Tray 922 also houses sled 917. Sled 917 is configured to be movable within tray 922 and has a cartridge receiving area 921 and an arm-like structure having openings 915 for engaging the teeth or gear 913 of mouthpiece 930 so that in closing the device for use, movement of mouthpiece 930 relative to housing 920 moves the sled in a proximal direction, which results in the sled abutting a cartridge container seated on inhaler holder or mounting area 908 and translocates the container from a containment position to a dosing position. In this embodiment, a cartridge seated in the cartridge holder 908 has the air inlet opening in a dosing configuration facing towards the proximal end of the inhaler or the user. Housing cover 925 is configured so that it can securely attach to tray 922 by having, for example, protrusions 926 extending from the bottom border as a securing mechanism. FIG. 50 illustrates inhaler 900 in the open configuration depicting the position and orientation of a cartridge 150 in a containment configuration for mounting on the inhaler. FIG. 51 further illustrates inhaler 900 in the open configuration with cartridge 150 seated in the cartridge holder in the containment configuration. FIG. 52 illustrates a mid-longitudinal section of the inhaler in FIG. 51 showing the position of the gear 913 relative to sled 917 in the containment configuration of the cartridge container 151, which abuts sled 917. In this embodiment, container 151 moves relative to cartridge top 156. Upon closing inhaler 900 (FIG. 53) and as mouthpiece 930 moves to attain a closed configuration, sled 917 pushes container 151 until the dosing configuration is attained and mouthpiece aperture 955 slides over cartridge boss 126 so that dispensing ports 127 are in communication with the mouthpiece conduit 940 and an air flow pathway is established for dosing through air inlet aperture 918, cartridge air inlet 919 and dispensing ports 127 in air conduit 940. As seen in FIG. 54, mouthpiece 930 and therefore, air conduit 940 have a relatively tapered, hour-glass shape configuration at approximately mid to distal end. In this embodiment, sled 917 is configured so that when the inhaler is open after use, the sled cannot reconfigure a cartridge to the containment configuration. In some variations of this embodiment, it may be possible or desirable to reconfigure the cartridge.

In embodiments disclosed herein, inhaler apertures, for example, 155, 255, 355, 955 can be provided with a seal, for example, crushed ribs, conformable surfaces, gaskets, and o-rings to prevent air flow leakage into the system so that the airflow only travels through the cartridge. In other embodiment, to effectuate the seal, the seal can be provided to the cartridge. The inhalers are also provided with one or more zones of deagglomeration, which are configured to minimize build-up of powder or deposition. Deagglomeration zones are provided, for example, in the cartridge, including, in the container and the dispensing ports, and at one or more locations in the air conduit of the mouthpiece.

Figure 55:
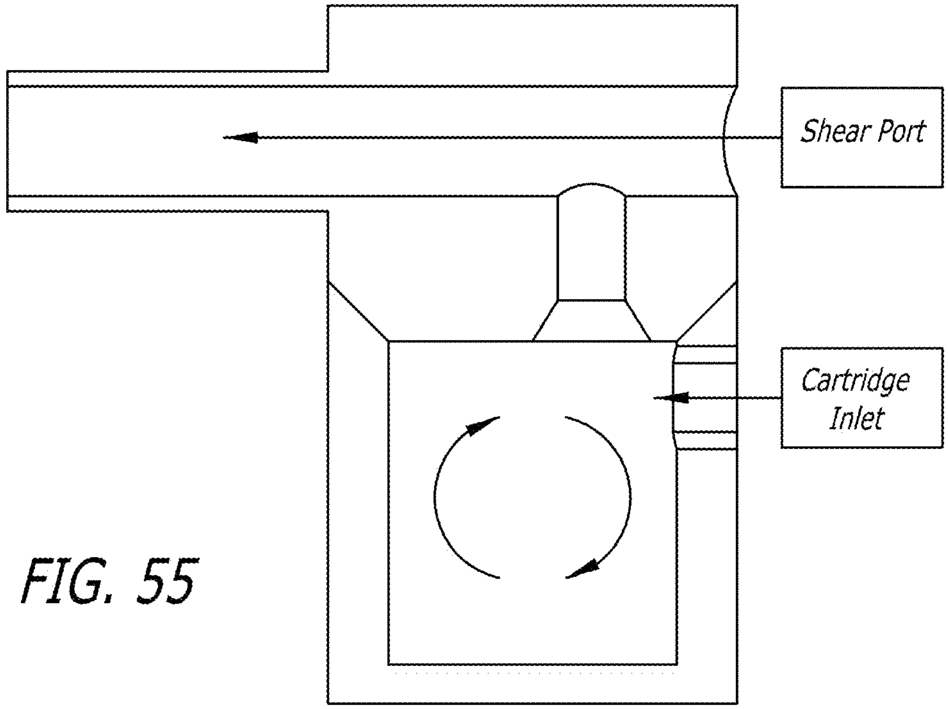
FIG. 55 is a schematic representation of the movement of flow within the powder containment area of a dry powder inhaler as indicated by the arrows.
Figure 56:
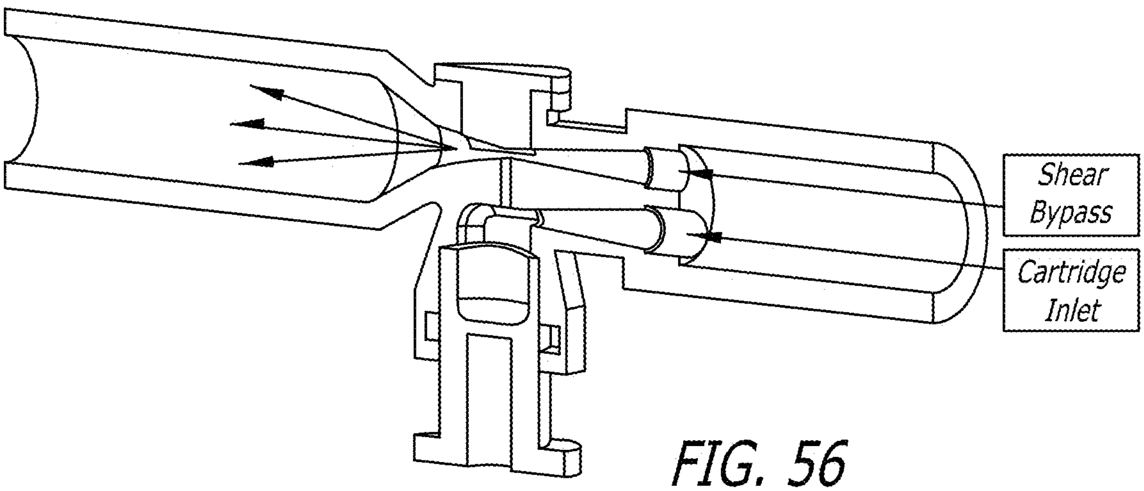
FIG. 56 is a schematic representation of an embodiment of a dry powder inhaler showing the flow pathways and direction of flow through the inhaler as indicated by the arrows.

In the embodiments disclosed herein, the dry powder inhaler system is configured to have a predetermined flow balance distribution in use, having a first flow pathway through the cartridge and second flow pathway through, for example, the mouthpiece air conduit. FIG. 55 and FIG. 56 depict a schematic representation of air conduits established by the cartridge and inhaler structural configurations which direct the balance of flow distribution. FIG. 55 depicts the general direction of flow within a cartridge in the dispensing or dosing position of a dry powder inhaler as shown by the arrows. FIG. 56 illustrates the movement of flow of an embodiment of a dry powder inhaler showing the flow pathways of the inhaler in the dosing position as indicated by the arrows.

The balance of mass flow within an inhaler is approximately 10% to 70% of the volume going through the cartridge flow pathway, and about 30% to 90% through the beginning portion of the mouthpiece conduit. In this embodiment, the airflow distribution through the cartridge mixes the medicament in a tumbling manner to fluidize or aerosolize the dry powder medicament in the cartridge container. Airflow fluidizing the powder within the container then lifts the powder and gradually letting it exit the cartridge container through the dispensing ports, then shear from the airflow entering the mouthpiece conduit converges with the airflow containing medicament emanating from the cartridge container. Predetermined or metered exiting airflow from the cartridge converge with bypass airflow entering the air conduit of the mouthpiece to further dilute and deagglomerate the powder medicament prior to exiting the mouthpiece outlet port and entering the patient.

In yet another embodiment, an inhalation system for delivering a dry powder formulation to a patient is provided, comprising an inhaler comprising a container mounting area configured to receive a container, and a mouthpiece having at least two inlet apertures and at least one exit aperture; wherein one inlet aperture of the at least two inlet apertures is in fluid communication with the container area, and one of the at least two inlet apertures is in fluid communication with the at least one exit aperture via a flow path configured to bypass the container area to deliver the dry powder formulation to the patient; wherein the flow conduit configured to bypass the container area delivers 30% to 90% of the total flow going through the inhaler during an inhalation.

In another embodiment, an inhalation system for delivering a dry powder formulation to a patient is also provided, comprising a dry powder inhaler comprising a container region and a container; said dry powder inhaler and container combined are configured to have rigid flow conduits in a dosing configuration and a plurality of structural regions that provide a mechanism for powder deagglomeration of the inhalation system in use; wherein at least one of the plurality of mechanisms for deagglomeration is an agglomerate size exclusion aperture in the container region having a smallest dimension between 0.5 mm and 3 mm.

In an alternate embodiment, an inhalation system for delivering a dry powder formulation to a patient is provided, comprising a dry powder inhaler comprising a mouthpiece and a container; said dry powder inhaler and container combined are configured to have rigid flow conduits in a dosing configuration and a plurality of structural regions that provide a mechanism for powder deagglomeration of the inhalation system in use; wherein at least one of the plurality of mechanisms for deagglomeration is an air conduit configured in the mouthpiece which directs flow at an exit aperture in fluid communication with the container. In particular embodiments, the inhalation system of includes a container further comprising a mechanisms for cohesive powder deagglomeration which comprises a cup-like structure configured to guide a flow entering the container to rotate, re-circulating in the internal volume of the cup-like structure and lifting up a powder medicament so as to entrain the powder agglomerates in the flow until the powder mass is small enough prior to exiting the container. In this embodiment, the cup-like structure has one or more radii configured to prevent flow stagnation.

In embodiments describe herein, the cartridge is structurally configured having the inlet opening in close proximity to the dispensing ports in a horizontal and vertical axis. For example, the proximity of the inlet to the dispensing ports can be immediately next to the air inlet to about within one cartridge width, although this relationship can vary depending on the flow rate, the physical and chemical properties of the powder. Because of this proximity, flow from the inlet crosses the opening to the dispensing ports within the cartridge creating a flow configuration that inhibits fluidized powder or powder entrained within the airflow, from exiting the cartridge. In this manner, during an inhalation maneuver, flow entering the cartridge container can effectuate tumbling of the dry powder formulation in the cartridge container, and fluidized powder approaching the exit or dispensing ports of a cartridge can be impeded by flow entering the inlet port of the cartridge, thereby, flow within the cartridge can be restricted from exiting the cartridge container. Due to differences in inertia, density, velocity, charge interaction, position of the flow, only certain particles can navigate the path needed to exit the dispensing ports. Particles that do not pass through the exit port must continue to tumble until they possess the proper mass, charge, velocity or position. This mechanism, in effect, can meter the amount of medicament leaving the cartridge and can contribute to deagglomeration of powder. To further help meter the exiting fluidized powder, the size and number of dispensing ports can be varied. In one embodiment, two dispensing ports are used, configured to be circular in shape, each 0.10 cm in diameter and positioned near the inlet aperture about middle center line of the container to about 0.2 cm from the centerline towards the air inlet port. Other embodiments can, for example, have dispensing ports of various shapes including rectangular wherein the cross-sectional area of the one or more dispensing ports ranges from 0.05 $cm^2$ to about 0.25 $cm^2$. In some embodiments, the sizes ranging of the dispensing ports can be from about 0.05 cm to about 0.25 cm in diameter. Other shapes and cross-sectional areas can be employed as long as they are similar in cross-sectional area to the values given herewith. Alternatively, for more cohesive powders larger cross sectional area of the dispensing port can be provided. In certain embodiments, the cross sectional area of the dispensing port can be increased depending on the size of the agglomerates relative to the minimum opening dimension of the port or ports so that the length relative to the width of the port remains large. In one embodiment, the intake aperture is wider in dimension than the width of the dispensing port or ports. In embodiments wherein the intake aperture is rectangular, the air inlet aperture comprises a width ranging from about 0.2 cm to about the maximal width of the cartridge. In one embodiment the height is about 0.15 cm, and width of about 0.40 cm. In alternate embodiments, the container can have a height of from about 0.05 cm to about 0.40 cm. In particular embodiments, the container can be from about 0.4 cm to about 1.2 cm in width, and from about 0.6 cm to about 1.2 cm in height. In an embodiment, the container comprise one or more dispensing ports having and each of the ports can have a diameter between 0.012 cm to about 0.25 cm.

In particular inhalation systems, a cartridge for a dry powder inhaler, comprising a cartridge top and a container is provided, wherein the cartridge top configured relatively flat and having one or more openings and one or more flanges having tracks configured to engage the container; said container having an inner surface defining an internal volume and is moveably attached to the tracks on the one or more flanges on the cartridge top and configurable to attain a containment position and a dispensing or dosing position by moving along the tracks of the one or more flanges.

In another embodiment, the inhalation system comprises an enclosure having one or more exit ports configured to exclude a powder mass of a dry powder composition having a smallest dimension greater than 0.5 millimeters and less than 3 mm. In one embodiment, a cartridge for a dry powder inhaler, comprising an enclosure having two or more rigid parts; the cartridge having one or more inlet ports and one or more dispensing ports, wherein one or more inlet ports have a total cross-sectional area which is larger than the total cross-sectional area of the dispensing ports, including wherein the total cross-sectional area of one or more dispensing ports ranges from 0.05 $cm^2$ to about 0.25 $cm^2$.

In one embodiment, a method for deagglomerating and dispersing a dry powder formulation for inhalation, comprising the steps of: generating an airflow in a dry powder inhaler comprising a mouthpiece and a container having at least one inlet port and at least one dispensing port and containing a dry powder formulation; said container forming an air conduit between the at least one inlet port and the at least one dispensing port and said inlet port directs a portion of the airflow entering said container to the at least one dispensing port; allowing airflow to tumble powder within the container so as to lift and mix the dry powder medicament in the container to form an airflow medicament mixture; and accelerating the airflow exiting the container through the at least one dispensing port. In this embodiment, the powder medicament that passes through the dispensing ports can immediately accelerate due to reduction in cross-sectional area of the exit ports relative to the inlet port. This change in velocity may further deagglomerate the fluidized and aerosolized powder medicament during inhalation. Additionally, because of the inertia of the particles or groups of particles in the fluidized medicament, the velocity of the particles leaving the dispensing ports is not the same. The faster moving air flow in the mouthpiece conduit imparts a drag or shear force on each particle or group of particles of the slower moving fluidized powder leaving the exit or dispensing port or ports, which can further deagglomerate the medicament.

The powder medicament that passes through the dispensing port or ports immediately accelerates due to reduction in cross-sectional area of the exit or dispensing ports relative to the container, which are designed to be narrower in cross-sectional area than the air inlet of the container. This change in velocity may further deagglomerate the fluidized powder medicament. Additionally, because of the inertia of the particles or groups of particles in the fluidized medicament, the velocity of the particles leaving the dispensing ports and the velocity of the flow passing the dispensing ports is not the same.

In embodiments described herein, powder exiting the dispensing ports can further accelerate, for example, by an imparted change in direction and/or velocity of the fluidized medicament. Directional change of fluidized powder leaving the dispensing port and entering the mouthpiece conduit can occur at an angle of approximately 0° to about 180°, for example approximately 90°, to the axis of the dispensing port. Change in flow velocity and direction may further deagglomerate the fluidized powder through the air conduits. The change in direction can be accomplished through geometric configuration changes of the air flow conduit and/or by impeding the air flow exiting the dispensing ports with a secondary air flow entering the mouthpiece inlet. The fluidized powder in the mouthpiece conduit expands and decelerates as it enters the oral placement portion of the mouthpiece prior to exiting due to a cross-sectional area increase in the conduit. Gas trapped within agglomerates also expands and may help to break apart the individual particles. This is a further deagglomeration mechanism of the embodiments described herein. Airflow containing medicament can enter the patient's oral cavity and be delivered effectively, for example, into the pulmonary circulation.

Each of the deagglomeration mechanisms described herein and part of the inhalation system represent a multistage approach which maximizes powder deagglomeration. Maximal deagglomeration and delivery of powder can be obtained by optimizing the effect of each individual mechanism, including, one or more acceleration/deceleration conduits, drag, or expansion of gas trapped within the agglomerates, interactions of powder properties with those of the inhaler components material properties, which are integral characteristics of the present inhaler system. In the embodiments described herein, the inhalers are provided with relatively rigid air conduits or plumbing system to maximize deagglomeration of powder medicament so that there is consistency of the powder medicament discharge from the inhaler during repeated use. Since the present inhalers are provided with conduits which are rigid or remain the same and cannot be altered, variations in the air conduit architecture resulting from puncturing films or peeling films associated with prior art inhalers using blister packs are avoided.

In one embodiment, there is provided a method of deagglomerating a powder formulation in a dry powder inhalation system, comprising: providing the dry powder formulation in a container having an internal volume to a dry powder inhaler; allowing a flow to enter said container which is configured to direct a flow to lift, entrain and ciruclate the dry powder formulation until the powder formulation comprises powder masses sufficiently small to pass through one or more dispensing apertures into a mouthpiece. In this embodiment, the method can further comprise the step of accelerating the powder masses entrained in the flow leaving the one or more dispensing apertures and entering the mouthpiece.

In embodiments disclosed herein, a dry powder medicament is dispensed with consistency from the inhaler in less than about 2 seconds. The present inhaler system has a high resistance value of approximately 0.065 to about 0.20 ($\sqrt{kPa}$)/liter per minute. Therefore, in the system comprising a cartridge, peak inhalation pressure drops applied of between 2 and 20 kPa produce resultant peak flow rates of about through the system of between 7 and 70 liters per minute. These flow rates result in greater than 75% of the cartridge contents dispensed in fill masses between 1 and 30 mg of powder. In some embodiments, these performance characteristics are achieved by end users within a single inhalation maneuver to produce cartridge dispense percentage of greater than 90%. In certain embodiments, the inhaler and cartridge system are configured to provide a single dose by discharging powder from the inhaler as a continuous flow, or as one or more pulses of powder delivered to a patient. In an embodiment, an inhalation system for delivering a dry powder formulation to a patient's lung is provided, comprising a dry powder inhaler configured to have flow conduits with a total resistance to flow in a dosing configuration ranging in value from 0.065 to about 0.200 ($\sqrt{kPa}$)/liter per minute. In this and other embodiments, the total resistance to flow of the inhalation system is relatively constant across a pressure differential range of between 0.5 kPa and 7 kPa.

The structural configuration of the inhaler allows the deagglomeration mechanism to produce respirable fractions greater than 50% and particles of less than 5.8 μm. The inhalers can discharge greater than 85% of a powder medicament contained within a container during an inhalation maneuver. Generally, the inhalers herein depicted in FIG. 15I can discharge greater that 90% of the cartridge contents or container contents in less than 3 seconds at pressure differentials between 2 and 5 kPa with fill masses ranging up to 30 mg.

While the present inhalers are primarily described as breath-powered, in some embodiments, the inhaler can be provided with a source for generating the pressure differential required to deagglomerate and deliver a dry powder formulation. For example, an inhaler can be adapted to a gas powered source, such as compressed gas stored energy source, such as from a nitrogen can, which can be provided at the air inlet ports. A spacer can be provided to capture the plume so that the patient can inhale at a comfortable pace.

In embodiments described herewith, the inhaler can be provided as a reusable inhaler or as a single use inhaler. In alternate embodiments, a similar principle of deagglomeration can be adapted to multidose inhalers, wherein the inhaler can comprise a plurality of, for example, cartridge like structures in a single tray and a single dose can be dialed as needed. In variations of this embodiment, the multidose inhaler can be provided with enough doses for example for a day, a week or a month supply of a medication. In the multidose embodiments described herein, end-user convenience is optimized. For example, in prandial regimens breakfast, lunch and dinner dosing is achieved for a course of 7 days in a single device. Additional end-user convenience is provided by an indicator mechanism that indicates the day and dosing, for example, day 3 (D3), lunchtime (L). An exemplary embodiment is illustrated in FIGS. 57-68, wherein the inhaler 950 comprises a relatively circular shape comprising a plurality of dosing units as part of a disk-like cartridge system. Inhaler 950 comprises a mouthpiece 952 having air inlet 953 and air outlet 954 and housing subassembly 960. Mouthpiece 952 is configured to have a relatively hour glass shape and therefore air conduit 980 (FIG. 67) is configured with a corresponding shape. Mouthpiece 952 also comprises a cover for engaging with housing subassembly 960 and an air conduit 980 having an opening 985 (FIG. 67) which communicates with the interior of housing subassembly 960.

Figure 57:
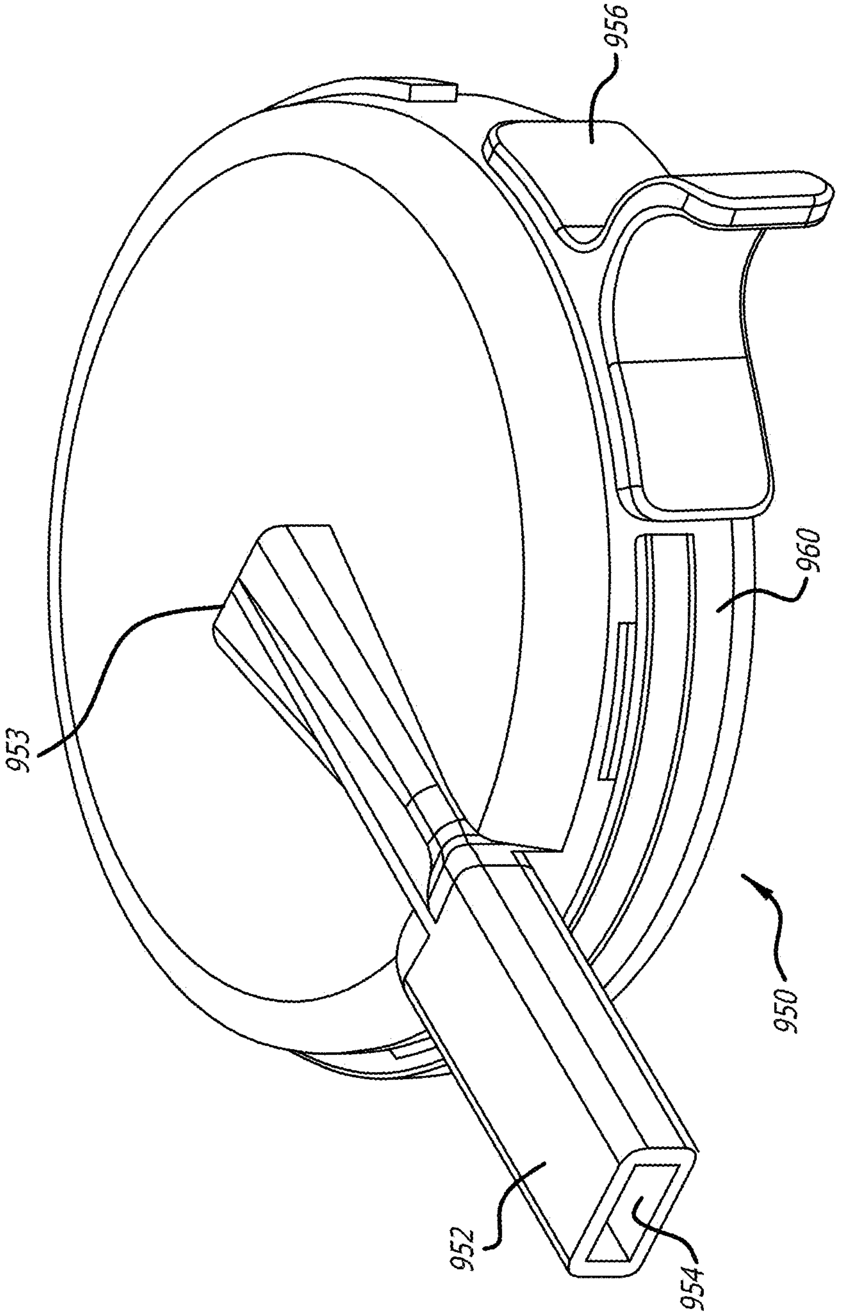
FIG. 57 illustrates a perspective view of a multidose embodiment of a dry powder inhaler.
Figure 58:
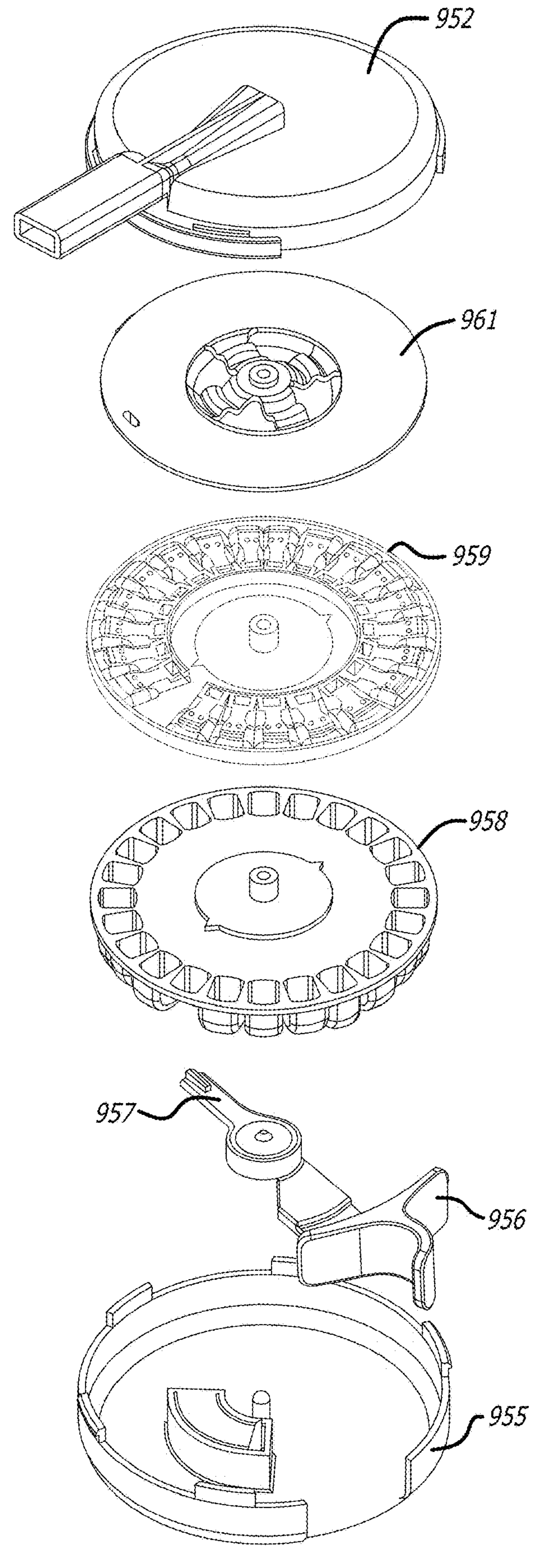
FIG. 58 illustrates an exploded view of the inhaler embodiment of FIG. 57 showing the inhaler component parts.
Figure 59:
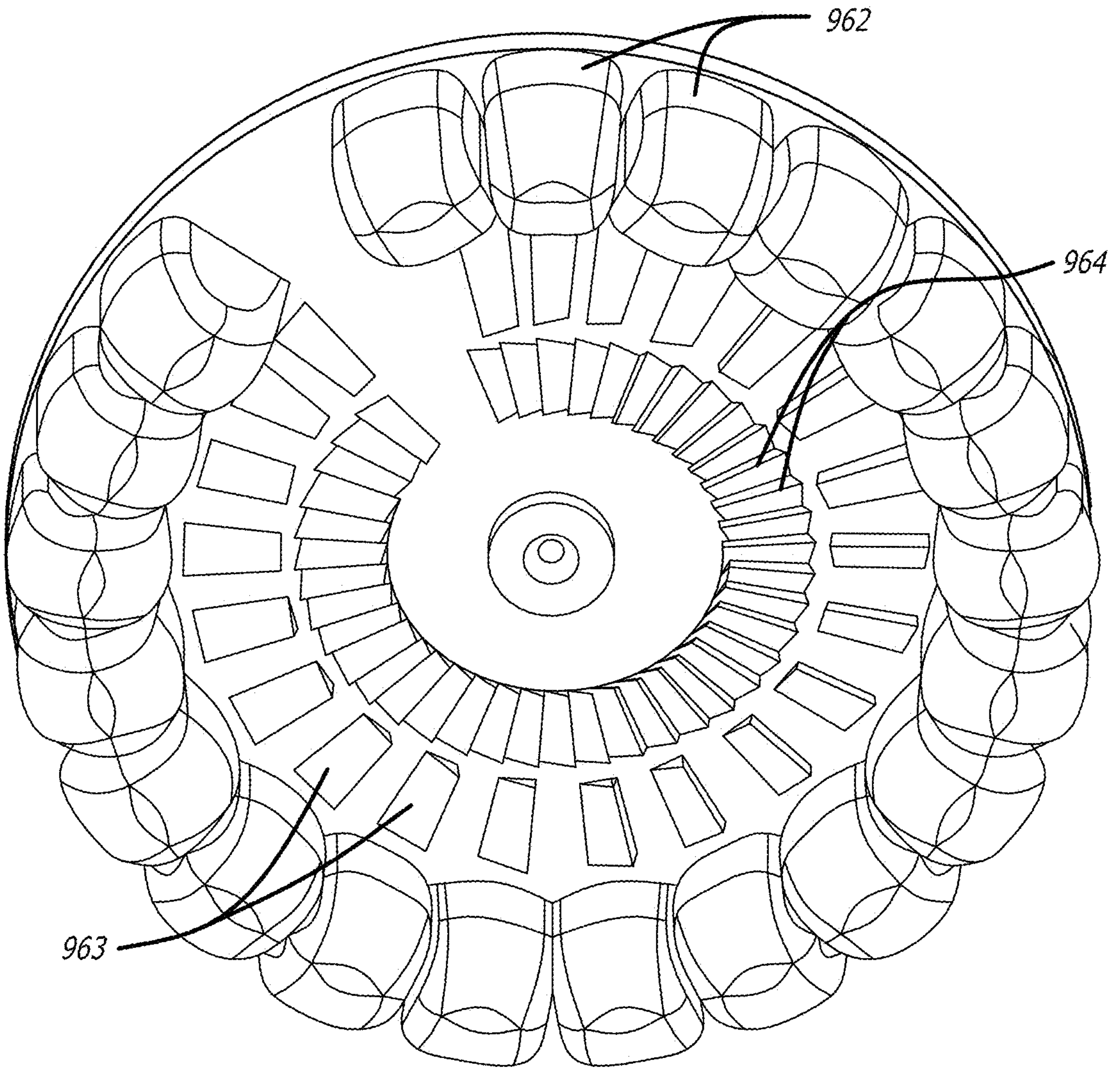
FIG. 59 illustrates a perspective bottom view of component part 958 of the inhaler depicted in FIG. 58.
Figure 60:
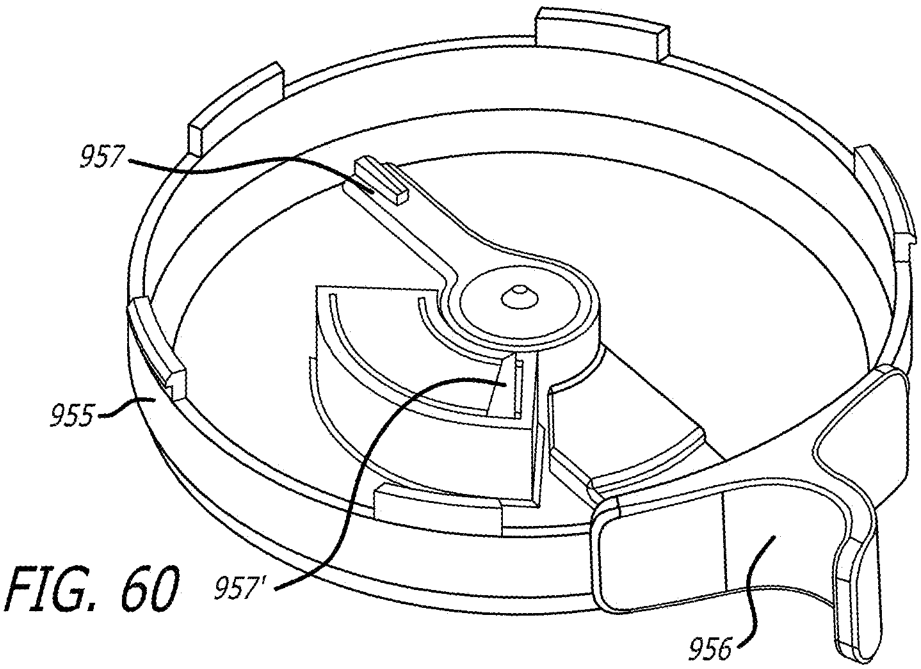
FIG. 60 illustrates a perspective top view of component parts assembled of the inhaler depicted in FIG. 58.
Figure 61:
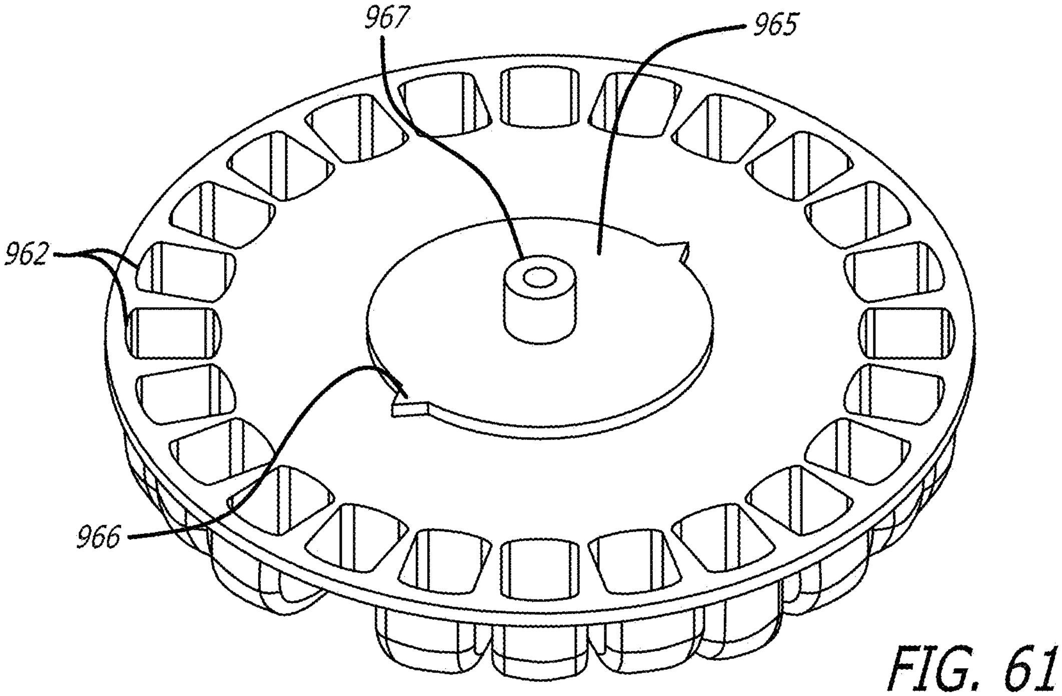
FIG. 61 illustrates a perspective top view of component part 958 of the inhaler depicted in FIG. 58.
Figure 62:
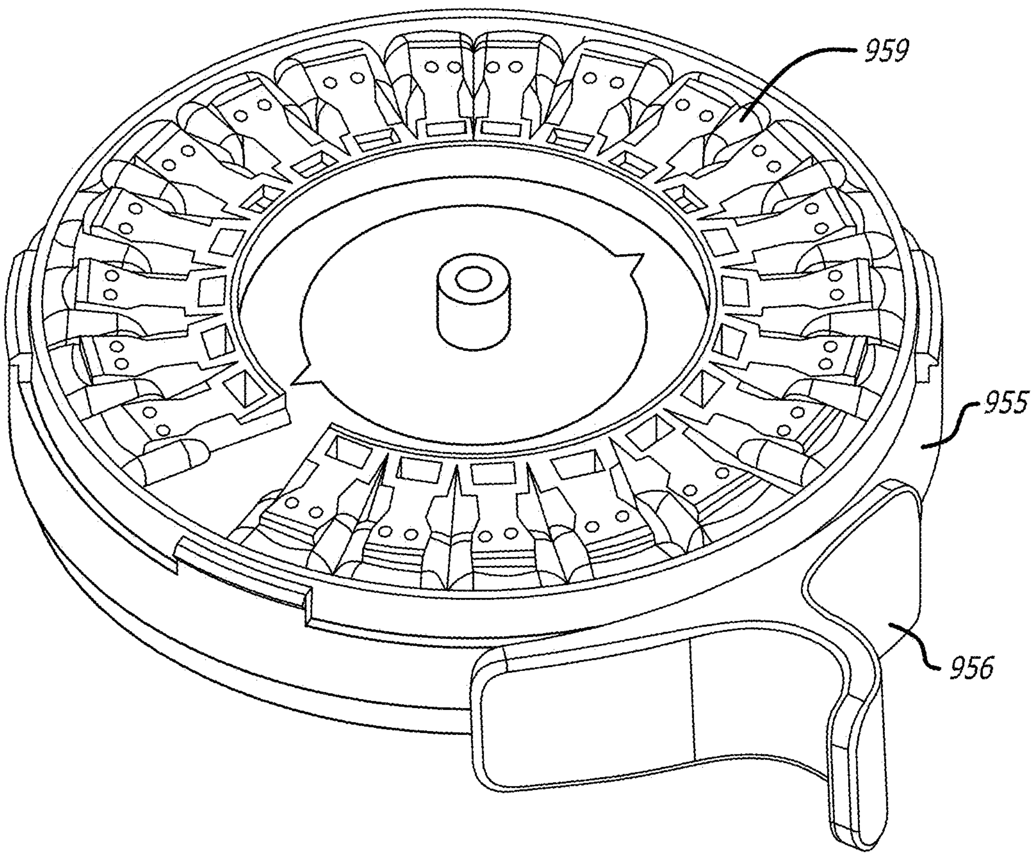
FIG. 62 illustrates a perspective top view of component parts of the housing assembly of the inhaler depicted in FIG. 58.

FIG. 58 is an exploded view of the inhaler of FIG. 57 showing the component parts, including mouthpiece 952; housing subassembly 960 comprising multiple parts, including bottom cover or tray 955, an actuator 956 having a ratchet 957, a cartridge disk system with a bottom tray portion 958 and a lid portion 959 and a seal disk or plate 961. In one embodiment, a spring can be provided with ratchet 957 to index tray 958. Housing tray 955 is structurally configured so that it can engage securely with the mouthpiece, for example, snap fits, ultrasonic weld, threads and the like. FIG. 59 illustrates the bottom tray portion 958 of the cartridge disk system showing an outer gear mechanism 963 and an inner gear mechanism 964 with relative position around the center axis of the cartridge disk. The cartridge system is configured to have a centrally located aperture for engaging with the actuator. FIG. 59 also shows the position of the plurality of unit dose containers 962, each configured of the same dimension and shape and are radially located towards the periphery of the cartridge disk system. FIG. 60 illustrates the housing tray showing the actuator 956 and the ratchet system 957, 957' in place without a return spring. FIG. 61 depicts the bottom portion 958 of the cartridge disk system showing the plurality of containers 962 radially located within the disk and also showing a relatively circular raised area 965 comprising two projections 966 place in the horizontal plane of the disk and a second projection 967 located in the central axis and projecting upwards and perpendicular to the disk. FIG. 62 illustrates housing tray 955 with the cartridge disk system 958, 959, actuator 956, and ratchet system assembled therein.

Figure 63:
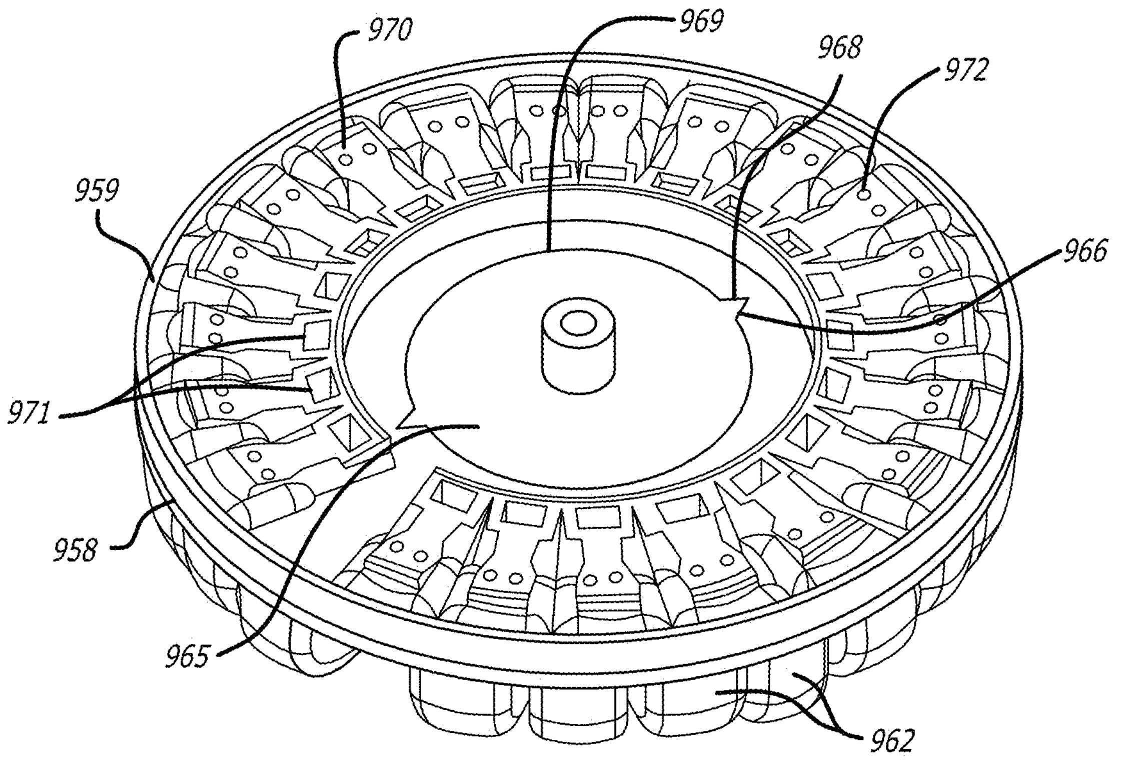
FIG. 63 illustrates a perspective view of the cartridge disk system of the inhaler depicted in FIG. 58.
Figure 64:
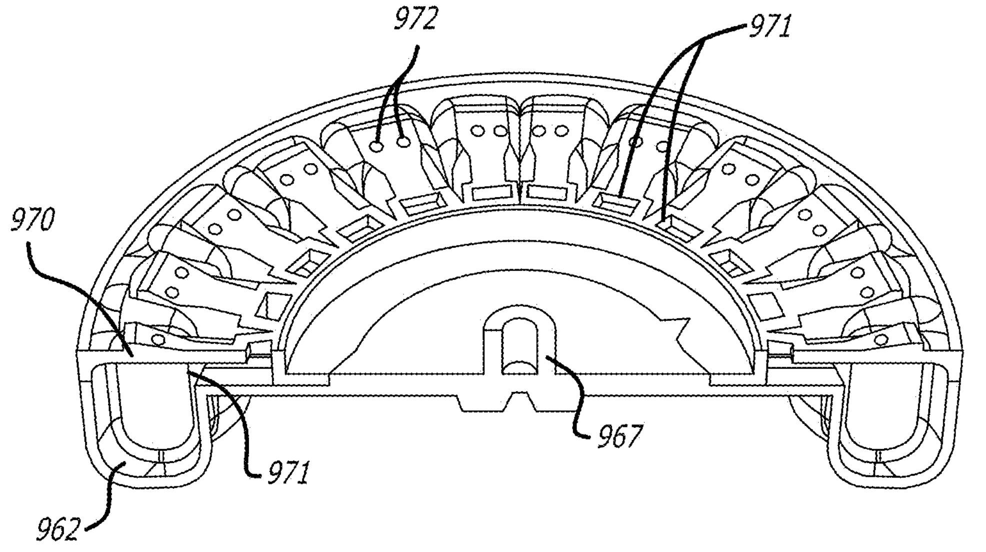
FIG. 64 illustrates a perspective view of the cartridge disk system illustrated in FIG. 63 in cross-section.

FIG. 63 depicts the cartridge disk system of inhaler 950 in an assembled configuration showing the plurality of containers 962 and can engageably attach to one another to provide powder containment. The cartridge system lid portion 959 comprises a plurality of cartridge-like tops 970 which in alignment correspond to the containers 962 of the bottom tray of the cartridge disk system to form a plurality of unit dose cartridge units within the cartridge disk system. Alignment of the cartridge system lid 959 and bottom tray portion is achieved by the lid portion 959 having a centrally located aperture 969 configured with two notches 968 which engage securely with the raised area of the bottom tray portion 958. In this embodiment, the cartridge disk system is also configured to have a plurality of air inlets 971 and a plurality of dispensing ports 972, wherein each unit dose cartridge comprises at least one air inlet 971 and one ore more dispensing ports 972. FIG. 64 shows a cross-section of a cartridge disk system 958, 959 showing air inlet 971 establishing an air conduit pathway in the interior compartment of the container with the dispensing ports 972 so that an airflow entering the unit compartment enters through air inlet 971, tumbles inside the container and exits through the dispensing ports.

Figure 65:
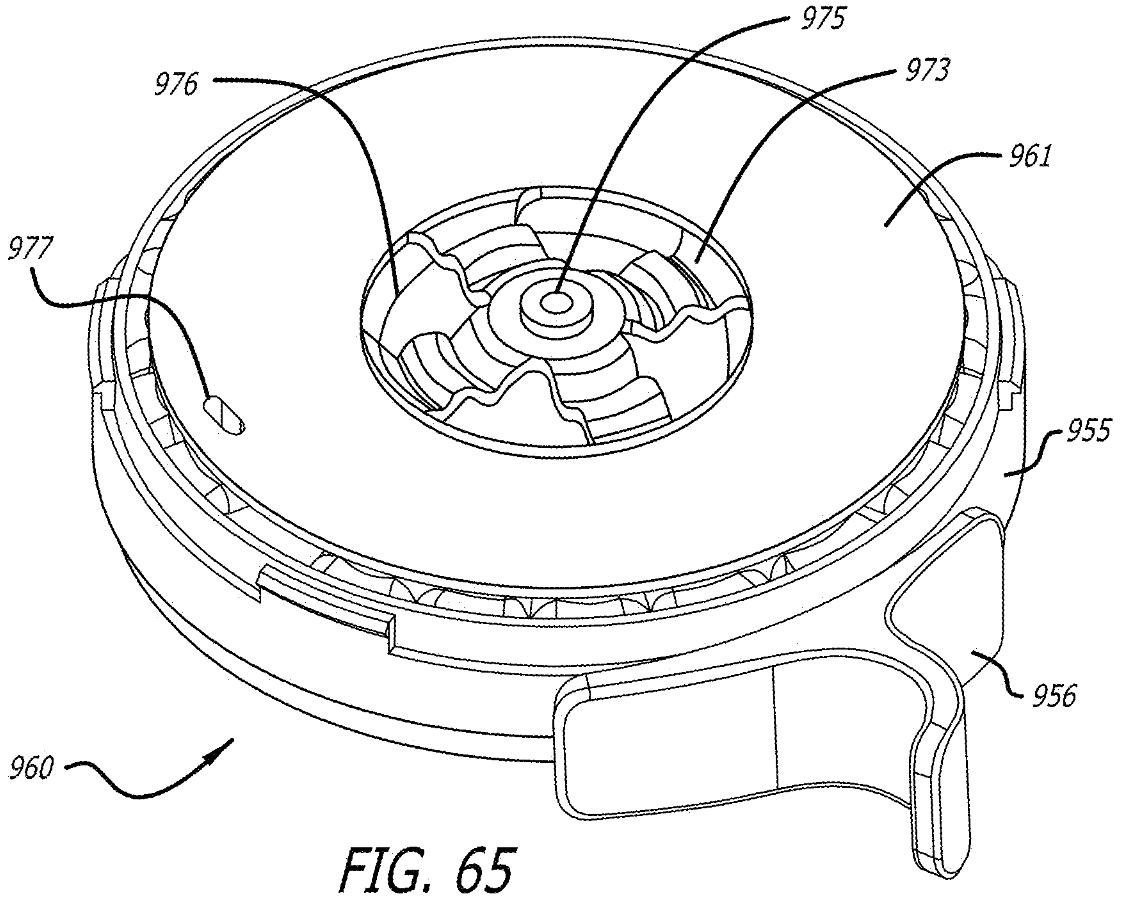
FIG. 65 illustrates a perspective top view of the housing subassembly of the inhaler depicted in FIGS. 57 and 58.
Figure 66:
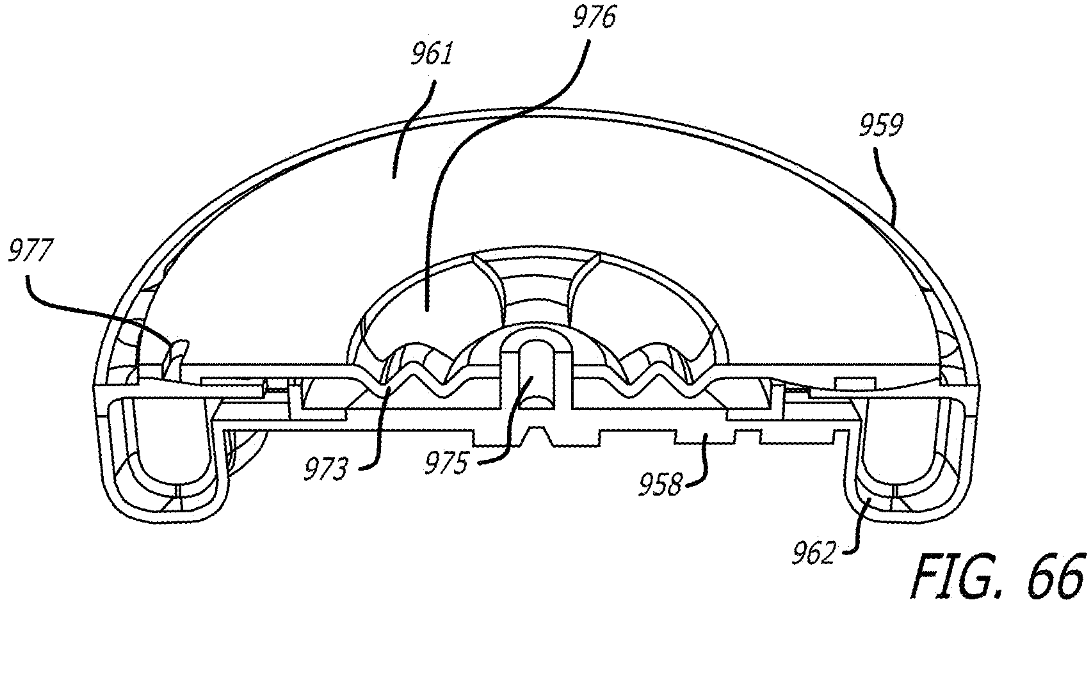
FIG. 66 illustrates a perspective cross-sectional view of component parts of the inhaler depicted in FIG. 58.
Figure 67:
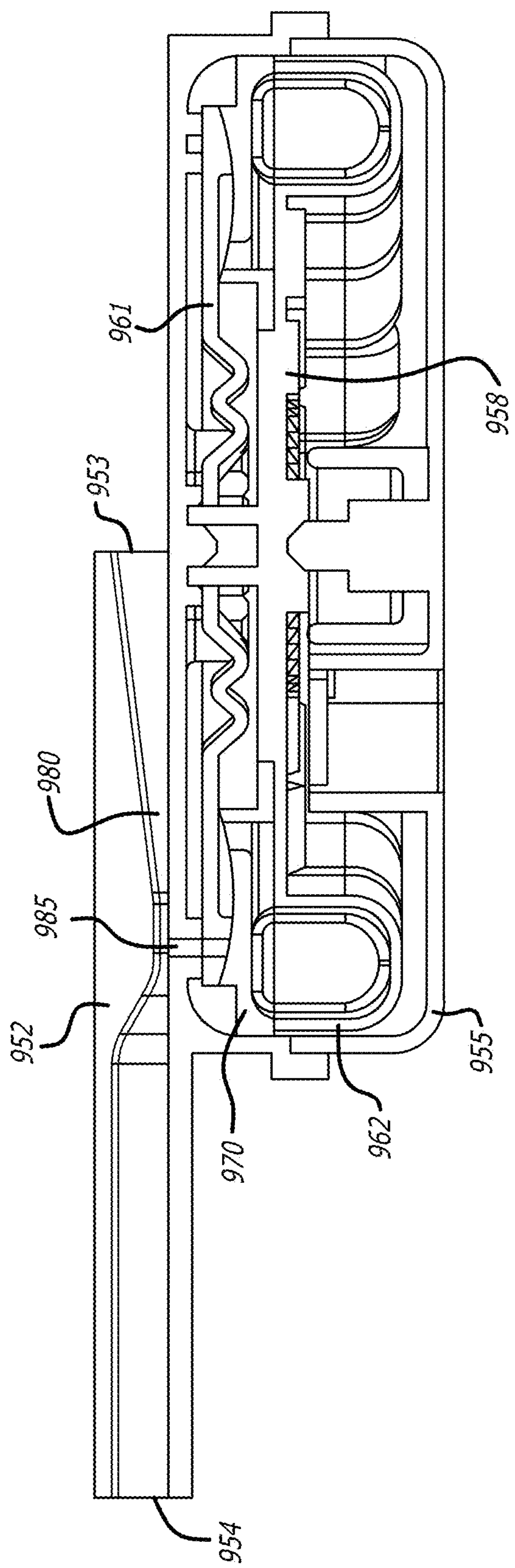
FIG. 67 illustrates a perspective view of the inhaler depicted in FIG. 57 in cross-section.
Figure 70:
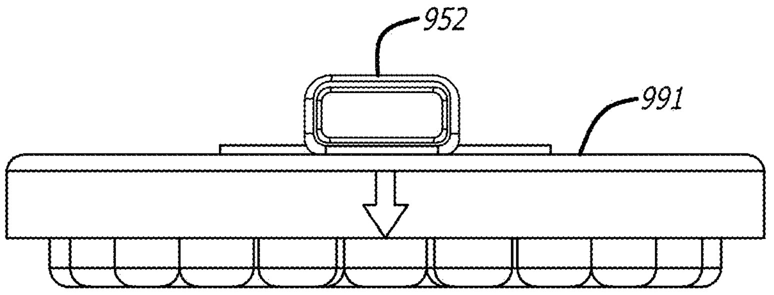
FIG. 70 illustrates a top view of the inhaler embodiment of FIG. 68 showing the inhaler body and the mouthpiece.
Figure 71:
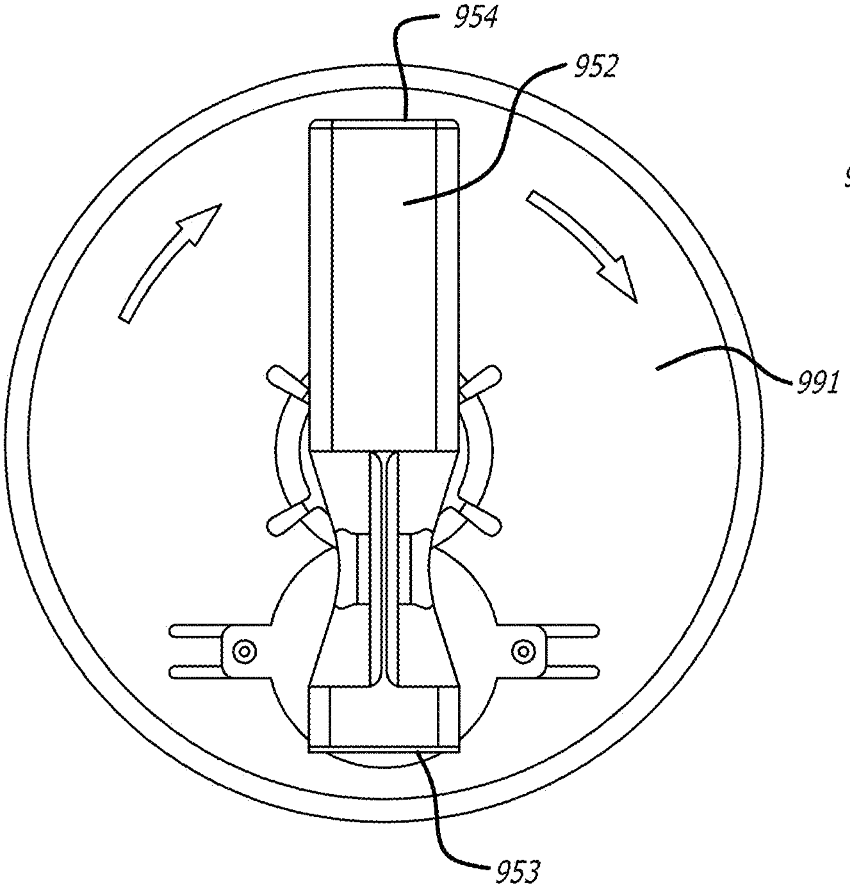
FIG. 71 illustrates a front view of the inhaler depicted in FIG. 68.
Figure 72:
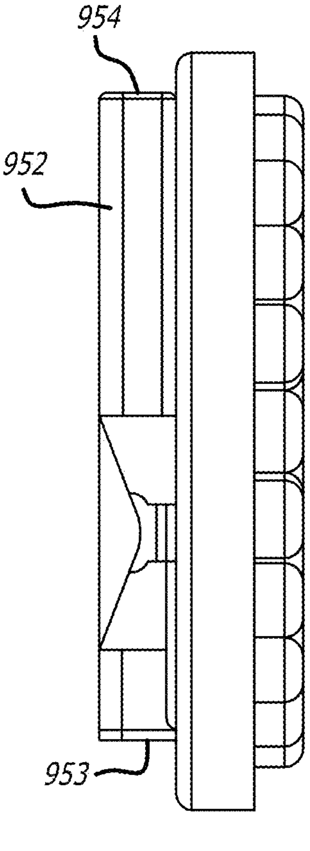
FIG. 72 illustrates a side view of the inhaler depicted in FIG. 68.
Figure 73:
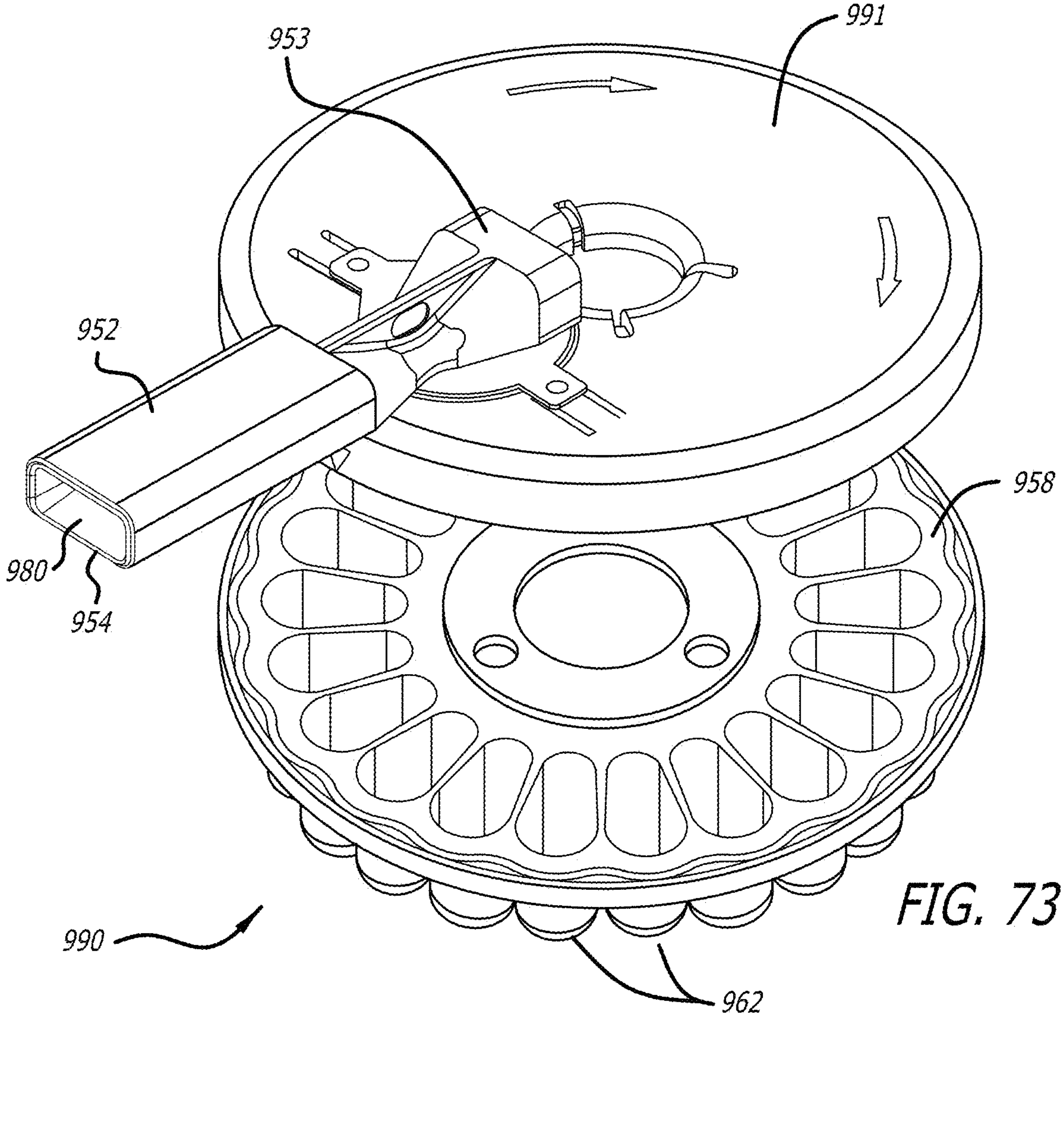
FIG. 73 illustrates a perspective explode view showing the bottom cartridge tray removed with not all component parts depicted.

FIG. 65 illustrates the housing subassembly 960 assembled with its component parts, in particular, the seal disk 961 is illustrated comprising an aperture 977 located toward the edge of the disk which aligns with the dispensing ports 972 of a unit dose cartridge of the cartridge disk system in the dosing position. Seal disk 961 is also configured to seal dispensing ports 972 and air inlets 971 into the unit dose cartridge of the cartridge disk system, except for the unit dose cartridge that is in alignment with aperture 977. In this manner, powder containment in a filled cartridge system is maintained. Seal disk 961 also has a central opening 975 and a plurality of spring-like structures, exemplified as undulating elements, or arms 973 extending from the disk inner portion with reference to the central axis, which form a plurality of openings 976 that allow air flow into the interior of the inhaler 950 and into the unit dose cartridge being dispensed when in use. FIG. 66 is a cross-section of the housing subassembly 960 showing seal disk 961 configuration which restricts air passage into the unit dose cartridge of all cartridge units except at aperture 977 of the seal disk cartridge disk system. FIG. 67 shows inhaler 950 in cross-section showing the dosing configuration, wherein the mouthpiece shows air conduit 980 and mouthpiece aperture 985 aligned with the dispensing ports 972 of a unit dose cartridge and aperture 977 of the seal disk. The other units in the cartridge are in containment by seal disk 961.

In this embodiment, the inhaler device 950 is simple to use and can be used one cartridge at a time and for dosing. After all dosages are dispensed the inhaler can be disposed or reloaded with a new cartridge disk system. In this embodiment, movement from an initial position to an adjacent cartridge is effectuated by actuator 956 through a complementary ratchet system 957. One ratchet which is attached to the actuator advances the cartridge disk, while another holds the cartridge disk in place while the actuator resets to its original position.

Figure 74:
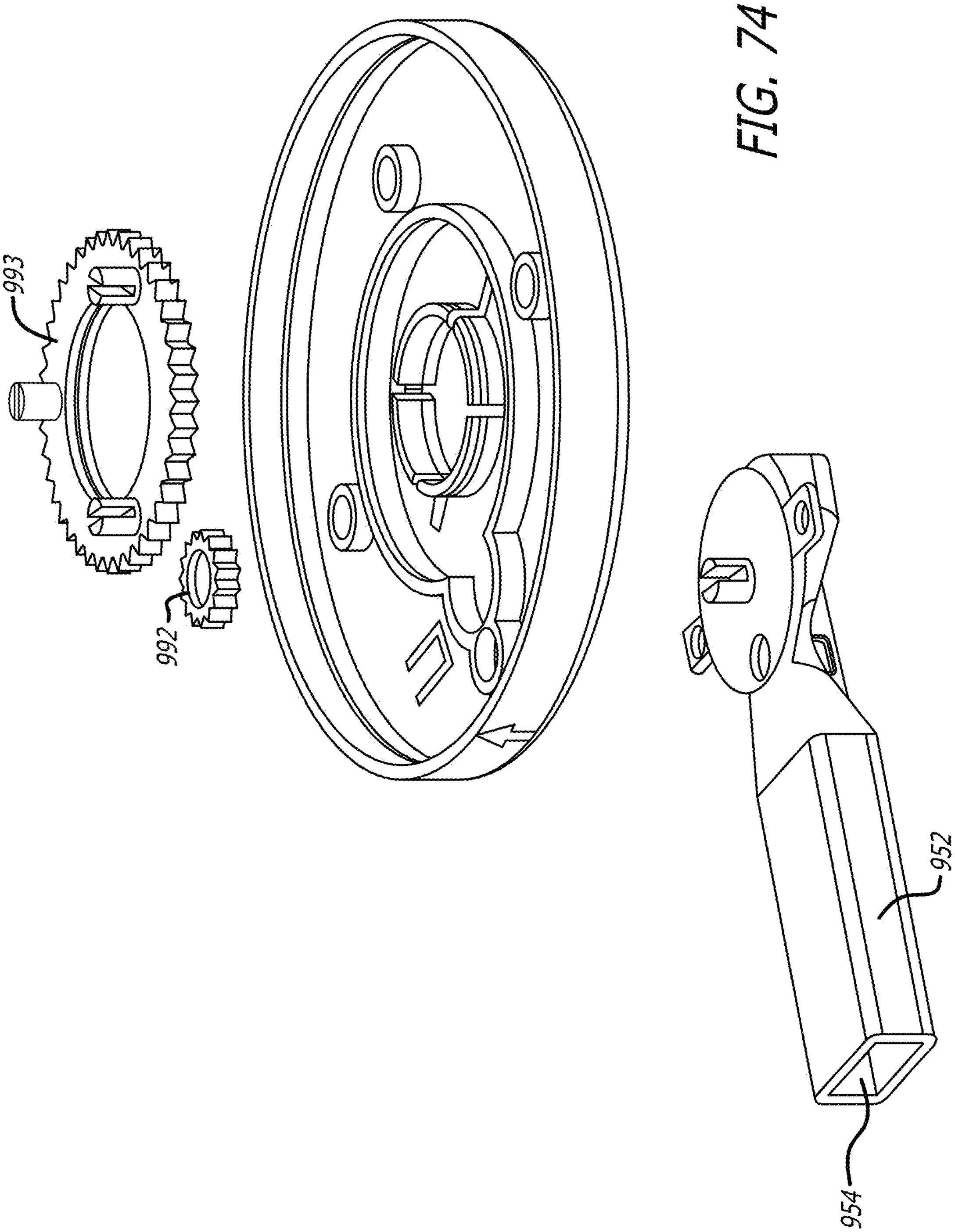
FIG. 74 illustrates an exploded view of the inhaler depicted in FIG. 68 showing the gear drive system.
Figure 75:
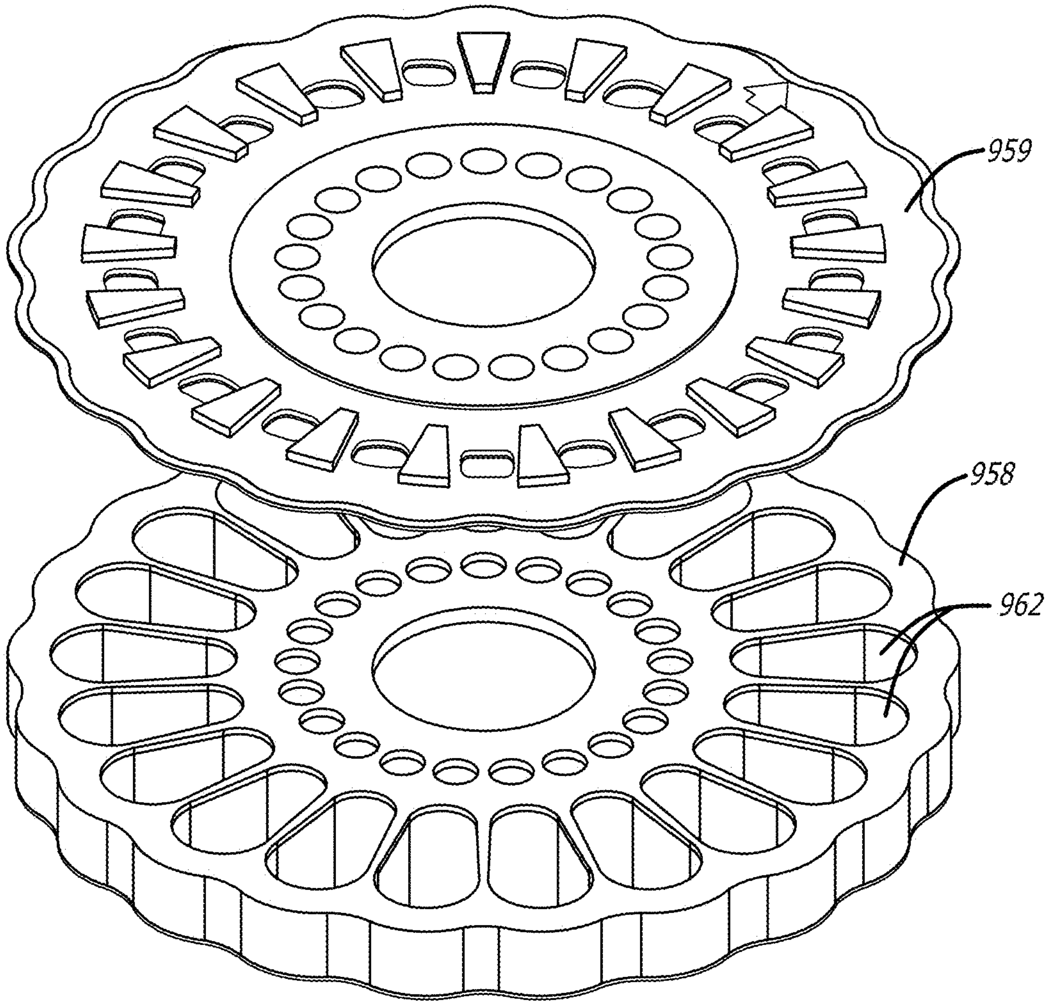
FIG. 75 illustrates a perspective view of cartridge disk system of the inhaler depicted in FIG. 68.
Figure 77:
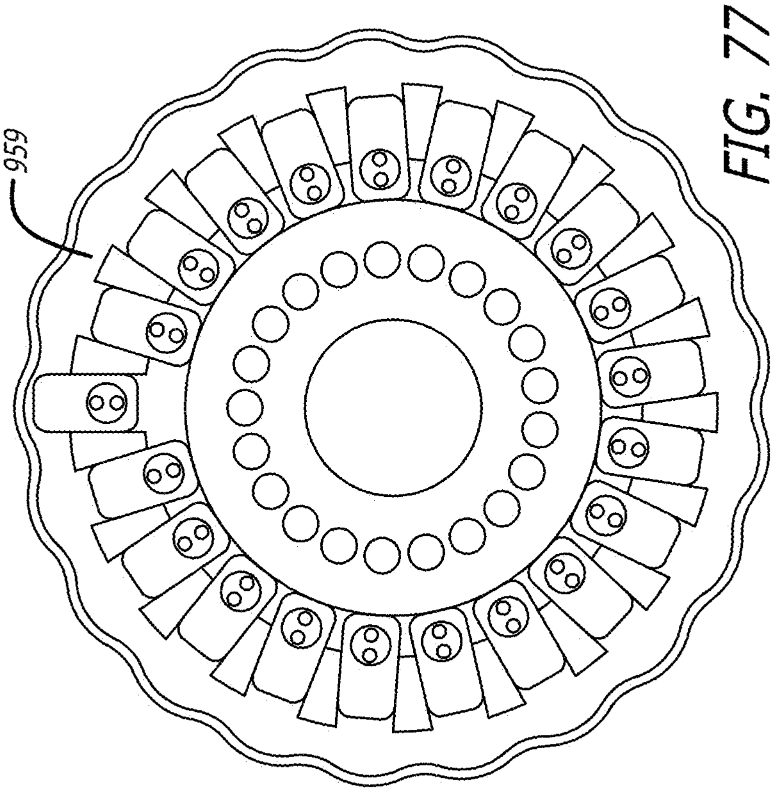
FIG. 77 illustrates a front view of cartridge disk system of the inhaler depicted in FIG. 68.
Figure 76:
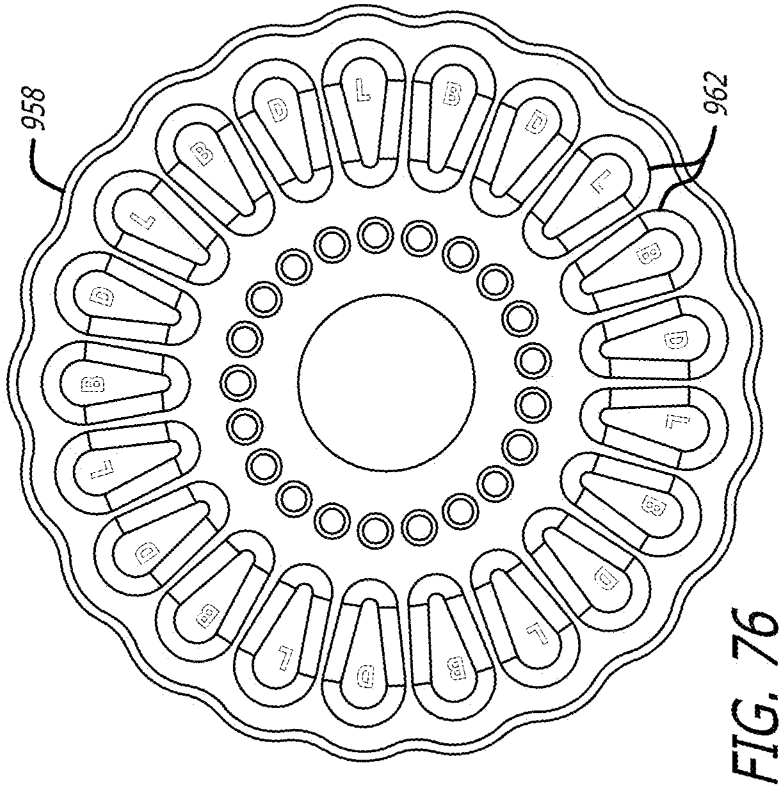
FIG. 76 illustrates a back view of cartridge disk system of the inhaler depicted in FIG. 68.
Figure 78:
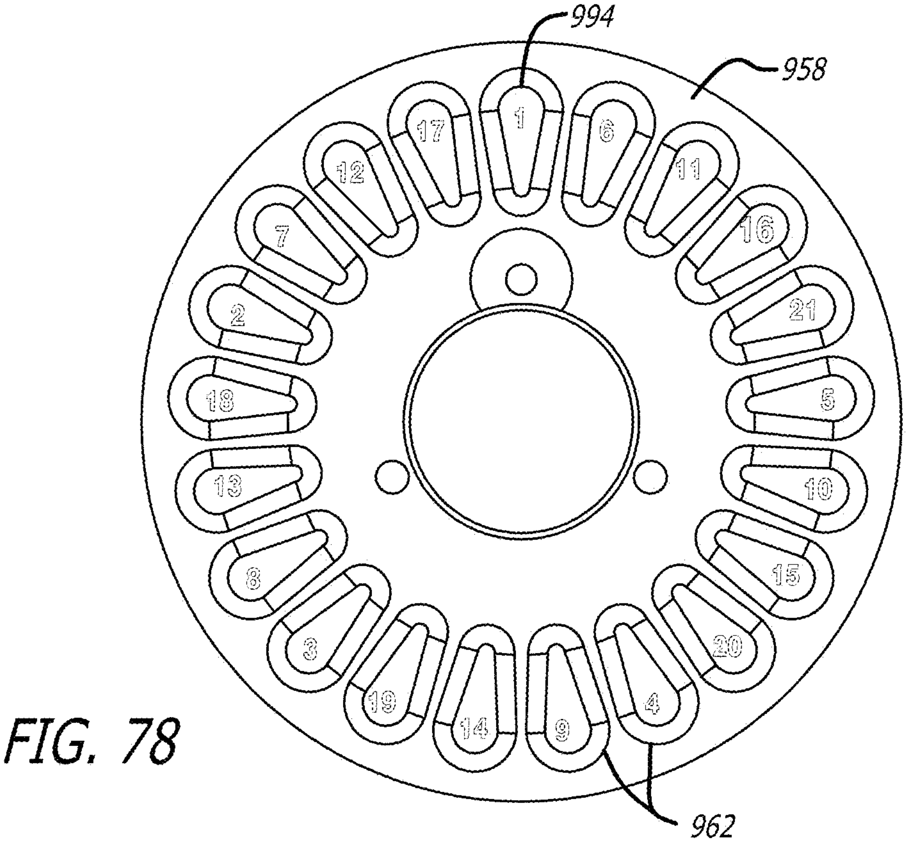
FIG. 78 illustrates a bottom view of cartridge disk system of the inhaler depicted in FIG. 68.
Figure 79:
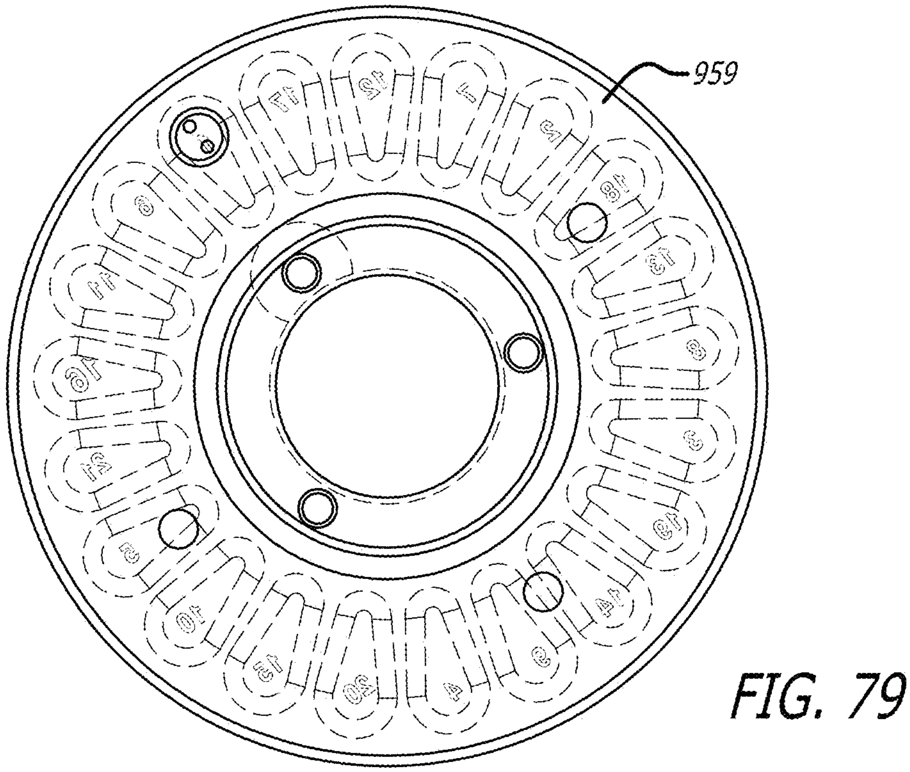
FIG. 79 illustrates a top view of seal disk of the inhaler depicted in FIG. 68.

FIGS. 68 through 79 illustrate an alternate embodiment of a multidose inhaler 990 comprising a mouthpiece 952 and an inhaler body 991. Mouthpiece 952 having an air inlet port 953, an air outlet port 954 and configured to have a relatively hour glass shape having an aperture for communicating with the body 991 and attached to inhaler body 991. FIGS. 69-73 disclosed the various component parts of inhaler 990. In this embodiment, inhaler body 991 comprises several parts with the cartridge disk system forming the bottom portion of the body 991. FIG. 74 shows a gear drive assembly comprising first gear 992 and second gear 993 is used to rotate a unit dose cartridge to alignment with the mouthpiece aperture for dispensing. An alphanumeric indicator system can be applied to the cartridge container to indicate the dose unit being dispensed. FIG. 75 shows the cartridge unit system comprising bottom tray portion 958 comprising a plurality of wells or unit dose containers 962 radially located and a plurality of air inlet ports, and a lid or top portion 959 comprising a cartridge cover plate that can be glued or welded permanently on the bottom disk containing the wells. FIG. 76 shows a back view of the cartridge disk system and FIG. 77 shows a front view of the cartridge disk comprising a plurality of cartridge tops which can be movable in the cartridge from a containment position to a dosing position. FIG. 78 shows a bottom view of the cartridge system of the inhaler 990 showing the position numerically, represented by at least one numeral 994 of the order in which the doses are dispensed. FIG. 79 shows a disk seal having an aperture to align with the dispensing ports of a unit dose cartridge of the cartridge disk system.

In one embodiment, the dry powder medicament may comprise, for example, a diketopiperazine and a pharmaceutically active ingredient. In this embodiment, the pharmaceutically active ingredient or active agent can be any type depending on the disease or condition to be treated. In another embodiment, the diketopiperazine can include, for example, symmetrical molecules and asymmetrical diketopiperazines having utility to form particles, microparticles and the like, which can be used as carrier systems for the delivery of active agents to a target site in the body. The term 'active agent' is referred to herein as the therapeutic agent, or molecule such as protein or peptide or biological molecule, to be encapsulated, associated, joined, complexed or entrapped within or adsorbed onto the diketopiperazine formulation. Any form of an active agent can be combined with a diketopiperazine. The drug delivery system can be used to deliver biologically active agents having therapeutic, prophylactic or diagnostic activities.

One class of drug delivery agents that has been used to produce microparticles that overcome problems in the pharmaceutical arts such as drug instability and/or poor absorption, are the 2,5-diketopiperazines. 2,5-diketopiperazines are represented by the compound of the general Formula 1 as shown below where E=N. One or both of the nitrogens can be replaced with oxygen to create the substitution analogs diketomorpholine and diketodioxane, respectively.

Formula 1

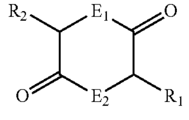

These 2,5 diketopiperazines have been shown to be useful in drug delivery, particularly those bearing acidic R groups (see for example U.S. Pat. No. 5,352,461 entitled "Self Assembling Diketopiperazine Drug Delivery System;" U.S. Pat. No. 5,503,852 entitled "Method For Making Self-Assembling Diketopiperazine Drug Delivery System;" U.S. Pat. No. 6,071,497 entitled "Microparticles For Lung Delivery Comprising Diketopiperazine;" and U.S. Pat. No. 6,331,318 entitled "Carbon-Substituted Diketopiperazine Delivery System," each of which is incorporated herein by reference in its entirety for all that it teaches regarding diketopiperazines and diketopiperazine-mediated drug delivery). Diketopiperazines can be formed into drug adsorbing microparticles. This combination of a drug and a diketopiperazine can impart improved drug stability and/or absorption characteristics. These microparticles can be administered by various routes of administration. As dry powders these microparticles can be delivered by inhalation to specific areas of the respiratory system, including the lungs.

Methods for synthesizing diketopiperazines are described in, for example, Katchalski, et al., J. Amer. Chem. Soc. 68, 879-880 (1946) and Kopple, et al., J. Org. Chem. 33(2), 862-864 (1968), the teachings of which are incorporated herein by reference in their entirety. 2,5-diketo-3,6-di(aminobutyl)piperazine (Katchalski et al. refer to this as lysine anhydride) can also be prepared via cyclodimerization of N-ε-P-L-lysine in molten phenol, similar to the Kopple method, followed by removal of the blocking (P)-groups with 4.3 M HBr in acetic acid. This route can be preferred because it uses a commercially available starting material, it involves reaction conditions that are reported to preserve stereochemistry of the starting materials in the product and all steps can be easily scaled up for manufacture. Methods for synthesizing diketopiperazines are also described in U.S. Patent Publication No. 2006/004133 entitled, "Catalysis of Diketopiperazine Synthesis," which is also incorporated by reference herein for its teachings regarding the same.

The fumaryl diketopiperazine (3,6-bis(N-fumaryl-4-aminobutyl)-2,5-diketopiperazine; FDKP) is one preferred diketopiperazine for pulmonary applications:

FDKP

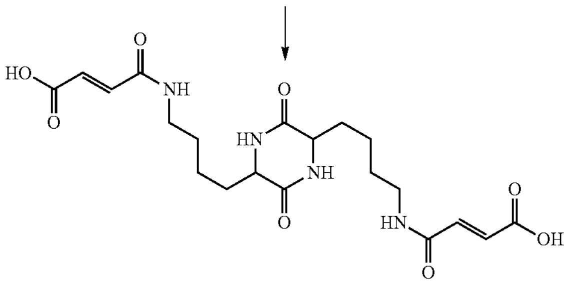

FDKP provides a beneficial microparticle matrix because it has low solubility in acid but is readily soluble at neutral or basic pH. These properties allow FDKP to crystallize under acidic conditions and the crystals self-assemble to form particles. The particles dissolve readily under physiological conditions where the pH is neutral. As noted, microparticles having a diameter of between about 0.5 and about 10 microns can reach the lungs, successfully passing most of the natural barriers. Particles in this size range can be readily prepared from FDKP. In one embodiment, the microparticles disclosed herein are FDKP microparticles loaded with an active agent such as insulin.

FDKP is a chiral molecule having trans and cis isomers with respect to the arrangement of the substituents on the substituted carbons on the DKP ring. As described in U.S. Provisional Patent Application No. 61/186,779 entitled DIKETOPIPERAZINE MICROPARTICLES WITH DEFINED ISOMER CONTENTS filed on date even with the present disclosure, more robust aerodynamic performance and consistency of particle morphology can be obtained by confining the isomer content to about 45-65% trans. Isomer ratio can be controlled in the synthesis and recrystallization of the molecule. Exposure to base promotes ring epimerization leading to racemization, for example during the removal of protecting groups from the terminal carboxylate groups. However increasing methanol content of the solvent in this step leads to increased trans isomer content. The trans isomer is less soluble than the cis isomers and control of temperature and solvent composition during recrystallization can be used to promote or reduce enrichment for the trans isomer in this step.

FDKP possesses two asymmetric centers in the diketopiperazine ring. FDKP is manufactured as a mixture of geometric isomers that are identified as "cis-FDKP" and "trans-FDKP" according to the arrangement of side chains relative to the central "ring" of the diketopiperazine. The R,R and S,S enantiomers have the propenyl(amidobutyl) "side arms" projecting from the same planar side of the diketopiperazine ring (A and B below) and are thus referred to as the cis isomers while the R,S compound has the "side arms" projecting from opposite planar sides of the diketopiperazine ring (C below) and is referred to as the trans isomer.

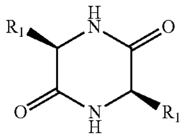

A

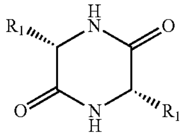

B

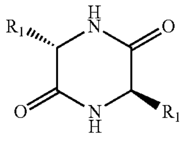

C

Figure 82:
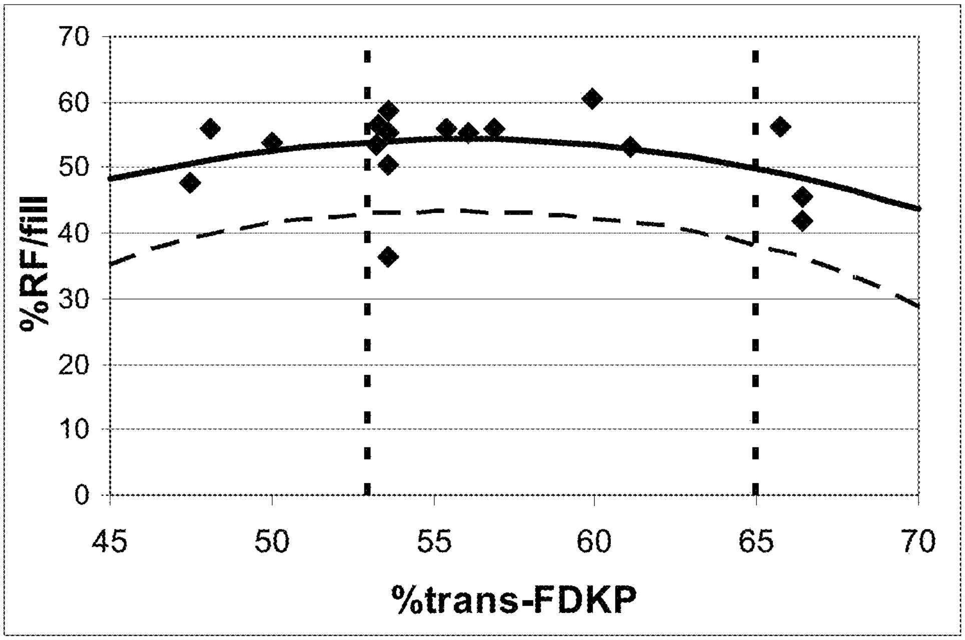
FIG. 82 depicts aerodynamic powder performance as a function of % trans isomer content.

FDKP microparticle powders with acceptable aerodynamic performance, as measured by RF/fill with moderately efficient inhalers such as the MEDTONE® inhaler disclosed in U.S. Pat. No. 7,464,706 entitled, "Unit Dose Cartridge and Dry Powder Inhaler," which is incorporated by reference herein for its teachings regarding the same, have been produced from FDKP with a trans isomer content ranging from about 45 to about 65%. Particles with isomer content in this range also perform well with high efficiency inhalers such as that disclosed in U.S. patent application Ser. No. 12/484,137 entitled, "A Dry Powder Inhaler and System for Drug Delivery," filed on Jun. 12, 2009, which is incorporated by reference herein for its teachings regarding the same. Microparticle powders containing more than 65% trans-FDKP tend to have lower and more variable RF/fill (FIG. 82). Trans-enriched particles have altered morphology and also lead to viscous suspensions which are difficult to process.

In other experiments done under comparable conditions to those reported in FIG. 82, microparticles made from about 95% trans-enriched FDKP and loaded with insulin gave an RF/fill of about 24% whereas control samples with a trans isomer content of about 59% gave an RF/fill of about 49-52% (data not shown). Accordingly, a microparticle powder having a trans isomer content of about 45 to about 65% provides a powder with acceptable aerodynamic properties. In alternate embodiments the trans isomer content ranges from about 53 to about 65% (see FIG. 82) or from about 53 to about 63%, or from about 50 to about 56%, or from about 54 to about 56%.

Based on the foregoing, it is desirable to produce microparticle powders having a trans isomer content within the range of about 45 to about 65%. That isomer content would affect the aerodynamic performance of FDKP microparticles was not anticipated. However, it was discovered that improved consistency could be obtained by carefully controlling the isomer content of the FDKP used to make the microparticles. In FIG. 82, the solid curved line represents predicted RF/fill and the dashed curved line represents the one-sided lower 95% confidence limit of obtaining an appropriate RF/fill score. The vertical dashed lines provide limits on the trans isomer content for one exemplary embodiment disclosed herein.

Figure 83:
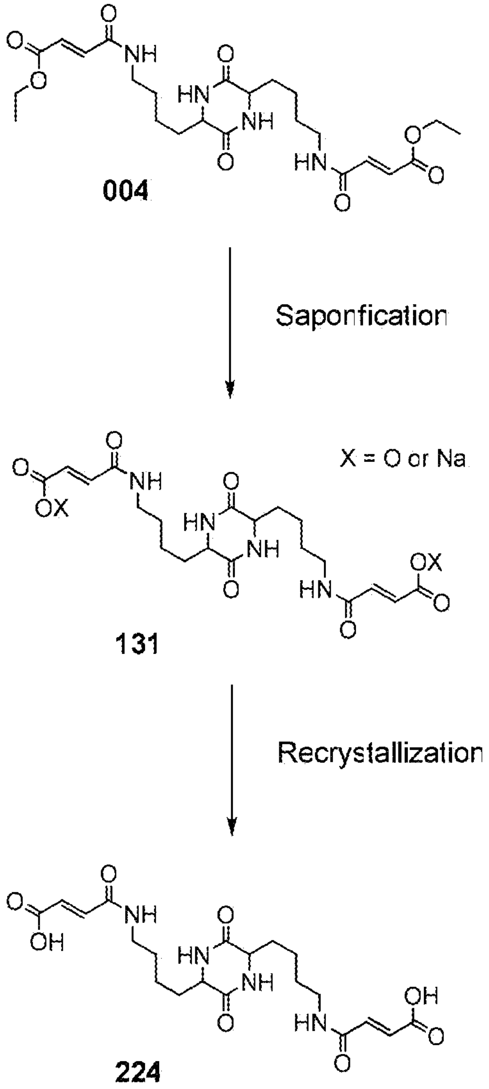
FIG. 83 depicts steps in a synthetic scheme that can be controlled so as to produce FDKP with a trans isomer content of about 45 to about 65%.

The FDKP cis/trans isomer ratio is established during the manufacturing steps depicted in FIG. 83.

Control of the Lower End of the Trans Isomer Content

Figure 84:
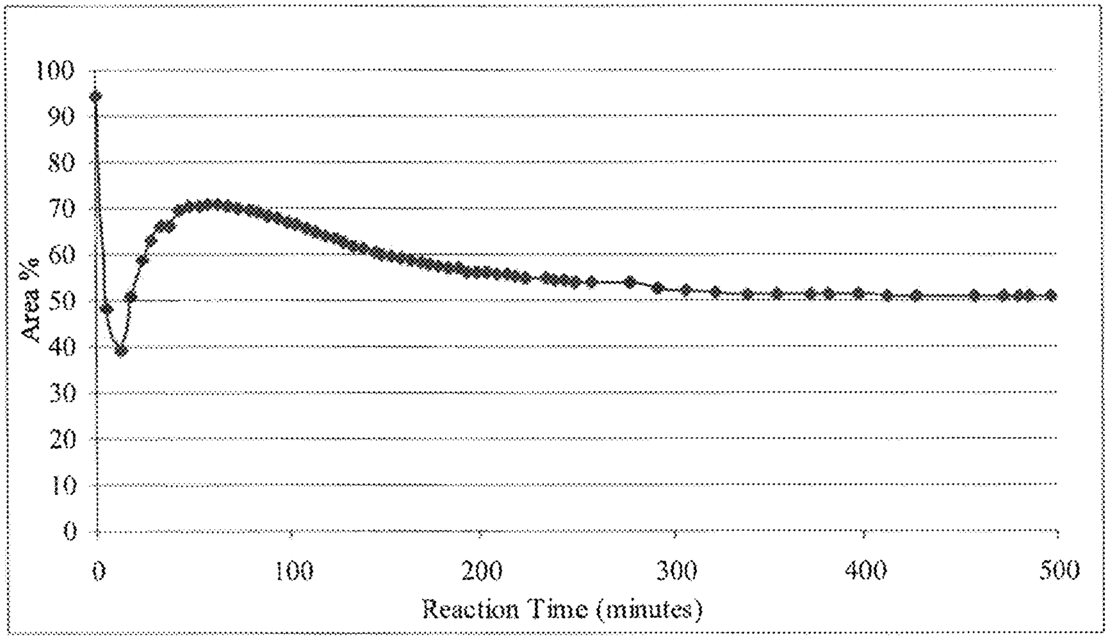
FIG. 84 depicts % trans isomer content as a function of slow NaOH addition during the saponification step of the scheme depicted in FIG. 2.

The lower end of the trans isomer content is controlled by exposing the DKP ring to a strong base. In one manufacturing step, ethyl protecting groups are removed by saponification with sodium hydroxide. These basic conditions promote ring epimerization between isomers as shown below, without regard for which isomer is in excess. Thus, the addition of base to material with 95% trans isomer appeared to favor an approximate 50/50 mixture of cis and trans isomers (FIG. 84). Other factors, such as concentration of co-solvents like methanol, may also affect isomer content.

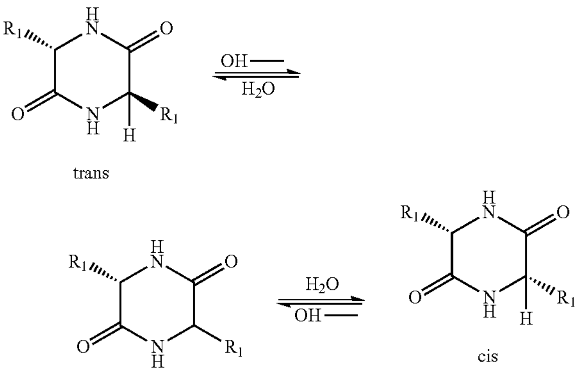

Control of the Upper End of the Trans Isomer Range

Figure 85:
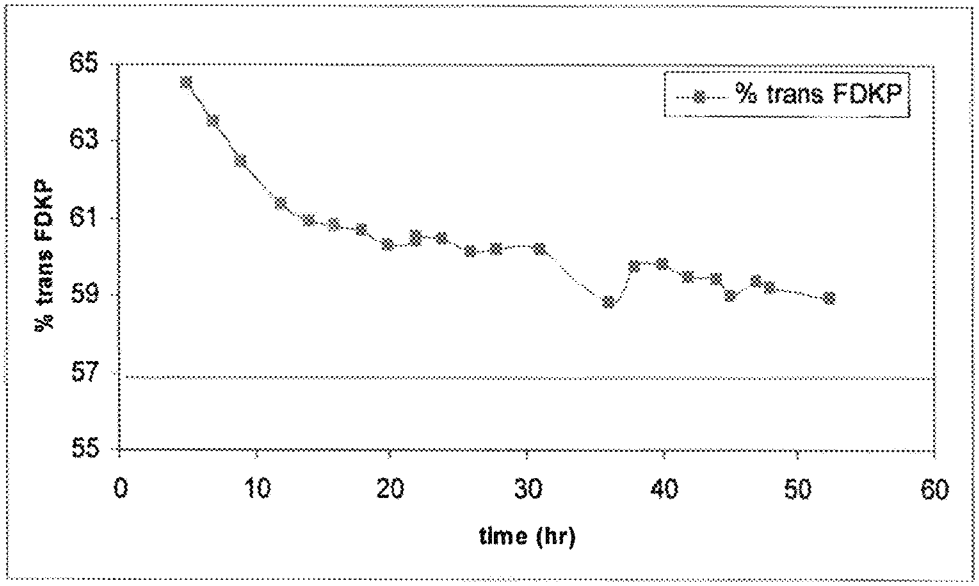
FIG. 85 depicts % trans isomer content after trifluoroacetic acid (TFA) recrystallization using a fast cooling ramp.

Differences in solubility between the isomers affect the FDKP isomer content. For instance, FDKP can be recrystallized from trifluoroacetic acid (TFA) and glacial acetic acid (GAA). Trans FDKP is less soluble in this solvent system than cis FDKP. Accordingly, conditions that favor selective precipitation of the less soluble trans isomer can be used to increase the trans isomer content of the final product. Such conditions include decreased recrystallization time, anti-solvent addition at low temperature and/or rapid cooling of the TFA-GAA mixture (FIG. 85). It will also be appreciated that elevating the trans isomer content by such methods provides a residual solution of FDKP enriched in the cis isomers.

TABLE 1

| Exemplary Manufacturing Ranges | |
|---|---|
| Parameter | Suggested Operating Range |
| TFA/GAA Ratio | 0.67 ± 0.05 |
| Crystallization Time (hrs) | 6 ± 0.5 |
| Crystallization Temp (° C.) | 15-25 |
| Cooling Ramp Post GAA Addition (° C./hr) | 7-10 |

Providing microparticles with an isomer content in the about 45 to about 65% range provides microparticles with beneficial aerodynamic characteristics.

As long as the microparticles described herein retain the required isomer content, they can adopt other additional characteristics beneficial for delivery to the lung and/or drug adsorption. U.S. Pat. No. 6,428,771 entitled “Method for Drug Delivery to the Pulmonary System” describes DKP particle delivery to the lung and is incorporated by reference herein for its teachings regarding the same. U.S. Pat. No. 6,444,226, entitled, “Purification and Stabilization of Peptide and Protein Pharmaceutical Agents” describes beneficial methods for adsorbing drugs onto microparticle surfaces and is also incorporated by reference herein for its teachings regarding the same. Microparticle surface properties can be manipulated to achieve desired characteristics as described in U.S. patent application Ser. No. 11/532,063 entitled “Method of Drug Formulation based on Increasing the Affinity of Crystalline Microparticle Surfaces for Active Agents” which is incorporated by reference herein for its teachings regarding the same. U.S. patent application Ser. No. 11/532,065 entitled “Method of Drug Formation based on Increasing the Affinity of Active Agents for Crystalline Microparticle Surfaces” describes methods for promoting adsorption of active agents onto microparticles. U.S. patent application Ser. No. 11/532,065 is also incorporated by reference herein for its teachings regarding the same.

Selection and Incorporation of Active Agents

The microparticles described herein can be loaded with one or more active agents. As used herein “active agent”, used interchangeably with “drug” refers to pharmaceutical substances, small molecule pharmaceuticals, biologicals and bioactive agents. Active agents can be naturally occurring, recombinant or synthetic proteins, polypeptides, peptides, nucleic acids, organic macromolecules, synthetic organic compounds, polysaccharides and other sugars, fatty acids, and lipids, and antibodies and fragments thereof, including, but not limited to, humanized or chimeric antibodies, F(ab), $F(ab)_2$, a single-chain antibody alone or fused to other polypeptides or therapeutic or diagnostic monoclonal antibodies to cancer antigens. The active agents can fall under a variety of biological activity classes, such as vasoactive agents, neuroactive agents, hormones, anticoagulants, immunomodulating agents, cytotoxic agents, antibiotics, antiviral agents, antigens, infectious agents, inflammatory mediators, hormones, and cell surface antigens. More particularly, active agents can include, in a non-limiting manner, cytokines, lipokines, enkephalins, alkynes, cyclosporins, anti-IL-8 antibodies, IL-8 antagonists including ABX-IL-8; prostaglandins including PG-12, LTB receptor blockers including LY29311, BIIL 284 and CP105696; triptans such as sumatriptan and palmitoleate, insulin and analogs thereof, growth hormone, parathyroid hormone (PTH), parathyroid hormone related peptide (PTHrP), ghrelin, granulocyte macrophage colony stimulating factor (GM-CSF), amylin, amylin analogs, glucagon-like peptide 1 (GLP-1), Texas Red, clopidogrel, PPACK (D-phenylalanyl-L-prolyl-L-arginine chloromethyl ketone), oxyntomodulin (OXN), peptide YY(3-36) (PYY), adiponectin, cholecystokinin (CCK), secretin, gastrin, glucagon, motilin, somatostatin, brain natriuretic peptide (BNP), atrial natriuretic peptide (ANP), IGF-1, growth hormone releasing factor (GHRF), integrin beta-4 precursor (ITB4) receptor antagonist, nociceptin, nocistatin, orphanin FQ2, calcitonin, CGRP, angiotensin, substance P, neurokinin A, pancreatic polypeptide, neuropeptide Y, delta-sleep-inducing peptide and vasoactive intestinal peptide.

The range of loading of the drug to be delivered is typically between about 0.01% and about 20%, depending on the form and size of the drug to be delivered. For insulin, preferred loads are about 10-15% (corresponding to 3-4 U/mg).

The following describes a manufacturing process that can be used to produce insulin-loaded FDKP microparticles with a trans isomer content from about 45 to about 65%.

Insulin-loaded FDKP microparticles can be prepared according to the schematic depicted in FIG. 5. Using a Dual-feed Sonolator™, equal masses of about 10.5 wt % acetic acid and about 2.5 wt % FDKP solutions at about 16° C.±about 2° C. (Table 2 and 3) can be fed at 2000 psi through a 0.001-$in^2$ orifice. The precipitate can be collected in a DI water reservoir of about equal mass and temperature. At this point the suspension contains about 0.8% solids. The precipitate can be concentrated and washed by tangential flow filtration. The precipitate can be first concentrated to about 4% solids then washed with DI water. The suspension can be finally concentrated to about 10% solids based on the initial mass of FDKP. The concentrated suspension can be assayed for solids content by an oven drying method.

A concentrated insulin stock solution can be prepared with 1 part insulin and 9 parts about 2% wt acetic acid. The insulin stock can be added gravimetrically to the suspension to obtain a load of about 11.4% wt. The insulin-loaded suspension can be mixed at least about 15 minutes, and then titrated with about 14 to about 15 wt % aqueous ammonia to a pH of about 4.5 from an initial pH of about 3.5. The suspension can be flash frozen in liquid nitrogen to form pellets and lyophilized to yield the bulk insulin-loaded FDKP microparticles with a % trans isomer content of between about 45% and 65%. Blank FDKP microparticles can be manufactured identically minus the insulin loading and pH adjustment steps.

TABLE 2

| 10.5% Acetic Acid Solution | |
|---|---|
| Component | wt % |
| DI Water | 89.00 |
| GAA | 10.50 |
| 10% Polysorbate 80 | 0.50 |

0.2 μm filtered

TABLE 3

| 2.5% FDKP Solution | |
|---|---|
| Component | wt % |
| DI Water | 95.40 |
| FDKP | 2.50 |
| $NH_4OH$ | 1.60 |
| 10% Polysorbate 80 | 0.50 |

0.2 μm filtered

As used herein, "solvent" refers to the fluid medium in which the active agent and microparticle are "bathed." It should not be interpreted to require that all components are in solution. Indeed in many instances it may be used to refer to the liquid medium in which the microparticles are suspended.

As is evident from the foregoing disclosure, microparticles of embodiments disclosed herein can take many different forms and incorporate many different drugs or active agents. The common attribute of each of these embodiments, however, is that the formed microparticles have a trans isomer content of about 45 to about 65%.

Microparticles having a diameter of between about 0.5 and about 10 microns can reach the lungs, successfully passing most of the natural barriers. A diameter of less than about 10 microns is required to navigate the turn of the throat and a diameter of about 0.5 microns or greater is required to avoid being exhaled. DKP microparticles with a specific surface area (SSA) of between about 35 and about 67 m2/g exhibit characteristics beneficial to delivery of drugs to the lungs such as improved aerodynamic performance and improved drug adsorption.

As described in U.S. Provisional Patent Application No. 61/186,773 entitled DIKETOPIPERAZINE MICROPARTICLES WITH DEFINED SPECIFIC SURFACE AREAS filed on date even with the present disclosure, the size distribution and shape of FDKP crystals are affected by the balance between the nucleation of new crystals and the growth of existing crystals. Both phenomena depend strongly on concentrations and supersaturation in solution. The characteristic size of the FDKP crystal is an indication of the relative rates of nucleation and growth. When nucleation dominates, many crystals are formed but they are relatively small because they all compete for the FDKP in solution. When growth dominates, there are fewer competing crystals and the characteristic size of the crystals is larger.

Crystallization depends strongly on supersaturation which, in turn, depends strongly on the concentration of the components in the feed streams. Higher supersaturation is associated with the formation of many small crystals; lower supersaturation produces fewer, larger crystals. In terms of supersaturation: 1) increasing the FDKP concentration raises the supersaturation; 2) increasing the concentration of ammonia shifts the system to higher pH, raises the equilibrium solubility and decreases the supersaturation; and 3) increasing the acetic acid concentration increases the supersaturation by shifting the endpoint to lower pH where the equilibrium solubility is lower. Decreasing the concentrations of these components induces the opposite effects.

Temperature affects FDKP microparticle formation through its effect on FDKP solubility and the kinetics of FDKP crystal nucleation and growth. At low temperatures, small crystals are formed with high SSA. Suspensions of these particles exhibit high viscosity indicating strong interparticle attractions. A temperature range of about 12 to about 26° C. produced particles with acceptable (or better) aerodynamic performance with various inhaler systems including inhaler systems disclosed herein.

These present devices and systems are useful in the pulmonary delivery or powders with a wide range of characteristics. Embodiments of the invention include systems comprising an inhaler, an integral or installable unit dose cartridge, and powder of defined characteristic(s) providing an improved or optimal range of performance. For example, the devices constitute an efficient deagglomeration engine and thus can effectively deliver cohesive powders. This is distinct from the course pursued by many others who have sought to develop dry powder inhalation systems based on free flowing or flow optimized particles (see for example U.S. Pat. Nos. 5,997,848 and 7,399,528, US Patent Application No. 2006/0260777; and Ferrari et al. AAPS PharmSciTech 2004; 5 (4) Article 60). Thus embodiments of the invention include systems of the device plus a cohesive powder.

Cohesiveness of a powder can be assessed according to its flowability or correlated with assessments of shape and irregularity such as rugosity. As discussed in the US Pharmacopeia USP 29, 2006 section 1174 four techniques commonly used in the pharmaceutical arts to assess powder flowability: angle of repose; compressibility (Carr's) index and Hausner ratio; flow through an orifice; and shear cell methods. For the latter two no general scales have been developed due to diversity of methodology. Flow through an orifice can be used to measure flow rate or alternatively to determine a critical diameter that allows flow. Pertinent variables are the shape and diameter of the orifice, the diameter and height of the powder bed, and the material the apparatus is made of. Shear cell devices include cylindrical, annular, and planar varieties and offer great degree of experimental control. For either of these two methods description of the equipment and methodology are crucial, but despite the lack of general scales they are successfully used to provide qualitative and relative characterizations of powder flowability.

Angle of repose is determined as the angle assumed by a cone-like pile of the material relative to a horizontal base upon which it has been poured. Hausner ratio is the unsettled volume divided by the tapped volume (that is the volume after tapping produces no further change in volume), or alternatively the tapped density divided by the bulk density. The compressibility index (CI) can be calculated from the Hausner ratio (HR) as $$CI=100\times(1-(1/HR)).$$

Despite some variation in experimental methods generally accepted scales of flow properties have been published for angle of repose, compressibility index and Hausner ratio (Carr, R L, Chem. Eng. 1965, 72:163-168).

| Flow Character | Angle of Repose | Hausner Ratio | Compressibility Index (%) |
|---|---|---|---|
| Excellent | 25-30° | 1.00-1.11 | ≤10 |
| Good | 31-35° | 1.12-1.18 | 11-15 |
| Fair | 36-40° | 1.19-1.25 | 16-20 |
| Passable | 41-45° | 1.26-1.34 | 21-25 |
| Poor | 46-55° | 1.35-1.45 | 26-31 |
| Very Poor | 56-65° | 1.46-1.59 | 32-27 |
| Very, Very Poor | ≥66° | ≥1.60 | ≥38 |

The CEMA code provides a somewhat different characterization of angle of repose.

| Angle of repose | Flowability |
|---|---|
| ≤19° | Very free flowing |
| 20-29° | Free flowing |
| 30-39° | Average |
| ≥40° | Sluggish |

Powders with a flow character according to the table above that is excellent or good can be characterized in terms of cohesiveness as non- or minimally cohesive, and the powders with less flowability as cohesive and further dividing them between moderately cohesive (corresponding to fair or passable flow character) and highly cohesive (corresponding to any degree of poor flow character). In assessing angle of repose by the CEMA scale powders with an angle of repose≥30° can be considered cohesive and those≥40° highly cohesive. Powders in each of these ranges, or combinations thereof, constitute aspects of distinct embodiments of the invention.

Cohesiveness can also be correlated with rugosity, a measure of the irregularity of the particle surface. The rugosity is the ratio of the actual specific surface area of the particle to that for an equivalent sphere:

$$\text{Rugosity} = \frac{(SSA)_{particle}}{(SSA)_{sphere}}$$

Methods for direct measurement of rugosity, such as air permeametry, are also known in the art. Rugosity of 2 or greater has been associated with increased cohesiveness. It should be kept in mind that particle size also affects flowability so that larger particles (for example on the order of 100 microns) can have reasonable flowability despite somewhat elevated rugosity. However for particles useful for delivery into the deep lung, such as those with primary particle diameters of 1-3 microns, even modestly elevated rugosity or 2-6 may be cohesive. Highly cohesive powders can have rugosities≥10 (see example A below).

Many of the examples below involve the use of dry powders comprising fumaryl diketopiperazine (3,6-bis(N-fumaryl-4-aminobutyl)-2,5-diketopiperazine; FDKP). The component microparticles are self-assembled aggregates of crystalline plates. Powders comprised of particles with plate-like surfaces are known to have generally poor flowability, that is, they are cohesive. Indeed smooth spherical particles generally have the best flowability, with flowability generally decreasing as the particles become oblong, have sharp edges, become substantially two dimensional and irregularly shaped, have irregular interlocking shapes, or are fibrous. While not wanting to be bound, it is the applicants' present understanding that the crystalline plates of the FDKP microparticles can interleave and interlock contributing to the cohesiveness (the inverse of flowability) of bulk powders comprising them and additionally making the powder more difficult to deagglomerate than less cohesive powders. Moreover factors affecting the structure of the particles can have effects on aerodynamic performance. It has been observed that as specific surface area of the particles increases past a threshold value their aerodynamic performance, measured as respirable fraction, tends to decrease. Additionally FDKP has two chiral carbon atoms in the piperazine ring, so that the N-fumaryl-4-aminobutyl arms can be in cis or trans configurations with respect to the plane of the ring. It has been observed that as the trans-cis ratio of the FDKP used in making the microparticles departs from an optimal range including the racemic mixture respirable fraction is decreased and at greater departures from the preferred range the morphology of the particles in SEM becomes visibly different. Thus embodiments of the invention include systems of the device plus DKP powders with specific surface areas within preferred ranges, and the device plus FDKP powders with trans-cis isomer ratios within preferred ranges.

FDKP microparticles either unmodified or loaded with a drug, for example insulin, constitute highly cohesive powders. FDKP microparticles have been measured to have a Hausner ratio of 1.8, a compressibility index of 47%, and an angle of repose of 40°. Insulin loaded FDKP microparticles (TECHNOSPHERE® INSULIN; TI) have been measured to have a Hausner ratio of 1.57, a compressibility index of 36%, and an angle of repose of 50°±3°. Additionally in critical orifice testing it was estimated that to establish flow under gravity an orifice diameter on the order of 2 to 3 feet (60-90 cm) would be needed (assumes a bed height of 2.5 feet; increased pressure increased the size of the diameter needed). Under similar conditions a free flowing powder would require an orifice diameter on the order of only 1-2 cm (Taylor, M. K. et al. *AAPS PharmSciTech* 1, art. 18).

Accordingly, in one embodiment, the present inhalation system comprises a dry powder inhaler and a container for deagglomerating cohesive powder is provided, comprising a cohesive dry powder having a Carr's index ranging from 16 to 50. In one embodiment, the dry powder formulation comprises a diketopiperazine, including, FDKP and a peptide or protein including an endocrine hormone such as insulin, GLP-1, parathyroid hormone, oxyntomodulin, and others as mentioned elsewhere in this disclosure.

Microparticles having a diameter of between about 0.5 and about 10 microns can reach the lungs, successfully passing most of the natural barriers. A diameter of less than about 10 microns is required to navigate the turn of the throat and a diameter of about 0.5 microns or greater is required to avoid being exhaled. Embodiments disclosed herein show that microparticles with a specific surface area (SSA) of between about 35 and about 67 $m^2/g$ exhibit characteristics beneficial to delivery of drugs to the lungs such as improved aerodynamic performance and improved drug adsorption.

Disclosed herein are also fumaryl diketopiperazine (FDKP) microparticles having a specific trans isomer ratio of about 45 to about 65%. In this embodiment, the microparticles provide improved flyability.

In one embodiment, there is also provided a system for the delivery of an inhalable dry powder comprising: a) a cohesive powder comprising a medicament, and b) an inhaler comprising an enclosure defining an internal volume for containing a powder, the enclosure comprising a gas inlet and a gas outlet wherein the inlet and the outlet are positioned so that gas flowing into the internal volume through the inlet is directed at the gas flowing toward the outlet. In an embodiment, the system is useful for deagglomerating a cohesive powder having a Carr's index of from 18 to 50. The system can also be useful for delivering a powder when the cohesive powder has an angle of repose from 30° to 55°. The cohesive powder can be characterized by a critical orifice dimension of ≤3.2 feet for funnel flow or ≤2.4 feet for mass flow, a rugosity>2. Exemplary cohesive powder particles include particles comprising of FDKP crystals wherein the ratio of FDKP isomers in the range of 50% to 65% trans:cis.

In another embodiment, the inhalation system can comprise an inhaler comprising a mouthpiece and upon applying a pressure drop of ≥2 kPa across the inhaler to generate a plume of particles which is emitted from the mouthpiece wherein 50% of said emitted particles have a VMAD of ≤10 micron, wherein 50% of said emitted particles have a VMAD of ≤8 microns, or wherein 50% of said emitted particles have a VMAD of ≤4 microns.

In yet another embodiment, a system for the delivery of an inhalable dry powder comprising: a) a dry powder comprising particles composed of FDKP crystals wherein the ratio of FDKP isomers in the range of 50% to 65% trans:cis, and a medicament; and b) an inhaler comprising a powder containing enclosure, the chamber comprising a gas inlet and a gas outlet; and a housing in which to mount said chamber and defining two flow pathways, a first flow pathway allowing gas to enter the gas inlet of the chamber, a second flow pathway allowing gas to bypass the chamber gas inlet; wherein flow bypassing the enclosure gas inlet is directed to impinge upon the flow exiting the enclosure substantially perpendicular to the gas outlet flow direction.

In certain embodiments, a system for the delivery of an inhalable dry powder is provided, comprising: a) a dry powder comprising particles composed of FDKP crystals wherein the microparticles have a specific surface area (SSA) of between about 35 and about 67 $m^2/g$ which exhibit characteristics beneficial to delivery of drugs to the lungs such as improved aerodynamic performance and improved drug adsorption per milligram, and a medicament; and b) an inhaler comprising a powder containing enclosure, wherein the enclosure comprises a gas inlet and a gas outlet; and a housing in which to mount said chamber and defining two flow pathways, a first flow pathway allowing gas to enter the gas inlet of the chamber, a second flow pathway allowing gas to bypass the chamber gas inlet; wherein flow bypassing the chamber gas inlet is directed to impinge upon the flow exiting the enclosure substantially perpendicular to the gas outlet flow direction.

A system for the delivery of an inhalable dry powder is also provided, comprising: a) a dry powder comprising a medicament, and b) an inhaler comprising a powder containing cartridge, the cartridge comprising a gas inlet and a gas outlet, and a housing in which to mount the cartridge and defining two flow pathways, a first flow pathway allowing gas to enter the gas inlet of the cartridge, a second flow pathway allowing gas to bypass the enclosure gas inlet, and a mouthpiece and upon applying a pressure drop of ≥2 kPa across the inhaler plume of particles is emitted from the mouthpiece wherein 50% of said emitted particles have a VMAD of ≤10 microns, wherein flow bypassing the cartridge gas inlet is directed to impinge upon the flow exiting the enclosure substantially perpendicular to the gas outlet flow direction.

Active agents for use in the compositions and methods described herein can include any pharmaceutical agent. These can include, for example, synthetic organic compounds, proteins and peptides, polysaccharides and other sugars, lipids, inorganic compound, and nucleic acid sequences, having therapeutic, prophylactic, or diagnostic activities. Peptides, proteins, and polypeptides are all chains of amino acids linked by peptide bonds.

Examples of active agents that can be delivered to a target or site in the body using the diketopiperazine formulations, include hormones, anticoagulants, immunomodulating agents, vaccines, cytotoxic agents, antibiotics, vasoactive agents, neuroactive agents, anaesthetics or sedatives, steroids, decongestants, antivirals, antisense, antigens, and antibodies. More particularly, these compounds include insulin, heparin (including low molecular weight heparin), calcitonin, felbamate, sumatriptan, parathyroid hormone and active fragments thereof, growth hormone, erythropoietin, AZT, DDI, granulocyte macrophage colony stimulating factor (GM-CSF), lamotrigine, chorionic gonadotropin releasing factor, luteinizing releasing hormone, beta-galactosidase, exendin, vasoactive intestinal peptide, and argatroban. Antibodies and fragments thereof can include, in a non-limiting manner, anti-SSX-$2_{41-49}$ (synovial sarcoma, X breakpoint 2), anti-NY-ESO-1 (esophageal tumor associated antigen), anti-PRAME (preferentially expressed antigen of melanoma), anti-PSMA (prostate-specific membrane antigen), anti-Melan-A (melanoma tumor associated antigen) and anti-tyrosinase (melanoma tumor associated antigen).

In certain embodiments, a dry powder formulation for delivering to the pulmonary circulation comprises an active ingredient or agent, including a peptide, a protein, a hormone, analogs thereof or combinations thereof, wherein the active ingredient is insulin, calcitonin, growth hormone, erythropoietin, granulocyte macrophage colony stimulating factor (GM-CSF), chorionic gonadotropin releasing factor, luteinizing releasing hormone, follicle stimulating hormone (FSH), vasoactive intestinal peptide, parathyroid hormone (including black bear PTH), parathyroid hormone related protein, glucagon-like peptide-1 (GLP-1), exendin, oxyntomodulin, peptide YY, interleukin 2-inducible tyrosine kinase, Bruton's tyrosine kinase (BTK), inositol-requiring kinase 1 (IRE1), or analogs, active fragments, PC-DAC-modified derivatives, or O-glycosylated forms thereof. In particular embodiments, the pharmaceutical composition or dry powder formulation comprises fumaryl diketopiperazine and the active ingredient is one or more selected from insulin, parathyroid hormone 1-34, GLP-1, oxyntomodulin, peptide YY, heparin and analogs thereof.

In one embodiment, a method of self-administering a dry powder formulation to one's lung with a dry powder inhalation system is also provided, comprising: obtaining a dry powder inhaler in a closed position and having a mouthpiece; obtaining a cartridge comprising a premetered dose of a dry powder formulation in a containment configuration; opening the dry powder inhaler to install the cartridge; closing the inhaler to effectuate movement of the cartridge to a dose position; placing the mouthpiece in one's mouth, and inhaling once deeply to deliver the dry powder formulation.

In one embodiment, a method of delivering an active ingredient comprising: a) providing dry powder inhaler containing a cartridge with a dry powder formulation comprising a diketopiperazine and the active agent; and b) delivering the active ingredient or agent to an individual in need of treatment. The dry powder inhaler system can deliver a dry powder formulation such as insulin FDKP having a respirable fraction greater than 50% and particles sizes less than 5.8 μm.

In still yet a further embodiment, a method of treating obesity, hyperglycemia, insulin resistance, and/or diabetes is disclosed. The method comprises the administration of an inhalable dry powder composition or formulation comprising a diketopiperazine having the formula 2,5-diketo-3,6-di (4-X-aminobutyl)piperazine, wherein X is selected from the group consisting of succinyl, glutaryl, maleyl, and fumaryl. In this embodiment, the dry powder composition can comprise a diketopiperazine salt. In still yet another embodiment of the present invention, there is provided a dry powder composition or formulation, wherein the diketopiperazine is 2,5-diketo-3,6-di-(4-fumaryl-aminobutyl)piperazine, with or without a pharmaceutically acceptable carrier, or excipient.

An inhalation system for delivering a dry powder formulation to a patient's lung, comprising a dry powder inhaler configured to have flow conduits with a total resistance to flow in a dosing configuration ranging in value from 0.065 to about 0.200 (√kPa)/liter per minute.

In one embodiment, a dry powder inhalation kit is provided comprising a dry powder inhaler as described above, one or more medicament cartridge comprising a dry powder formulation for treating a disorder or disease such as respiratory tract disease, diabetes and obesity.

Example 1

Measuring the resistance and flow distribution of a dry powder inhaler—cartridge system: Several dry powder inhaler designs were tested to measure their resistance to flow—an important characteristic of inhalers. Inhalers exhibiting high resistance require a greater pressure drop to yield the same flow rate as lower resistance inhalers. Briefly, to measure the resistance of each inhaler and cartridge system, various flow rates are applied to the inhaler and the resulting pressures across the inhaler are measured. These measurements can be achieved by utilizing a vacuum pump attached to the mouthpiece of the inhaler, to supply the pressure drop, and a flow controller and pressure meter to change the flow and record the resulting pressure. According to the Bernoulli principle, when the square root of the pressure drop is plotted versus the flow rate, the resistance of the inhaler is the slope of the linear portion of the curve. In these experiments, the resistance of the inhalation system, comprising a dry powder inhaler and cartridge as described herein, were measured in the dosing configuration using a resistance measuring device. The dosing configuration forms an air pathway through the inhaler air conduits and through the cartridge in the inhaler.

Figure 80:
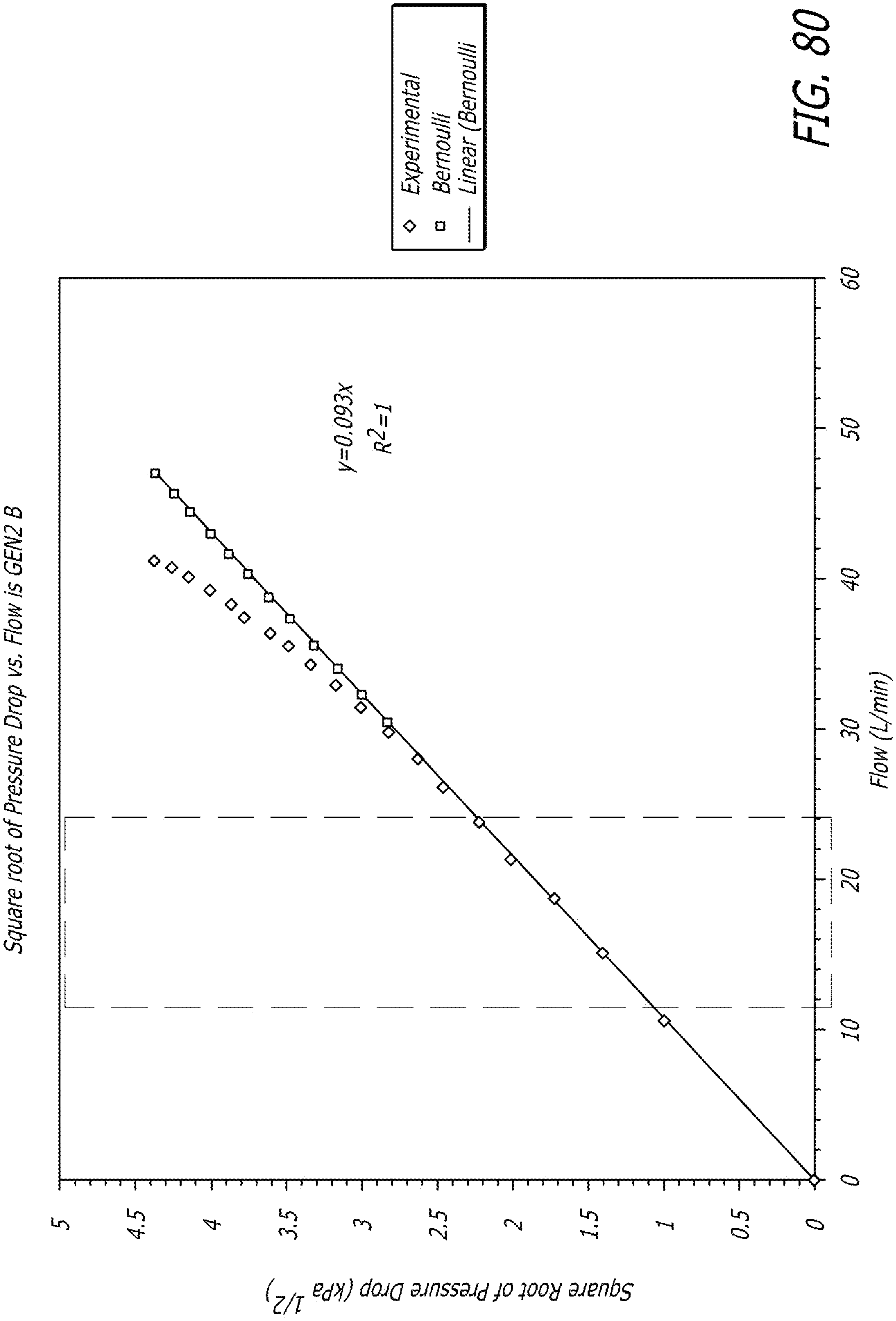
FIG. 80 illustrates a graph of measurements of flow and pressure relationship based on the Bernoulli principle for an exemplary embodiment of the resistance to flow of an inhaler.

Since different inhaler designs exhibit different resistance values due to slight variations in geometries of their air pathways, multiple experiments were conducted to determine the ideal interval for pressure settings to use with a particular design. Based on the Bernoulli principle of linearity between square root of pressure and flow rate, the intervals for assessing linearity were predetermined for the three inhalers used after multiple tests so that the appropriate settings could be used with other batches of the same inhaler design. An exemplary graph for an inhaler can be seen in FIG. 80 for an inhalation system depicted in FIG. 15I. The graph depicted in FIG. 80 indicates that the resistance of the inhalation system as depicted in FIG. 15I can be measured with good correlation to the Bernoulli principle at flow rates ranging from about 10 to 25 L/min. The graph also shows that the resistance of the exemplary inhalation system was determined to be 0.093 √kPa/LPM. FIG. 80 illustrates that flow and pressure are related. Therefore, as the slope of the line in square root of pressure versus flow graph decreases, i.e., inhalation systems exhibiting lower resistance, the change in flow for a given change in pressure is greater. Accordingly, higher resistance inhalation systems would exhibit less variability in flow rates for given changes in pressure provided by the patient with a breath powered system.

The data in Tables 1 show the results of a set of experiments using the inhalers described in FIG. 50 (DPI 1), and FIGS. 15C-15K (DPI 2). For the dry powder inhaler 1 (DPI 1), the cartridge illustrated in design 150, FIGS. 35-38, was used, and the cartridge illustrated in design 170, FIG. 39A-I was used with DPI 2. Accordingly, DPI 1 used Cartridge 1 and DPI 2 used Cartridge 2.

TABLE 1

| Device Tested | Total Device Resistance | Cartridge Resistance | % of Total Flow Through Cartridge |
|---|---|---|---|
| MedTone ® | 0.1099 | 0.368 | 15.28 |
| DPI 1 | 0.0874 | 0.296 | 29.50 |
| DPI 2 | 0.0894 | 0.234 | 35.56 |

Table 1 illustrates the resistance of the inhalation system tested herewith is 0.0874 and 0.0894 √kPa/LPM, respectively for DPI 1 and DPI 2. The data show that the resistance of the inhalation system to flow is in part determined by the geometry of the air conduits within the cartridge.

Example 2

Measurement of particle size distribution using an inhaler system with an insulin formulation: Measurements of the particle size distribution with a laser diffraction apparatus (Helos Laser Diffraction system, Sympatec Inc.) with an adaptor (MannKind Corp.) were made of a formulation of various amounts in milligram (mg) of an insulin and fumaryl diketopiperazine particles provided in a cartridge-inhaler system as described herewith (inhaler of FIGS. 15C-15K with cartridge 170 shown in FIGS. 39A-39I). The device is attached at one end to a tubing, which is adapted to a flow meter (TSI, Inc. Model 4043) and a valve to regulate pressure or flow from a compressed air source. Once the laser system is activated and the laser beam is ready to measure a plume, a pneumatic valve is actuated to allow the powder to be discharged from the inhaler. The laser system measures the plume exiting the inhaler device automatically based on predetermined measurement conditions. The laser diffraction system is operated by software integrated with the apparatus and controlled by computer program. Measurements were made of samples containing different amounts of powder and different powder lots. The measurement conditions are as follows:

Laser measurement start trigger conditions: when ≥0.6% laser intensity is detected on a particular detector channel;

Laser measurement end trigger conditions: when ≤0.4% laser intensity is detected on a particular detector channel;

Distance between vacuum source and inhaler chamber is approximately 9.525 cm.

Multiple tests were carried out using different amounts of powders or fill mass in the cartridges. Cartridges were only used once. Cartridge weights were determined before and after powder discharge from the inhaler to determine discharged powder weights. Measurements in the apparatus were determined at various pressure drops and repeated multiple times as indicated in Table 2 below. Once the powder plume is measured, the data is analyzed and graphed. Table 2 depicts data obtained from the experiments, wherein CE denotes cartridge emptying (powder discharged) and Q3 (50%) is the geometric diameter of the $50^{th}$ percentile of the cumulative powder particle size distribution of the sample, and q3(5.8 μm) denotes the percentage of the particle size distribution smaller than 5.8 μm geometric diameter.

TABLE 2

| Test No. | Pressure Drop (kPa) | Discharge Time (s) | Fill Mass (mg) | Sample Size | % CE | Q3 (50%) | q3 (5.8 μm) |
|---|---|---|---|---|---|---|---|
| 1 | 4 | 3 | 6.7 | 30 | 98.0 | 4.020 | 63.8 |
| 2 | 4 | 3 | 6.7 | 20 | 97.0 | 3.700 | 67.4 |
| 3 | 4 | 3 | 6.7 | 20 | 98.4 | 3.935 | 64.6 |
| 4 | 4 | 3 | 3.5 | 20 | 97.8 | 4.400 | 61.0 |
| 5 | 2 | 4 | 6.7 | 7 | 92.9 | 4.364 | 61.0 |
| 6 | 2 | 4 | 6.7 | 7 | 95.1 | 4.680 | 57.9 |
| 7 | 4 | 4 | 6.7 | 7 | 97.0 | 3.973 | 64.4 |
| 8 | 4 | 4 | 6.7 | 7 | 95.5 | 4.250 | 61.7 |
| 9 | 6 | 4 | 6.7 | 7 | 97.3 | 3.830 | 65.3 |
| 10 | 6 | 4 | 6.7 | 7 | 97.8 | 4.156 | 62.2 |

The data in Table 2 showed that 92.9% to 98.4% of the total powder fill mass was emitted from the inhalation system. Additionally, the data indicate that regardless of the fill mass, 50% of the particles emitted from the inhalation system had a geometric diameter of less than 4.7 μm as measured at the various times and pressure drops tested. Moreover, between 60% and 70% of the particles emitted had a geometric diameter of less than 5.8 μm.

Figure 81:
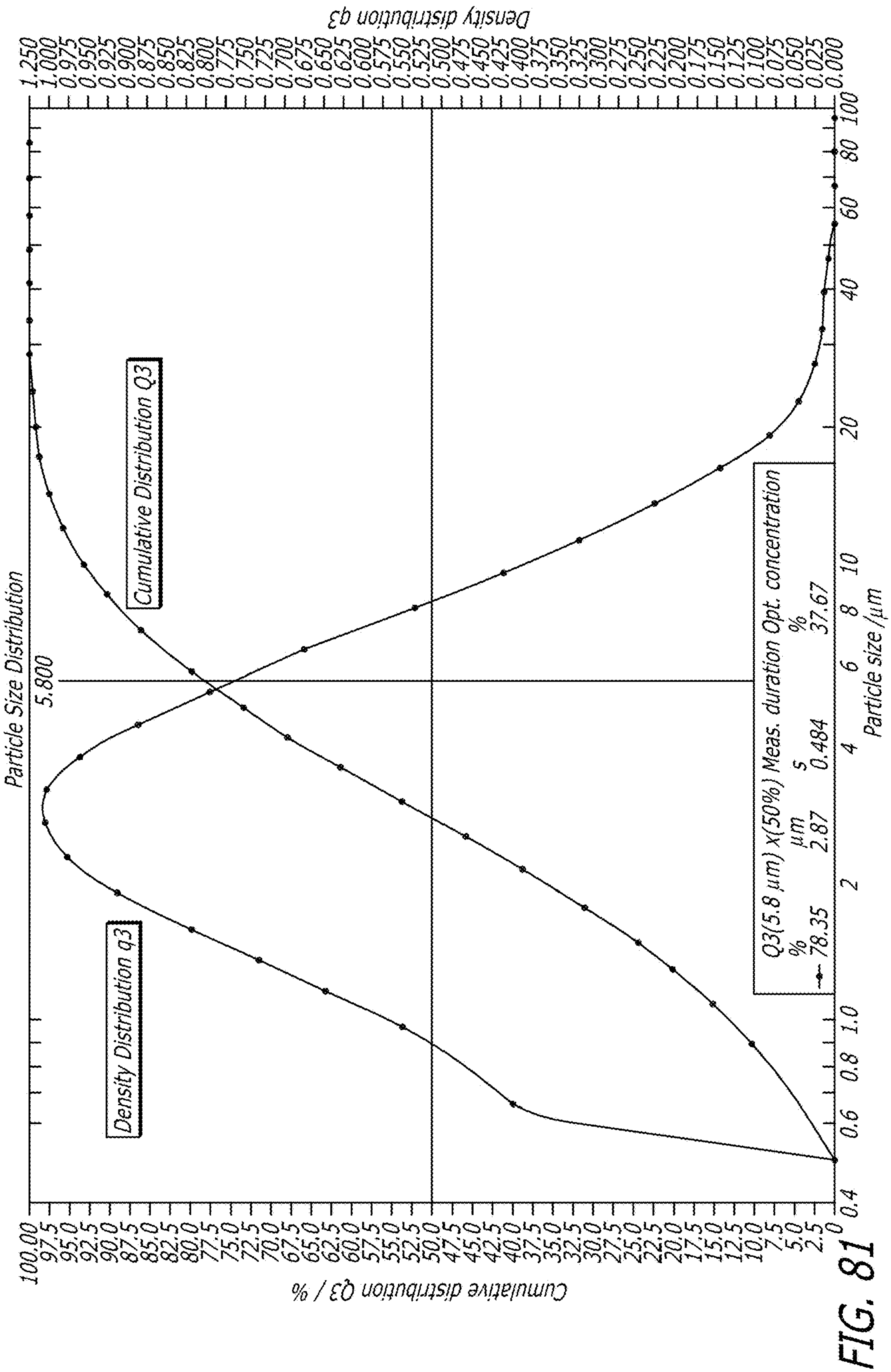
FIG. 81 depicts the particle size distribution obtained with a laser diffraction apparatus using an inhaler and cartridge containing a dry powder formulation for inhalation comprising insulin and fumaryl diketopiperizine particles.

FIG. 81 depicts data obtained from another experiment in which 10 mg of powder fill mass was used. The graph shows the particle size distribution of the sample containing particles of a formulation comprising insulin and fumaryl diketopiperazine resulted in 78.35% of the measured particles had a particle size of ≤5.8 μm. The laser detected 37.67% optical concentration during the measurement duration of 0.484 seconds at the above measurement conditions. The data show that the inhalation system effectively deagglomerates the insulin-FDKP formulation to small sizes over a relevant and lower range of user inhalation capacities, i.e., pressure drops. These small geometric sizes for this cohesive (Carr's index=36%) formulation are believed to be respirable.

Example 3

Measurement of Powder Discharge from a Cartridge as a Measure of Inhalation System Performance.

The experiments were conducted using the inhalation system described herewith using multiple inhaler prototypes depicted in FIGS. 15C-15K with cartridge 170 prototypes as shown in FIGS. 39A-39I. Multiple cartridges were used with each inhaler. Each cartridge was weighed in an electronic balance prior to fill. The cartridges were filled with a predetermined mass of powder, again weighed and each filled cartridge was placed in an inhaler and tested for efficiency of emptying a powder formulation, i.e., Technosphere® Insulin (insulin-FDKP; typically 3-4 U insulin/mg powder, approximately 10-15% insulin w/w) powder batches. Multiple pressure drops were used to characterize the consistency of performance. Table 3 depicts results of this testing using 35 cartridge discharge measurements per inhaler. In the data in Table 3, all tests were carried out using the same batch of a clinical grade insulin-FDKP powder. The results show that relevant user pressure drops, ranging from 2 through 5 kPa demonstrated a highly efficient emptying of the powder from the cartridge.

TABLE 3

| Test No. | Pressure Drop (kPa) | Discharge Time (s) | Fill Mass (mg) | Sample Size | Mean % CE | % CE SD |
|---|---|---|---|---|---|---|
| 1 | 5.00 | 3.00 | 3.08 | 35 | 99.42 | 0.75 |
| 2 | 5.00 | 3.00 | 3.00 | 35 | 98.11 | 1.11 |
| 3 | 5.00 | 3.00 | 6.49 | 35 | 99.49 | 0.81 |
| 4 | 5.00 | 3.00 | 6.55 | 35 | 99.05 | 0.55 |
| 5 | 5.00 | 2.00 | 6.57 | 35 | 98.69 | 0.94 |
| 6 | 5.00 | 2.00 | 6.57 | 35 | 99.33 | 1.03 |
| 7 | 4.00 | 3.00 | 6.47 | 35 | 98.15 | 1.15 |
| 8 | 4.00 | 3.00 | 6.50 | 35 | 99.37 | 0.46 |
| 9 | 4.00 | 3.00 | 3.28 | 35 | 98.63 | 0.93 |
| 10 | 4.00 | 3.00 | 3.18 | 35 | 98.63 | 1.48 |
| 11 | 4.00 | 2.00 | 6.61 | 35 | 92.30 | 3.75 |
| 12 | 4.00 | 2.00 | 6.58 | 35 | 98.42 | 1.71 |
| 13 | 3.00 | 3.00 | 6.55 | 35 | 92.91 | 5.04 |
| 14 | 3.00 | 3.00 | 6.56 | 35 | 98.88 | 0.63 |
| 15 | 3.00 | 2.00 | 6.56 | 35 | 96.47 | 3.19 |
| 16 | 3.00 | 2.00 | 6.59 | 35 | 99.49 | 0.54 |
| 17 | 3.00 | 1.00 | 6.93 | 35 | 98.06 | 2.37 |
| 18 | 3.00 | 1.00 | 6.95 | 35 | 98.74 | 0.67 |
| 19 | 3.00 | 1.00 | 3.12 | 35 | 97.00 | 1.06 |
| 20 | 3.00 | 1.00 | 3.15 | 35 | 96.98 | 0.99 |
| 21 | 2.00 | 1.00 | 6.53 | 35 | 97.24 | 1.65 |
| 22 | 2.00 | 1.00 | 6.49 | 35 | 98.48 | 2.27 |

Example 4

Measurement of Predictive Deposition by Andersen Cascade Impaction:

The experiments were conducted using an Andersen Cascade Impactor to collect stage plate powder deposits during a simulated dose delivery using flow rates of 28.3 LPM. This flow rate resulted in a pressure drop across the inhalation system (DPI plus cartridge) of approximately 6 kPa. Depositions on the plate stages were analyzed gravimetrically using filters and electronic balances. Fill weights of a cohesive powder in 10 mg, 6.6 mg and 3.1 mg fill mass were evaluated for inhalation system performance. Each impaction test was conducted with five cartridges. The cumulative powder mass collected on stages 2-F was measured in accordance with aerodynamic particle sizes less than 5.8 μm. The ratio of the collected powder mass to the cartridge fill content was determined and is provided as percent respirable fraction (RF) over the fill weight. The data is presented in Table 4.

The data show that a respirable fraction ranging from 50% to 70% was achieved with multiple powder batches. This range represents a normalized performance characteristic of the inhalation system.

The inhaler system performance measurements were repeated 35 times with a different cartridge. Fill mass (mg) and discharge time (seconds) were measured for each inhaler cartridge system used. Additionally, the percent of respirable fraction, i.e., particles suitable for pulmonary delivery, in the powder was also measured. The results are presented in Table 4 below. In the table, the % RF/fill equals the percent of particles having a size (≤5.8 μm) that would travel to the lungs in the powder; CE indicates cartridge emptying or powder delivered; RF indicates respirable fraction. In Table 4, Test Nos. 1-10 were conducted using a second batch of a clinical grade of the insulin-FDKP powder, but the test powder for 11-17 used the same powder as the tests conducted and presented in Table 3.

TABLE 4

| No. | Pressure Drop (kPa) | Discharge Time (s) | Fill Mass (mg) | Sample Size | Mean % CE | % RF/ Fill | % RF/ Delivered |
|---|---|---|---|---|---|---|---|
| 1 | 6.4 | 8 | 9.7 | 5 | 98.9 | 56.6 | 58.3 |
| 2 | 6.4 | 8 | 9.9 | 5 | 88.8 | 53.7 | 60.4 |
| 3 | 6.4 | 8 | 8.2 | 5 | 97.5 | 54.9 | 56.9 |
| 4 | 6.4 | 8 | 6.7 | 5 | 98.4 | 56.8 | 58.1 |
| 5 | 6.4 | 8 | 10.0 | 5 | 89.2 | 60.4 | 67.8 |
| 6 | 6.4 | 8 | 9.6 | 5 | 99.3 | 53.5 | 53.9 |
| 7 | 6.4 | 8 | 9.6 | 5 | 98.2 | 57.3 | 58.4 |
| 8 | 6.4 | 8 | 9.6 | 5 | 99.0 | 56.9 | 57.5 |
| 9 | 6.4 | 8 | 9.6 | 5 | 95.4 | 59.3 | 62.1 |
| 10 | 6.4 | 8 | 6.6 | 5 | 99.4 | 61.7 | 62.1 |
| 11 | 6.4 | 8 | 6.6 | 5 | 99.6 | 59.0 | 59.2 |
| 12 | 6.4 | 8 | 6.6 | 5 | 96.5 | 62.6 | 64.8 |
| 13 | 6.4 | 8 | 6.6 | 5 | 98.7 | 59.8 | 60.6 |
| 14 | 6.4 | 8 | 3.1 | 5 | 99.5 | 66.3 | 66.6 |
| 15 | 6.4 | 8 | 3.1 | 5 | 99.7 | 70.7 | 70.9 |
| 16 | 6.4 | 8 | 3.1 | 5 | 97.6 | 65.9 | 67.5 |
| 17 | 6.4 | 8 | 3.1 | 5 | 98.2 | 71.6 | 73.0 |

The data above show that the present inhalation system comprising a dry powder inhaler and a cartridge containing a cohesive powder, i.e., TECHNOSPHERE® Insulin (FDKP particles comprising insulin) can discharge effectively almost all of the powder content, since greater than 85% and in most cases greater than 95% of the total powder content of a cartridge at variable fill masses and pressure drops were obtained with consistency and significant degree of emptying. The Andersen cascade impaction measurements indicated that greater than 50% of the particles are in the respirable range wherein the particles are less than 5.8 μm and ranging from 53.5% to 73% of the total emitted powder.

Example 5

Rugosity of TECHNOSPHERE® Insulin (TI).

The rugosity is the ratio of the actual specific surface area of the particle to that for an equivalent sphere. The specific surface area of a sphere is:

$$SSA_{sphere} = \frac{\pi d_{eff}^2}{\rho \frac{\pi}{6} d_{eff}^3} = \frac{6}{\rho d_{eff}}$$

where $d_{eff}$=1.2 μm is the surface-weighted diameter of TI particles from Sympatec/RODOS laser diffraction measurements.

An average sphere with the same density as the TI particle matrix (1.4 g/cm$^3$) would therefore have an SSA of $$SSA_{sphere} = \frac{6}{\rho d_{eff}} = \frac{6}{\left(1.4\frac{g}{cm^3}\right)(1.2\times10^{-6}\ m)}\left(\frac{m^3}{10^6\ cm^3}\right) = 3.6\ m^2/g$$

Thus for TI particles with specific surface area (SSA) of approximately 40 m$^2$/g $$\text{Rugosity} = \frac{(SSA)_{TI}}{(SSA)_{particle}} = \frac{40\ m^2/g}{3.6\ m^2/g} \approx 11.$$

For similarly sized particles with specific surface area of 50 or 60 m$^2$/g the rugosity would be roughly 14 and 16 respectively.

Example 6

Geometric Particle Size Analysis of Emitted Formulations by Volumetric Median Geometric Diameter (VMGD) Characterization Laser diffraction of dry powder formulations emitted from dry powder inhalers is a common methodology employed to characterize the level of de-agglomeration subjected to a powder. The methodology indicates a measure of geometric size rather than aerodynamic size as occurring in industry standard impaction methodologies. Typically, the geometric size of the emitted powder includes a volumetric distribution characterized by the median particle size, VMGD. Importantly, geometric sizes of the emitted particles are discerned with heightened resolution as compared to the aerodynamic sizes provided by impaction methods. Smaller sizes are preferred and result in greater likelihood of individual particles being delivered to the pulmonary tract. Thus, differences in inhaler de-agglomeration and ultimate performance can be easier to resolve with diffraction. In these experiments, an inhaler as specified in Example 3 and a predicate inhaler are tested with laser diffraction at pressures analogous to actual patient inspiratory capacities to determine the effectiveness of the inhalation system to de-agglomerate powder formulations. Specifically, the formulations included cohesive diketopiperazine powders with an active insulin loaded ingredient and without. These powder formulations possessed characteristic surface areas, isomer ratios, and Carr's indices. Reported in Table 5 are a VMGD and an efficiency of the container emptying during the testing. FDKP powders have an approximate Carr's index of 50 and TI powder has an approximate Carr's index of 40.

TABLE 5

| Inhaler system | powder | % trans | SSA | pressure drop (kPa) | sample size | % CE | VMGD (micron) |
|---|---|---|---|---|---|---|---|
| DPI 2 | FDKP | 56 | 55 | 4 | 15 | 92.5 | 6.800 |
| MedTone ® | FDKP | 56 | 55 | 4 | 30 | 89.5 | 21.200 |
| DPI 2 | FDKP + active | 56 | 45 | 4 | 30 | 98.0 | 4.020 |
| DPI 2 | FDKP + active | 56 | 45 | 4 | 20 | 97.0 | 3.700 |
| DPI 2 | FDKP + active | 56 | 45 | 4 | 20 | 98.4 | 3.935 |
| DPI 2 | FDKP + active | 56 | 45 | 4 | 20 | 97.8 | 4.400 |
| MedTone ® | FDKP + active | 56 | 45 | 4 | 10 | 86.1 | 9.280 |
| MedTone ® | FDKP + active | 56 | 45 | 4 | 10 | 92.3 | 10.676 |
| DPI 2 | FDKP + active | 56 | 45 | 2 | 7 | 92.9 | 4.364 |
| DPI 2 | FDKP + active | 56 | 45 | 2 | 7 | 95.1 | 4.680 |
| DPI 2 | FDKP + active | 56 | 45 | 4 | 7 | 97.0 | 3.973 |

TABLE 5-continued

| Inhaler system | powder | % trans | SSA | pressure drop (kPa) | sample size | % CE | VMGD (micron) |
|---|---|---|---|---|---|---|---|
| DPI 2 | FDKP + active | 56 | 45 | 4 | 7 | 95.5 | 4.250 |
| DPI 2 | FDKP + active | 56 | 56 | 4 | 10 | 99.6 | 6.254 |
| DPI 2 | FDKP + active | 56 | 14 | 4 | 10 | 85.5 | 4.037 |
| MedTone ® | FDKP + active | 56 | 56 | 4 | 20 | 89.7 | 12.045 |
| MedTone ® | FDKP + active | 56 | 14 | 4 | 20 | 37.9 | 10.776 |
| DPI 2 | FDKP + active | 54 | 50 | 4 | 10 | 97.1 | 4.417 |
| DPI 2 | FDKP + active | 54 | 44 | 4 | 10 | 96.0 | 4.189 |
| DPI 2 | FDKP + active | 56 | 35 | 4 | 10 | 92.0 | 3.235 |
| DPI 2 | FDKP + active | 50 | 34 | 4 | 10 | 93.2 | 5.611 |
| DPI 2 | FDKP + active | 66 | 33 | 4 | 10 | 79.0 | 4.678 |
| DPI 2 | FDKP + active | 45 | 42 | 4 | 10 | 93.2 | 5.610 |
| DPI 2 | FDKP + active | 56 | 9 | 4 | 10 | 78.9 | 5.860 |

These data in Table 5 show an improvement in powder de-agglomeration over a predicate inhaler system as compared to the inhaler system described herein. Diketopiperazine formulations with surface areas ranging from 14-56 $m^2/g$ demonstrated emptying efficiencies in excess of 85% and VMGD less than 7 microns. Similarly, formulations possessing an isomer ratio ranging from 45-66% trans demonstrated improved performance over the predicate device. Last, performance of the inhaler system with formulations characterized with Carr's indices of 40-50 were shown to be improved over the predicate device as well. In all cases, the reported VMGD values were below 7 microns.

Example 7

Relationship Between Trans Isomer Content and RF/Fill

Microparticles were manufactured from FDKP and insulin. FDKP was dissolved in aqueous $NH_4OH$ to form a solution. A feed stream of this solution was combined with a feed stream of an aqueous HOAc solution in a high shear mixer to form an aqueous suspension of microparticles.

The FDKP feed solution was prepared with about 2.5 wt % FDKP, about 1.6 wt % concentrated $NH_4OH$ (about 28 to about 30 wt % $NH_3$) and about 0.05 wt % polysorbate 80. The acetic acid feed solution was prepared at about 10.5 wt % GAA and about 0.05 wt % polysorbate 80. Both feed solutions were filtered through an about 0.2 μm membrane prior to use.

Equal amounts (by mass) of each feed solution were pumped through a Dual-Feed Sonolator™ equipped with the #5 orifice (0.0011 sq. inch). The minor pump was set to 50% for equal flow rates of each feed stream and the feed pressure was about 2000 psi. The receiving vessel contained DI water equal to the mass of either feed solution (e.g. 4 kg FDKP feed solution and 4 kg HOAc feed solution would be pumped through the Sonolator™ into the receiving vessel containing 4 kg of DI water).

The resulting suspension was concentrated and washed by means of tangential flow filtration using a 0.2 $m^2$ PES membrane. The suspensions were first concentrated to about 4% solids then diafiltered with DI water and finally concentrated to about 16% nominal solids. The actual percent solids of the washed suspension was determined by "loss on drying."

Insulin stock solutions were prepared containing about 10 wt % insulin (as received) in a solvent comprising about 2 wt % HOAc in DI water and sterile filtered. The stock solution was filtered through a 0.22 μm filter prior to use. Based on the solids content of the suspension, the appropriate amount of stock solution was added to the mixed suspension. The resulting microparticle/insulin was then adjusted from a pH of about 3.6 to a pH of about 4.5 using an ammonia solution.

The microparticle/insulin suspension was then flash frozen by pelletizing (cryo-granulating) into liquid nitrogen. The ice pellets were lyophilized until the drying was complete.

The respirable fraction (RF/fill) of bulk powders is a measure of aerodynamic microparticle size distribution and is determined by testing with the Andersen cascade impacter. To obtain RF/fill values, cartridges are filled with bulk powder and discharged through a MEDTONE® inhaler at 30 L/min. The powder collected on each inhaler stage is weighed and the total powder collected is normalized to the total amount filled in the cartridges. Accordingly, RF/fill is powder collected on those stages of the impacter representing the respirable fraction divided by powder loaded into cartridges.

As shown in FIG. 1, FDKP powders with acceptable aerodynamic performance measured as RF/fill have been produced from FDKP with as little as 45% trans isomer (FIG. 1). Powders containing more than 65% trans-FDKP tended to have lower and more variable RF/fill.

This study determined the upper end of the trans isomer content range with beneficial aerodynamic properties. The next sections describe experiments conducted to evaluate processing conditions that can generate the specified isomer contents.

Example 8

Saponification Solvent

Experiments were conducted to determine the effect, if any, of the saponification solvent on % trans isomer FDKP (FIG. 83).

A mixture of 004 and 590 mL of reaction solvent (see Table 5) was heated to about 57° C. After the reaction temperature had stabilized, about 50% NaOH solution was added dropwise via addition funnel over about 60 minutes. The reaction was held for about 30 minutes after the NaOH addition was complete and then filtered to remove any unreacted solids. The filtrate was acidified with acetic acid to a pH of about 5 and the resulting solids isolated by filtration, washed with water and acetone, dried in a vacuum oven, and analyzed by HPLC to determine cis and trans isomer content.

Accordingly, five different solvent systems ranging from aqueous (Table 5, A) to organic (Table 5, E) were evaluated. In general, the results showed that as methanol content in the methanol/water solvent system increased, the percent of trans FDKP also increased, although saponification in 100% methanol gave FDKP with low trans isomer content and was complicated by low FDKP solubility in methanol:

TABLE 5

| Affect of water:methanol Solvent Ratio in Step 5 on FDKP Isomer Content | | |
|---|---|---|
| Sample ID | Water:Methanol Ratio (v:v) | % Trans FDKP |
| A | 4:0 | 51 |
| B | 3:1 | 53 |
| C | 2:2 | 55 |
| D | 1:3 | 78 |
| E | 0:4 | 33 |

Example 9

Recrystallization Conditions

Figure 86:
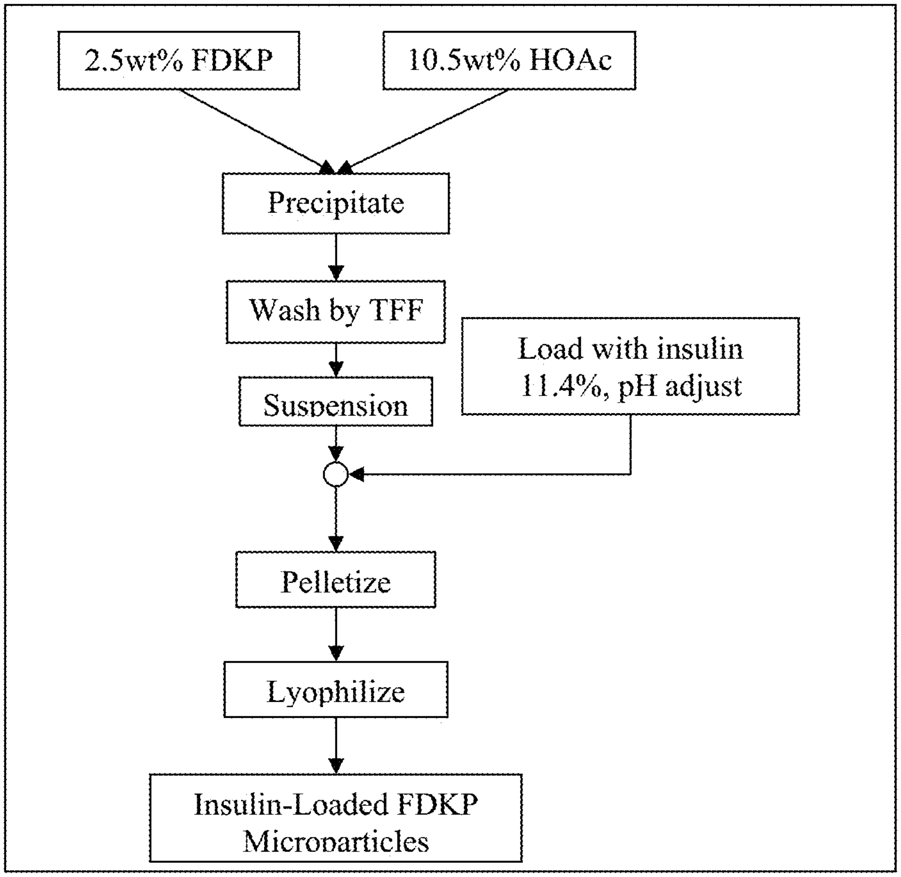
FIG. 86 depicts a schematic of a process to manufacture insulin-loaded FDKP microparticles with a trans isomer content of about 45 to about 65%.

FDKP can be recrystallized from a TAA (solvent)/GAA (anti-solvent) mixture (FIG. 86; step 6). Controlled process parameters were evaluated to characterize this recrystallization process and its effects on FDKP isomer contents. The effect of each parameter on the isomer content varied as a function of reaction yield. That is, low product recovery resulted in elevated trans isomer levels because cis FDKP has a greater solubility in TFA. These yield effects complicated data interpretation, so it was difficult to characterize the effect of a given parameter on % trans FDKP alone. However, the data suggest that an about 40 to about 65% yield is necessary to meet the about 45 to about 65% trans FDKP range. Accordingly, data points that did not meet this required minimum yield were excluded.

The following experiments used the following procedure unless a parameter was modified to examine its effect on FDKP isomer contents and yield.

A reactor was charged with crude FDKP (about 75 g) and TFA (about 250 mL) and stirring was initiated. The suspension was heated to reflux (about 80 to about 85° C.) and held for about 10 minutes or until all solids were dissolved. The mixture was cooled to below about 60° C. Glacial acetic acid (about 375 mL) was added to the solution. The mixture was cooled and held for a minimum of about 6 hours at about 10 to about 20° C. The precipitated product was filtered and washed with GM (3×about 100 mL), acetone (3×about 100 mL) and water (1×about 100 mL). The product was dried at about 55° C. under vacuum (about 22 to about 25 in. Hg) for about 12 to about 18 hours.

Initially, four factors were tested including solvent quantity, anti-solvent quantity, crystallization time and crystallization temperature. A solvent quantity of about 2.68 or about 3.34 mL/g FDKP provided acceptable % trans isomer. At around 6.68 mL solvent/g FDKP, an unacceptably high trans isomer content was produced. The amount of anti-solvent did not significantly affect % trans FDKP isomer content at up to 5.0 mL/g FDKP. Reducing anti-solvent quantity from the control quantity substantially produced a % trans FDKP above the desired range.

In these experiments crystallization time did not significantly affect % trans FDKP isomer content at up to about 6 hours. Isomer content (% trans FDKP) fell outside the about 45 to about 65% range at the high (35° C.) and low (0° C.) crystallization temperatures tested.

Figure 87:
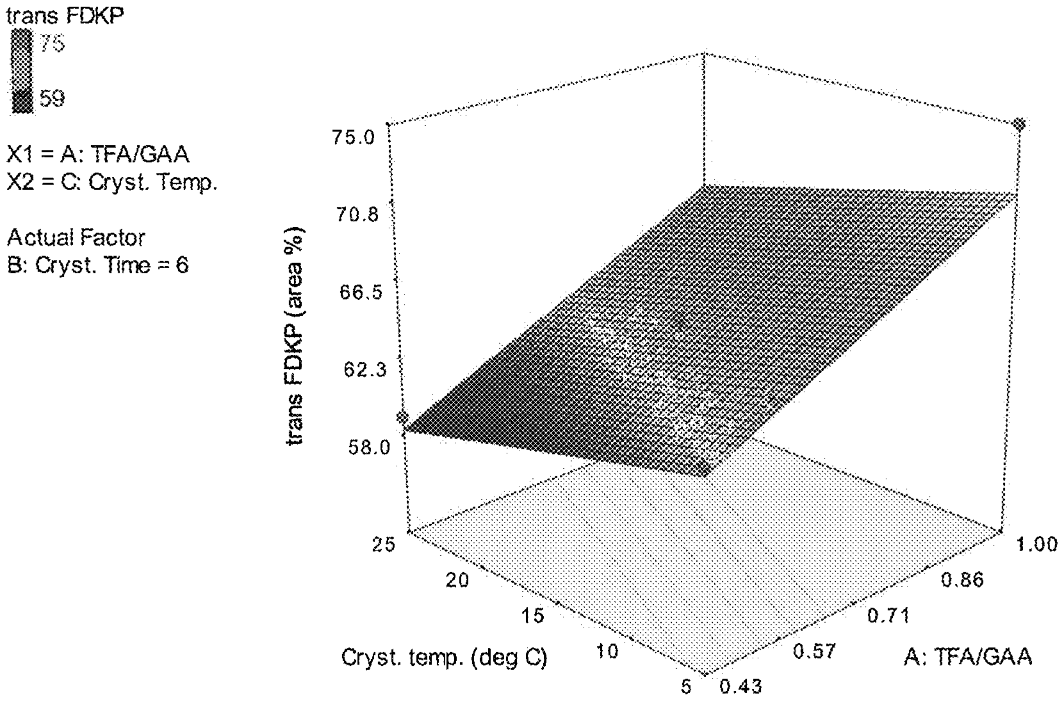
FIG. 87 depicts a response surface methodology analysis for trans isomer content.

Subsequent experiments supported these findings. FIG. 87 shows a surface depicting FDKP isomer content, measured as % trans FDKP, as a function of solvent:anti-solvent ratio (TFA:GAA) and crystallization temperature. Over the ranges tested in these experiments the values for % trans FDKP varied from 59-75%. The data suggest that trans FDKP is within the desired range at a low solvent ratio (0.43) and high crystallization temperatures (25° C.). Predicted values for trans FDKP in this area of the response surface are 58-60%. These observations suggest that using a crystallization temperature of 25° C. could be advantageous.

The preceding disclosures are illustrative embodiments. It should be appreciated by those of skill in the art that the devices, techniques and methods disclosed herein elucidate representative embodiments that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A dry powder inhaler comprising:

a sled or slide tray, a mouthpiece, and a cartridge including two or more rigid parts, wherein at least one of the two or more rigid parts is a container and another of the two or more rigid parts is a lid, wherein movement of the mouthpiece actuates movement of the sled or slide tray and the sled or slide tray is operably configured to move the container relative to the lid from a powder containment position to a dosing position, wherein the cartridge has at least one opening configured as an inlet and at least one opening configured as an outlet, and wherein the container includes a dry powder including a prostaglandin.

2. The dry powder inhaler of claim 1, wherein the prostaglandin is PG-I2.

3. The dry powder inhaler of claim 1, wherein the dry powder includes a di ketopiperazine.

4. The dry powder inhaler of claim 3, wherein the diketopiperazine is

FDKP

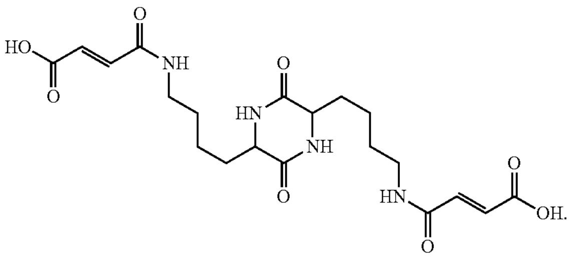

5. The dry powder inhaler of claim 1, wherein the mouthpiece is configured to engage the sled or slide tray.

6. The dry powder inhaler of claim 1, further comprising a housing.

7. The dry powder inhaler of claim 6, wherein the inhaler has a proximal end and a distal end, and the housing, mouthpiece and sled or slide tray are attached at the distal end of the inhaler; and the mouthpiece pivots on the housing to attain an open or loading position or a closed or dosing position.

8. The dry powder inhaler of claim 6, wherein the inhaler comprises a gear mechanism mounted in said inhaler housing.

9. The dry powder inhaler of claim 6, wherein the mouthpiece further has an internal volume extending from the first inlet port to the exit port greater than 0.2 cubic centimeters.

10. The dry powder inhaler of claim 6, wherein the housing has one or more openings to allow ambient air into its interior compartment.

11. The dry powder inhaler of claim 6, wherein the housing is substantially rectangular in shape and has an upper surface, side walls and a bottom wall forming an enclosure and comprises one or more flanges projecting in an upwardly direction from the upper surface of the housing.

12. The dry powder inhaler of claim 6, wherein the housing has a substantially rectangular, oval, circular, or square shape.

13. The dry powder inhaler of claim 6, wherein the housing comprises one or more grasping surfaces.

14. The dry powder inhaler of claim 6, wherein the sled or slide tray is positioned between the mouthpiece and the housing.

15. The dry powder inhaler of claim 1, wherein the mouthpiece actuates the sled or slide tray by rotation or translation.

16. The dry powder inhaler of claim 1, wherein the dry powder inhaler is configured to attain an open or container loading position, and a closed or dosing position.

17. The dry powder inhaler of claim 16, wherein the mouthpiece actuates the sled or slide tray during movement between the open position and the closed position or from the closed position to the open position.

18. The dry powder inhaler of claim 1, wherein the sled or slide tray is attached to the mouthpiece by a hinge mechanism.

19. The dry powder inhaler of claim 18, wherein the hinge mechanism comprises a gear or rack and pinion mechanism.

20. The dry powder inhaler of claim 1, wherein the sled or slide tray comprises a cam.

* * * * *